United States Patent
Sun et al.

(10) Patent No.: US 10,508,103 B2
(45) Date of Patent: Dec. 17, 2019

(54) BENZIMIDAZOLE-LINKED INDOLE COMPOUND ACTING AS NOVEL DIVALENT IAP ANTAGONIST

(71) Applicant: MEDSHINE DISCOVERY INC., Nanjing, Jiangsu (CN)

(72) Inventors: Fei Sun, Shanghai (CN); Charles Z. Ding, Shanghai (CN); Zhe Cai, Shanghai (CN); Wenyuan Qian, Shanghai (CN); Guoping Hu, Shanghai (CN); Jian Li, Shanghai (CN); Shuhui Chen, Shanghai (CN)

(73) Assignee: MEDSHINE DISCOVERY INC., Nanjing, Jiangsu (CN)

( * ) Notice: Subject to any disclaimer, the term of this patent is extended or adjusted under 35 U.S.C. 154(b) by 0 days.

(21) Appl. No.: 16/096,848

(22) PCT Filed: Apr. 27, 2017

(86) PCT No.: PCT/CN2017/082227
§ 371 (c)(1),
(2) Date: Oct. 26, 2018

(87) PCT Pub. No.: WO2017/186147
PCT Pub. Date: Nov. 2, 2017

(65) Prior Publication Data
US 2019/0135794 A1 May 9, 2019

(30) Foreign Application Priority Data
Apr. 27, 2016 (CN) .......................... 2016 1 0271073

(51) Int. Cl.
C07D 403/14 (2006.01)
A61P 35/00 (2006.01)
A61P 31/20 (2006.01)
A61K 31/4184 (2006.01)

(52) U.S. Cl.
CPC ........ C07D 403/14 (2013.01); A61K 31/4184 (2013.01); A61P 31/20 (2018.01); A61P 35/00 (2018.01)

(58) Field of Classification Search
CPC ...... A61K 31/4184; A61P 35/00; A61P 31/20; C07D 403/14
See application file for complete search history.

(56) References Cited

U.S. PATENT DOCUMENTS

| | | | |
|---|---|---|---|
| 8,283,372 | B2 | 10/2012 | Condon et al. |
| 2011/0305777 | A1 | 12/2011 | Condon et al. |
| 2014/0303090 | A1 | 10/2014 | Condon et al. |

FOREIGN PATENT DOCUMENTS

| | | |
|---|---|---|
| CN | 101516904 A | 8/2009 |
| CN | 102471275 A | 5/2012 |
| WO | 2006091972 A2 | 8/2006 |
| WO | 2008014252 A2 | 1/2008 |
| WO | 2008014263 A2 | 1/2008 |
| WO | 2011002684 A1 | 1/2011 |

OTHER PUBLICATIONS

International Search Report of the International Searching Authority issued in PCT/CN2017/082227, dated Aug. 8, 2017; ISA/CN.
Written Opinion of the International Searching Authority issued in PCT/CN2017/082227, dated Aug. 8, 2017; ISA/CN.
English Translation of Priority Application No. CN201610271073.3.
Fulda, S., et al.,"Targeting IAP proteins for therapeutic intervention in cancer", Nature Reviews Drug Discovery, 2012, 11, p. 109-124.
Bai, L. et al., "Small-molecule SMAC mimetics as new cancer therapeutics", Pharmacology & Therapeutics, 2014, 144, p. 82-95.
Condon, S. et al., "Birinapant, a Smac-Mimetic with Improved Tolerability for the Treatment of Solid Tumors and Hematological Malignancies", Journal of Medicinal Chemistry, 2014, 57, p. 3666-3677.
Ebert, E. et al., "Cellular inhibitor of apoptosis proteins prevent clearance of hepatitis B virus", PNAS, 2015, 112, p. 5797-5802.

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

The present invention discloses a benzimidazole-linked indole compound acting as novel divalent IAP antagonist, specifically disclosing the compound shown in formulas (I) or a pharmaceutically acceptable salt thereof.

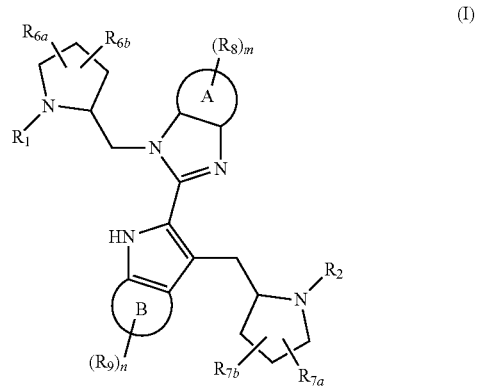

32 Claims, No Drawings

BENZIMIDAZOLE-LINKED INDOLE COMPOUND ACTING AS NOVEL DIVALENT IAP ANTAGONIST

CROSS-REFERENCE TO RELATED APPLICATIONS

This application is a 371 National Phase of PCT/CN2017/082227 filed Apr. 27, 2017, which claims the benefit of Chinese Patent Application No. 201610271073.3, filed on Apr. 27, 2016. The entire disclosures of the above applications are incorporated herein by reference.

FIELD OF INVENTION

The present invention relates to a kind of benzimidazole-linked indole compound acting as novel divalent IAP antagonist and specially discloses the compound shown in formula (I) or a pharmaceutically acceptable salt thereof.

BACKGROUND OF INVENTION

Cell apoptosis is an autonomic ordered programmed cell death controlled by genes in order to maintain homeostasis which plays an important role in organism evolution, homeostasis and multi-system development. Cell apoptosis signal transduction is divided into internal (mediated by interaction between death receptor and ligand) and exterior (mediated by cell stress and mitochondria permeability) transduction and these two transduction converge on Caspase. Once apoptosis signal is activated, Caspase will dissociate lots of substrates associated with cell death which causes cells die.

Inhibitor of apoptosis proteins (IAPB) is a family of highly conserved endogenous anti-apoptosis factors which suppresses apoptosis through inhibiting Caspase activation and participating in mediating nuclear factor NF-κB. Roy et al. found IAP was a neuronal apoptosis inhibitor protein (NAIP) in research of spinal muscular atrophy firstly in 1995. Subsequently, cellular inhibitor of apoptosis protein (cellular TAP, c-IAP1 and c-IAP2), X chromosome linked inhibitory of apoptosis factor(XIAP), Survivin, melanoma inhibitor of apoptosis protein (melanoma-TAP, ML-IAP/Livin), testi-specific inhibitor of apoptosis protein (hILP) and BIR repeat containing ubiquitin-conjugating enzyme, and eight human IAPB family protein members has been found so far. Among these eight IAP family, cIAP1, cIAP2, XIAP were sufficiently studied. They contain three structural functional domains, named BIR1, BIR2 and BIR3, which play roles in apoptosis suppression through inhibiting Caspase 3, 7, 9 and so on.

Smac, fully named second mitochondria-derived activator of caspases, is a protein mediating cellular apoptosis in mitochondrial which promotes apoptosis through reversing inhibitor of apoptosis proteins (IAPs), particular X chromosome linked inhibitory of apoptosis factor (XIAP). When cells are activated by apoptosis, mitochondrial releases Smac into cytoplasm, which binds to IAPs and results in IAPB losing suppression on caspase and promoting cellular apoptosis. Smac binds to multi-IAPB directly with tetrapeptide in N-terminus which blocks IAPs' roles in apoptosis suppression and promoting cellular apoptosis effectively. Various IAP inhibitors, also named Smac mimetics were reported by lots of references which inhibited proliferation of cancer cells and promoted apoptosis of infected cells in vivo and in vitro. Among them, Birinapant, LCL-161, AT-406 and so on have entered into clinical phase I or phase II. However, novel IAP antagonists with better activity, selectivity and safety are still in a huge demand.

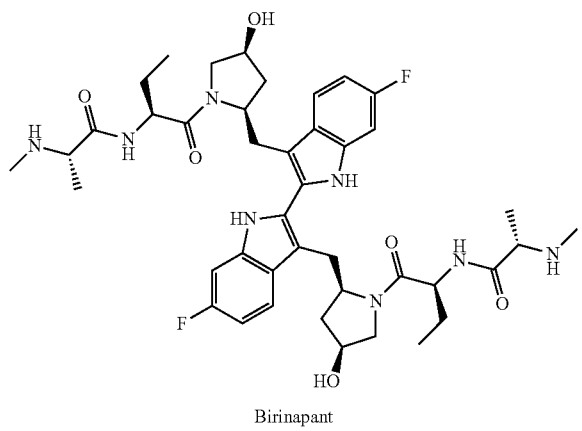

Birinapant

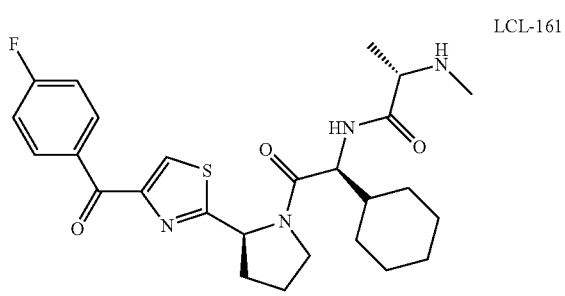

LCL-161

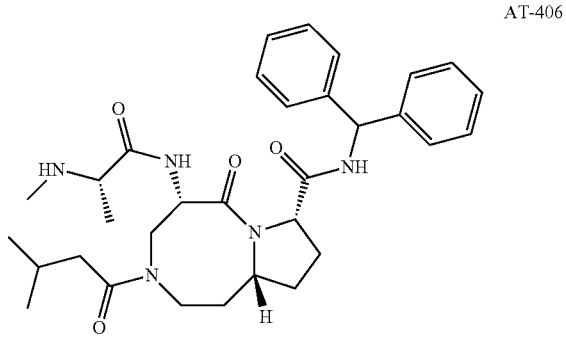

AT-406

Background information referred to references below:

Nat.rev.Drug Discov.2012, 11, p 109-124; Pharmacology & Therapeutics, 2014, 144, p 82-95; J.Med.Chen.2014, 57, p 3666-3677; Proc.Natl.Sci.Acad.USA2015, 112, p 5759-5802; CONDON, Stephen, M. etc, WO/2006/091972.

CONTENT OF THE PRESENT INVENTION

The present invention provides a compound shown in formula (I) or a pharmaceutically acceptable salt thereof,

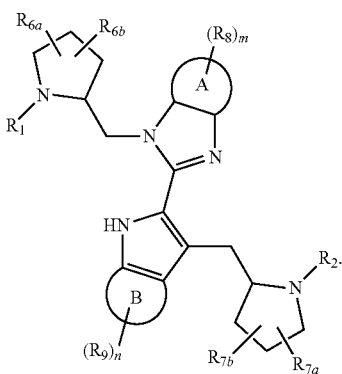

(I)

wherein,

R₁ and R₂ are independently selected from

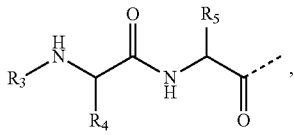

respectively;

R₃, R₄ and R₅ are independently selected from the group consisting of $C_{1-6}$ alkyl, $C_{1-6}$ heteroalkyl, $C_{3-12}$ cycloalkyl, 3-12membered heterocycloalkyl, 5-12membered aryl or heteroaryl, 5-12membered aralkyl or heteroaralkyl, each of which is optionally substituted with 1, 2 or 3 of R;

$R_{6a}$ and $R_{6b}$ are independently selected from the group consisting of H, F, Cl, Br, I, OH, CN, NH₂, COOH, or $C_{1-6}$ alkyl, $C_{1-6}$ heteroalkyl, $C_{3-6}$ cycloalkyl, 3-6membered heterocycloalkyl, 5-6membered aryl or heteroaryl and 5-6membered aralkyl or heteroaralkyl, the $C_{1-6}$ alkyl, $C_{1-6}$ heteroalkyl, $C_{3-6}$ cycloalkyl, 3-6membered heterocycloalkyl, 5-6membered aryl or heteroaryl and 5-6membered aralkyl or heteroaralkyl are optionally substituted with 1, 2 or 3 of R;

optionally, $R_{6a}$ and $R_{6b}$ are linked together to form a 3-6membered ring optionally substituted with 1, 2 or 3 of R;

$R_{7a}$ and $R_{7b}$, are independently selected from the group consisting of H, F, Cl, Br, I, OH, CN, NH₂, COOH, or $C_{1-6}$ alkyl, $C_{1-6}$ heteroalkyl, $C_{3-6}$ cycloalkyl, 3-6membered heterocycloalkyl, 5-6membered aryl or heteroaryl and 5-6membered aralkyl or heteroaralkyl, the $C_{1-6}$ alkyl, $C_{1-6}$ hetero alkyl, $C_{3-6}$ cycloalkyl, 3-6-membered hetero cycloalkyl, 5-6 membered aryl or hetero aryl and 5-6membered aralkyl or hetero aralkyl are optionally substituted with 1, 2 or 3 of R;

optionally, $R_{7a}$ and $R_{7b}$, are linked together to form a 3-6membered ring optionally substituted with 1, 2 or 3 of R;

ring A and ring B are independently selected from the group consisting of 5-6membered aryl or heteroaryl, 5-6membered aralkyl or heteroaralkyl;

R₈ and R₉ are independently selected from the group consisting of halogen, hydroxy or $C_{1-6}$ alkyl, $C_{1-6}$ heteroalkyl, $C_{3-6}$ cycloalkyl and 3-6membered heterocycloalkyl, the $C_{1-6}$ alkyl, $C_{1-6}$ heteroalkyl, $C_{3-6}$ cycloalkyl and 3-6membered heterocycloalkyl are optionally substituted with 1, 2 or 3 of R;

m and n are independently selected from 0,1,2 or 3;

R is selected from the group consisting of F, Cl, Br, I, CN, OH, NH₂, COOH, or $C_{1-6}$ alkyl, $C_{1-6}$ heteroalkyl, $C_{3-6}$ cycloalkyl, 3-6membered heterocycloalkyl,phenyl and 5-6membered heteroaryl, the $C_{1-6}$ alkyl, $C_{1-6}$ heteroalkyl, $C_{3-6}$ cycloalkyl, 3-6membered heterocycloalkyl,phenyl and 5-6 membered heteroaryl are optionally substituted with 1, 2 or 3 of R';

R' is selected from the group consisting of F, Cl, Br, I, OH, CN, NH₂, COOH, Me, Et, CF₃, CHF₂, CH₂F, NHCH₃ and N(CH₃)₂;

"hetero" means hetero atom or hetero group, which is selected from the group consisting of —C(=O)N(R)—, —N(R)—, —C(=NR)—, —S(=O)₂N(R)—, —S(=O) N(R), —O—, —S—, =O, =S, —O—N=, —C(=O) O—, —C(=O)—, —C(=S)—, —S(=O)—, —S(=O)₂— and —N(R)C(=O)N(R)—;

In any case above, the number of hetero atom or hetero group is independently selected from 1,2 or 3.

In certain embodiment of this invention, R is selected from the group consisting of F, Cl, Br, I, CN, OH, NH₂, COOH, or $C_{1-3}$ alkyl, $C_{1-3}$ alkoxy, $C_{1-3}$ alkylthiol, $C_{1-3}$ alkylamino and N,N-di($C_{1-2}$ alkyl)amino, the $C_{1-3}$ alkyl, $C_{1-3}$ alkoxy, $C_{1-3}$ alkylthiol, $C_{1-3}$ alkylamino and N,N-di ($C_{1-2}$ alkyl)amino are optionally substituted with 1, 2 or 3 R'.

In certain embodiment of this invention, R is selected from the group consisting of F, Cl, Br, I, CN, OH, NH₂, COOH, Me, Et, CF₃, CHF₂, CH₂F, NHCH₃, N(CH₃)₂,

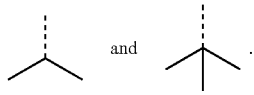

In certain embodiment of this invention, R₃ and R₄ are independently selected from the group consisting of $C_{1-4}$ alkyl, $C_{1-4}$ heteroalkyl, $C_{3-6}$ cycloalkyl, 3-6membered heterocycloalkyl, 5-6membered aryl or heteroaryl and 5-6membered aralkyl or heteroaralkyl; the $C_{1-4}$ alkyl, $C_{1-4}$ heteroalkyl, $C_{3-6}$cycloalkyl, 3-6membered heterocycloalkyl, 5-6membered aryl or heteroaryl and 5-6 membered aralkyl or heteroaralkyl are optionally substituted with 1, 2 or 3 of R.

In certain embodiment of this invention, R₃ and R₄ are independently selected from the group consisting of $C_{1-3}$ alkyl, $C_{1-3}$ heteroalkyl, phenyl, pyridinyl, pyrimidyl, pyrazinyl, pyridaziny, furyl, imidazolyl, oxazolyl, isoxazolyl, thienyl and pyrazolyl.

In certain embodiment of this invention, R₃ and R₄ are independently selected from Me.

In certain embodiment of this invention, R₅ is selected from the group consisting of $C_{1-4}$ alkyl, $C_{1-4}$ heteroalkyl, $C_{3-6}$ cycloalkyl, 3-6membered heterocycloalkyl, 5-6membered aryl or heteroaryl and 5-6-membered aralkyl or heteroaralkyl; the $C_{1-4}$ alkyl, $C_{1-4}$ heteroalkyl, $C_{3-6}$ cycloalkyl, 3-6membered heterocycloalkyl, 5-6membered aryl or heteroaryl and 5-6-membered aralkyl or heteroaralkyl are optionally substituted with 1, 2 or 3 of R.

In certain embodiment of this invention, R₅ is selected from the group consisting of $C_{1-4}$ alkyl, $C_{3-6}$ cycloalkyl, 3-6membered heterocycloalkyl, phenyl, pyridinyl, pyrimidyl, pyrazinyl, pyridaziny, furyl, imidazolyl, oxazolyl, isoxazolyl, thienyl and pyrazolyl.

In certain embodiment of this invention, R₅ is selected from

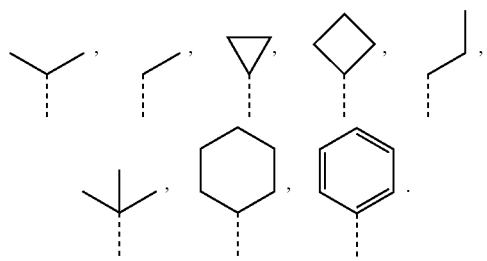

In certain embodiment of this invention, the structural unit

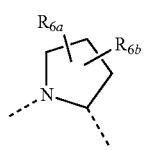

is selected from

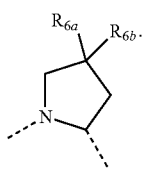

In certain embodiment of this invention, the structural unit

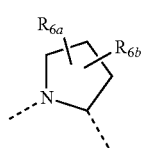

is selected from

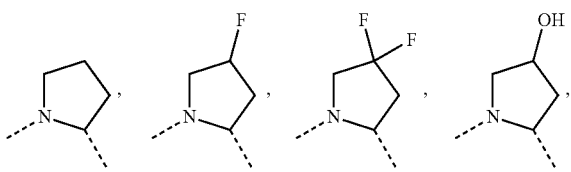

In certain embodiment of this invention, the structural unit

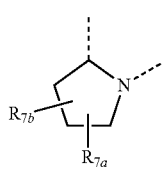

is selected from

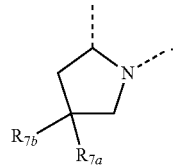

In certain embodiment of this invention, the structural unit

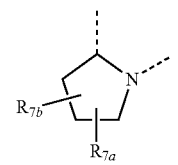

is selected from

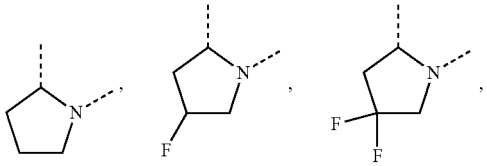

In certain embodiment of this invention, $R_{6a}$ and $R_{6b}$ are linked together to form a 3-6-membered cycloalkyl optionally substituted with 1, 2 or 3 of R.

In certain embodiment of this invention, $R_{6a}$ and $R_{6b}$ are linked, the structural unit

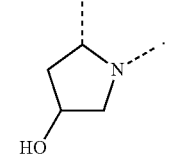

is selected from

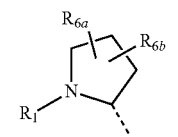

In certain embodiment of this invention, $R_{6a}$ and $R_{6b}$ are linked, the structural unit

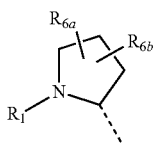

is selected from

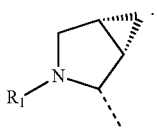

In certain embodiment of this invention, $R_{7a}$ and $R_{7b}$ are linked to form a 3-6-membered cycloalkyl optionally substituted with 1, 2 or 3 of R.

In certain embodiment of this invention, $R_{7a}$ and $R_{7b}$ are linked, the structural unit

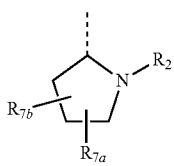

is selected from

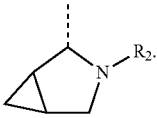

In certain embodiment of this invention, the structural unit

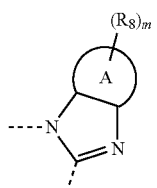

is selected from

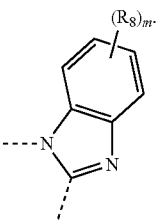

In certain embodiment of this invention, the structural unit

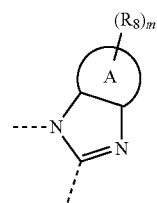

is selected from

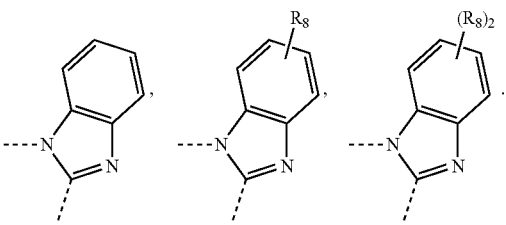

In certain embodiment of this invention, the structural unit

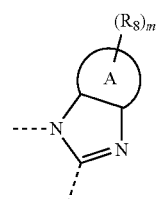

is selected from

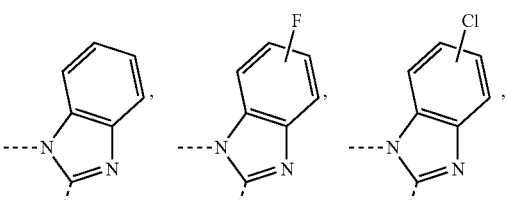

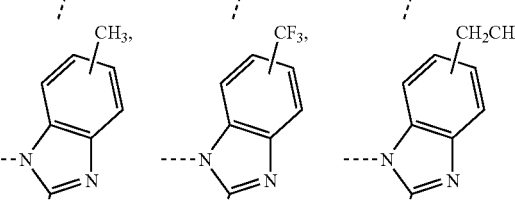

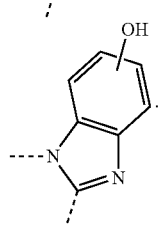

In certain embodiment of this invention, the structural unit is selected from

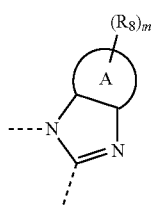

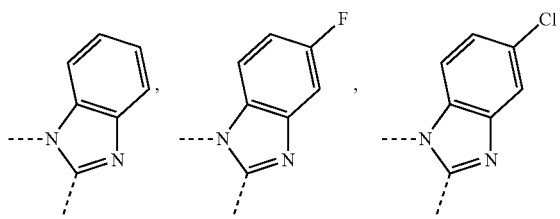

In certain embodiment of this invention, the structural unit

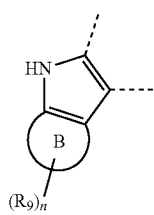

is selected from

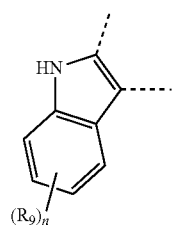

In certain embodiment of this invention, the structural unit

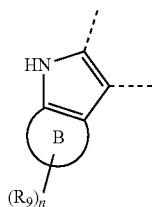

is selected from

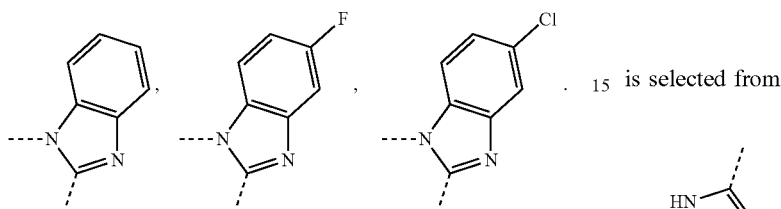

In certain embodiment of this invention, the structural unit

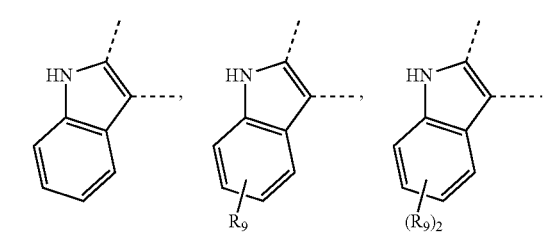

In certain embodiment of this invention, the structural unit

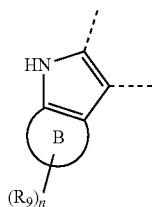

is selected from

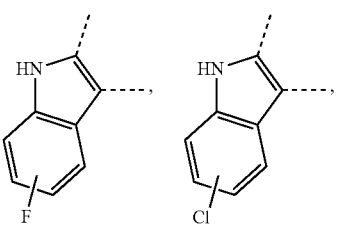

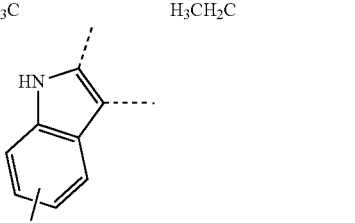

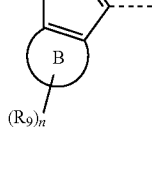

In certain embodiment of this invention, the structural unit

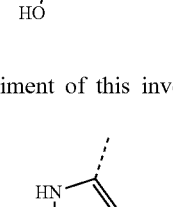

is selected from

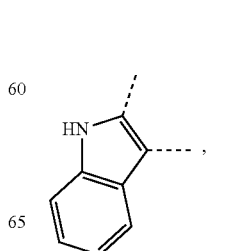

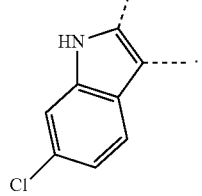
The present invention also provides the compound or the pharmaceutically acceptable salt thereof, wherein the compound is
(II)
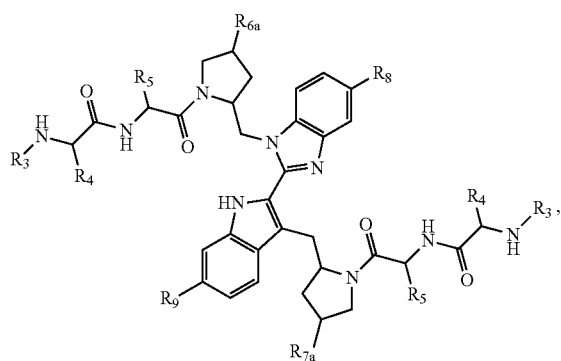
R$_3$, R$_4$, R$_5$, R$_{6a}$, R$_{7a}$, R$_8$, R$_9$ are as defined above.
The present invention also provides the compound or the pharmaceutically acceptable salt thereof which is selected from the group consisting of
1
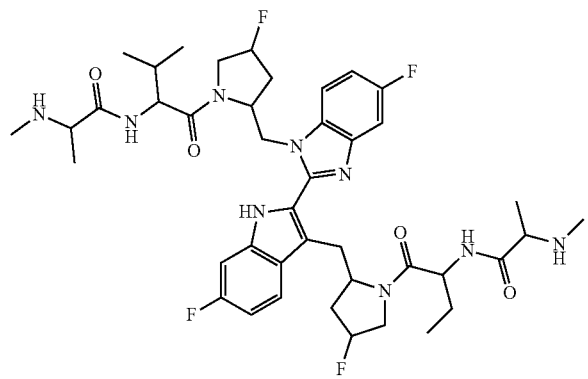
2
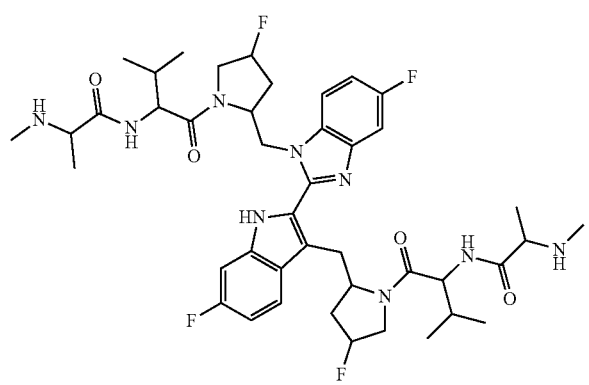
3
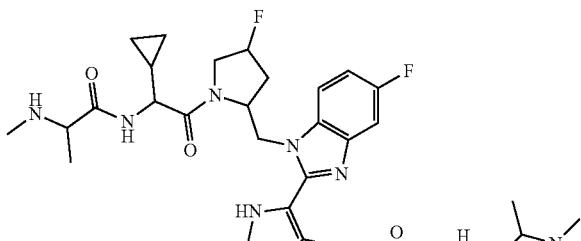
4
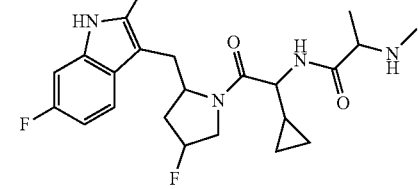
5
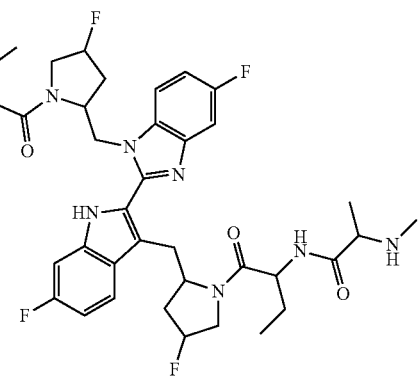
6
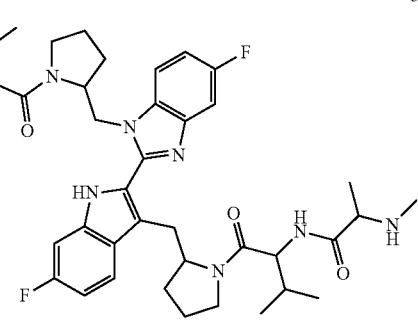

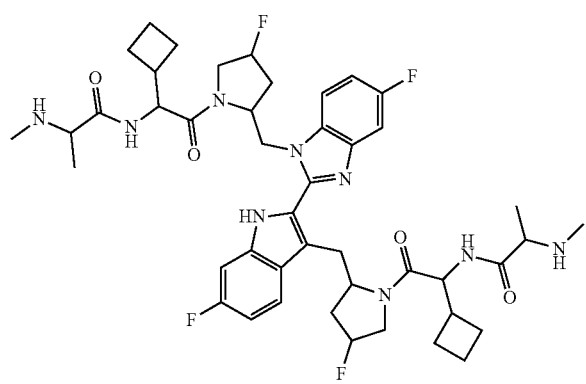
7
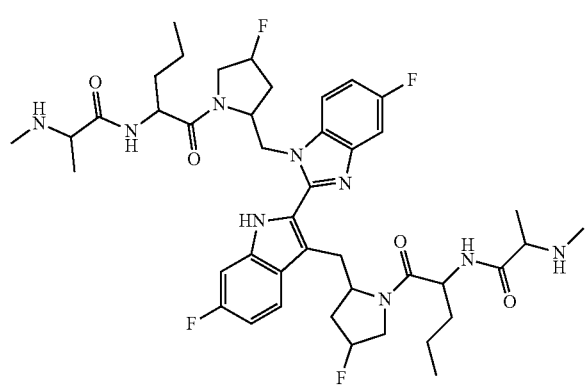
8
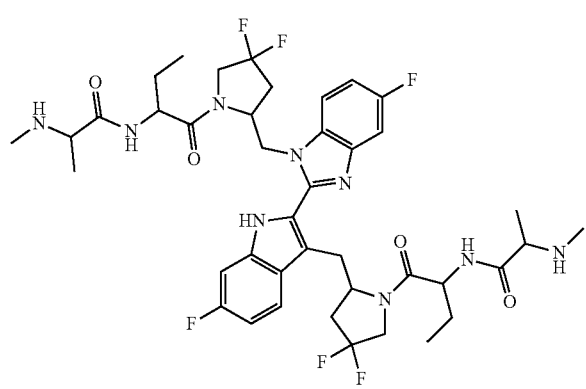
9
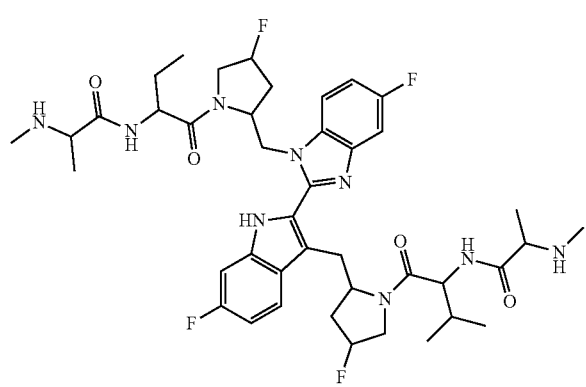
10
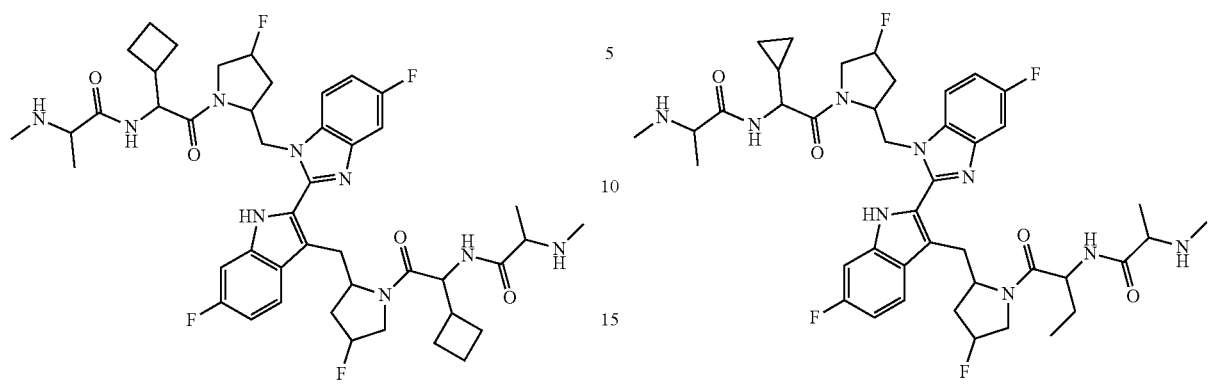
11
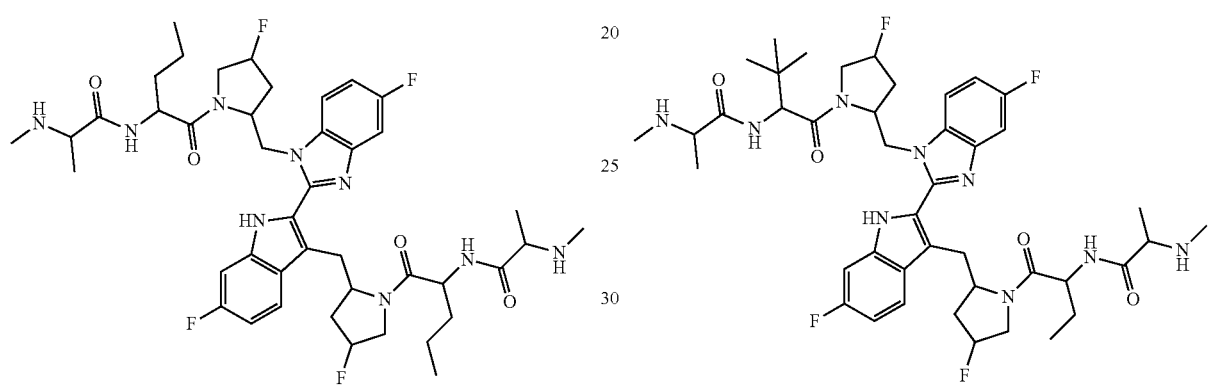
12
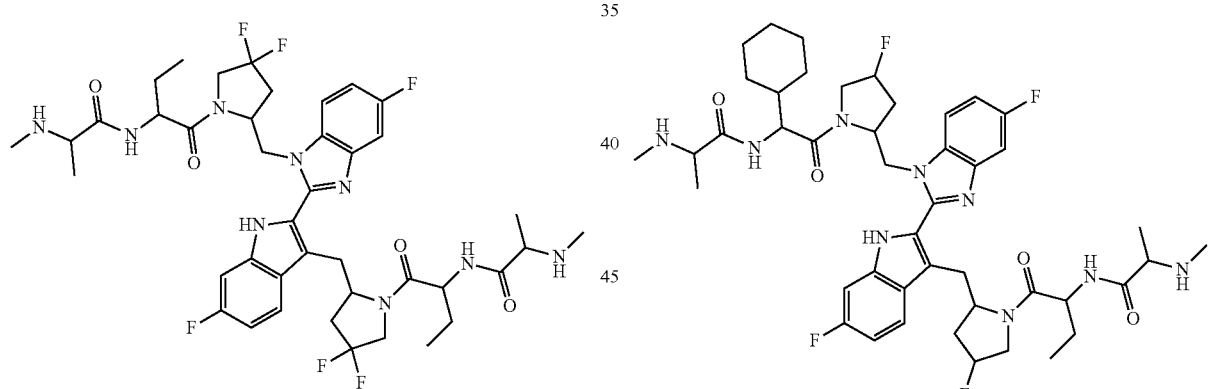
13
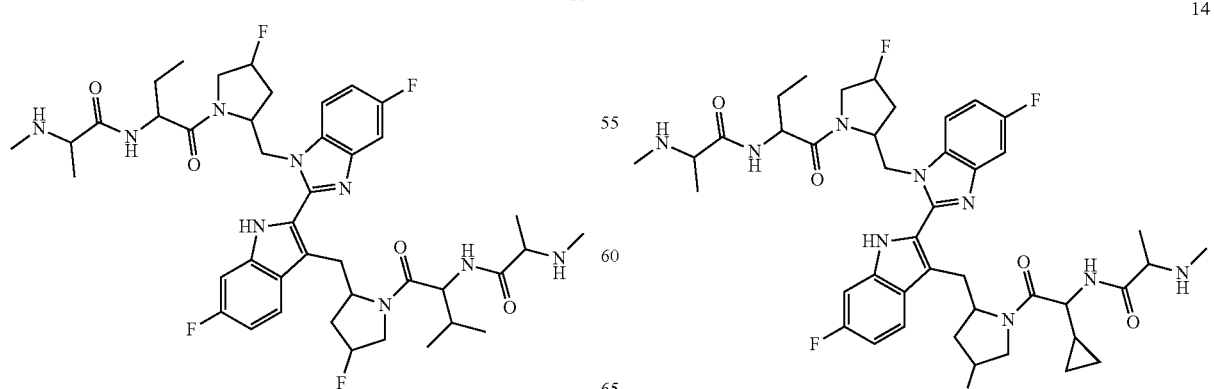
14

15
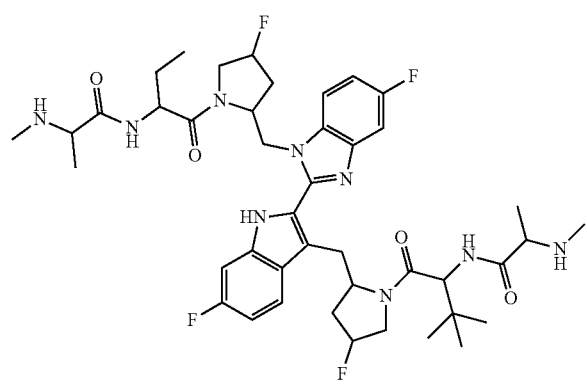
16
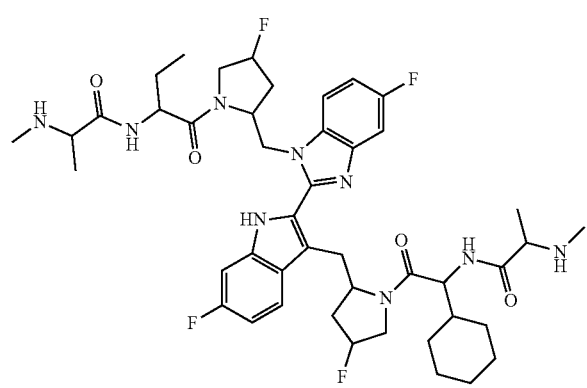
17
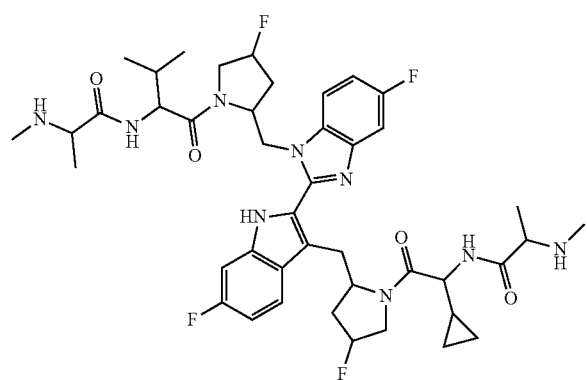
18
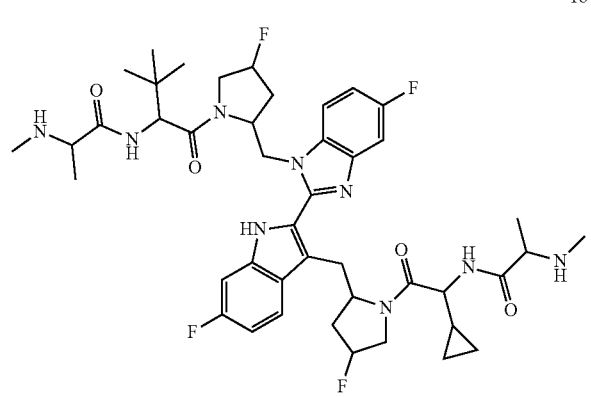
19
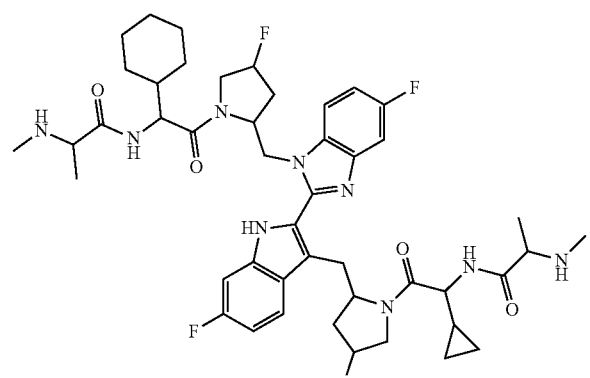
20
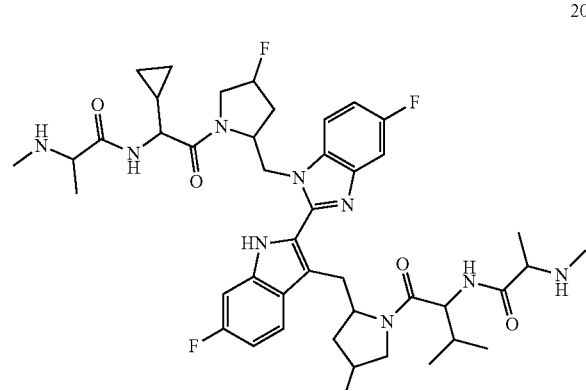
21
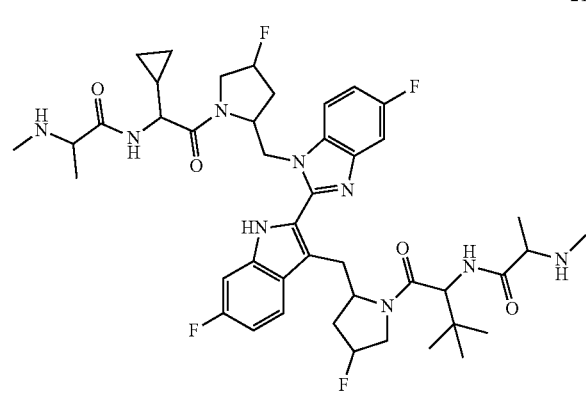
22
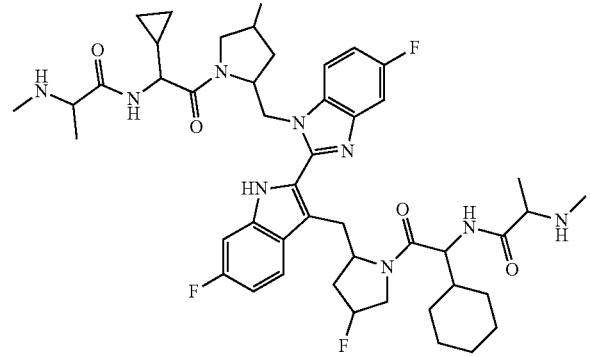

23
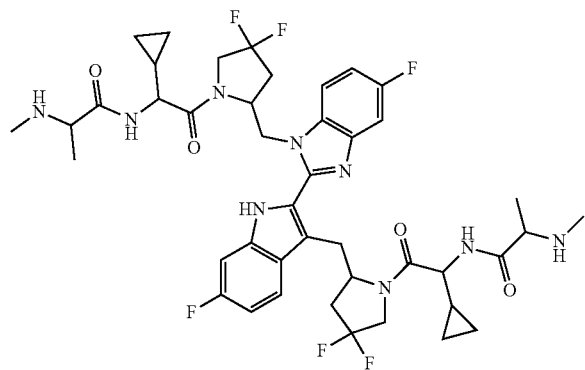
24
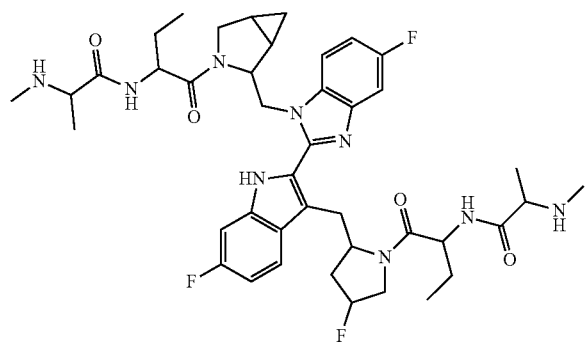
25
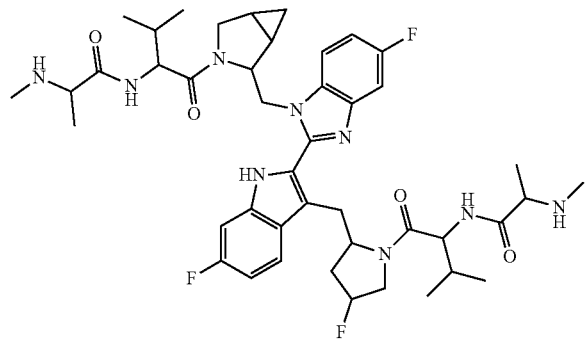
26
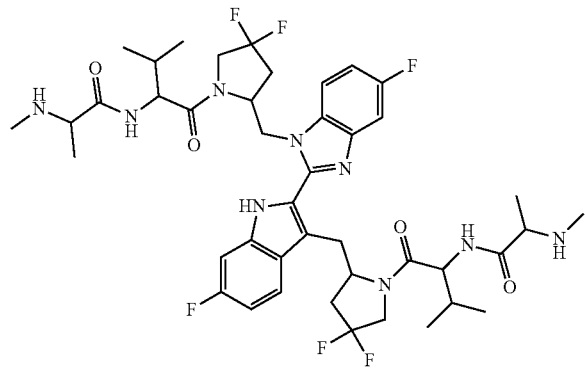
27
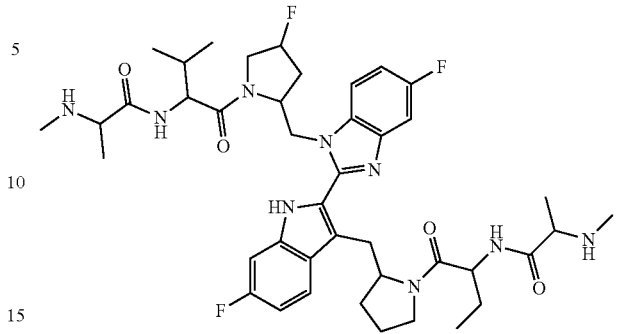
28
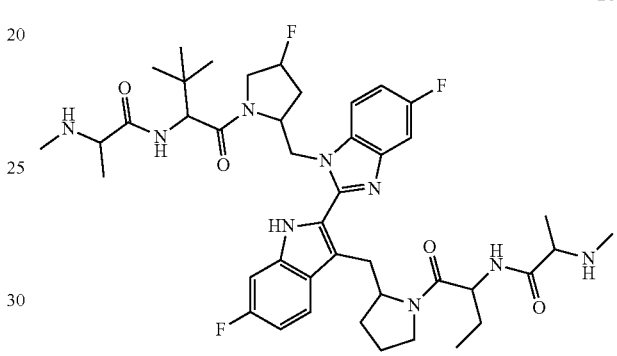
29
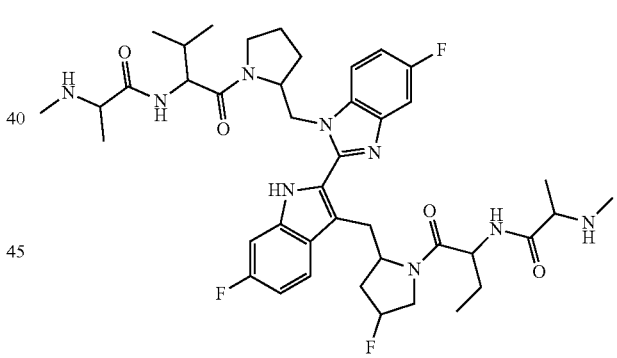
30
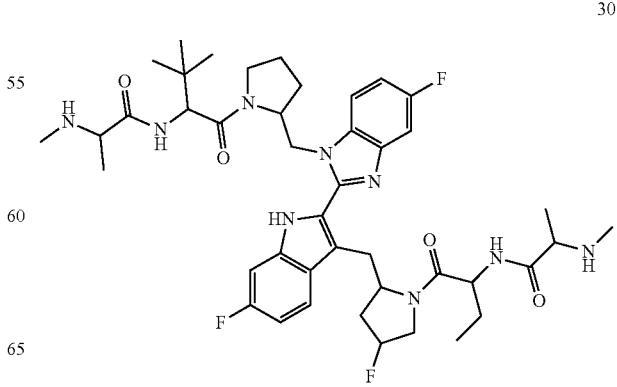

31
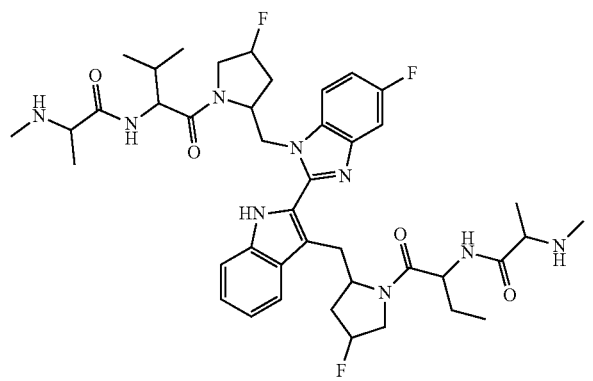
32
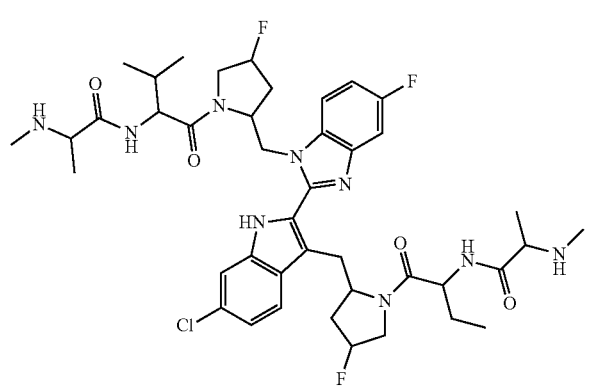
33
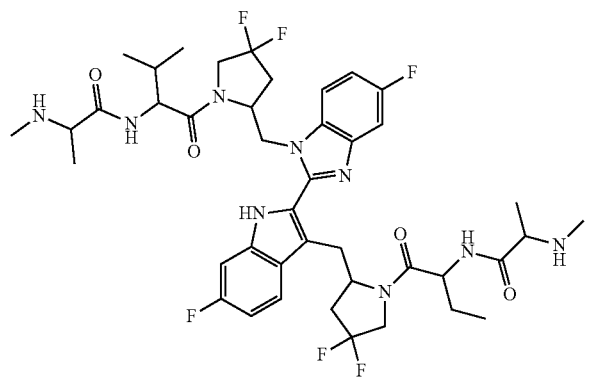
34
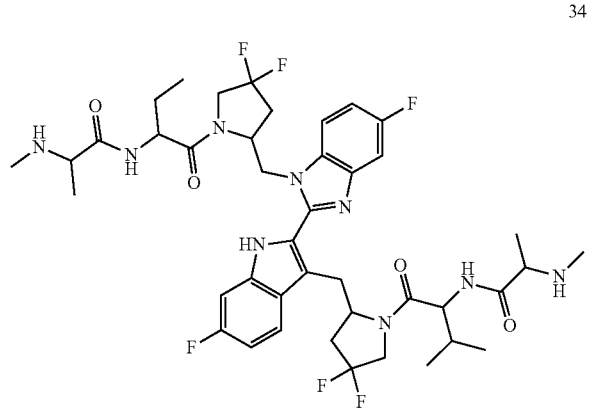
35
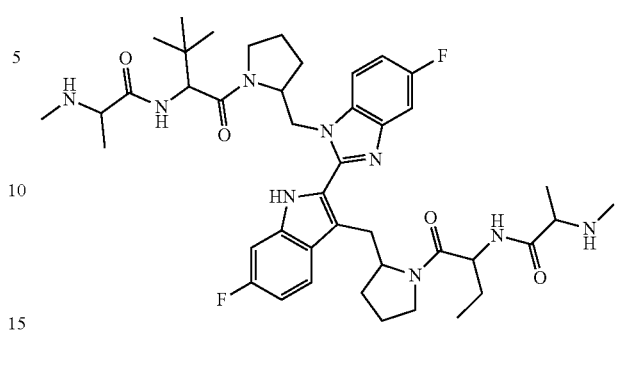
36
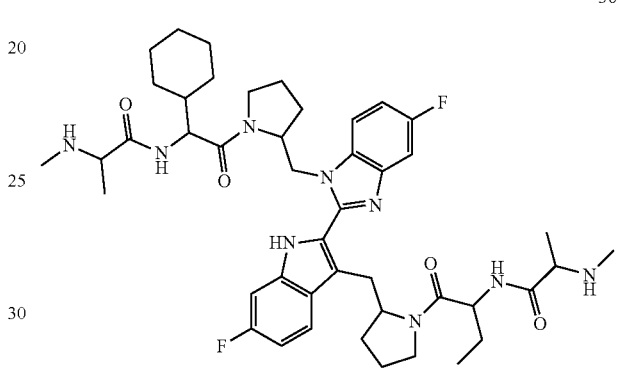
37
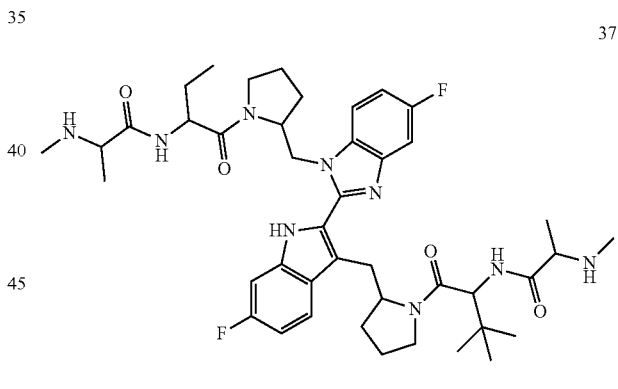
38
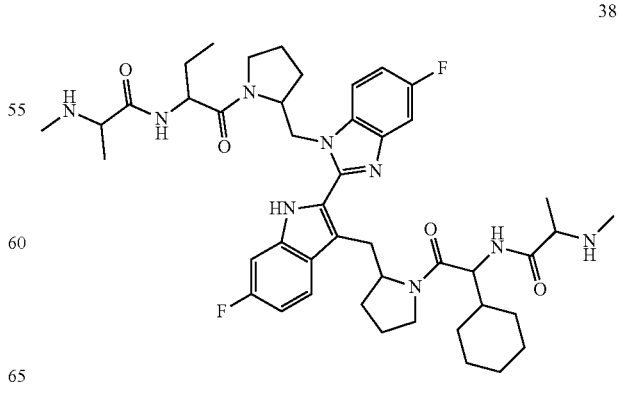

39
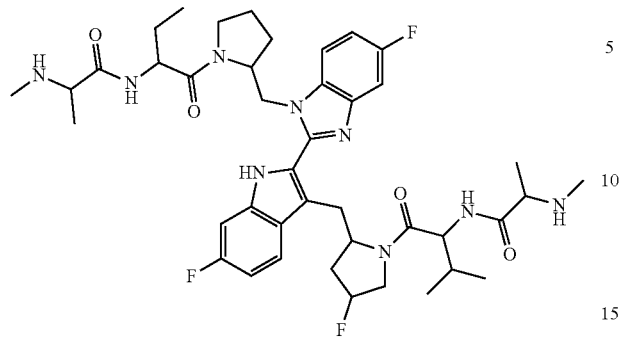
40
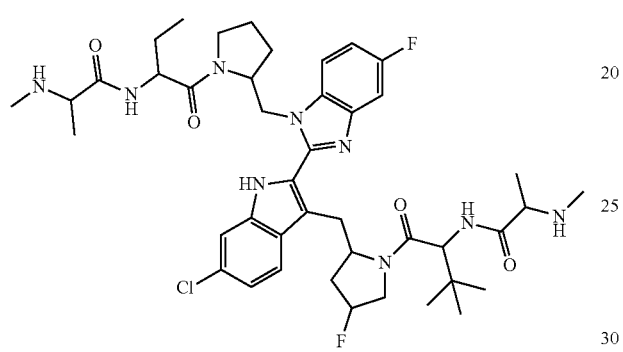
41
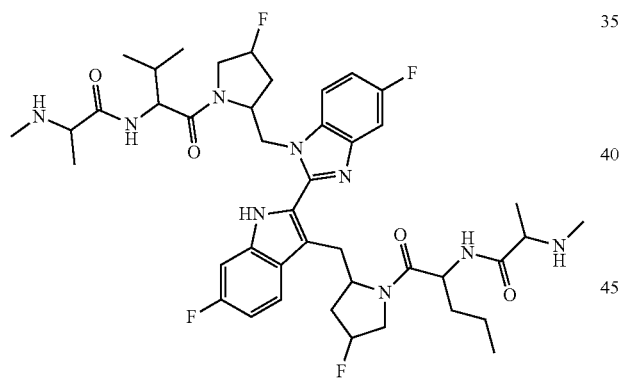
42
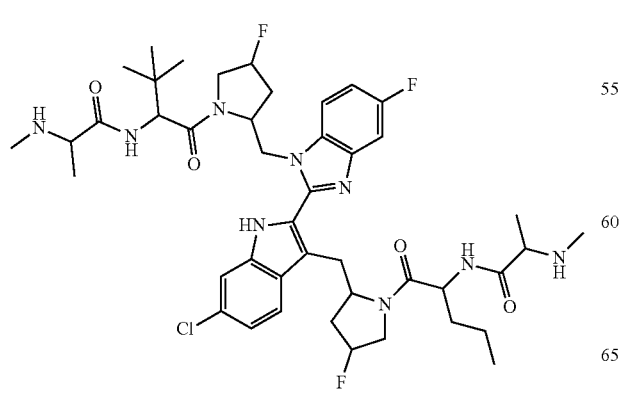
43
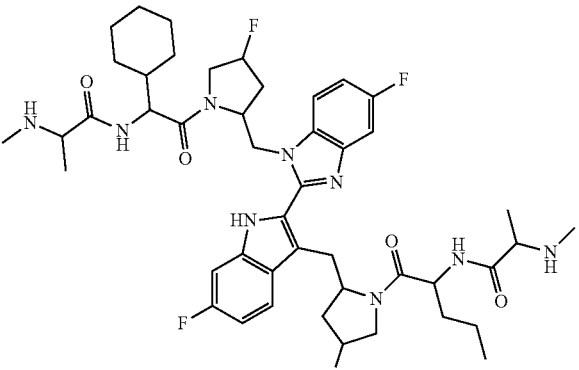
44
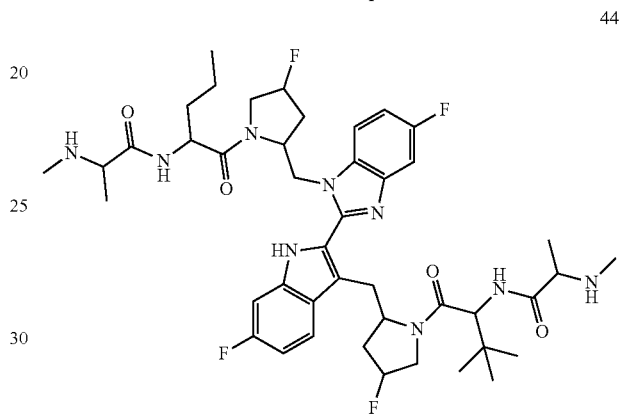
45
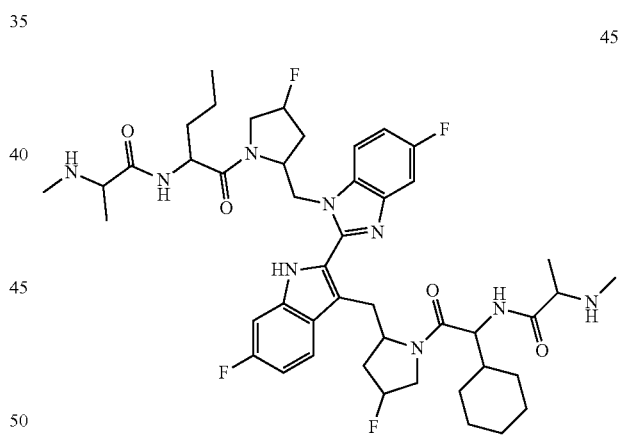
46
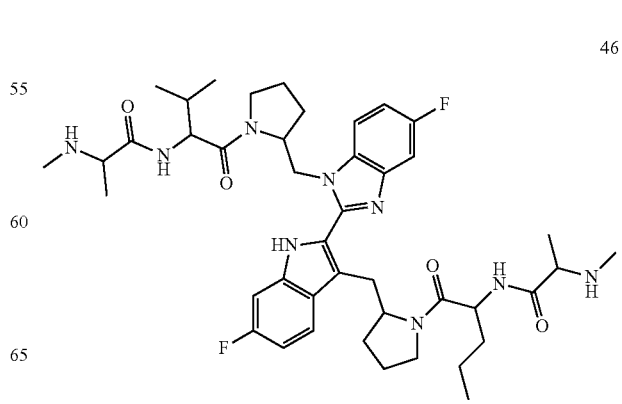

47
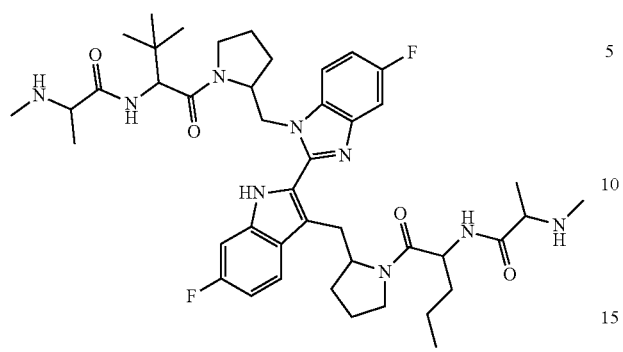
48
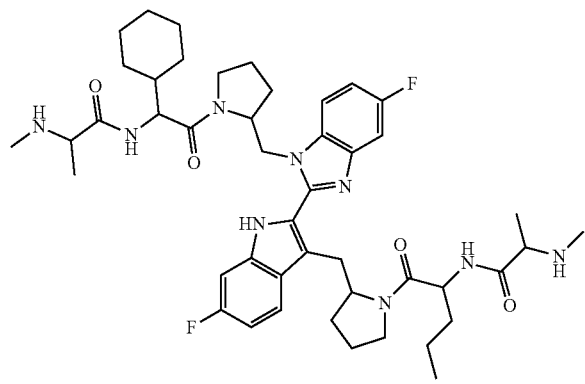
49
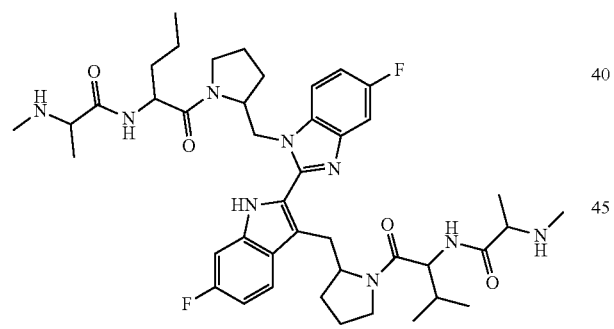
50
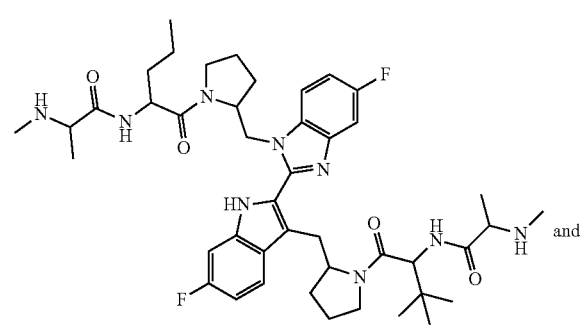
and
51
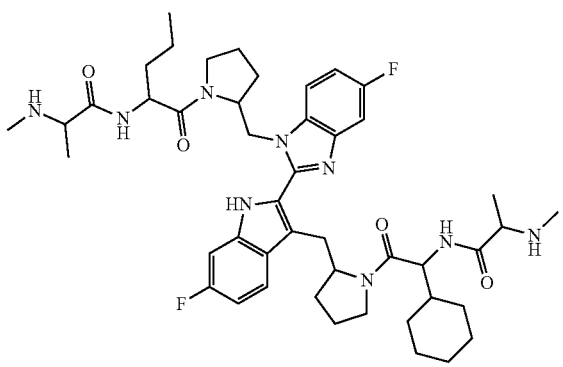
In some embodiments of the present invention, the compound or the pharmaceutically acceptable salt thereof is selected from
52
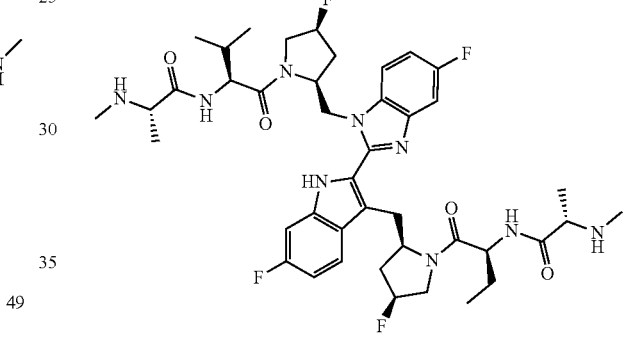
53
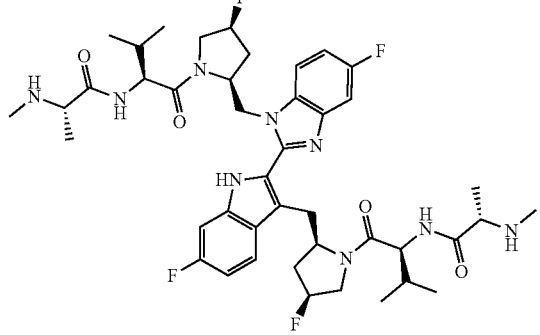
54
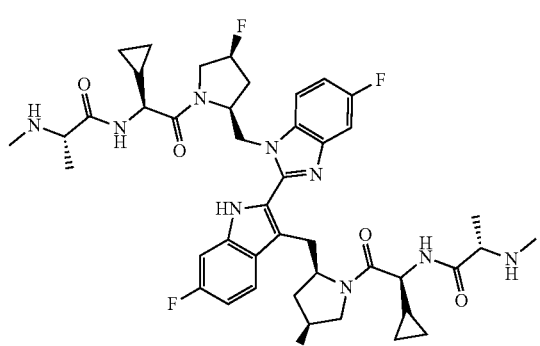

25
-continued
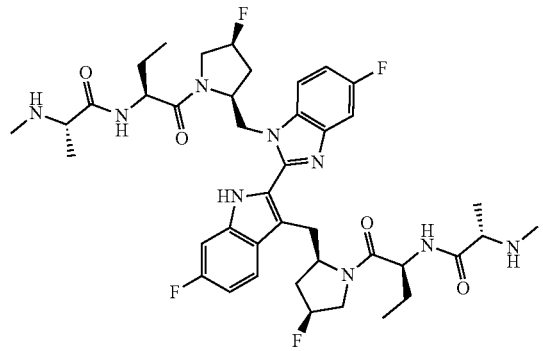
55
26
-continued
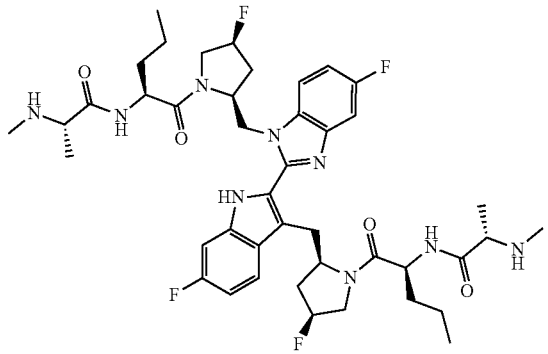
59
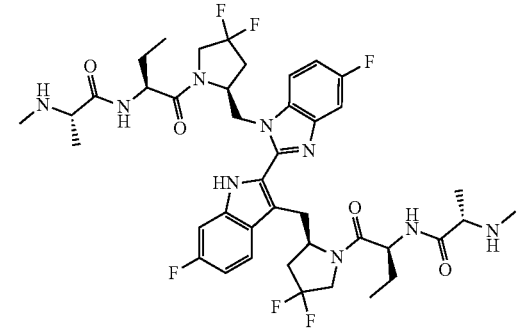
60
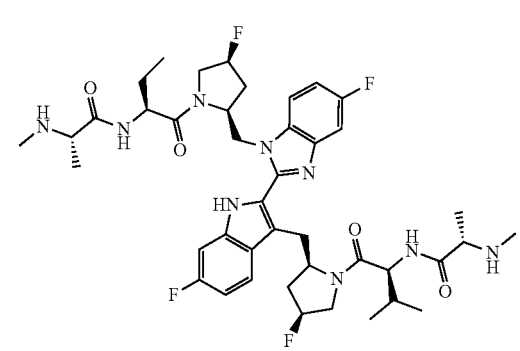
61
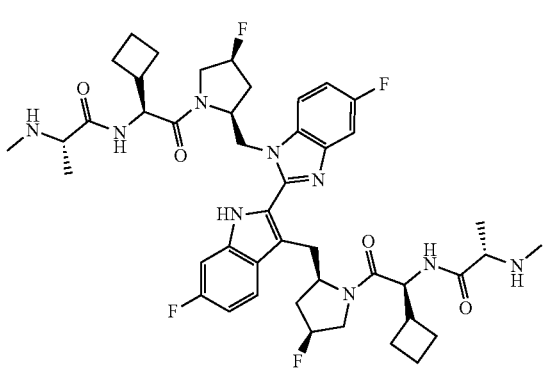
56
57
58
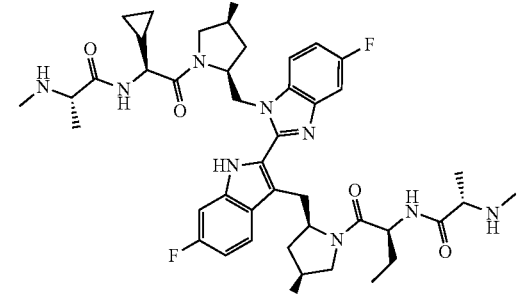
62

63
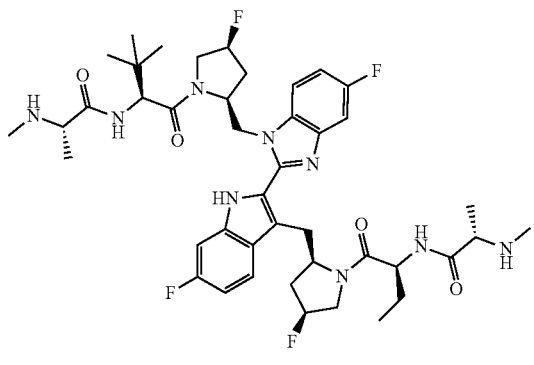
64
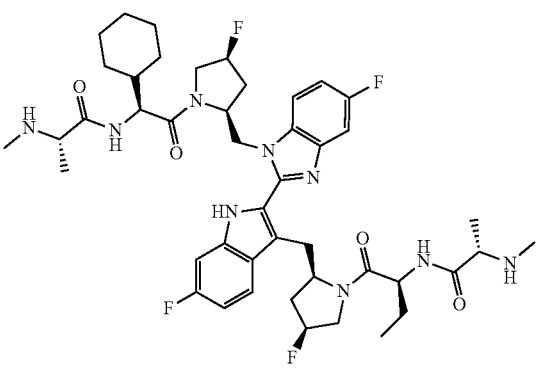
65
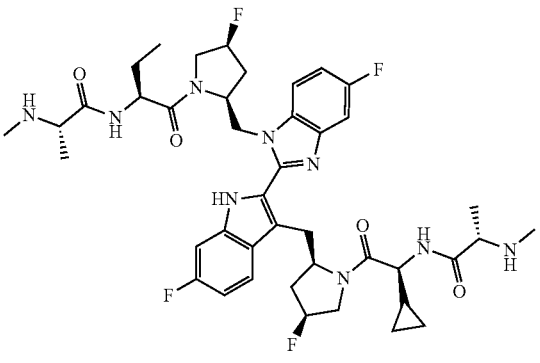
66
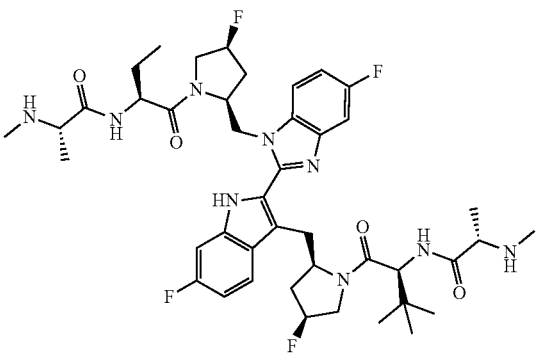
67
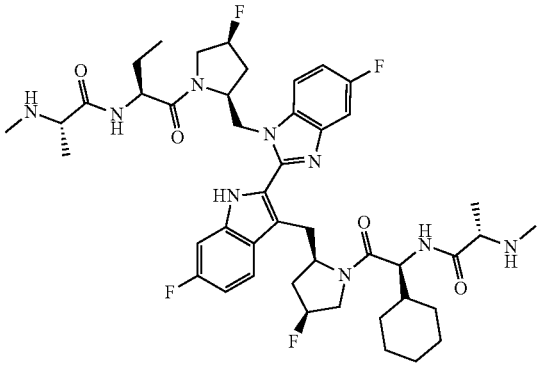
68
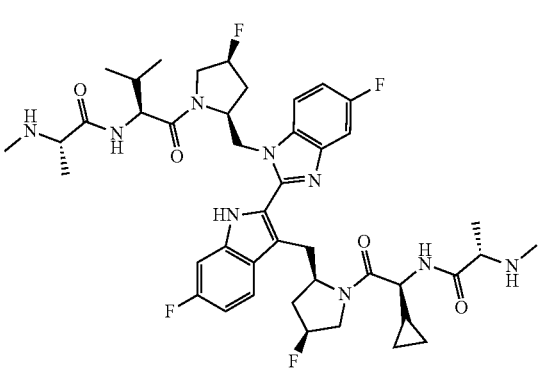
69
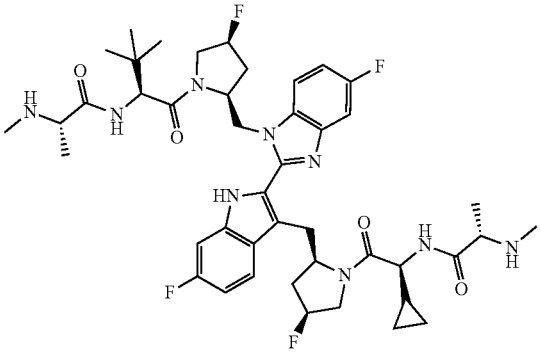
70
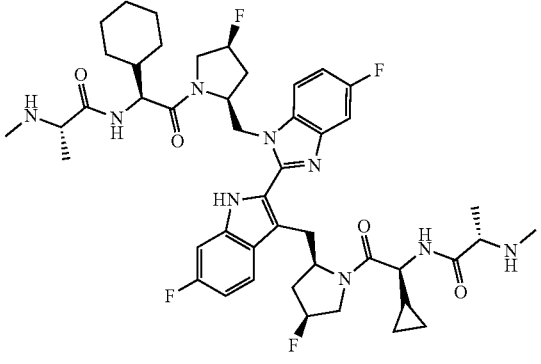

71
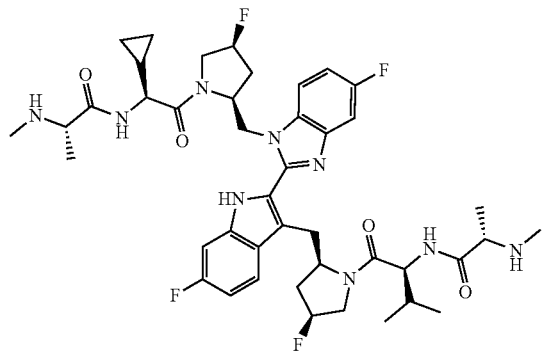
72
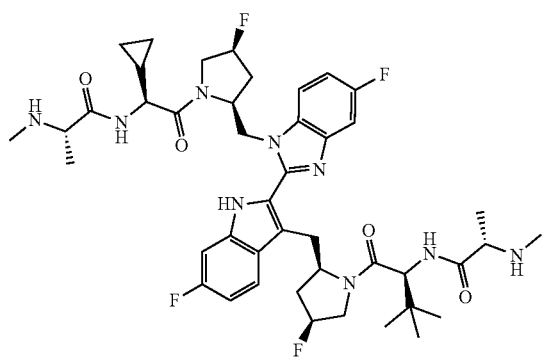
73
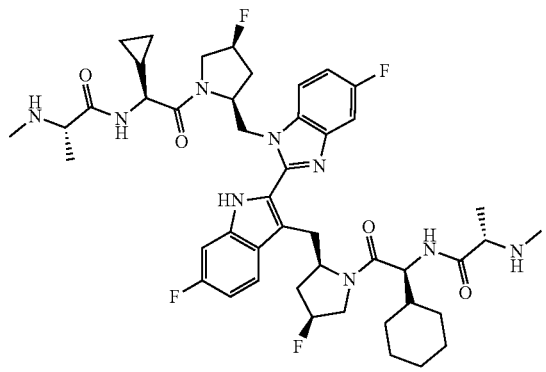
74
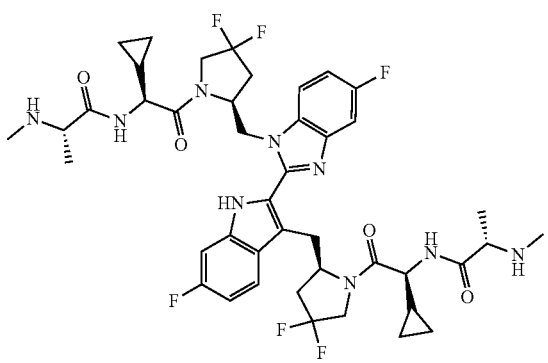
75
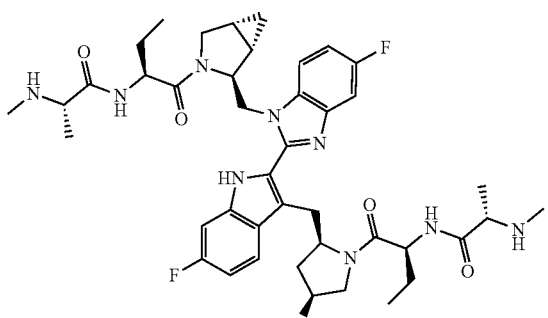
76
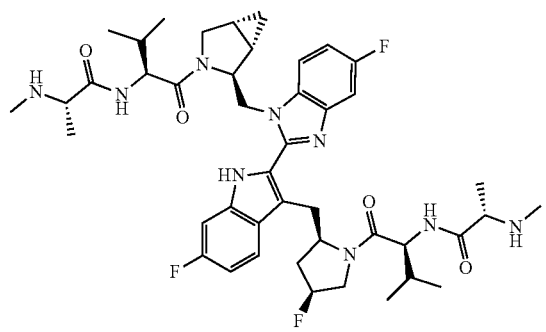
77
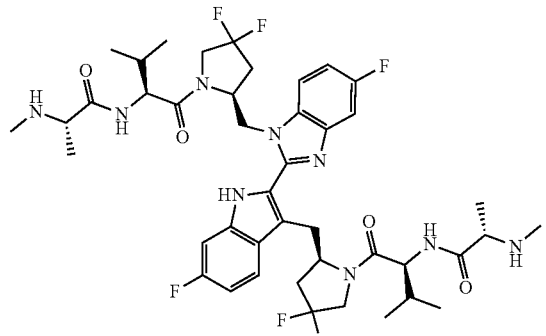
78
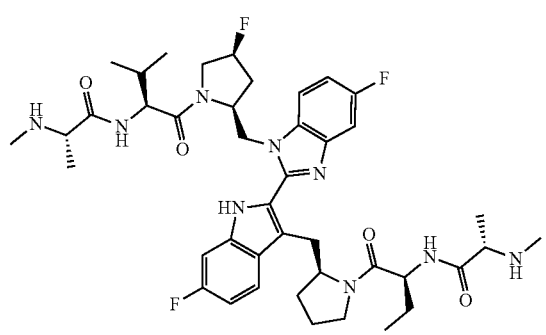

79
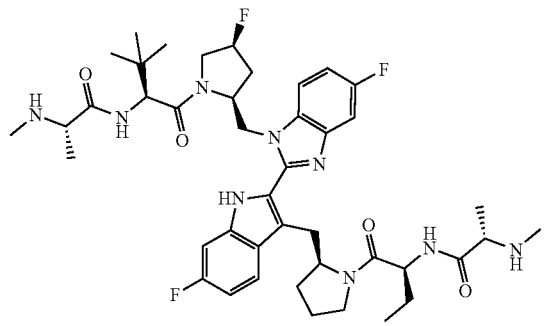
80
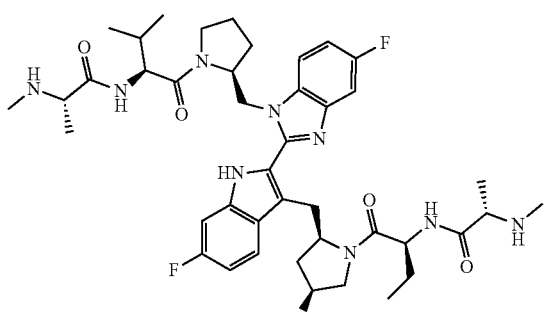
81
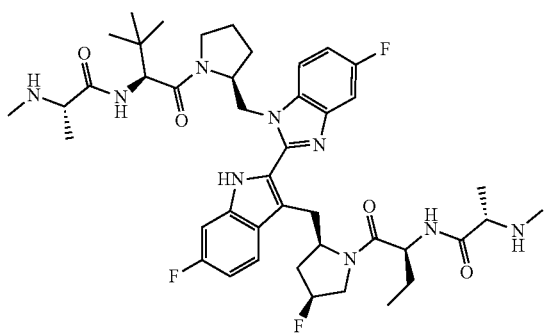
82
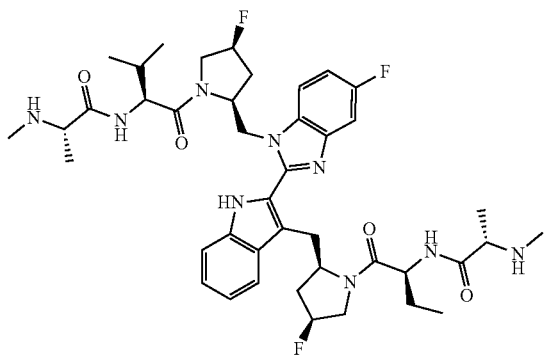
83
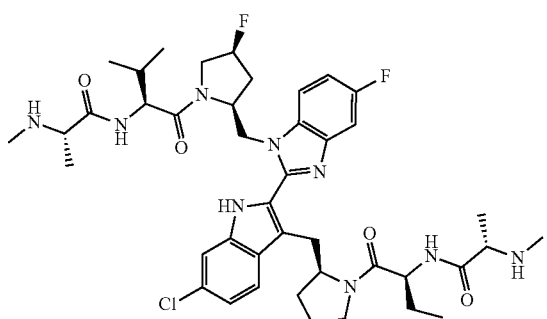
84
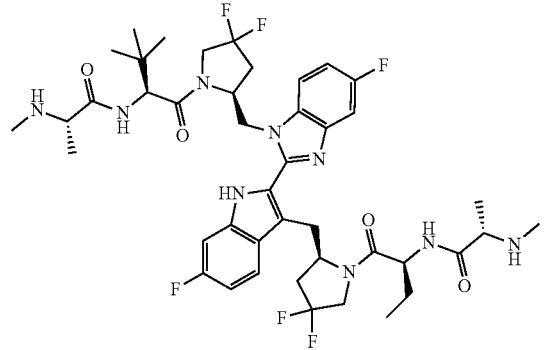
85
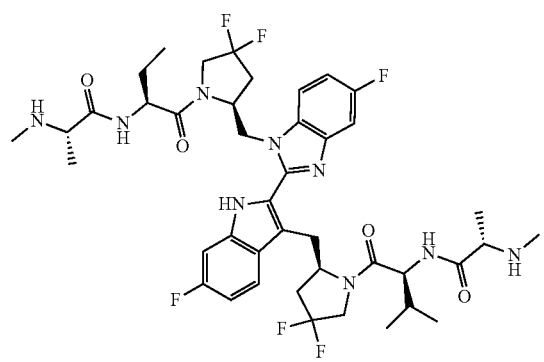
86
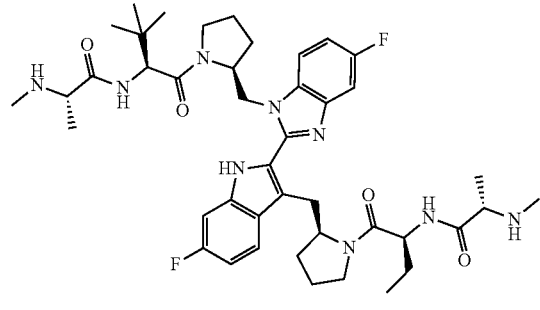

87
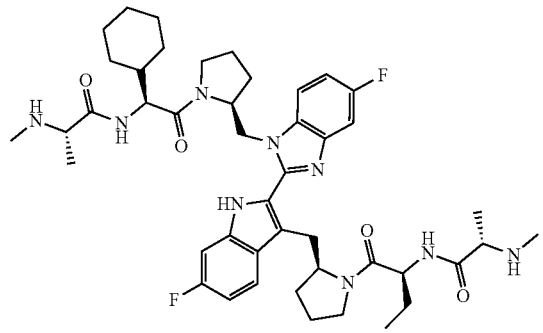
88
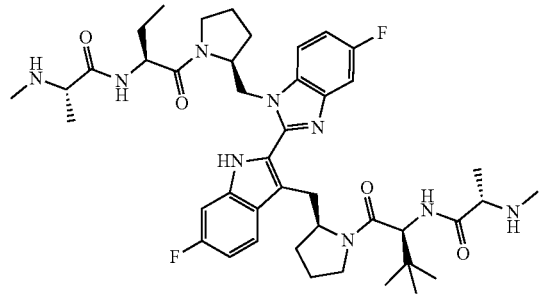
89
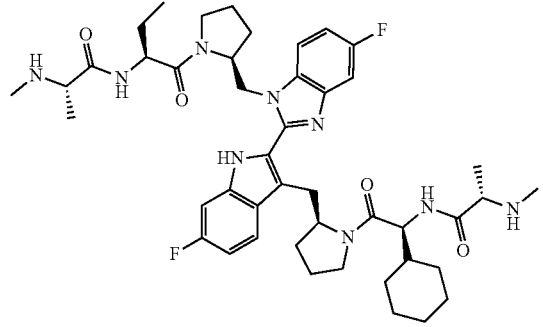
90
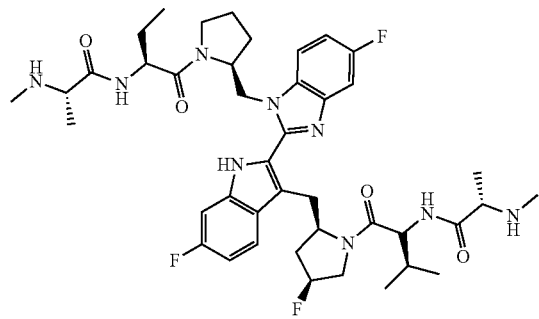
91
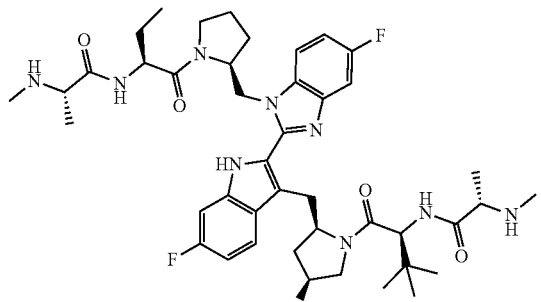
92
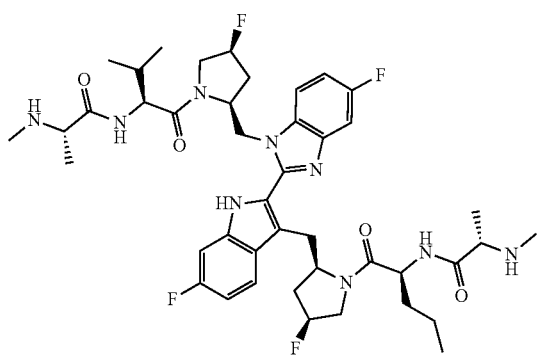
93
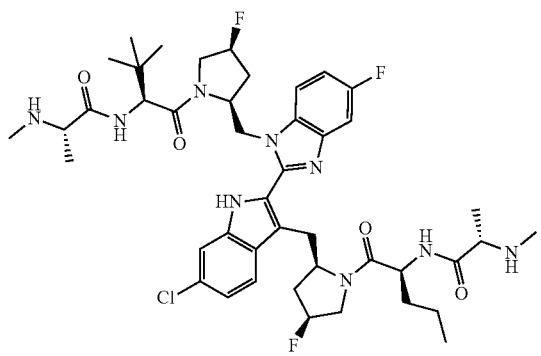
94
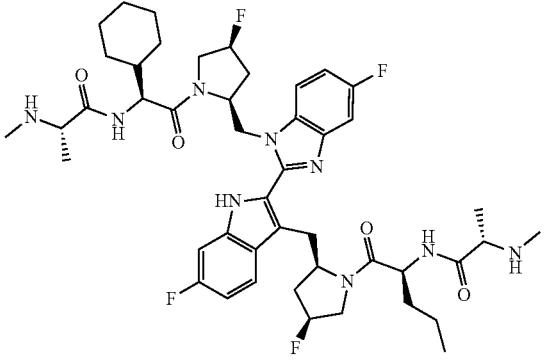

95

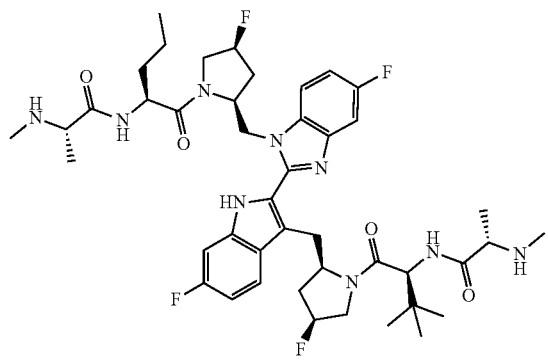

96

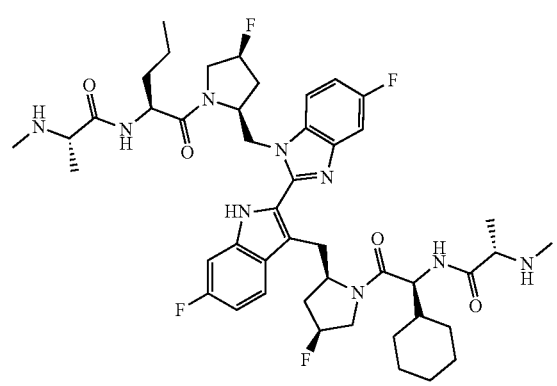

97

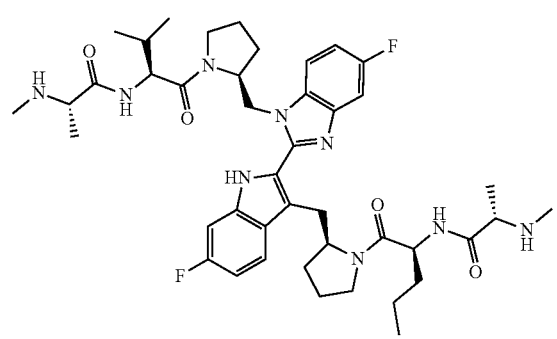

98

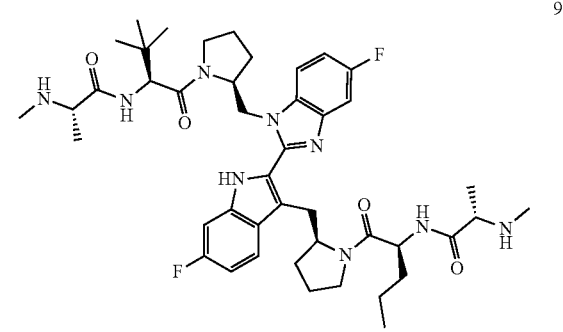

99

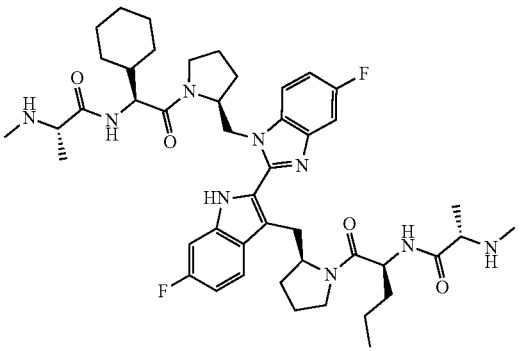

100

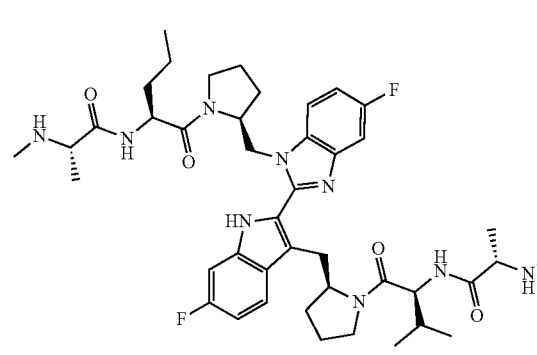

101

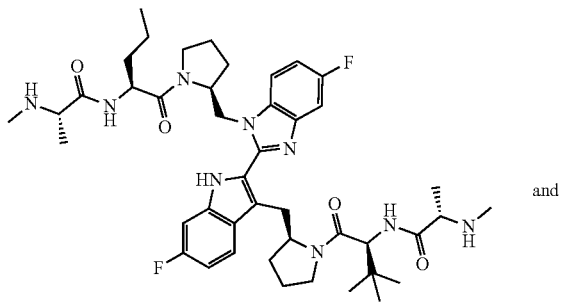

and

102

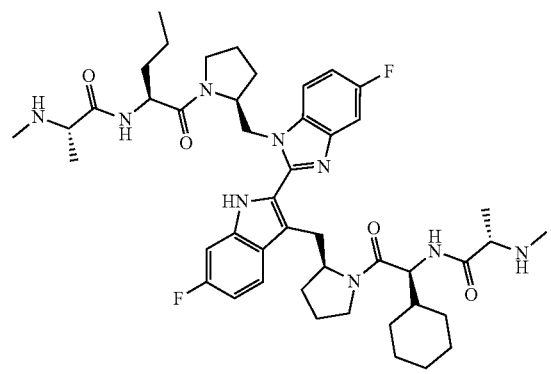

The present invention also provides a pharmaceutical composition comprising a therapeutically effective amount of the compound or the pharmaceutically acceptable salt thereof and a pharmaceutically acceptable carrier.

The present invention also provides a use of the compound or the pharmaceutically acceptable salt thereof or the pharmaceutical composition in the preparation of a medicament for the treatment of diseases caused by IAP disorder.

In certain embodiment of this invention, the diseases caused by IAP disorder are selected from cancers or hepatitis B virus infection.

In certain embodiment of this invention, R is selected from the group consisting of F, Cl, Br, I, CN, OH, $NH_2$, COOH, or $C_{1-3}$ alkyl, $C_{1-3}$ alkoxy, $C_{1-3}$ alkylthiol, $C_{1-3}$ alkylamino and N,N-di($C_{1-2}$ alkyl)amino, the $C_{1-3}$ alkyl, $C_{1-3}$ alkoxy, $C_{1-3}$ alkylthiol, $C_{1-3}$ alkylamino and N,N-di ($C_{1-2}$ alkyl)amino are optionally substituted with 1, 2 or 3 of R', and other variables are as defined above.

In certain embodiment of this invention, R is selected from the group consisting of F, Cl, Br, I, CN, OH, $NH_2$, COOH, Me, Et, $CF_3$, $CHF_2$, $CH_2F$, $NHCH_3$, $N(CH_3)_2$,

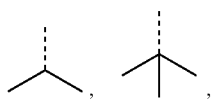

and other variables are as defined above.

In certain embodiment of this invention, $R_3$ and $R_4$ are independently selected from the group consisting of $C_{1-4}$ alkyl, $C_{1-4}$ heteroalkyl, $C_{3-6}$cycloalkyl, 3-6membered heterocycloalkyl, 5-6membered aryl or heteroaryl and 5-6memberedaralkyl or heteroaralkyl; the $C_{1-4}$ alkyl, $C_{1-4}$ heteroalkyl, $C_{3-6}$cycloalkyl, 3-6membered heterocycloalkyl, 5-6membered aryl or heteroaryl and 5-6membered aralkyl or heteroaralkyl are optionally substituted with 1, 2 or 3 of R, and other variables are as defined above.

In certain embodiment of this invention, $R_3$ and $R_4$ are independently selected from the group consisting of $C_{1-3}$ alkyl, $C_{1-3}$ heteroalkyl, phenyl, pyridinyl, pyrimidyl, pyrazinyl, pyridaziny, furyl, imidazolyl, oxazolyl, isoxazolyl, thienyl and pyrazolyl, and other variables are as defined above.

In certain embodiment of this invention, $R_3$ and $R_4$ are independently selected from Me, and other variables are as defined above.

In certain embodiment of this invention, $R_5$ is selected from the group consisting of $C_{1-4}$ alkyl, $C_{1-4}$ heteroalkyl, $C_{3-6}$ cycloalkyl, 3-6membered heterocycloalkyl, 5-6membered aryl or heteroaryl and 5-6membered aralkyl or heteroaralkyl, each of which is optionally substituted with 1, 2 or 3 of R, and other variables are as defined above.

In certain embodiment of this invention, $R_5$ is selected from the group consisting of $C_{1-4}$ alkyl, $C_{3-6}$cycloalkyl, 3-6membered heterocycloalkyl, phenyl, pyridinyl, pyrimidyl, pyrazinyl, pyridaziny, furyl, imidazolyl, oxazolyl, isoxazolyl, thienyl and pyrazolyl, and other variables are as defined above.

In certain embodiment of this invention, $R_5$ is selected from

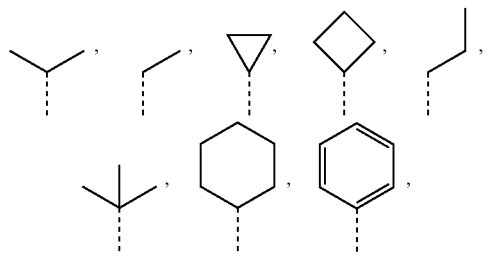

and other variables are as defined above.

In certain embodiment of this invention, the structural unit

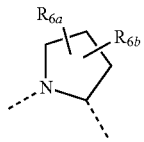

is selected from

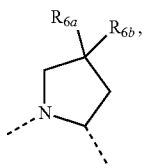

and other variables are as defined above.

In certain embodiment of this invention, the structural unit

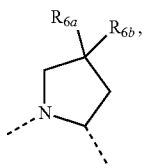

is selected from

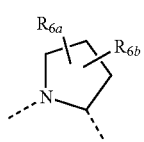

and other variables are as defined above.

In certain embodiment of this invention, the structural unit

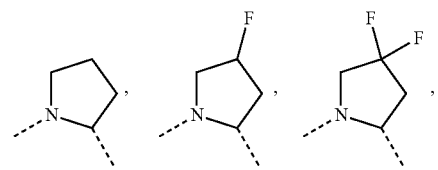

is selected from

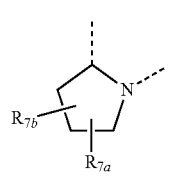

and other variables are as defined above.

In certain embodiment of this invention, the structural unit

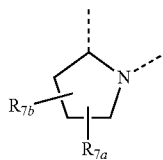

is selected from

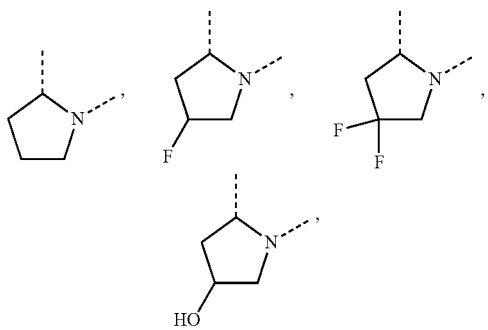

and other variables are as defined above.

In certain embodiment of this invention, $R_{6a}$ and $R_{6b}$ are linked together to form a 3-6membered cycloalkyl optionally substituted with 1, 2 or 3 of R, and other variables are as defined above.

In certain embodiment of this invention, $R_{6a}$ and $R_{6b}$ are linked, the structural unit

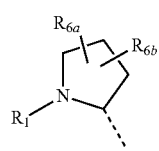

is selected from

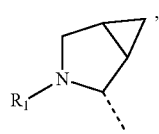

and other variables are as defined above.

In certain embodiment of this invention, $R_{7a}$ and $R_{6b}$ are linked, the structural unit

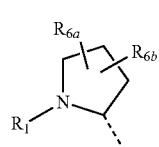

is selected from

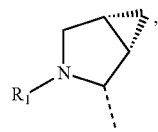

and other variables are as defined above.

In certain embodiment of this invention, $R_{7a}$ and $R_{7b}$, are linked together to form a 3-6membered cycloalkyl optionally substituted with 1, 2 or 3 of R, and other variables are as defined above.

In certain embodiment of this invention, $R_{7a}$ and $R_{7b}$ are linked, the structural unit

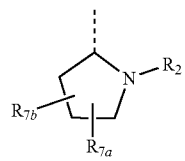

is selected from

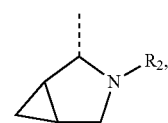

and other variables are as defined above.

In certain embodiment of this invention, the structural unit

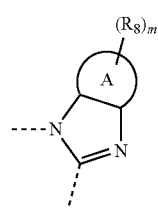

is selected from

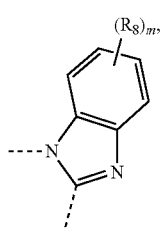

and other variables are as defined above.

In certain embodiment of this invention, the structural unit

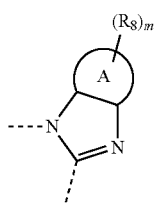

is selected from

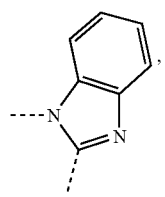 , 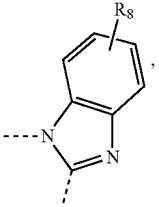 and 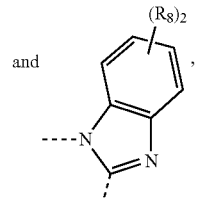 , and other variables are as defined above.

In certain embodiment of this invention, the structural unit

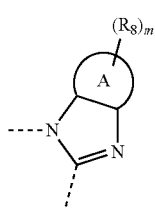

is selected from

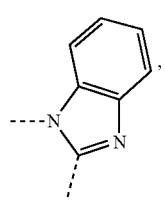 , 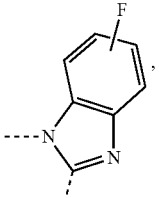 , 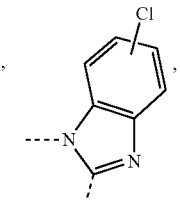 ,

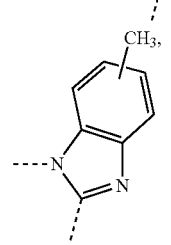 , 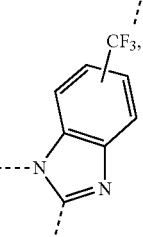 ,

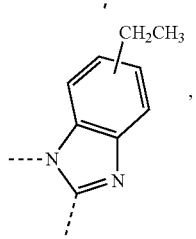 , 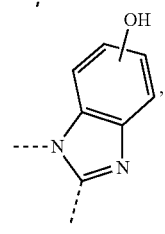 , and other variables are as defined above.

In certain embodiment of this invention, the structural unit

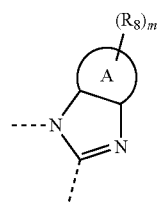

is selected from

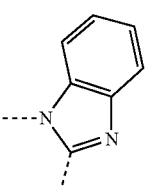 , 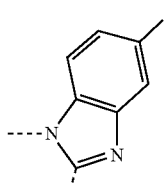 , 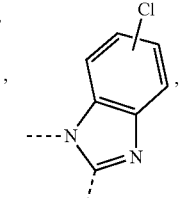 , and other variables are as defined above.

In certain embodiment of this invention, the structural unit

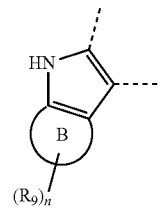

is selected from

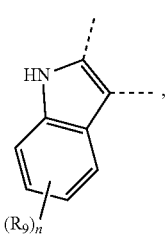 , and other variables are as defined above.

In certain embodiment of this invention, the structural unit

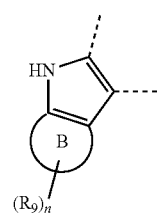

is selected from

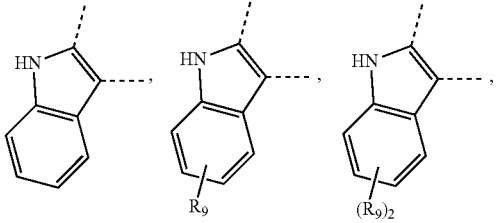

and other variables are as defined above.

In certain embodiment of this invention, the structural unit

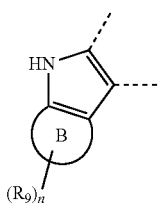

above is selected from

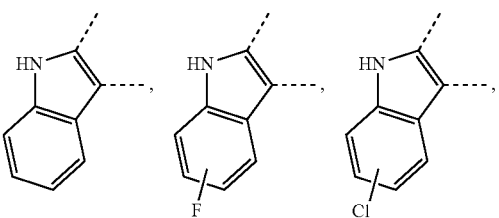

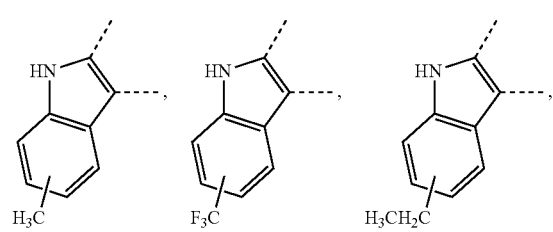

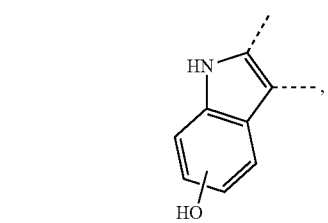

and other variables are as defined above.

In certain embodiment of this invention, the structural unit

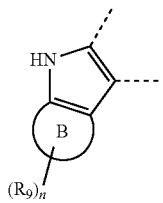

is selected from

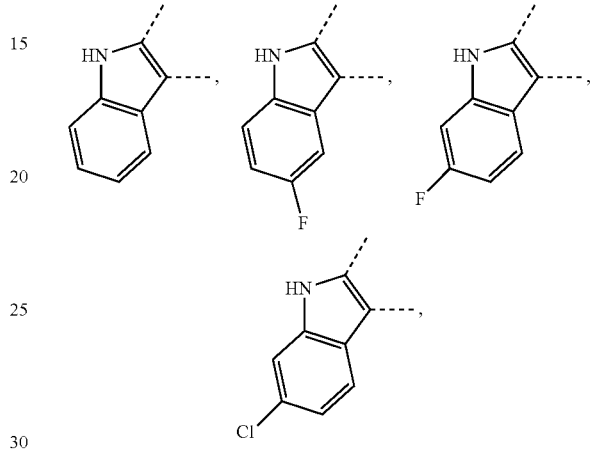

and other variables are as defined above.

The present invention contains embodiments which are formed by the arbitrary combination with the aforesaid variables.

Technical Effect of Invention

In this invention, the core structure of the compound is designed as benzimidazole-linked indole, which improves total solubility of the compound. The innovation of the core structure, benzimidazole-linked indole, is to have less hydrogen bond donators thereon, thereby resulting in lower XIAP binding force and higher cIAP/XIAP selectivity. Higher selective compound will show lower toxicity and better tolerance in human and animal body.

Definitions and Explanations

Unless otherwise stated, the terms and phrases listed below used in this article bear the meanings assigned thereto. One certain terms or phrases shouldn't be deemed to being uncertain or unclear without special definition, but be understood according to normal meanings. When trade names appear in this article, they are deem to corresponding goods or their effective components.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

$C_{1-12}$ alkyl or hetero alkyl, $C_{1-12}$ cycloalkyl or hetero cycloalkyl, $C_{1-12}$ alkyl or hetero alkyl substituted with $C_{1-12}$ cycloalkyl or hetero cycloalkyl include, but not limited to $C_{1-12}$ alkyl, $C_{1-12}$ alkylamino, N,N-di($C_{1-12}$ alkyl)amino, $C_{1-12}$ alkoxy, $C_{1-12}$ alkylacyl, $C_{1-12}$ carbalkoxy, $C_{1-12}$ alkylsulfonyl, $C_{1-12}$ alkylsulfinyl, $C_{3-12}$ cycloalkyl, $C_{3-12}$ cycloalkylamino, $C_{3-12}$ hetero cycloalkylamino, $C_{3-12}$ cycloalkoxy, $C_{3-12}$cycloalkylacyl, $C_{3-12}$ cyclocarbalkoxy, $C_{3-12}$cycloalkylsulfonyl, $C_{3-12}$ cycloalkylsulfinyl, 5-12 members aryl or hetero aryl, 5-12 members aralkyl or hetero aralkyl;

methyl, ethyl, n-propyl, i-propyl, —$CH_2C(CH_3)(CH_3)$(OH), cyclopropyl, cyclobutyl, propyl methylene, cyclopropyl acyl, benzyloxy, triflurine methyl, aminomethyl, hydroxy methyl, methoxyl, methylacyl, methoxycarbonyl, methyl sulfonyl, methyl sulfinyl, ethoxyl, ethylacyl, ethyl sulfonyl, ethoxycarbonyl, dimethylamino, diethylamino, dimethylaminocarbonyl, di ethyl aminocarbonyl;

$N(CH_3)_2$, $NH(CH_3)$, —$CH_2CF_3$, —$CH_2CH_2CF_3$, —$CH_2CH_2F$, —$CH_2CH_2S(=O)_2CH_3$, —$CH_2CH_2CN$, —$CH_2CH(OH)(CH_3)_2$, —$CH_2CH(F)(CH_3)_2$, —$CH_2CH_2F$, —$CH_2CF_3$, —$CH_2CH_2CF_3$, —$CH_2CH_2NH_2$, —$CH_2CH_2OH$, —$CH_2CH_2OCH_3$, —$CH_2CH_2CH_2OCH_3$, —$CH_2CH_2N(CH_3)_2$, —$S(=O)_2CH_3$, and phenyl, thiazolyl, biphenyl, naphthyl, cyclopentyl, furyl, 3-pyrrolinyl, pyrrolidyl, 1,3-dioxolanyl, pyrazolyl, 2-pyrrolinyl, pyrazolidinyl, imidazolyl, oxazolyl, thiazolyl, 1,2,3-azolyl, 1,2,3-triazolyl, 1,2,4-triazolyl, 1,3,4-thidiazolyl, 4H-pyranyl, pyridyl, piperidyl, 1,4-dioxanyl, morpholinyl, pyridazinyl, pyrimidyl, pyrazinyl, piperazinyl, 1,3,5-trithioohanyl, 1,3,5-triazinyl, benzofuryl, benzothienyl, indolyl, benzimidazolyl, benzothiazolyl, purinyl, quinolyl, isoquinolyl, cinnolinyl or quinoxalinyl;

The term "pharmaceutically acceptable" used herein is in allusion to those compounds, materials, compositions and/or dosages which are applied to contact to human and animal tissues without excessive toxicity, irritation, anaphylaxis, or other issues or complication, and suit to rational interest and risk ratio within the bounds of reliable medical judgment.

The term "pharmaceutically acceptable" refers to salt of the compounds in this invention which are prepared by compounds with certain substituents and relatively nontoxic acids or alkalis. When compounds contain relatively acidic functional group, alkalis-addtive salts are prepared by enough alkalis contacting with these compounds in neutral form in pure solutions or appropriate intetia solvents. Pharmaceutically acceptable alkalis-additive salts include sodium, potassium, calcium, ammonium or magnesium salts, or analogous salts. When compounds contain relatively alkaline functional group, acid-addtive salts are prepared by enough acids contacting with these compounds in neutral form in pure solutions or appropriate intetia solvents. Examples of pharmaceutically acceptable acid-additive salts include inorganic acid salts, the aforesaid inorganic acids include hydrochloric acid, hydrobromic acid, nitric acid, carbonic acid, bicarbonate radical, phosphoric acid, monohydrogen phosphate, dihydrogen phosphate, sulphuric acid, bisulfate, hydroiodic acid, phosphorous acid and so on; and organic acid, the aforesaid organic acids include acetic acid, propionic acid, isobutyric acid, maleic acid, malonic acid, benzoic acid, succinic acid, octandioic acid, allomaleic acid, lactate, amygdalic acid, alizaric acid, benzenesulfonic acid, p-methylbenzenesulfonic acid, citric acid, tartaric acid, methylsulforic acid and so on; also include amino acid (like arginine) salts, and organic acid salts like glucuronic acid and so on (refer to Berge et al., "pharmaceutical Salts", Journal of pharmaceutical Science 66: 1-19 (1977)). The certain compounds containing alkaline and acidic functional groups in this invention can be transferred into any one of alkaline- or acidic-addtive salts.

Preferably, salts contact with alkalis or acids in normal ways, and then maternal compounds are separated to give regenerated compounds in neutral form. The differences between maternal forms and various saline forms of compounds are certain physical properties, such as different solubility in polar solvents.

The term "pharmaceutically acceptable salts" used herein is derivatives of compounds in this invention, including, maternal compounds modified through salifying with acids or alkalis. Examples of pharmaceutically acceptable salts include, but are not limited to, alkali bases, such as inorganic acid salts or organic acid salts of amines, acid radicals, such as alkali metal salts or organic salts of carboxylic acids, and so on. Pharmaceutically acceptable salts include normal nontoxic salts or quaternary ammonium salts of maternal compounds, such as nontoxic salts formed from inorganic or organic acids. Normal nontoxic salts include, but are not limited to, those salts derived from inorganic or organic acids, and the aforesaid inorganic or organic acids are selected from 2-acetoxy benzoic acid, 2-hydroxyl ethanesulfonic acid, acetic acid, ascorbic acid, benzenesulfonic acid, benzoic acid, bicarbonate radical, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxyl, hydroxy naphthalene, isethionic acid, lactic acid, lactose, dodecyl sulfonic acid, maleic acid, malic acid, mandelic acid, methanesulfonic acid, nitric acid, oxalic acid, dihydroxy naphthalene acid, pantothenic acid, phenylacetic acid, phosphoric acid, polygalactose aldehyde, propionic acid, salicylic acid, stearic acid, subacetic acid, succinic acid, sulfamic acid, sulfanilic acid, sulfuric acid, tannin, tartaric acid and p-methylbenzenesulfonic acid.

Pharmaceutically acceptable salts in this invention can be synthesized through conventional chemical methods with maternal compounds containing acid radical or alkaline base. In general, the preparation methods of these salts is that in water or organic solvents or the mixture of both, dissociated acidic or alkaline forms of these compounds react with stoichiometric proper acids or alkalis to give salts. In general, preferably, ether, ethyl acetate, ethanol, isopropanol or acetonitrile, and the like non-aqueous media.

Including forms of salts, compounds provided in this invention also exist forms of prodrugs. Prodrugs of compounds described herein are transferred into compounds in this invention easily through chemical reaction in physiological conditions. Besides, prodrugs can be transferred into compounds in this invention easily through chemical or biochemical methods in vivo environment.

Certain compounds in this invention can exist in non-solvent or solvent forms, including hydrate forms. In general, solvent forms are comparable to non-solvent forms, which are included in this invention.

Certain compounds in this invention can contain the asymmetric carbon (optical center) or double bond. Racemic mixtures, asymmetric isomers, geometric isomers, and single isomers are all included in this invention.

The diagram method of racemates, ambiscalemic and scalemic or enantiomer pure compounds comes from Machr, J.Chem.Ed. 1985, 62: 114-120. 1985,62: 114-120. Unless otherwise stated, the wedge key and dashed key represent a stereocentric absolute configuration. When the aforesaid compounds in this article contain olefinic double bonds or other geometric asymmetry centers, unless otherwise stated, they include E, Z geometrical isomers. Similarly, all the tautomeric forms are included in this invention.

The compounds in this invention can exist specific geometrical or stereo isomer forms. This invention conceives all this kind compounds, which include cis- and trans-isomers, (–)- and (+)-enantiomers, (R)- and (S)-enantiomers, diastereomers, (D)-isomers, (L)-isomers, their racemic mixtures and other mixtures, such as the mixture rich in symmetric isomers and diastereomers, and all these mixtures are included in this invention. Substituents such as alkyl may exist other asymmetric carbon, and all these isomers and their mixture are included in this invention.

The optically active (R)- and (S)-enantiomers, and (D)- and (L)-isomers can be prepared through chiral synthesis, or chiral reagents or other conventional techniques. If a kind of enantiomers is needed in this invention, they can be prepared through asymmetric synthesis or derivatization of chiral auxiliary, where obtained mixtures of diastereomers are separated and then auxiliary groups are ruptured to give pure needed enantiomers. Or, when compounds contain alkaline groups (such as amino) or acidic groups (such as carboxyl), they form salts of diastereomers with appropriate optically active acids or alkalis which are splitted through conventional methods known in this field to gine pure enantiomers. Besides, the separate of enantiomers and diastereomers is through chromatography, and the aforesaid chromatography uses chiral stationary phases, and combines with chemical derivatization optionally (such as amine forming carbamate).

Compounds in this invention can contain unnatural ratio atomic isotopes in one or multi-atoms forming compounds. For example, compounds can be labeled with radioactive isotopes, such as tritium ($^3H$), iodine-125 ($^{125}I$) or carbon-14 ($^{14}C$). The conversion of all the isotopes constituting compounds in this invention, whether radioactivity or not, are included in this invention.

The term "pharmaceutically acceptable carrier" means any preparation or supported media that can deliver effective amount of active substance in this invention, don't interfere biological active of active substance and is nontoxic to hosts or patients, and representative carriers include water, oil, vegetable and mineral, cream base, lotion base, ointment base and so on. These bases include suspending agent, tackifier and penetration enhancer and so on. Their preparations are known to technicians in cosmetic and topical medication fields. Other information about carriers, can refer to the literature Remington: The Science and Practice of Pharmacy, 21st ED., Loppincott, Williams&Wilkins (2005), and contents of this literature merge into this article by quoting.

The term "excipient" usually means carrier, diluent and/or media which are needed for preparation of effective pharmaceutical compositions.

In allusion to medicine or pharmacological activator, the term "effective amount" or "therapeutically effective amount" means enough amount of medicine or agent which can achieve the desired affect without toxin. For the oral preparation in this invention, "effective amount" of a kind of active substance in compositions means the amount needed to achieve the desired affect when combining with another active substance in compositions. The effective amount varies with each individual, and depends on ages of receptors and general situations, also specific active substances. In individual cases, appropriate effective amount can be determined according to routine tests by technicians in this field.

The term "active constituent", "therapeutic agents", "active substance" or "active agent" mean a kind of chemical entities which treat targeted disorders, diseases or symptoms.

The term "substituted", as used herein, means that any one or more hydrogens on the desigated atom is replaced with a selection from the indicated group, including deuterium "D" atom, a variant hydrogen, provided that the designated atom's normal valency is not exceeded, and that the substitution results in a stable compound. When a substituent is keto (i.e., =O), then two hydrogens on the atom are replaced. Keto substituents are not present on aromatic moieties. The term "optionally substituted", as used herein, means that the designated atom can be substituted or unsubstituted by the substituents, and unless otherwise stated, the species and number of the substituents are not defined provided that they can be achieved in Chemistry.

When any variable (e.g. R) occurs more than one time in any constituents or formula for a compound, its definition at each occurrence is independent of its definition at every other occurrence. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When the number of a bonding group is zero, for example, —(CRR)$_0$—, then this bonding group is a single bond.

When one of variants is selected from single bond, then two group bonding by this variant is bonded directly, for example, when "L" in "A-L-Z" represents a single bond, this formula is "A-Z" actually.

When a substituent is vacant, then this substituent doesn't exist, for example, when "X" in "A-X" is vacant, this formula is "A" actually.

When a bond to a substituent is shows to cross a bond connecting two atoms in a ring, then such substituent may be bonded to any atom on the ring. When a substituent is listed without indicating the atom via which such substituent is bonded to the rest of compound of a given formula, then such substituent may be bonded via any atom in such substituent. Combinations of substituents and/or variables are permissible only if such combinations result in stable compounds. For example, structural units

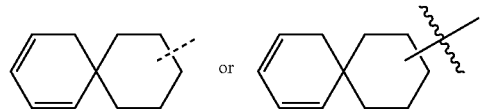

mean any site of cyclohexyl or cyclohexadiene can be substituted.

The terms "halo" or "halogen", by themselves or as a part of another substituent, mean, unless otherwise stated, a fluorine, chlorine, bromine, or iodine atom. Additionally, terms such as "haloalkyl", are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$ and $C_6$ alkoxy groups. Examples of alkoxy include, but are not limited to, methoxy, ethoxy, n-propoxy, i-propoxy, n-butoxy, s-butoxy, t-butoxy, n-pentoxy, and a-pentoxy. "Cycloalkyl" is intended to include saturated ring groups, such as cyclopropyl, cyclobutyl, or cyclopentyl. 3-7 cycloalkyl is intended to include hydrocarbom chains of either straight or branched configuration and one or more unsaturated carbon-carbon bonds that may occur in any stable point along the chain, such as ethenyl and propenyl.

"Halo" or "halogen" as used herein refers to fluoro, chilro, bromo, and iodo.

As used herein, the term "hetero", mean, unless otherwise stated, "heteroatom" or "heteroadical" (namely radical containing heteroatom), including atoms other than carbon (C) and hydrogen (H), also including the radicals containing these aforesaid heteroatoms. Examples include oxygen (O), nitrogen (N), sulfur (S), silicon (Si), germanium (Ge), aluminum (Al), and boron (B), also include optically substituted —C(=O)N(H)—, —N(H)—, —C(=NH)—, —S(=O)$_2$N(H)—, or S(=O)N(H)—.

"Ring" as used herein, means a substituted or unsubstituted cycloalkyl, heterocyclalkyl, cycloalkenyl, heterocycloalkenyl, cycloalkynyl, heterocycloalkybyl, aryl, or heteroaryl. A ring includes mono, bi, sprio, fused, and bridged ring moieties. The number of atoms in a ring is typically defined by the number of the members in the ring. For example, a "5- to 7-membered ring", means there are 5 to 7 atoms in the encircling arrangement. Unless otherwise specified, the ring optically includes one to three heteroatoms. Thus, the term "5- to 7-membered ring" includes, for example, phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heterocycle" or "heterocyclic group" is intended to mean a stable monocyclic, bicyclic, or tricyclic ring containing heteroatom or heteroadical, which is saturated, partially saturated or unsaturated (aromatic), and which consists of carbon atoms and 1,2,3, or 4 ring heteroatoms independently selected from the groups consisting of N, O and S and including any bicyclic groups in which any of the above-defined heterocyclic rings is fused to a benzene ring. The nitrogen and sulfur heteroatoms may optically be oxidized (i.e. NO and S (O) p, p is 1 or 2). The nitrogen atom may be substituted or unsubstitued (i.e. N or NR wherein R is H or another substituent, if define). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not more than 1. As used herein, the term "aromatic heterocyclic group" or "heteroaryl" is tended to mean a stable 5,6, or 7-membered monocyclic or bicyclic or 7,8,9, or 10-membered bicyclic heterocyclic aromatic ring which consists of carbon atoms and 1,2,3 or 4 heteroatoms independently selected from the group consisting of N, O and S. The nitrogen atom may be substituted or unsubstituted (i.e. N or NR wherein R is H or another substituent, if defined). The nitrogen and sulfur heteroatoms may optionally be oxidized (i.e., NO and S (O) p). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen, two nitrogen atoms, and a carbon-nitrogen group. It is noted that a bridge always converts a monocyclic ring into a tricyclic ring. When a ring is bridged, the substituents recited for the ring may also be present on the bridge.

Example of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, decahydroquinolinyl, 2H, 6H-1,5-2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indoliziny, indolyl, 3H-indolyl, isobenzofuranyl, isoindolinyl, isoindolyl, isoquinolinyl, isothiazolyl, isoxazolyl, methylenedioxyphenyl, morpholiny, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phthalazinyl, piperazinyl, piperidinyl, piperidonyl, 4-piperidonyl, piperonyl, pteridinyl, purinyl, pyranyl, pyrazinyl, pyrazolidinyl, pyrodazinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroidoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthiophenyl, thienooxazolyl, thienothiazolyl, thienoimidazole, thienyl, triazinyl, 1,2,3-triazolyl, 1,2,4-triazolyl, 1,2,5-triazolyl, 1,3,4-triazolyl, and xanthenyl. Also included are fused ring and spiro compounds.

The term "hydrocarbyl" or it lower concept (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). "hydrocarbyl" include, but are not limited to, aliohatic hydrocarbyl and aromatic hydrocarbyl, and the aliohatic hydrocarbyl include linear and cyclic ones, specifically including but not limited to, alkyl, alkenyl, and alkynyl, and the aromatic hydrocarbyl includes, but is not limited to, 6-12 membered aromatic hydrocarbyl, for example, benzene, and naphthalene. In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of, for example, n-pentyl, n-hexyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its lower concept (such as heteroalkyl, heteroalkeneyl, heteroalkynyl and heteroaryl etc.) by itself or in combination with another term, means, unless otherwise stated, a stable straight or branched chain, or cyclic hydrocarbon radical,or combinations thereof, consisting of the stated number of carbon atoms and at least one heteroatom. In some embodiments, the term "heteroalkyl", by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heterohydrocarbyl group (including the position at which the hydrocarbyl group is attached to the remaider of the molecule). Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH=CH-O-CH_3$, $-CH_2-CH=N-OCH_3$, and $-CH=CH-N(CH_3)-CH_3$. Up to two heteroatoms may be consecutive, such as, for example, $-CH_2-NH-OCH_3$.

The term "alkoxy", "alkylamino" and "alkylthio" (or thioalkoxy) are used in their conventional sense, and refer to those alkyl groups attached to the remaider of the molecule via an oxygen atom, an amino group, or a sulfur atom, respectively.

The term "cyclohydrocarbyl", "heterocyclohydrocarbyl", or their lower concept (such as aryl, heteroaryl, cycloalkyl, heterocycloalkyl, cycloalkenyl, heterocycloalkenyl, cycloalkynyl, and heterocycloalkynyl etc.) by themselves or in combination with other terms mean cyclized hydrocarbyl and heterohydrocarbyl, respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Example of cycloalkyl include, but are not limited to, cyclopentyl, cyclohexyl, 1-cyclohexenyl, 3-cyclohexenyl, cycloheptyl, and the like. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl and 2-piperazinyl.

The term "aryl" means, unless otherwise stated, a polyunsaturated aromatic substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidy, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Unless otherwise stated, the term "aryl" when used in combination with other terms (e.g., aryloxy, arylthio, aralkyl) includes both aryl and heteroaryl rings as defined above. Thus, the term "aralkyl" is meant to include those radicals in which an aryl group is attached to an alkyl group (e.g., benzyl, phenethyl, pyridylmethyl and the like) including those alkyl group in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "leaving group" means a functional group or atom which can be displaced by another functional group or atom in a substitution reaction, such as a nucleophilic substitutiom reaction. By way of example, representative leaving groups include triflate, chloro, bromo and iodo group; sulfobic ester groups, such as mesylate, tosylate, brosylate, nosylate and the like; and acyloxy groups, such as acetoxy, trifluoroc=acetoxy and the like.

The term "protecting group" includes but is not limited to "amino-protecting group", "hydroxyl-protecting group" and "thiol-protecting group". The term "amino-protecting group" means a protecting group suitable for preventing undesired reactions at an amino nitrogen. Representative amino-protecting groups include, but are not limited to, formyl; acyl group, for example alkanoyl groups, such as acetyl, trichloroacetul or trifluoroacetyl; alkoxycarbonyl groups, such as tert-butoxycarbonyl (Boc); arylmethoxycarbonyl groups, such as benzyloxycarbobyl (Cbz) and 9-fluorenylmethoxycarbonyl (Fmoc); arylmethyl groups, such as benzyl (Bn), trityl (Tr), and 1,1-di-(4'-methoxyphenyl) methyl; silyl groups, such as trimethylsilyl (TMS) and tert-butylsimethylsilyl (TBS); and the like. The term "hydroxyl-protecting group" means a protecting group suitable for preventing undesired reactions at a hydroxyl group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butylsimethylsilyl (TBS); and the like.

The compounds of this invention can be prepared in a number of ways known to one skilled in the art of organic synthesis. The examples of this invention can be synthesized using the methods described below, together with synthetic methods known in the art of synthetic organic chemistry, or by variations thereon as appreciated by those skilled in the art. Concrete methods include, but are not limited to, those describe below.

This present invention adopts following abbreviating words:

| List of abbreviating words | |
|---|---|
| Pd/C | Pd/C catalyst |
| HATU | 2-(7-Azabenzotriazol-1-yl)-N,N,N',N'-tetramethyluroniumhexafluorophosphate |
| TEMPO | 2,2,6,6-tetramethylpiperidine-1-oxyl |
| DIAD | diisopropyl azodiformate |
| NMM | N-methylmorpholine |
| DCM | dichloromethane |
| THF | tetrahydrofuran |
| Boc | t-butyloxy carbonyl |
| Oxone | potassium peroxymonosulfate |
| Cbz | carbobenzyloxy |
| DMF | N,N-dimethylformamide |
| LiBH4 | lithium borohydride |
| TFA | trifluoroacetic acid |
| EDCI | 1-ethyl-(3-Dimethylaminopropyl)carbodiimide hydrochloride |
| aq | aqueous |
| EDC | N-(3-Dimethylaminopropyl)-N'-ethylcarbodiimide hydrochloride |
| m-CPBA | 3-chloroperoxybenzoic acid |

-continued

| | List of abbreviating words |
|---|---|
| eq | equivalent |
| CDI | carbonyldiimidazole |
| DCM | dichloromethane |
| PE | petroleum ether |
| DMSO | dimethyl sulfoxide |
| EtOAc | ethyl acetate |
| EtOH | ethanol |
| MeOH | methanol |
| CBz | carbobenzyloxy, a kind of protecting group for amine |
| HOAc | acetic acid |
| NaCNBH$_3$ | sodium cyanoborohydride |
| r.t. | room temperature |
| O/N | overnight |
| Boc$_2$O | di-tert-butyl dicarbonate |
| TFA | trifluoroacetic acid |
| DIPEA | Ethyldiisopropylamine |
| SOCl$_2$ | thionyl chloride |
| CS$_2$ | carbon disulfide |
| TsOH | p-toluenesulfonic acid |
| NFSI | N-Fluorobenzenesulfonimide |
| NCS | N-Chlorosuccinimide |
| n-Bu$_4$NF | Tetrabutylammonium fluoride |
| iPrOH | 2-propanol |
| Mp | melting point |
| LDA | lithium diisopropylamide |

Compounds are named either manually or by using ChemDraw®, or using vendors catalogue name if commercially available.

All solvents used are commercially available and are used without any further purification. Reactions are typically run using anhydrous solvents under an inert atmosphere of nitrogen. Proton NMR are recorded on Bruker Avance III 400(400 MHz) spectrometer and chemical shifts are reported as (ppm) down field from tetramethylsilane. Mass spectra are determined on Agilent 1200 series plus 6110 (& 1956A). LC/MS, or shimadzu MS consisting of a DAD: SPD-M20A(LC) and shimadzu Micromass 2010 detector. The mass spectrometer is equipped with an electrospray ion source (ESI) operated in a positive or negative mode.

Analysis of high performance liquid chromatography uses shimadzu LC20AB system equipped Shimadzu SIL-20A automatic sampler and Shimadzu DAD; SPD-M20A detector, and adopts Xtimate C18 (3 m filler, standard is 2.1×300 mm) chromatographic column. Method 0-60AB_6 min: adopting linear gradient, washing is started with 100% A (A is 0.0675% TFA aqueous solution) and ended with 60% B (B is 0.0625% TFA in MeCN solution), and all the process costs 4.2 min, then washing is running with 60% B for 1 min. The chromatographic column is balanced for 0.8 min to reach 100:0, and total running time is 6 min. Method 0-80AB_6 min: adopting linear gradient, washing is started with 90% A (A is 0.0675% TFA aqueous solution) and ended with 80% B (B is 0.0625% TFA in MeCN solution), and all the process costs 4.2 min, then washing is running with 80% B for 1 min. The chromatographic column is balanced for 0.8 min to reach 90:10, and total running time is 6 min. The column temperature is 50° C., and the flow velocity is 0.8 mL/min. The scanning wavelength of DAD is 200-400 nm.

Thin-layer chromatography (TLC) is running on Sanpontgroup silica gel GF254, and the spot is detected by ultraviolet light irradiation usually or by other ways on certain cases, and on these cases, compounds are viewed by spreading thin layer plate with iodine (1g iodine is added into 10 g silica and mixture completely), vanillin (about 1 g vanillin solute into 100 ml L 10% H$_2$SO$_4$), ninhydrin (brought from Aldrich) or special chromogenic agent (25 g (NH$_4$)$_6$Mo$_7$O$_{24}$.4H$_2$O, 5 g (NH$_4$)$_2$Ce(IV)(NO$_3$)$_6$ solute into 450 mL H$_2$O and 50 mL H$_2$SO$_4$ completely). Adopting similar ways of disclosed technology in Still, W. C.; Kahn, M.; and Mitra, M. Journal of Organic Chemistry, 1978, 43, 2923-2925, flash column chromatography is running on Silicycle 40-63 μm silica (230-400 mesh). Common solvents used in flash column chromatography or thin-layer chromatography are mixtures of dichloromethane/methanol, ethyl acetate/methanol, and hexane/ethyl acetate. Preparation chromatography is running on Gilsom-281 Prep LC 322system using Gilson UV/VIS-156 detector, and chromatographic columns used are Agella Venusil ASB Prep C18 (5 m filler, standard is 150×21.2 mm), Phenomenex Gemini C18 (5 m filler, standard is 150×30 mm), Boston Symmetrix C18 (5 m filler, standard is 150×30 mm) or Phenomenex Synergi C18 (4 m filler, standard is 150×30 mm). When flow velocity is 25 mL/min, compounds are washed off with low gradient acetonitrile/water (0.05% HCl, 0.25% HCOOH or 0.5% NH$_3$.H$_2$O in water), and total running time is 8-15 min.

EMBODIMENTS

The invention is now further described by examples given below, but the protective scope of which is not limited thereto. The present invention has been described in detail, and the embodiments have also been disclosed. For one skilled in the art, it is obvious to modify and improve the embodiment of the present invention without departing from the spirit and range of the present invention.

Embodiment 1

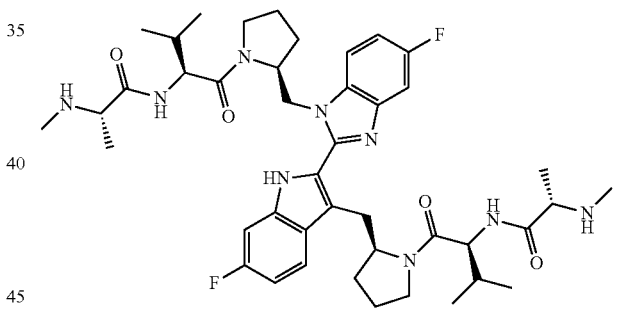

Reaction Process: Preparation of Intermediates 1-5

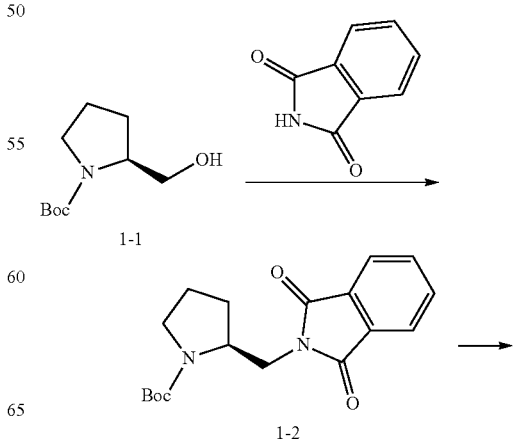

-continued

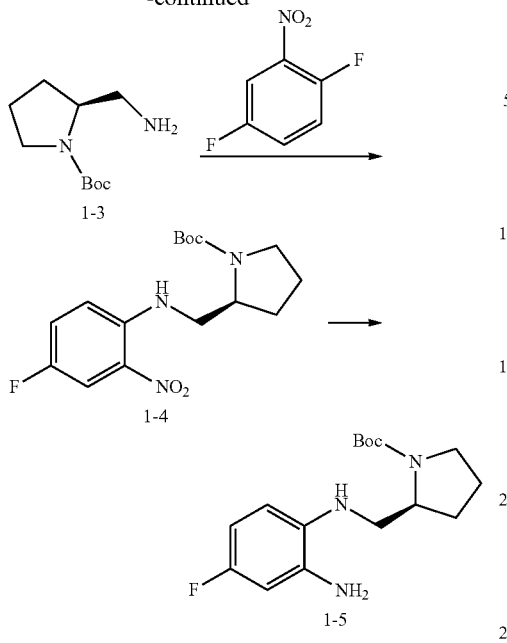

Step A: To a solution of N-Boc-L-prolinol (50 g, 248.43 mmol), phthalimide (43.86 g, 298.12 mmol) and triphenylphosphine (65.16 g, 248.43 mmol) in tetrahydrofuran (1 L) at 0° C. under N₂ was added DIAD (48.31 mL, 248.43 mmol) dropwise. The mixture was then warmed to room temperature and stirred for 16 h, quenched with water (200 mL), stirred for 10 min and extracted with EtOAc (250 mL×2). The combined organic phase was washed with aq saline, dried over anhydrous Na₂SO₄ and concentrated in vacuo. The residue was purified by flash column chromatography eluted with Pet. Ether/EtOAc (50/1 to 30/1) to give tert-butyl (S)-2-((1,3-dioxoisoindolin-2-yl)methyl)pyrrolidine-1-carboxylate (51 g, 62.14%).

Step B: To a solution of tert-butyl (2S)-2-((1,3-dioxoisoindolin-2-yl)methyl)pyrrolidine-1-carboxylate (51 g, 154.37 mmol) in ethanol (350 mL) at 80° C. was added hydrazine hydrate (22.07 mL, 385.93 mmol, 85%) dropwise and then stirred for 16 h at this temperature. The mixture was cooled to room temperature, filtered and the filtrate was concentrated in vacuo to give tert-butyl (2S)-2-(aminomethyl)pyrrolidine-1-carboxylate (29 g, 93.8%).

Step C: To a solution of tert-butyl (2S)-2-(aminomethyl)pyrrolidine-1-carboxylate (15 g, 74.9 mmol), and potassium carbonate (20.7 g, 149.8 mmol) in acetonitrile (300 mL) was added 1,4-difluoro-2-nitrobenzene (13.11 mL, 82.39 mmol) at room temperature. The mixture was warmed to 80° C. and then stirred for 1 h under N₂, quenched with water (200 ml), extracted with EtOAc (250×2). The combined organic phase was washed with aq saline, dried over anhydrous Na₂SO₄ and concentrated in vacuo. The residue was purified by flash column chromatography eluted with Pet.Ether/EtOAc (50/1 to 30/1) to give tert-butyl (2S)-2-(((4-fluoro-2-nitrophenyl)amino)methyl)pyrrolidine-1-carboxylate (28 g, crude product) without further purification.

Step D: To a solution of tert-butyl (2S)-2-(((4-fluoro-2-nitrophenyl)amino)methyl)pyrrolidine-1-carboxylate (11 g, crude product) in methanol (100 mL) and EtOAc (100 mL) was added wet Pd/C under N₂, and the mixture was reacted for 10 h at the atmosphere of 50 psi H₂. The reaction mixture was filtered and concentrated to give tert-butyl (2S)-2-(((2-amino-4-fluorophenyl)amino)methyl)pyrrolidine-1-carboxylate (9 g, crude product).

Reaction Process: Preparation of Intermediates 1-10

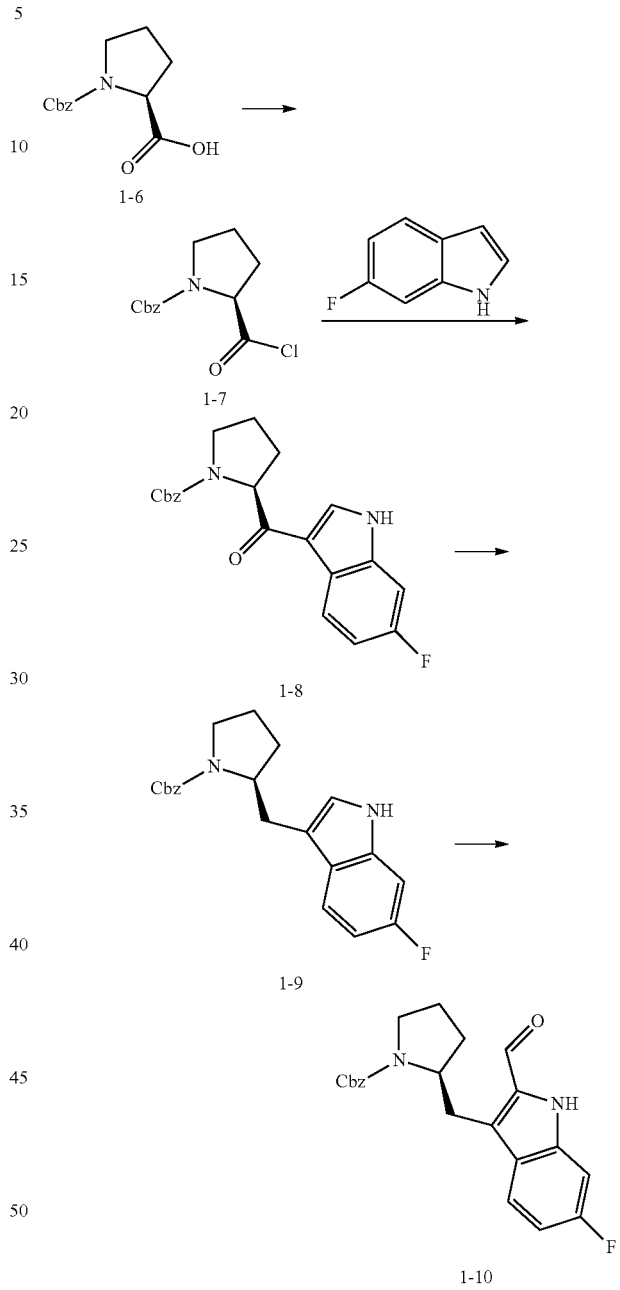

Step A: To a solution of N-Cbz-L-proline (50.00 g, 200.59 mmol) in 500 ml toluene was added DMF (146.61 mg, 2.01 mmol) and then added oxalylchloride (30.55 g, 240.71 mmol) dropwise at 10-20° C. The mixture was stirred for 16 h at 10-30° C., concentrated in vacuo and solvents were removed. Crude product N-Cbz-L-prolylchloride (53.70 g, 200.59 mmol) was used for next step.

Step B: To a solution of 6-fluoro-1H-indole (40.66 g, 300.88 mmol) in toluene (300 mL) was added ethylmagnesium bromide (3 mol/L, 106.98 mL) dropwise at −4-5° C. After the addition, the mixture was stirred for 30 min at the same temperature and then added N-Cbz-L-prolylchloride (53.70 g, 200.59 mmol) in 200 ml toluene at 0-10° C.

dropwise. The mixture was stirred for 2 h at 20-30° C., and then adjusted pH to 3 with HOAc, quenched with 1 L water, extracted with 1 L EtOAc. The organic phase was separated, dried over anhydrous Na₂SO₄, filtered and the filtrate was concentrated in vacuo to give crude product. The crude product was purified by flash column chromatography eluted with Pet. Ether/EtOAc (1/1) to give benzyl (2S)-2-(6-fluoro-1H-indole-3-carbonyl)pyrrolidine-1-carboxylate (47.00 g, 125.72 mmol, 62.67%) as orange solid.

¹HNMR (DMSO, 400 MHz): δ 12.06 (br.s., 1H), 8.45 (d, J=12.0 Hz, 1H), 8.17 (ddd, J=5.6, 8.7, 17.5 Hz 1H), 7.41-7.25 (m, 3H), 7.13-6.99 (m, 3H), 5.26-5.15 (m, 1H), 5.11-5.02 (m, 1H), 5.00-4087 (m, 1H), 3.57-3.45 (m, 2H), 2.45-2.27 (m, 1H), 1.95-1.79 (m, 3H).

Step C: To a solution of benzyl (2S)-2-(6-fluoro-1H-indole-3-carbonyl)pyrrolidine-1-carboxylate (58.00 g, 158.31 mmol) in 600 ml THF was added LiBH₄ (2 mol/L, 158.31 ml) dropwise at 5-15° C. and the mixture was stirred for 2.5 h at the same temperature. Then the mixture was cooled to 5° C., and added with methylsulphonic acid (27.39 g, 284.96 mmol) dropwise over 30 min. The mixture was stirred for 16.5 h at 10-30° C., then quenched with 100 mL ice water carefully, following adjusting pH to 1 and THF was removed in vacuo. Aqueous solution was extracted with 100 mL EtOAc twice, and the organic phase was concentrated in vacuo to give crude product. Crude product was purified by flash column chromatography eluted with EtOAc/Pet. Ether (3/1) to give benzyl (S)-24(6-fluoro-1H-indol-3-yl)methyl)pyrrolidine-1-carboxylate (49.00 g, 139.05 mmol, 87.83%).

¹HNMR (DMSO, 400 MHz): δ 10.98-10.84 (m, 1H), 7.69-7.04 (m, 8H), 6.89-6.52 (m, 1H), 5.22-5.09 (m, 2H), 4.09-3.93 (m, 1H), 3.36-3.27 (m, 2H), 3.18-2.96 (m, 1H), 2.72-2.56 (m, 1H), 1.88-1.62 (m, 4H).

Step D: The mixture of DMF (7.78 g, 106.41 mmol) and phosphoryl chloride (17.68 g, 115.31 mmol) was stirred for 30 min at 0°C., and then added with benzyl (S)-2-((6-fluoro-1H-indol-3-yl)methyl)pyrrolidine-1-carboxylate (12.50 g, 35.47 mmol) in 100mL 1,2-dichloroethane at the same temperature. The mixture was stirred for 5.5 h at 20-30° C., and then quenched with sat. aq. Na₂CO₃ (200 mL), extracted with EtOAc twice(500 mL). The combined organic phase was washed with sat.aq NaCl (500 mL), dried over anhydrous Na₂SO₄, filtered and the filtrate was concentrated in vacuo to give benzyl (2S)-2-((6-fluoro-2-formyl-1H-indol-3-yl)methyl)pyrrolidine-1-carboxylate (17.00 g, crude product).

Reaction Process: Preparation of Embodiment 1

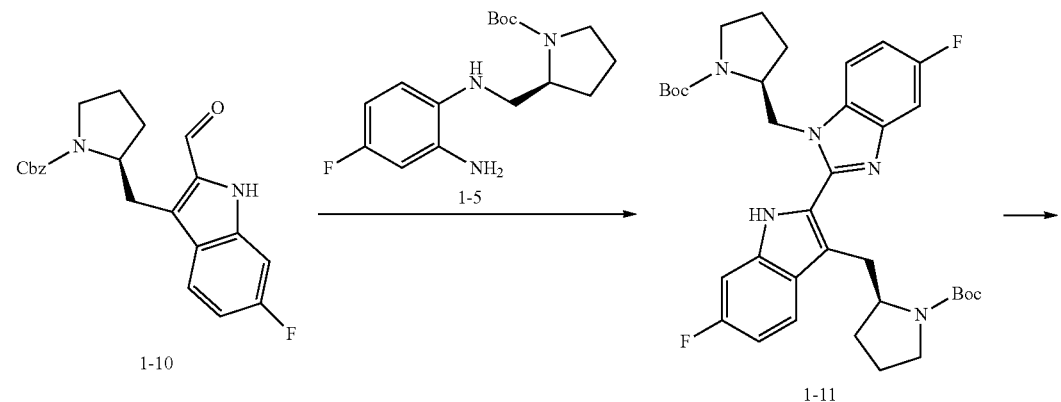

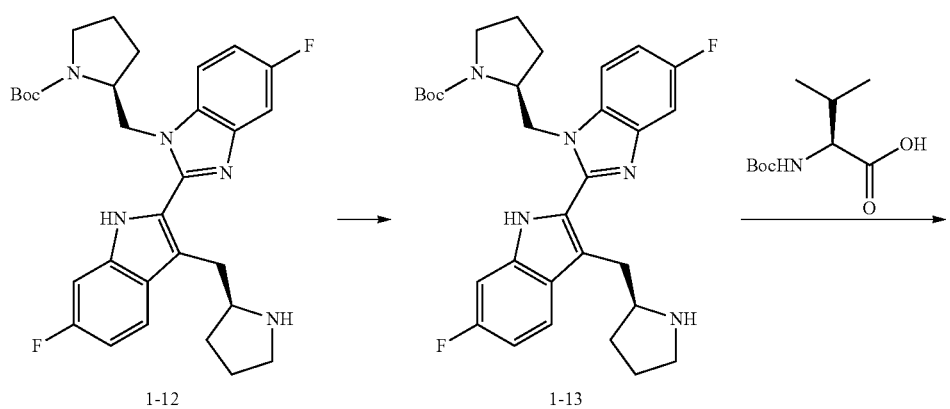

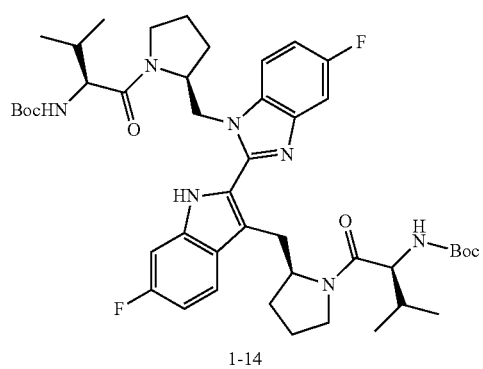

1-14

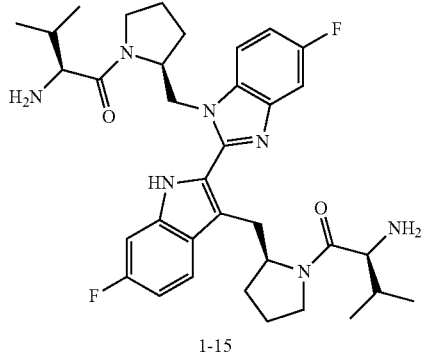

1-15

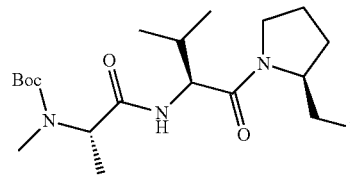

1-16

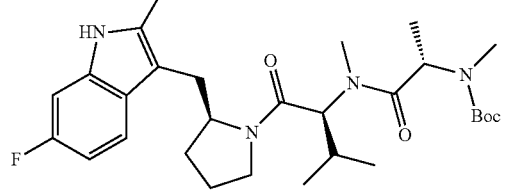

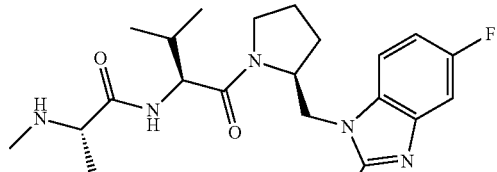

1-17

Step A: benzyl (2S)-2-((6-fluoro-2-formyl-1H-indol-3-yl)methyl)pyrrolidine-1-carboxylate (7 g, crude product) and tert-butyl (2S)-2-(((2-amino-4-fluorophenyl)amino)methyl)pyrrolidine-1-carboxylate (6.26 g, 20.24 mmol) were dissolved in DMF (30 mL) and water (1 mL), oxone (8.4 g, 55.2 mmol) was added in one portion at 25° C. After stirring for 1 h at room temperature, the mixture was quenched with sat.aq Na$_2$SO$_3$ (100 mL) solution, diluted with water (250 mL) and extracted with EtOAc (250 mL×2). The combined organic phase was washed with aq. NaCl, dried over anhydrous Na$_2$SO$_4$ and concentrated in vacuo. The residue was purified by flash column chromatography elution with Pet. Ether/EtOAc (50/1 to 30/1) to give benzyl (S)-2-((2-(1-(((S)-1-(tert-butoxycarbonyl)pyrrolidin-2-yl)methyl)-5-fluoro-1H-benzo[d]imidazol-2-yl)-6-fluoro-1H-indol-3-yl)methyl)pyrrolidine-1-carboxylate (15 g, crude product).

MS (ESI) m/z: 670.5 [M+H$^+$]

Step B: benzyl (2S)-2-((2-(1-(((S)-1-(tert-butoxycarbonyl)pyrrolidin-2-yl)methyl)-5-fluoro-1H-benzo[d]imidazo 1-2-yl)-6-fluoro-1H-indol-3-yl)methyl)pyrrolidine-1-carboxylate (1 g, 1.49 mmol) was dissolved in methanol (30 mL) and EtOAc (30 mL), wet Pd/C (100 mg) was added under N$_2$, and the mixture was reacted for 3 h at the atmosphere of 40 psi H$_2$. The reaction mixture was filtered and the filtrate was concentrated to give tert-butyl (S)-2-((5-fluoro-2-(6-fluoro-3-(((S)-pyrrolidin-2-yl)methyl)-1H-indol-2-yl)-1H-benzo[d]imidazo 1-1-yl)methyl)pyrrolidine-1-carboxylate (750 mg, 93.97%).

Step C: tert-butyl (2S)-2-((5-fluoro-2-(6-fluoro-3-(((S)-pyrrolidin-2-yl)methyl)-1H-indol-2-yl)-1H-benzo[d]imidazol-1-yl)methyl)pyrrolidine-1-carboxylate (610 mg, 1.14 mmol) was dissolved in HCl dioxane solution (3 mL, 4 mol/L), the mixture was stirred for 0.5 h at room temperature. The mixture was concentrated in vacuo to give tert-butyl (S)-2-((5-fluoro-2-(6-fluoro-3-(((S)-pyrrolidin-2-yl)methyl)-1H-indol-2-yl)-1H-benzo[d]imidazol-1-yl)methyl)pyrrolidine-1-carboxylate (579.6 mg, 100%, hydrochloride).

MS (ESI) m/z: 436.2 [M+H$^+$]

Step D: To a stirring solution of N-Boc-L-valine(743.53 mg, 3.42 mmol) in DMF (2 mL) were added N-methylmorpholine (691.87 mg, 6.84 mmol) and HATU (1.52 g, 3.99 mmol) and the mixture was stirred for 10 min at room temperature. Then a solution of 5-fluoro-2-(6-fluoro-3-(((2S)-pyrrolidin-2-yl)methyl)-1H-indol-2-yl)-1-((2S)-pyrrolidin-2-ylmethyl)benzo[d]imidazole (579.6mg, hydrochloride) in DMF (2 mL) was added to the mixture and the mixture was stirred for 2 h at room temperature. The mixture was diluted with water (100 mL) and extracted with EtOAc (100 mL×2).The combined organic phase was washed with aq. NaCl, dried over anhydrous Na$_2$SO$_4$ and concentrated in vacuo. The residue was purified by flash column chromatography eluted with EtOAc/Pet. Ether (3/1) to give tert-butyl ((S)-1-((S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)pyrrolidin-1-yl)-3-methyl-1-oxobutan-2-yl)carbamate (950 mg, 76.94%).

$^1$HNMR (DMSO, 400 MHz): δ8.14-8.06 (s, 0.5H), 8.00-7.85 (m, 1H), 7.58-7.45 (m, 1H), 7.58-7.45 (m, 1H), 7.32-7.19 (m, 1H), 7.05-6.91 (m, 2H), 6.84-6.76 (s, 0.5H), 4.31 (br.s., 1H), 4.08-3.94 (m, 2H), 3.60-3.47 (m, 1H), 3.27 (d, J=12.0 Hz, 1H), 3.08-2.80 (m, 1H), 2.70 (s, 11H), 2.00 (s, 2H), 1.48-1.43 (m, 2H), 1.41-1.31 (m, 17H), 1.30-1.14 (m, 5H), 0.93-0.82 (m, 12H).

MS (ESI) m/z: 834.3 [M+H$^+$]

Step E: tert-butyl ((S)-1-((S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)pyrrolidin-1-yl)-3-methyl-1-oxobutan-2-yl)carbamate (950 mg, 1.14 mmol) was dissolved in HCl dioxane (2 mL, 4 mol/L), the mixture was stirred for 0.5 h at room temperature, and then concentrated in vacuo to give (S)-1-((S)-2-((2-(1-(((S)-1-(L-valyl)pyrrolidin-2-yl)methyl)-5-fluoro-1H-benzo[d]imidazol-2-yl)-6-fluoro-1H-indol-3-yl)methyl)pyrrolidin-1-yl)-2-amino-3-methylbutan-1-one (800 mg, crude product) used for next step.

MS (ESI) m/z: 643.3 [M+H$^+$]

Step F: To a stirring solution of N-Boc-N-methyl-L-alanine (688.95 mg, 3.39 mmol) in DMF (2 mL) were added N-methylmorpholine (685.8 mg, 6.78 mmol) and HATU (1.5 g, 3.96 mmol), the mixture was stirred for 10 min at room temperature, and then added with (S)-1-((S)-2-((2-(1-(((S)-1-(L-valyl)pyrrolidin-2-yl)methyl)-5-fluoro-1H-benzo[d]imidazol-2-yl)-6-fluoro-1H-indol-3-yl)methyl)pyrrolidin-1-yl)-2-amino-3-methylbutan-1-one (800 mg, crude product) in DMF (2 mL) and the mixture was stirred for 2 h at room temperature. The mixture was diluted with water (100 mL) and extracted with EtOAc (100 mL×2). The combined organic phase was washed with aq. NaCl, dried over anhydrous Na$_2$SO$_4$ and concentrated in vacuo. The residue was purified by flash column chromatography eluted with Pet. Ether/EtOAc (2:1 to 1:1) to give tert-butyl ((S)-1-(((S)-1-((S)-2-((2-(3-(((S)-1-(N-(N-(tert-butoxycarbonyl)-N-methyl-L-alanyl)-N-methyl-L-valyl)pyrrolidin-2-yl)methyl)-6-fluoro-1H-indol-2-yl)-5-fluoro-1H-benzo[d]imidazol-1-yl)methyl)pyrrolidin-1-yl)-3-methyl-1-oxobutan-2-yl)amino)-1-oxopropan-2-yl)(methyl)carbamate (910 mg, 76.94%).

$^1$HNMR (DMSO, 400 MHz): δ 11.81 (s, 1H), 7.55 (dd, J=2.4,8.0 Hz, 1H), 7.26 (d, J=8.0 Hz, 2H), 7.05-6.97 (m, 1H), 4.49-4.20 (m, 4H), 2.90 (s, 6H), 2074-2.73 (m, 8H), 2.70 (s, 12H), 2.34 (s, 1H), 2.02-1.89 (m, 1H), 1.40 (d, J=3.8 Hz, 24H), 1.26-1.19 (m, 6H), 1.01-0.78 (m, 6H).

MS (ESI) m/z: 1004.4 [M+H$^+$]

Step G: tert-butyl ((S)-1-((S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)pyrrolidin-1-yl)-3-methyl-1-oxobutan-2-yl)carbamate (910 mg, 906.18mmol) was dissolved in dichloromethane (2 mL), trifluoroacetic acid (2mL, 27.01mmol) was added and the mixture was stirred for 0.5 h at room temperature. The mixture was concentrated in vacuo. The residue was purified by preparative HPLC to give embodiment 1 (233 mg, hydrochloride).

$^1$HNMR (DMSO, 400 MHz): δ 8.20 (dd, J=4.0,8.0 Hz, 1H), 8.01-7.91 (m, 2H), 7.59-7.49 (m, 2H), 7.12 (dt, J=4.0, 12.0 Hz, 1H), 5.04-4.97 (m, 1H), 4.87-4.79 (m, 1H), 4.58 (dd, J=4.0,8.0 Hz, 2H), 4.54-4.48 (m, 1H), 4.34 (brs, 1H), 4.09-3.76 (m, 6H), 3.59 (d, J=12.0 Hz, 1H), 3.29-3.18 (m, 1H), 2.71 (d, J=12.0 Hz, 6H), 2.26 (d, J=8.0 Hz, 3H), 2.06 (d, J=8.0 Hz, 6H), 1.82-1.73 (m, 1H), 1.54 (dd, J=8.0,8.0 Hz, 6H), 1.33 (dd, J=4.0, 8.0 Hz, 6H), 0.96 (t, J=8.0 Hz, 6H).

MS (ESI) m/z: 804.5 [M+H$^+$]

Embodiment 2

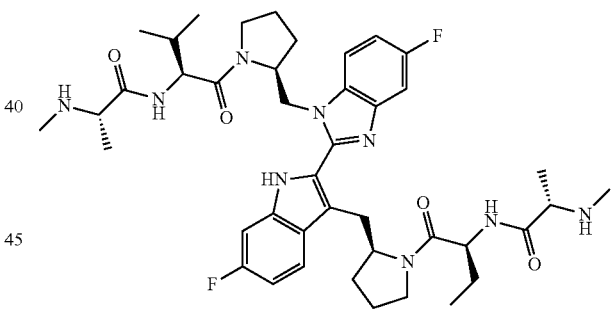

Reaction Process: Preparation of Embodiment 2

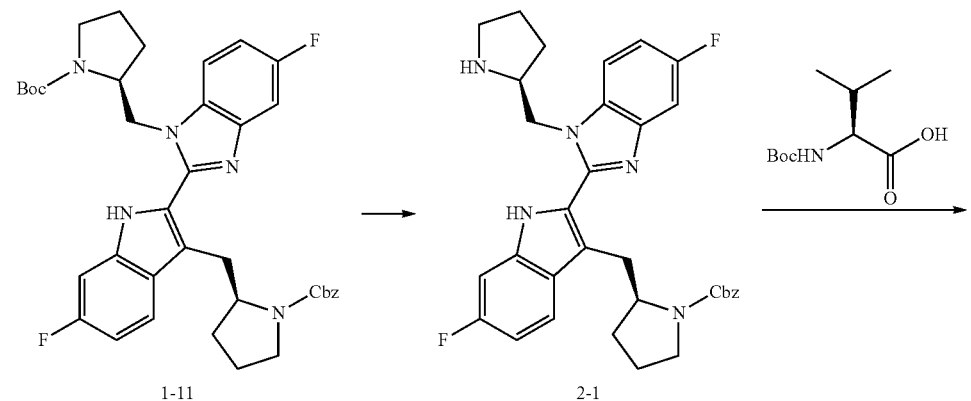

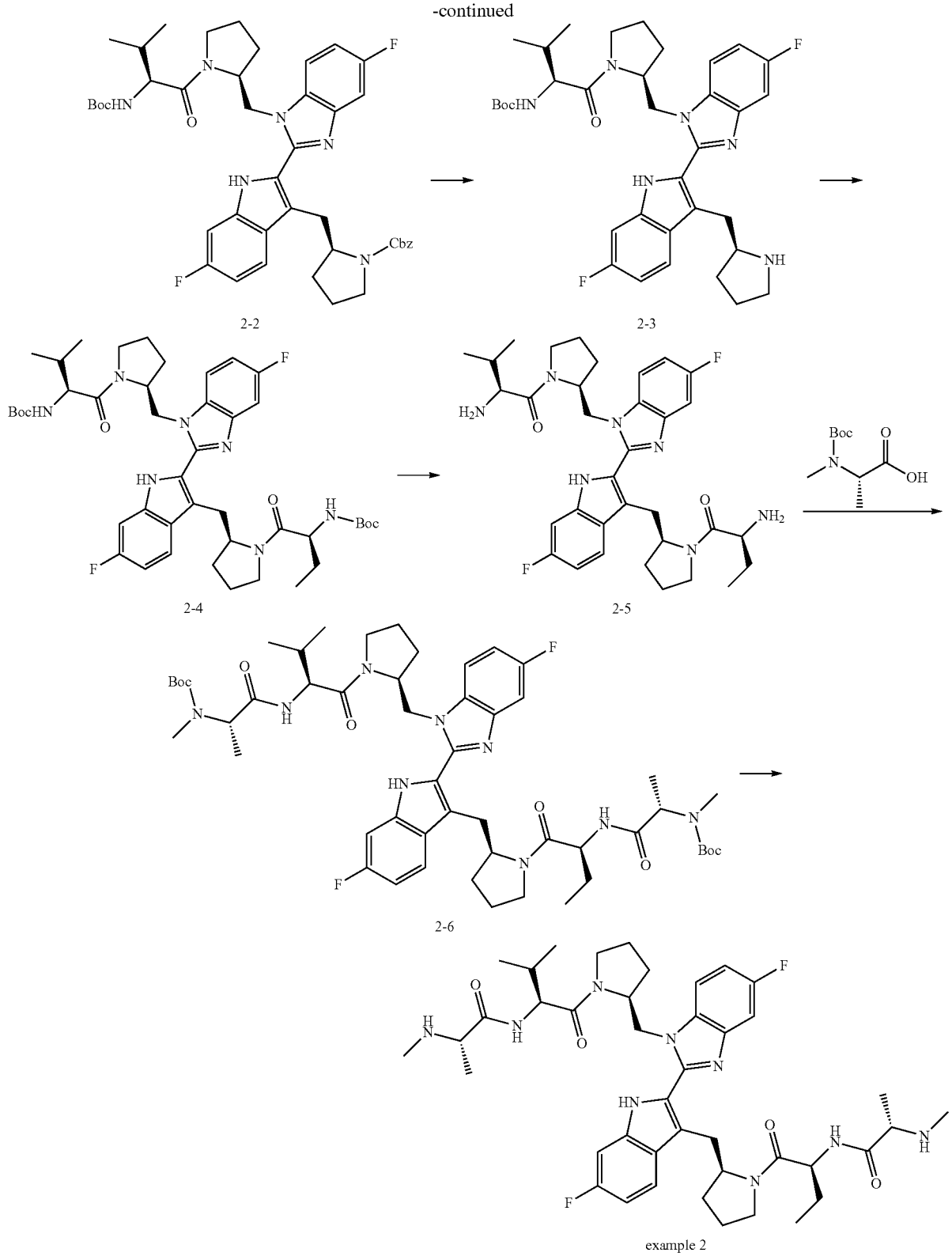

example 2

Step A: benzyl (S)-2-((2-(1-(((S)-1-(tert-butoxycarbonyl)pyrrolidin-2-yl)methyl)-5-fluoro-1H-benzo[d]imidazol-2-yl)-6-fluoro-1H-indol-3-yl)methyl)pyrrolidine-1-carboxylate (3 g, 4.48 mmol) was dissolved in HCl dioxane (10 mL, 4 mol/L), the mixture was stirred for 0.5 h at room temperature, and then concentrated in vacuo. The residue was mashed with EtOAc (50 mL) to give benzyl (S)-2-(((6-fluoro-2-(5-fluoro-1-(((S)-pyrrolidin-2-yl)methyl)-1H-benzo[d]imidazol-2-yl)-1H-indol-3-yl)methyl)pyrrolidine-1-carboxylate (1.7 g, crude product) used for next step.

¹HNMR (DMSO, 400 MHz): δ 11.95 (d, J=19.3 Hz, 1H), 9.71-9.21 (m, 2H), 8.10 (brs, 1H), 7.88 (dd, J=5.4,8.4 Hz, 1H), 7.67-7.57 (m, 1H), 7.41-7.29 (m, 7H), 7.08-6.67 (m, 1H), 5.00 (s, 2H), 4.26 (brs, 4H), 3.33-3.15 (m, 4H), 3.02 (brs, 1H), 1.99 (s, 1H), 1.75-1.46 (m, 8H).

Step B: To a stirring solution of N-Boc-L-valine (385.46 mg, 1.65 mmol) in DMF (1 mL) were added N-methylmorpholine (333.77 mg, 3.3 mmol) and HATU (690.08 mg, 1.81 mmol) and the mixture was stirred for 30 min at room temperature. Then a solution of benzyl (S)-2-((6-fluoro-2-(5-fluoro-1-(((S)-pyrrolidin-2-yl)methyl)-1H-benzo[d]imidazol-2-yl)-1H-indol-3-yl)methyl)pyrrolidine-1-carboxylate (500 mg, crude product) in DMF (1 mL) was added and the mixture was stirred for 2 h at room temperature, diluted with water (100 ml) and extracted with EtOAc (100 mL×2). The combined organic phase was washed with aq. NaCl, dried over anhydrous Na₂SO₄ and concentrated in vacuo. The residue was purified by flash column chromatography eluted with Pet. Ether/EtOAc (5/1 to 2/1) to give benzyl (S)-2-((2-(1-(((S)-1-((tert-butoxycarbonyl)-L-valyl)pyrrolidin-2-yl) methyl)-5-fluoro-1H-benzo[d]imidazol-2-yl)-6-fluoro-1H-indol-3-yl)methyl)pyrrolidine-1-carboxylate (570 mg, 89.86%).

¹HNMR (DMSO, 400 MHz): δ 11.77-11.98 (m, 1H), 7.48-7.55 (m, 1H), 7.36 (s, 7H), 7.20-7.28 (m, 2H), 6.92 (s, 1H), 5.03 (s, 2H), 4.34-4.39 (m, 1H), 4.03 (d, J=7.2 Hz, 1H), 2.69 (s, 4H), 2.31-2.35 (m, 1H), 1.99 (s, 2H), 1.45 (s, 2H), 1.36-1.40 (m, 6H), 1.36 (s, 9H), 1.18 (t, J=7.1 Hz, 2H), 0.96(d, J=6.9 Hz, 2H), 0.88(s, 6H).

MS (ESI) m/z: 769.4 [M+H⁺]

Step C: benzyl (S)-2-((2-(1-(((S)-1-((tert-butoxycarbonyl)-L-valyl)pyrrolidin-2-yl)methyl)-5-fluoro-1H-benzo[d] imidazol-2-yl)-6-fluoro-1H-indol-3-yl)methyl)pyrrolidine-1-carboxylate (570 mg, 741.33 µmol) was dissolved in methanol (15 mL) and EtOAc (15 mL), wet Pd/C (50 mg, 10%) was added under N₂, the mixture was reacted for 16 h at the atmosphere of 45 psi H₂. The reaction mixture was filtered and concentrated to give tert-butyl ((S)-1-((S)-2-((5-fluoro-2-(6-fluoro-3-(((S)-pyrrolidin-2-yl)methyl)-1H-indol-2-yl)-1H-benzo[d]imidazol-1-yl)methyl)pyrrolidin-1-yl)-3-methyl-1-oxobutan-2-yl)carbamate (380 mg, crude product), which was used for next step directly.

MS (ESI) m/z: 635.4 [M+H⁺]

Step D: To a stirring solution of N-Boc-L-n-butyric acid (243.34 mg, 1.2 mmol) in DMF (1 mL) were added N-methylmorpholine (302.77 mg, 2.99 mmol) and HATU (569.06 mg, 1.5 mmol), and a solution of tert-butyl ((S)-1-((S)-2-((5-fluoro-2-(6-fluoro-3-(((S)-pyrrolidin-2-yl)methyl)-1H-indol-2-yl)-1H-benzo[d]imidazol-1-yl)methyl)pyrrolidin-1-yl)-3-methyl-1-oxobutan-2-yl)carbamate (380 mg, crude product) in DMF (1 mL) was added and the mixture was stirred for 1 h at room temperature, then diluted with water (50 mL) and extracted with EtOAc (50 mL×2). The combined organic phase was washed with aq. NaCl, dried over anhydrous Na₂SO₄ and concentrated in vacuo. The residue was purified by flash column chromatography eluted with Pet. Ether/EtOAc (4/1 to 3/1) to give tert-butyl ((S)-1-((S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)pyrrolidin-1-yl)-1-oxobutan-2-yl) carbamate (380 mg, 77.41%).

MS (ESI) m/z: 820.5 [M+H⁺]

Step E: tert-butyl ((S)-1-((S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl) pyrrolidin-1-yl)-1-oxobutan-2-yl)carbamate (380 mg, 463.43 µmol) was dissolved in HCl dioxane (2 mL, 4 mol/L), the mixture was stirred for 0.5 h at room temperature, and then concentrated in vacuo to give (S)-2-amino-1-((S)-2-((2-(3-(S)-1-(S)-2-aminobutanoyl)pyrrolidin-2-yl)methyl)-6-fluoro-1H-indol-2-yl)-5-fluoro-1H-benzo[d]imidazol-1-yl)methyl)pyrrolidin-1-yl)-3-methylbutan-1-one (320 mg, hydrochloride), which is used directly for next step.

MS (ESI) m/z: 620.3 [M+H⁺]

Step F: To a stirring solution of N-Boc-N-methyl-alanine (281.68 mg, 1.39 mmol) in DMF (1 mL) were added N-methylmorpholine (233.65 mg, 2.31 mmol) and HATU (439.15 mg, 1.15 mmol), a solution of (S)-2-amino-1-((S)-2-((2-(3-(((S)-1-((S)-2-aminobutanoyl)pyrrolidin-2-yl) methyl)-6-fluoro-1H-indol-2-yl)-5-fluoro-1H-benzo[d]imidazol-1-yl)methyl)pyrrolidin-1-yl)-3-methylbutan-1-one (320 mg, 461.98 mmol, hydrochloride) in DMF (1 mL) was added and the mixture was stirred for 1 h at room temperature. The mixture was diluted with water (50 mL) and extracted with EtOAc (50 mL×2). The combined organic phase was washed with aq. NaCl, dried over anhydrous Na₂SO₄ and concentrated in vacuo. The residue was purified by flash column chromatography eluted with Pet. Ether/EtOAc (2/1 to 1/2) to give tert-butyl ((S)-1-(((S)-1-((S)-2-((2-(3-(((S)-1-((S)-2-((tert-butoxycarbonyl)(methyl) amino)propanamido)butanoyl)pyrrolidin-2-yl)methyl)-6-fluoro-1H-indol-2-yl)-5-fluoro-1H-benzo[d]imidazol-1-yl) methyl)pyrrolidin-1-yl)-3-methyl-1-oxobutan-2-yl)amino)-1-oxopropan-2-yl)(methyl)carbamate (450 mg, 98.37%).

MS (ESI) m/z: 990.3 [M+H⁺]

Step G: tert-butyl ((S)-1-(((S)-1-((S)-2-((2-(3-(((S)-1-((S)-2-((S)-2-((tert-butoxycarbonyl) (methyl)amino)propanamido)butanoyl)pyrrolidin-2-yl)methyl)-6-fluoro-1H-indol-2-yl)-5-fluoro-1H-benzo[d]imidazol-1-yl)methyl) pyrrolidin-1-yl)-3-methyl-1-oxobutan-2-yl)amino)-1-oxopropan-2-yl)(methyl)carbamate (450 mg, 454.46 mmol) was dissolved in dichloromethane (2 mL), trifluoroacetic acid (2 mL, 27.01 mmol) was added and the mixture was stirred for 0.5 h at room temperature. The mixture was concentrated in vacuo. The residue was purified by preparative HPLC to give embodiment 2 (117 mg, 28.84%, hydrochloride).

¹HNMR (MeOD, 400 MHz): δ 8.71 (d, J=8.0 Hz, 1H), 8.21 (dd, J=4.0,8.0 Hz, 1H), 7.58-7.50 (m, 2H), 7.58-7.50 (m, 2H), 7.12 (dt, J=4.0,8.0 Hz, 1H), 5.26-5.13 (m, 1H), 4.88-4.76 (m, 1H), 4.67 (dd, J=8.0,8.0 Hz, 2H), 4.60-4.45 (m, 2H), 4.33 (brs, 1H), 4.08-3.97 (m, 2H), 3.91-3.78 (m, 4H), 3.54 (d, J=12.0 Hz, 1H), 3.27-3.16 (m, 1H), 2.70 (d, J=12.0 Hz, 6H), 2.41-2.20 (m, 2H), 2.17-1.67 (m, 9H), 1.63-1.50 (m, 6H), 1.12 (t, J=8.0 Hz, 3H), 0.96 (dd, J=8.0, 16.0 Hz, 6H).

MS (ESI) m/z: 790.5 [M+H⁺]

Preparation of embodiment 3-12 can refer to preparation process of embodiment 2.

Embodiment 3

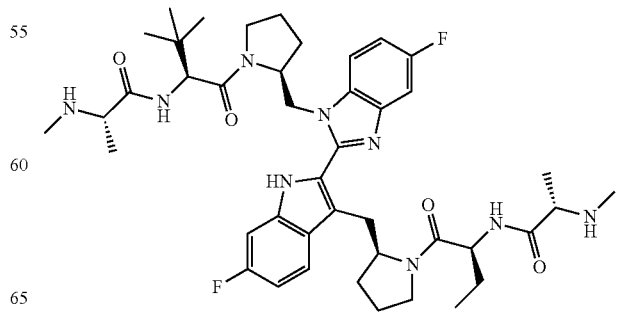

¹HNMR (MeOD, 400 MHz): δ 12.49 (s, 1H), 8.92 (d, J=6.7 Hz, 0.5H), 8.51 (d, J=7.7 Hz, 1H), 8.25-8.16 (m, 1H), 7.97-7.88 (m, 2H), 7.56-7.47 (m, 2H), 7.14-7.06 (m, 1H), 5.00-4.95 (m, 1H), 4.70-4.64 (m, 1H), 4.56 (d, J=6.8 Hz, 1H), 4.50 (brs, 1H), 4.33 (brs, 1H), 4.04 (d, J=6.8 Hz, 2H), 3.93-3.76 (m, 4H), 3.51 (d, J=13.9 Hz, 1H), 3.26-3.16 (m, 1H), 2.71 (s, 3H), 2.66 (s, 3H), 2.41-2.18 (m, 2H), 2.17-1.71 (m, 8H), 1.59 (d, J=7.0 Hz, 3H), 1.46 (d, J=6.8 Hz, 3H), 1.11 (t, J=7.3 Hz, 3H), 1.00 (s, 9H).

MS (ESI) m/z: 804.5 [M+H⁺]

Embodiment 4

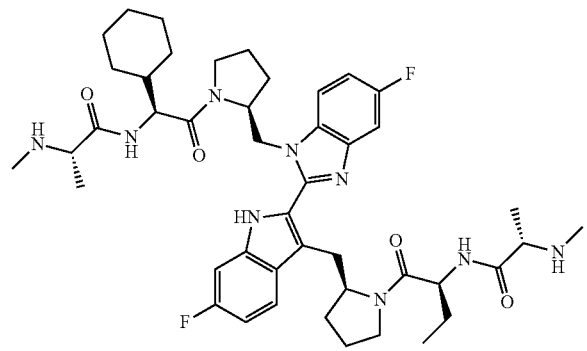

¹HNMR (MeOD, 400 MHz): δ 12.41 (s, 1H), 8.89 (d, J=7.0 Hz, 1H), 8.64 (d, J=7.7 Hz, 1H), 8.18 (dd, J=4.0,9.1 Hz, 1H), 7.99-7.84 (m, 2H), 7.57-7.44 (m, 2H), 7.10 (dt, J=2.1,9.2 Hz, 1H), 5.00-4.92 (m, 1H), 4.69-4.63 (m, 1H), 4.54-4.43 (m, 2H), 4.31 (brs, 1H), 4.04-3.76 (m, 6H), 3.52 (d, J=13.2 Hz, 1H), 3.18 (dd, J=11.2, 14.1 Hz, 1H), 2.71 (s, 3H), 2.66 (s, 3H), 2.38-2.17 (m, 2H), 2.10-1.62 (m, 14H), 1.57 (d, J=7.0 Hz, 3H), 1.48 (d, J=6.8 Hz, 3H), 1.38-0.91 (m, 9H). MS (ESI) m/z: 830.5 [M+H⁺]

Embodiment 5

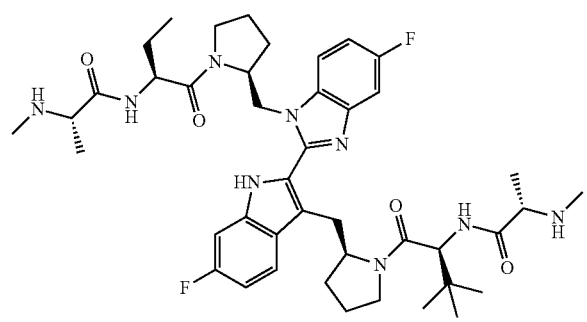

¹HNMR (MeOD, 400 MHz): δ 12.33 (s, 1H), 8.72-8.61 (m, 2H), 8.15 (dd, J=3.9,9.0 Hz, 1H), 7.99-7.90 (m, 2H), 7.55-7.44 (m, 2H), 7.09 (dt, J=2.0,9.2 Hz, 1H), 4.76-4.69 (m, 1H), 4.56-4.42 (m, 2H), 4.10 (q, J=6.5 Hz,1H), 3.96-3.84 (m, 3H), 3.75 (d, J=7.2 Hz, 2H), 3.54 (dd, J =13.9Hz, 1H), 3.26-3.12 (m, 1H),2.68 (d, J=13.9 Hz, 6H), 2.38-2.19 (m, 2H), 2.07-1.59 (m, 7H), 1.51 (t, J=6.8 Hz, 8H), 1.17 (s,9H), 1.03-0.38 (m, 3H).

MS (ESI) m/z: 804.2 [M+H⁺]

Embodiment 6

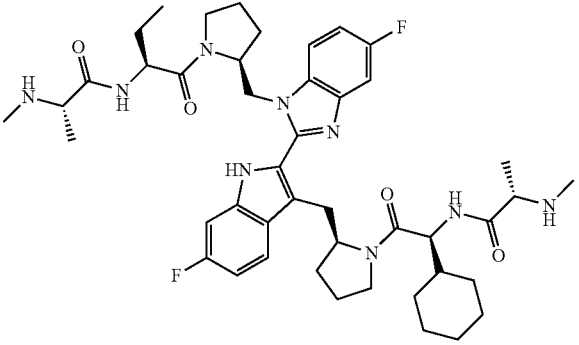

¹HNMR (MeOD, 400 MHz): δ 12.35 (s, 1H), 8.82 (d, J=7.7 Hz, 1H), 8.71 (d, J=6.8 Hz, 1H), 8.22-8.10 (m, 1H), 8.00-7.85 (m, 2H), 7.57-7.43 (m, 2H), 7.09 (t, J=8.3 Hz, 1H), 4.85-4.79 (m, 1H), 4.61-4.46 (m, 3H), 4.31 (brs, 1H), 4.05-3.73 (m, 6H), 3.61-3.49 (m, 1H), 3.25-3.12 (m, 1H), 2.68 (d, J=10.0 Hz, 6H), 2.28 (br.s, 3H), 2.08-1.62 (m, 14H), 1.61-1.41 (m, 8H), 1.41-1.01 (m, 6H), 0.94 (t, J=7.2 Hz, 3H).

MS (ESI) m/z: 830.3 [M+H⁺]

Embodiment 7

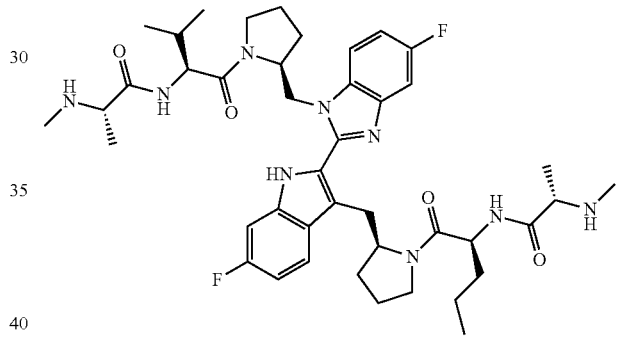

¹HNMR (MeOD, 400 MHz): δ12.45 (s, 1H), 8.91 (d, J=7.1 Hz, 1H), 8.67 (d, J=7.7 Hz, 1H), 8.20 (dd, J=3.8, 9.0 Hz, 1H), 7.97-7.86 (m, 2H), 7.56-7.46 (m, 2H), 7.10 (dt, J=2.1, 9.2 Hz, 1H), 5.00 (d, J=4.6 Hz, 1H), 4.83-4.78 (m, 1H), 4.71 (dd, J=5.4, 8.3 Hz, 1H), 4.58-4.46 (m, 2H),4.31 (brs, 1H), 4.01 (quin, J=6.9 Hz, 2H), 3.90-3.74 (m, 4H), 3.50 (d, J=13.4 Hz, 1H), 3.20 (dd, J=11.2, 13.9 Hz, 1H), 2.69 (d, J=12.8 Hz, 6H), 2.39-2.18 (m, 2H), 2.10-1.75 (m, 9H), 1.61-1.45 (m, 8H), 1.05-0.86 (m, 9H).

MS (ESI) m/z: 804.5 [M+H⁺]

Embodiment 8

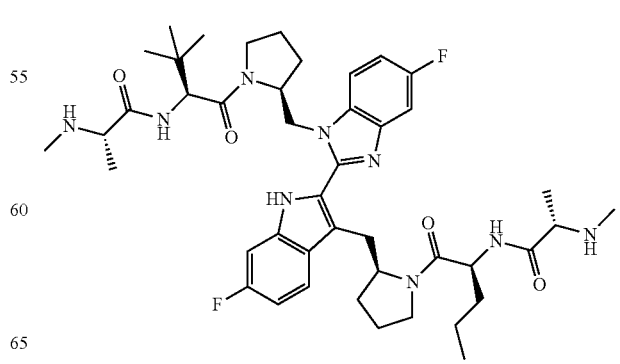

¹HNMR (MeOD, 400 MHz): δ8.94 (d, J=7.1 Hz, 1H), 8.54 (d, J=7.8 Hz, 1H), 8.21 (dd, J=3.9, 9.2 Hz, 1H), 7.97-7.87 (m, 2H), 7.56-7.46 (m, 2H), 7.10 (dt, J=2.0, 9.1 Hz, 1H), 5.03-4.92 (m, 2H), 4.76-4.71 (m, 1H), 4.61-4.46 (m, 2H), 4.32 (brs, 1H), 4.09-3.96 (m, 2H), 3.93-3.74 (m, 4H), 3.50 (d, J=13.8 Hz, 1H), 3.21 (dd, J=11.4, 13.9 Hz, 1H), 2.68 (d, J=19.2 Hz, 6H), 2.43-2.15 (m, 2H), 2.11-1.75 (m, 8H), 1.61-1.45 (m, 8H), 1.07-0.91 (m, 12H).

MS (ESI) m/z: 818.5 [M+H⁺]

Embodiment 9

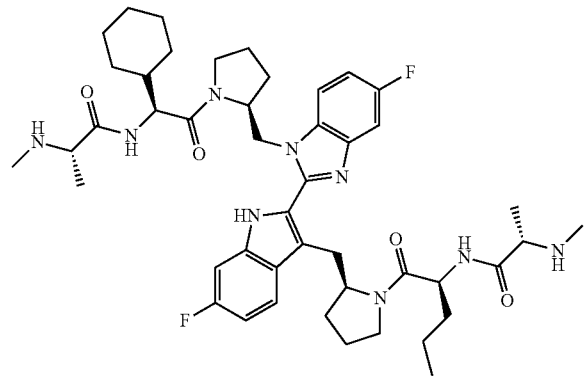

¹HNMR (MeOD, 400 MHz): δ 12.41 (s, 1H), 8.91 (d, J=6.8 Hz, 1H), 8.65 (d, J=7.6 Hz, 1H), 8.20 (dd, J=3.8, 9.0 Hz, 1H), 7.98-7.85 (m, 2H), 7.57-7.45 (m, 2H), 7.09 (dt, J=1.8, 9.1 Hz, 1H), 4.84 (dd, J=8.3, 14.8 Hz, 2H), 4.74-4.68 (m, 1H), 4.54-4.42 (m, 2H), 4.30 (brs, 1H), 4.05-3.93 (m, 2H), 3.90-3.73 (m, 4H), 3.49 (d, J=13.3 Hz, 1H), 3.19 (dd, J=11.2, 13.7 Hz, 1H), 2.73-2.61 (m, 6H), 2.41-2.16 (m, 2H), 2.06-1.67 (m, 12H), 1.60-1.36 (m, 10H), 1.20 (br.s, 3H), 1.11-0.97 (m, 5H).

MS (ESI) m/z: 844.5 [M+H⁺]

Embodiment 10

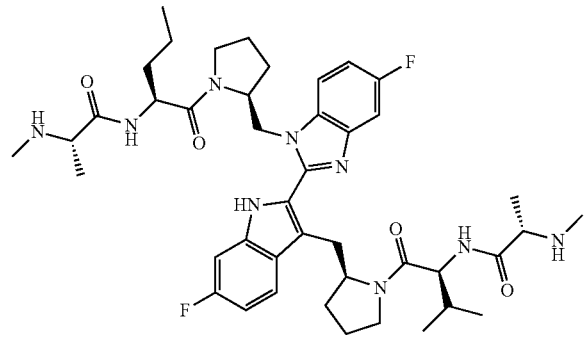

¹HMNR (MeOD, 400 MHz): δ8.16 (dd, J=3.8, 9.1 Hz, 1H), 8.01-7.87 (m, 2H), 7.56-7.40 (m, 2H), 7.09 (dt, J=2.0, 9.2 Hz, 1H), 4.88 (d, J=7.0 Hz, 2H), 4.55 (d, J=8.0 Hz, 1H), 4.47 (d, J=7.2 Hz, 2H), 4.31 (brs, 1H), 4.05 (q, J=6.9 Hz, 1H), 3.97-3.88 (m, 1H), 3.87-3.81 (m, 1H), 3.78-3.69 (m, 2H), 3.55 (d, J=13.3 Hz, 1H), 3.17 (dd, J=11.1, 14.0 Hz, 1H), 2.75-2.62 (m, 6H), 2.39-2.17 (m, 3H), 2.02 (d, J=3.0 Hz, 2H), 1.93-1.78 (m, 4H), 1.58-1.45 (m, 6H), 1.35-1.19 (m, 4H), 1.16-1.00 (m, 6H), 0.90 (t, J=6.4 Hz, 3H).

MS (ESI) m/z: 804.2 [M+H⁺]

Embodiment 11

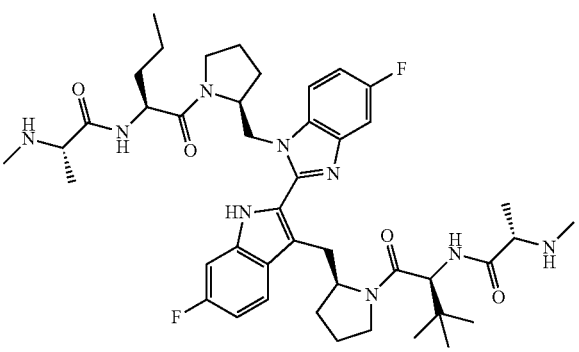

¹HNMR (MeOD, 400 MHz): δ8.73-8.54 (m, 1H), 8.15 (dd, J=3.8, 9.0 Hz, 1H), 8.01-7.88 (m, 2H), 7.60-7.42 (m, 2H), 7.09 (dt, J=2.0, 9.2 Hz, 1H), 4.74-4.70 (m, 1H), 4.47 (brs, 2H), 4.30 (brs, 1H), 4.15-4.06 (m, 1H), 3.96-3.85 (m, 3H), 3.80-3.68 (m, 2H), 3.54 (d, J=13.8 Hz, 1H), 3.18 (dd, J=11.3, 13.9 Hz, 1H), 2.73-2.63 (m, 6H), 2.30 (d, J=5.4 Hz, 2H), 2.16-1.66 (m, 7H), 1.56-1.46 (m, 6H), 1.34-1.22 (m, 4H), 1.17 (s, 9H), 1.03-0.82 (m, 4H).

MS (ESI) m/z: 818.3 [M+H⁺]

Embodiment 12

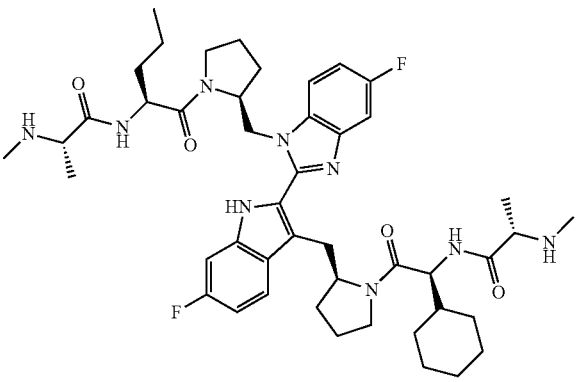

¹HNMR (MeOD, 400 MHz): δ8.81 (d, J=7.5 Hz, 1H), 8.67 (d, J=7.2 Hz, 1H), 8.16 (dd, J=3.7, 8.8 Hz, 1H), 7.96 (dd, J=5.1, 8.8 Hz, 1H), 7.92-7.85 (m, 1H), 7.58-7.43 (m, 2H), 7.09 (dt, J=1.9, 9.1 Hz, 1H), 4.62-4.46 (m, 3H), 4.30 (brs, 1H), 4.05-3.71 (m, 6H), 3.55 (d, J=13.7 Hz, 1H), 3.21-3.11 (m, 1H), 2.67 (d, J=14.6 Hz, 6H), 2.28 (brs, 2H), 2.06-1.59 (m, 13H), 1.58-1.46 (m, 6H), 1.44-1.13 (m, 10H), 0.97-0.85 (m, 3H).

MS (ESI) m/z: 844.3 [M+H⁺]

Embodiment 13

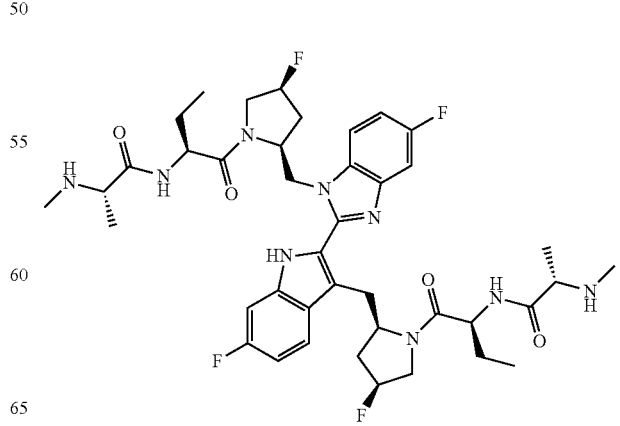

Reaction Process: Preparation of Intermediates 13-7

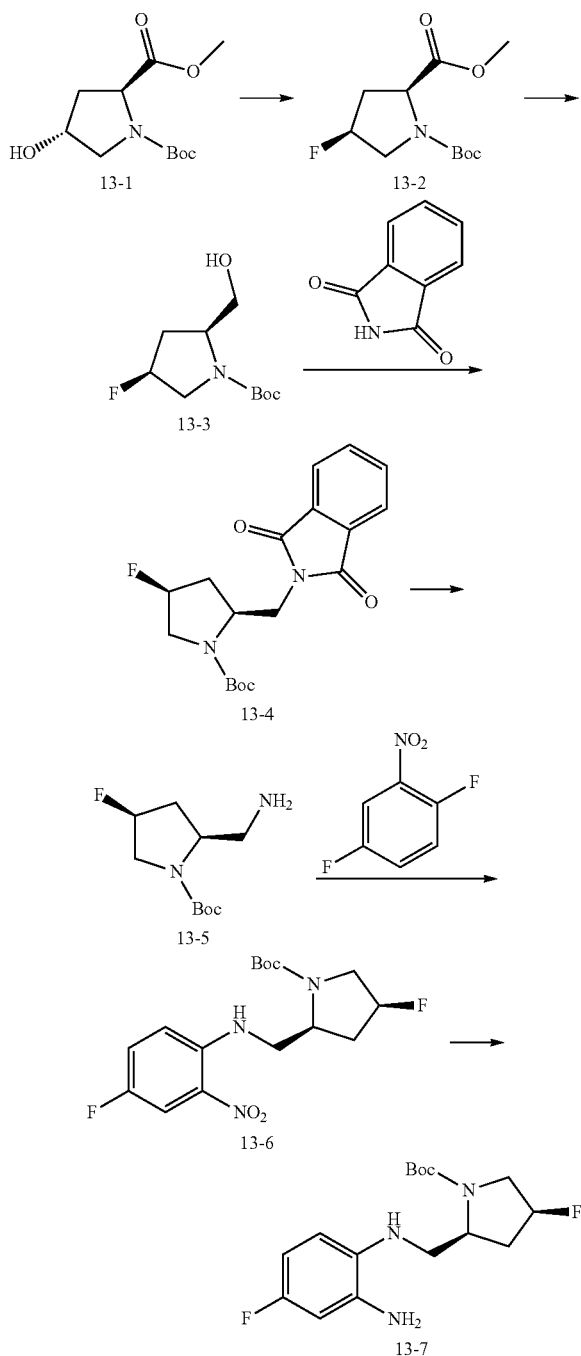

Step A: To a stirring solution of N-Boc-trans-4-hydroxyl-L-methylprolinate (262.00 g, 1.07 mol) in dichloromethane (2.5 L) was added DAST dropwise (258.28 g, 1.60 mol) at −78° C. under atmosphere of $N_2$. After stirring for 3 h at −78° C., the mixture was warmed to 10-20° C. and stirred for another 15 h. The mixture was poured into 0° C. sat.aq. $NaHCO_3$ (3 L)solution and quenched, and then extracted with dichloromethane twice (6 L). The organic phase was washed with sat.aq. NaCl (3 L), dried over $Na_2SO_4$, filtered and concentrated in vacuo to give crude product. The crude product was purified by flash column chromatography eluted with Pet. Ether/EtOAc (50/1 to 10/1) to give N-Boc-cis-4-fluor-L-methylprolinate (53.00 g, 214.35 mmol, 20.07%).

$^1$HNMR (CDCl3, 400 MHz): δ 5.30-5.11 (m, 1H), 4.58-4.39 (m, 1H), 3.94-3.55 (m, 5H), 2.56-2.24(m,2H), 1.53-1.40 (m, 9H).

Step B: To a solution of N-Boc-cis-4-fluoro-L-methylprolinate (80.00 g, 323.55 mmol) in THF (1 L) was added $LiBH_4$ (16.00 g, 734.62 mmol) in batch at 0-5° C. After stirring for 16 h at 10-20° C., the mixture was quenched with sat.aq. $NaHCO_3$ (1500 mL) solution, and then was extracted with EtOAc twice (3000 mL). The combined organic phase was concentrated in vacuo to give crude product. The crude product was dissolved in dichloromethane (500 mL) and washed with sat.aq. NaCl (500 mL), dried over anhydrous $Na_2SO_4$, filtered and the filtrate was concentrated in vacuo to give N-Boc-cis-4-fluor-L-prolinol (66.00 g, crude product).

$^1$HNMR (CDCl3, 400 MHz): δ 5.20-4.98 (m, 1H), 4.18 (brs, 1H), 4.14-4.04 (m, 1H), 3.83-3.74 (m, 1H), 3.69-3.60 (m, 1H), 3.59-3.48 (m, 2H), 2.28-2.07(m,1H), 2.02-1.87 (m, 1H), 1.41 (s, 9H).

Step C: To a solution of N-Boc-cis-4-fluoro-L-prolinol (66.00g, 301.03 mmol, crude product) in THF (700mL) were added phthalimide (46.50 g, 316.08 mmol) and triphenylphosphine (82.90 g, 316.08 mmol) at 10-20° C. Then the mixture was added with DIAD (63.91 g, 316.08 mmol) at 0-10° C. After the mixture was stirred for 16 h at 10-20° C., solvents were removed in vacuo. The residue was added with water (500 mL) and then extracted with dichloromethane twice (1000 mL). The combined organic phase was washed with sat.aq. NaCl, dried over anhydrous $Na_2SO_4$, filtered and concentrated in vacuo to give crude product. The crude product was purified by flash column chromatography eluted with Pet. Ether/EtOAc (10/1 to 5/1) to give tert-butyl (2S,4S)-2-((1,3-dioxoisoindolin-2-yl)methyl)-4-fluoropyrrolidine-1-carboxylate (133.00 g, crude product).

$^1$HNMR (CDCl3, 400 MHz): δ 7.93-7.64 (m, 4H), 4.55-4.31 (m, 1H), 4.10-4.01 (m, 1H), 3.87-3.55 (m, 3H), 2.32-2.07(m,2H), 1.27 (d, J=6.3 Hz, 9H).

MS (ESI) m/z: 249.1 [M+H$^+$-100]

Step D: To a solution of tert-butyl (2S,4S)-2-((1,3-dioxoisoindolin-2-yl)methyl)-4-fluoropyrrolidine-1-carboxylate (133.00 g, 381.78 mmol, crude product) in ethanol (1 L) was added hydrazine hydrate (48.75 g, 954.44 mmol). After reacting for 2 h at 60° C., the mixture was diluted with dichloromethane (1 L), filtered, and filter cake was washed with dichloromethane. The combined organic phase was concentrated in vacuo to give residue. The residue was dulited with dichloromethane (200 mL), filtered, and filter cake was washed with dichloromethane. The combined organic phase was concentrated in vacuo to give tert-butyl (2S,4S)-2-(aminomethyl)-4-fluoropyrrolidine-1-carboxylate (112.00 g, crude product).

$^1$HNMR (CDCl3, 400 MHz): δ 5.27-5.08 (m, 1H), 3.95-3.77 (m, 1H), 3.59 (d, J=10.6 Hz, 1H), 2.98 (brs, 1H), 2.73 (dd, J=7.8, 12.2 Hz, 1H), 2.55-2.41(m,2H), 2.19 (brs, 1H), 1.45 (s, 9H).

Step E: To a solution of tert-butyl (2S,4S)-2-(aminomethyl)-4-fluoropyrrolidine-1-carboxylate (66.00 g, crude product) in acetonitrile (1 L) were added 1,4-difluoro-2-nitrobenzene (45.70 g, 287.26 mmol) and potassium carbonate (3.85 g, 604.76 mmol) at 10-20° C. After reacting for 2 h at 80° C., the mixture was cooled to 10-20° C., filtered and then concentrated in vacuo to give crude product. The crude product was dissolved in methyl tert-butyl ether(500 mL), and stirred for 16 h. The yellow solid was precipitated and then filtered, the filter cake was dried over to give tert-butyl (2S,4S)-4-fluoro-2-(((4-fluoro-2-nitrophenyl)amino)methyl)pyrrolidine-1-carboxylate (68.00 g, 190.29 mmol, 62.93%).

¹HNMR (CDCl3, 400 MHz): δ 8.35-8.11(m, 1H), 7.89 (d, J=9.0 Hz, 1H), 7.35-7.16 (m, 2H), 5.40-5.17 (m, 1H), 4.33-4.16 (m, 1H), 3.88-3.52 (m, 3H), 3.45-3.30 (m, 1H), 2.37-2.06 (m, 2H), 1.59-1.48 (m, 9H).

MS (ESI) m/z: 380.1 [M+Na]

Step F: To a solution of tert-butyl (2S,4S)-4-fluoro-2-(((4-fluoro-2-nitrophenyl)amino)methyl)pyrrolidine-1-carboxylate (20.00 g, 55.97 mmol) in methanol (200 mL) and EtOAc (1 L) was added Pd/C (10%, 2 g) at the atmosphere of N₂ and the mixture was charged with H₂ for 3 times. The mixture was stirred for 4 h at 25-30° C. under the atmosphere of 40 psi H₂. The mixture was filtered and the filtrate was concentrated in vacuo to give tert-butyl (2S,4S)-2-(((2-amino-4-fluorophenyl)amino)methyl)-4-fluoropyrrolidine-1-carboxylate (18.00 g, 53.33 mmol, 95.29%).

MS (ESI) m/z: 328.1 [M+H⁺]

¹HNMR (CDCl3, 400 MHz): δ 6.48 (brs, 2H), 6.41-6.30 (m, 2H), 5.27-5.05 (m, 1H), 4.35-4.21 (m, 1H), 3.72-3.27 (m, 5H), 3.10 (dd, J=6.5, 12.0 Hz, 1H), 2.31-2.01 (m, 2H), 1.41 (brs, 9H).

Reaction Process: Preparation of Intermediates 13-14

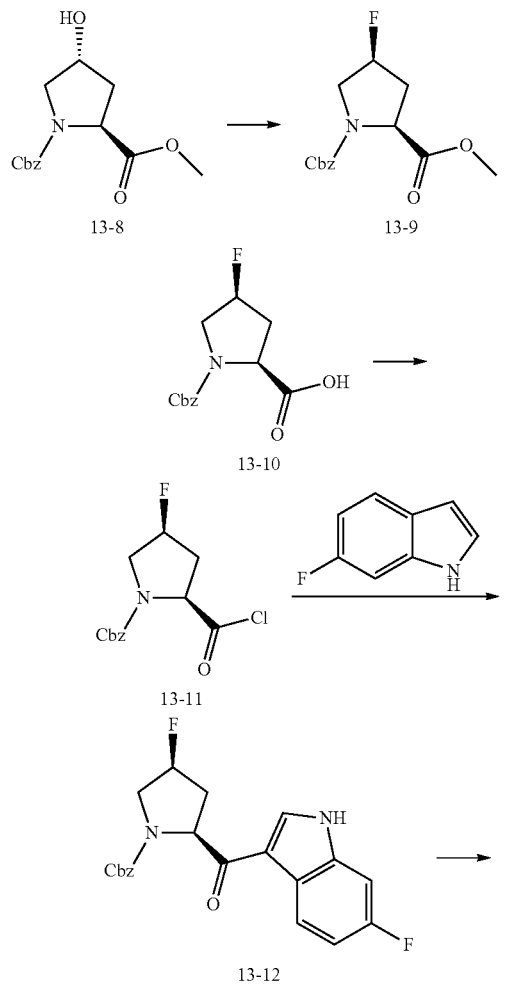

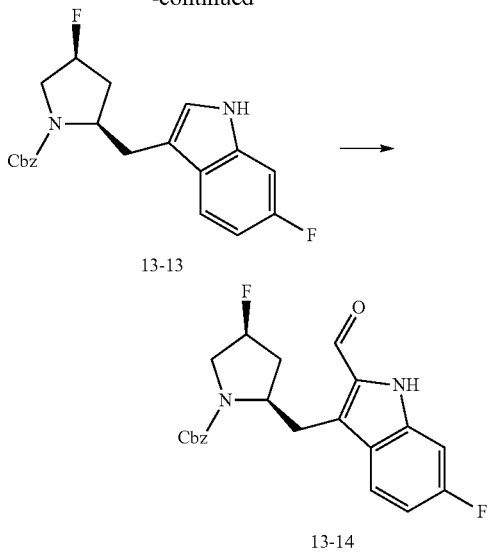

Step A: To a stirring solution of N-Cbz-trans-4-hydroxyl-L-methylprolinate (21.00 g, 57.14 mmol) in anhydrous dichloromethane (90 mL) was added DAST dropwise (21.65 g, 134.29 mmol) at −78° C. under N₂. After stirring for 3 h at −78° C., the mixture was warmed to room temperature (25° C.) and stirred for another 15 h. The mixture was quenched with sat.aq. NaHCO₃ (600 mL) at 0° C., and then was extracted with dichloromethane twice (600 mL×2). The organic phase was washed with sat.aq. NaCl (600 mL×1), dried over anhydrous Na₂SO₄, filtered and the filtrate was concentrated in vacuo at 45° C. The residue was purified by flash column chromatography eluted with Pet. Ether/EtOAc (1/0 to 4/1) to give N-carboxybenzyl-cis-4-fluor-L-methylprolinate (14.00 g, 85.80%).

¹HNMR (CDCl3, 400 MHz): δ 7.43-7.27 (m, 5H), 5.31-5.07 (m, 3H), 4.65-4.51 (m, 1H), 3.97-3.62 (m, 5H), 2.51 (d, J=18.4 Hz, 2H).

Step B: N-Cbz-cis-4-fluor-L-methylprolinate (14.00 g, 49.03 mmol) was dissolved in THF (70.00 mL), LiOH solution (1 mol/L, 69.13 mL) was added at 25° C. and the mixture was stirred for 14 h at the same temperature. The mixture was adjusted pH to 3 with hydrochloric acid solution (1 mol/L), added with water (200 mL) and extracted with EtOAc (200 mL×4). The organic phase was dried over anhydrous Na₂SO₄, filtered and the filtrate was concentrated at 45° C. in vacuo to give N-Cbz-cis-4-fluor-L-proline (13.00 g, 97.53%).

¹HNMR (CDCl3, 400 MHz): δ 13.33-12.02 (m, 1H), 7.49-7.12 (m, 5H), 5.43-5.19 (m, 1H), 5.17-5.00 (m, 2H), 4.56-4.31 (m, 1H), 3.85-3.50 (m, 2H), 2.49-2.20 (m, 2H).

Step C: To a solution of N-Cbz-cis-4-fluoro-L-proline (5.00 g, 18.39 mmol) in toluene (25.00 mL) were added DMF (13.44 mg, 183.91 μmol, 14.15 μL) and oxalyl chloride (2.80 g, 22.07 mmol, 1.93 mL) at 25° C. After stirring for 1 h at the same temperature, the mixture was concentrated at 45° C. in vacuo to give N-Cbz-cis-4-fluoro-L-proline chloride (5.30 g, crude product) as yellow oil, which was used for next step directly.

Step D: To a solution of 6-fluoro-1H-indole (5.01 g, 37.10 mmol) in toluene (60.00 mL) was added ethylmagnesium bromide (3 mol/L, 12.55 mL) dropwise in ice/acetone bath (−4° C.) under N₂. After stirring for 1 h at −4° C., a solution of N-Cbz-cis-4-fluoro-L-proline chloride (5.30 g, crude product) in toluene was added to the mixture dropwise. After stirring for another 2 h at −4° C., the mixture was warmed to 25° C. and stirred for 14 h. The mixture was quenched with acetic acid (1 mL), and diluted with EtOAc (300 mL) and water (300 mL). The organic phase was separated, washed with sat.aq NaCl (200 mL×2), dried over $Na_2SO_4$, filtered and the filtrate was concentrated at 45° C. in vacuo. The residue was purified by flash column chromatography eluted with Pet. Ether/EtOAc (1/0 to 1/1) to give benzyl (2S,4S)-4-fluoro-2-(6-fluoro-1H-indole-3-carbonyl)pyrrolidine-1-carboxylate (4.40 g, 11.45 mmol, 61.71%).

$^1$HNMR (DMSO, 400 MHz): δ 12.17-12.01 (m, 1H), 8.56-8.31 (m, 1H), 8.23-8.06 (m, 1H), 7.46-6.98 (m, 7H), 5.45-5.21 (m, 2H), 5.16-4.93 (m, 2H), 3.96-3.64 (m, 2H), 2.90-2.60 (m, 1H), 2.42-2.20 (m, 1H).

Step E: To a solution of benzyl (2S,4S)-4-fluoro-2-(6-fluoro-1H-indole-3-carbonyl)pyrrolidine-1-carboxylate (4.40 g, 11.45 mmol) in THF (44.00 mL) was added $LiBH_4$ (2 mol/L, 11.45 mL) dropwise at 25° C. (in 20 min). The mixture was stirred for 16 min at 25° C., and then was added methylsulphonic acid (2.04 g, 21.18 mmol, 1.51 mL) dropwise at 0° C., and further stirred for 2 h. Then the mixture was quenched with 200 mL water at 0° C., and extracted with EtOAc (200 mL×2). The combined organic phase was concentrated at 45° C. in vacuo. The residue was purified by flash column chromatography eluted with Pet. Ether/EtOAc (3/1 to 1/1) to give benzyl (2R,4S)-4-fluoro-2-((6-fluoro-1H-indol-3-yl)methyl)pyrrolidine-1-carboxylate (2.00 g, 4.64 mmol, 40.56%).

$^1$HNMR (DMSO, 400 MHz): δ 11.05-10.81 (m, 1H), 7.75-6.50 (m, 9H), 5.16 (s, 3H), 4.21-4.00 (m, 1H), 3.81-3.57 (m, 2H), 3.18 (d, J=5.3 Hz, 1H), 2.81-2.65 (m, 1H), 2.09 (m, 2H).

Step F: Phosphorus oxychloride(534.02 mg, 3.48 mmol) was added to DMF (254.56 mg, 3.48 mmol)dropwise at 0° C. under $N_2$, and the mixture was stirred for 1 h at 0° C. Then a solution of benzyl (2R,4S)-4-fluoro-2-((6-fluoro-1H-indol-3-yl)methyl)pyrrolidine-1-carboxylate (1.00 mg, 2.32 mmol) in 1,2-dichloroethane (5.00 mL) was added to the mixture dropwise at 0° C. After stirring for 18 h at 25° C., the mixture was poured into sat.aq $Na_2CO_3$ (100 mL) at 0° C. and extracted with EtOAc (150 mL×2). The organic phase was washed with sat.aq NaCl (100 mL×2), dried over $Na_2SO_4$, filtered and the filtrate was concentrated at 45° C. in vacuo to give crude product benzyl (2R,4S)-4-fluoro-2-((6-fluoro-2-formyl-1H-indol-3-yl)methyl)pyrrolidine-1-carboxylate (1.20 g, crude product).

MS ESI 399.0 [M+H$^+$]

Reaction Process: Preparation of Embodiment 13

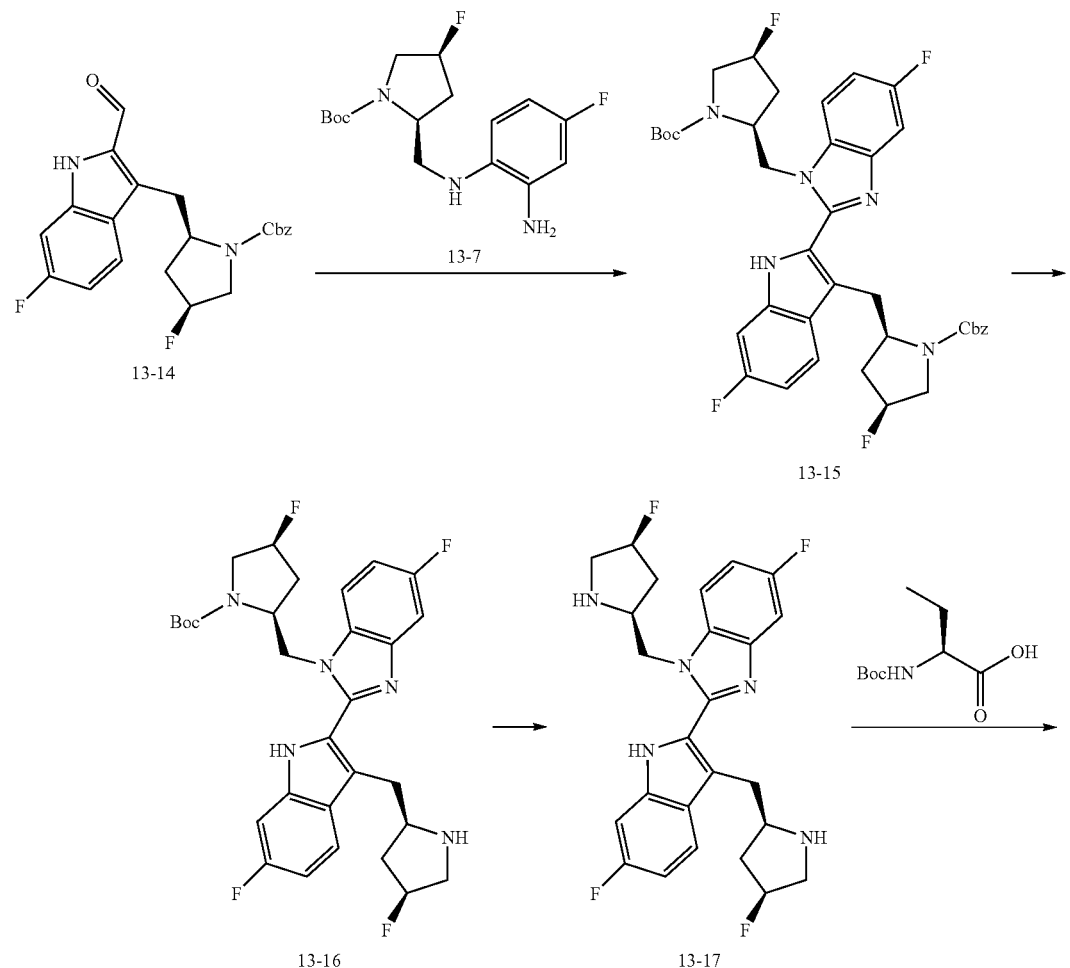

-continued

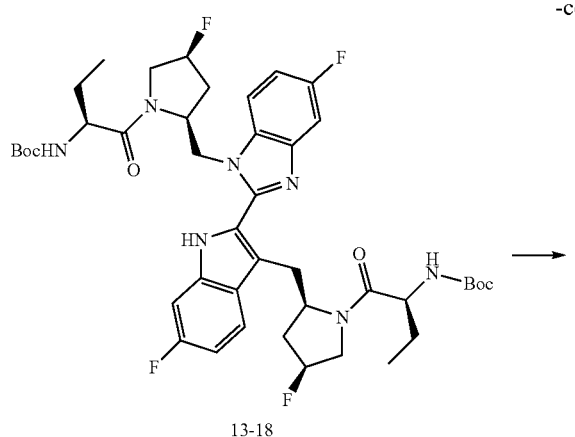

13-18

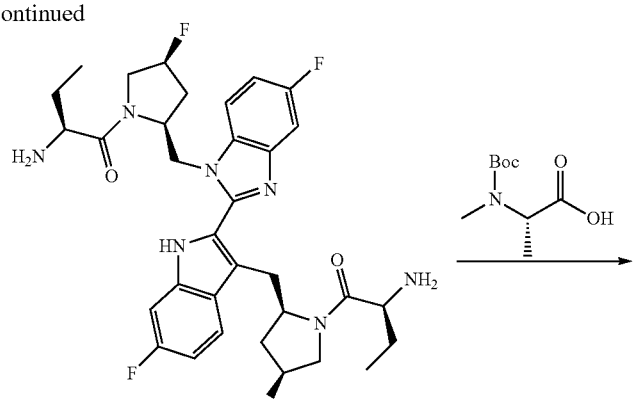

13-19

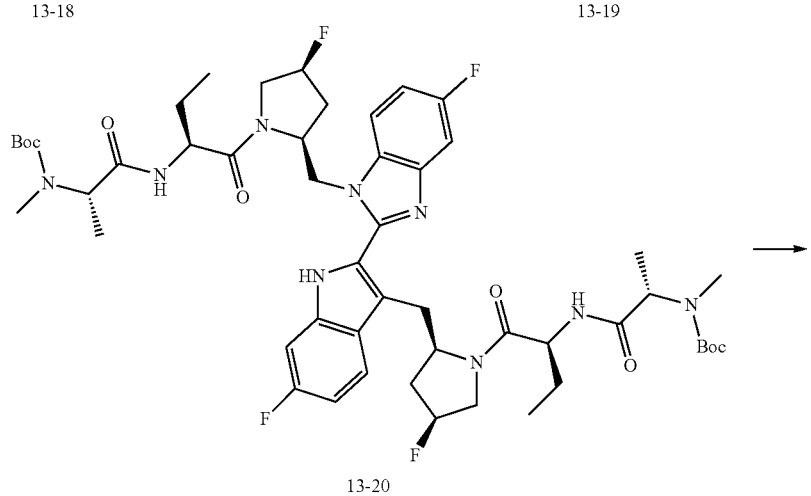

13-20

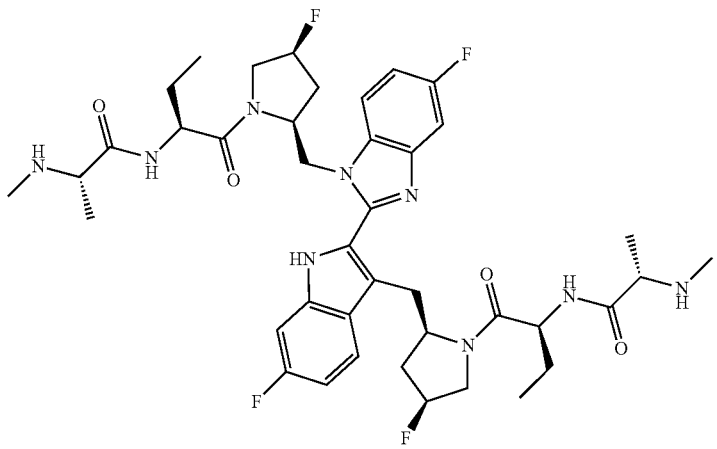

example 13

Step A: Benzyl (2R,4S)-4-fluoro-2-((6-fluoro-2-formyl-1H-indol-3-yl)methyl)pyrrolidine-1-carboxylate (1.00 g, 2.52 mmol) and tert-butyl (2S,4S)-2-(((2-amino-4-fluorophenyl)amino)methyl)-4-fluoropyrrolidine-1-carboxylate (800.00 mg, 2.39 mmol) were dissolved in DMF (12.00 mL) and water (1.00 mL), the mixture was added with Oxone (1.09 g, 7.18 mmol) one-time at 25° C. After stirring for 1 h at the same temperature, the mixture was diluted with sat.aq Na$_2$SO$_3$ (300 mL) and EtOAc (300 mL). The organic phase was separated, washed with aq. NaCl (200 mL×3), dried over anhydrous Na$_2$SO$_4$, filtered and the filtrate was concentrated at 45° C. in vacuo. The residue was purified by flash column chromatography eluted with Pet. Ether/EtOAc (1/0 to 3/1) to give benzyl (2R,4S)-2-((2-(1-(((2S,4S)-1-(tert-butoxycarbonyl)-4-fluoropyrrolidin-2-yl)methyl)-5-fluoro-1H-benzo[d]imidazol-2-yl)-6-fluoro-1H-indol-3-yl)methyl)-4-fluoropyrrolidine-1-carboxylate (1.40 g, 1.69 mmol, 70.55%) as a brown solid.

$^1$HNMR (DMSO, 400 MHz): δ 11.89-11.22 (m, 1H), 8.15-6.01 (m, 1H), 5.12 (brs, 4H), 4.71-4.43 (m, 1H), 4.40-4.09 (m, 3H), 3.76-3.38 (m, 4H), 3.03-2.63 (m, 4H), 1.94-1.68 (m, 2H), 1.62-1.19 (m, 9H).

Step B: Benzyl (2R,4S)-2-((2-(1-(((2S,4S)-1-(tert-butoxycarbonyl)-4-fluoropyrrolidin-2-yl)methyl)-5-fluoro- 1H-benzo[d]imidazol-2-yl)-6-fluoro-1H-indol-3-yl) methyl)-4-fluoropyrrolidine-1-carboxylate (1.40 g, 1.69 mmol) was dissolved in EtOAc (50.00 mL) and methanol (10.00 mL), Pd/C (200 mg, 10%) was added one-time under $N_2$ at 25° C. The suspensionwas degassed in vacuo, and then charged with $H_2$ for couple times and stirred for 6 h at 25° C. and an atmosphere of 40 psi $H_2$. The mixture was filtered with kieselguhr, washed with methanol (about 200 mL) and the filtrate was concentrated in vacuo to give tert-butyl (2S,4S)-4-fluoro-2-((5-fluoro-2-(6-fluoro-3-(((2R,4S)-4-fluoropyrrolidin-2-yl)methyl)-1H-indol-2-yl)-1H-benzo[d]imidazol-1-yl)methyl)pyrrolidine-1-carboxylate (900 mg, 1.42 mmol, 84.21%).

MS (ESI) m/z: 572.4 [M+H$^+$]

Step C: Tert-butyl (2S,4S)-4-fluoro-2-((5-fluoro-2-(6-fluoro-3-(((2R,4S)-4-fluoropyrrolidin-2-yl)methyl)-1H-indol-2-yl)-1H-benzo[d]imidazol-1-yl)methyppyrrolidine-1-carboxylate (200.00 mg, 314.90 μmol) was dissolved in dioxane (4.00 mL), the mixture was added with HCl/dioxane solution (4 mol/L, 3.60 mL) at 25° C. and stirred for 0.5 h at the same temperature. The mixture was concentrated in vacuo to remove solvent and give 5-fluoro-2-(6-fluoro-3-(((2R,4S)-4-fluoropyrrolidin-2-yl)methyl)-1H-indol-2-yl)-1-(((2S,4S)-4-fluoropyrrolidin-2-yl)methyl)-1H-benzo[d]imidazole (175.00 mg, 314.06 μmol, 99.73%, hydrochloride).

MS (ESI) m/z: 472.3 [M+H$^+$]

Step D: To a stirring solution of N-Boc-L-butyric acid (158.65 mg, 780.65 μmol) in DMF (3.00 mL) were added N-methylmorpholine (126.34 mg, 1.25 mmol, 137.33 μL) and HATU (124.67 mg, 327.87 μmol) and the mixture was stirred for 30 min at 25° C. Then the mixture was added with 5-fluoro-2-(6-fluoro-3-(((2R,4S)-4-fluoropyrrolidin-2-yl)methyl)-1H-indol-2-yl)-1-(((2S,4S)-4-fluoropyrrolidin-2-yl)methyl)-1H-benzo[d]imidazole (85.25 mg, 156.13 hydrochloride) and the mixture was stirred for further 30 min at 25° C., diluted with EtOAc (100 mL) and water (100 mL). The organic phase was separated, washed with aq. NaCl and concentrated in vacuo. The residue was purified by flash column chromatography eluted with Pet. Ether/EtOAc (1/1) to give tert-butyl-N-[(1S)-1-[(2R,4S)-2-[[2-[1-(((2S,4S)-1-[(2S)-2-((tert-butoxycarbonyl)amino)butanoyl]-4-fluoro-pyrrolidin-2-yl)methyl)-5-fluoro-benzimidazole-2-yl)-6-fluoro-1H-indol-3-yl)methyl)-4-fluoropyrrolidin-1-oxo)butyl)carbamate (110.00 mg, 127.65 81.76%).

MS (ESI) m/z: 842.1 [M+H$^+$]

Step E: To a solution of tert-butyl-N-[(1S)-1-[(2R,4S)-2-[[2-[1-(((2S,4S)-1-[(2S)-2-((tert-butoxycarbonyl)amino)butanoyl]-4-fluoro-pyrrolidin-2-yl)methyl)-5-fluoro-benzimidazole-2-yl)-6-fluoro-1H-indol-3-yl)methyl)-4-fluoropyrrolidin-1-oxo)butyl)carbamate (110.00 mg, 127.65 μmol) in dioxane (1.00 mL) was added HCl/dioxane (4 mol/L, 1 mL) dropwise at 25° C. After stirring for 30 min at 25° C., the mixture was concentrated in vacuo at 45° C. to give (S)-2-amino-1-((2R,4S)-2-((2-(1-(((2S,4S)-1-((S)-2-aminobutanoyl)-4-fluoropyrrolidin-2-yl)methyl)-5-fluoro-1H-benzo[d]imidazol-2-yl)-6-fluoro-1H-indol-3-yl)methyl)-4-fluoropyrrolidin-1-yl) butan-1-one (95.00 mg, 116.32 mmol, 91.12%, hydrochloride) as light yellow solid.

Step F: To a stirring solution of N-Boc-N-methyl-L-alanine (69.46 mg, 341.79 μmol) in DMF (2.00 mL) were added NMM (92.19 mg, 911.44 μmol, 100.21 μL) and HATU (134.29 mg, 353.18 μmol), the mixture was stirred for 30 min at 25 C. and then a solution of (S)-2-amino-1-((2R,4S)-2-((2-(1-(((2S,4S)-1-((S)-2-aminobutanoyl)-4-fluoropyrrolidin-2-yl)methyl)-5-fluoro-1H-benzo[d]imidazol-2-yl)-6-fluoro-1H-indol-3-yl)methyl)-4-fluoropyrrolidin-1-yl) butan-1-one (93.05 mg, 113.93 μmol) in DMF (2.00 mL) was added to the mixture. After stirred for 1 h at 25° C., the mixture was diluted with EtOAc (100 mL) and water (100 mL). The organic phase was separated, washed with aq. NaCl (100 mL×3) and concentrated at 45° C. in vacuo. The residue was purified by flash column chromatography eluted with Pet. Ether/EtOAc (1/1) to give tert-butyl ((S)-1-(((S)-1-((2R,4S)-2-((2-(1-(((2S,4S)-1-((S)-2-((S)-2-((tert-butoxycarbonyl)(methyl)amino) propanamido)butanoyl)-4-fluoropyrrolidin-2-yl)methyl)-5-fluoro-1H-benzo[d]imidazol-2-yl)-6-fluoro-1H-indol-3-yl)methyl)-4-fluoropyrrolidin-1-yl)-1-oxobutan-2-yl)amino)-1-oxopropan-2-yl) (methyl)carbamate (90.00 mg, 79.14 μmol, 69.46%) as yellow oil.

MS (ESI) m/z: 1012.2 [M+H$^+$]

Step G: To a solution of tert-butyl ((S)-1-(((S)-1-((2R,4S)-2-((2-(1-(((2S,4S)-1-((S)-2-((S)-2-((tert-butoxycarbonyl)(methyl)amino) propanamido)butanoyl)-4-fluoropyrrolidin-2-yl)methyl)-5-fluoro-1H-benzo[d]imidazol-2-yl)-6-fluoro-1H-indol-3-yl)methyl)-4-fluoropyrrolidin-1-yl)-1-oxobutan-2-yl)amino)-1-oxopropan-2-yl) (methyl) carbamate (90.00 mg, 79.14 μmol) in dichloromethane (1.00 mL) was added trifluoroacetic acid (1.54 g, 13.51 mmol, 1.00 mL) at 25° C. After stirring for 0.5 h at 25° C., the mixture was concentrated in vacuo. The residue was purified by prep HPLC to give embodiment 13 (40.00 mg, 48.77 61.63%).

$^1$HNMR (DMSO, 400 MHz): δ 8.99-8.81 (m, 2H), 8.75-8.51 (m, 1H), 8.14-8.04 (m, 1H), 7.93 (dd, J=4.0,8.0 Hz, 1H), 7.81 (dd, J=4.0,8.0 Hz, 1H), 7.54 (td, J=4.0,8.0 Hz, 1H), 7.43 (dd, J=4.0, 8.0 Hz, 1H), 7.10 (td, J=4.0, 8.0 Hz, 1H), 5.56-5.40 (m, 1H), 5.39-5.28 (m, 1H), 4.99-4.92 (m, 1H), 4.83-4.76 (m, 1H), 4.47-4.60 (m, 1H), 4.58-4.45 (m, 2H), 4.42-4.25 (m, 1H), 4.23-3.75 (m, 6H), 3.68-3.50 (m, 1H), 3.32-3.08 (m, 1H), 2.72-2.55 (m, 6H), 2.27-1.98 (m, 4H), 1.98-1.75 (m, 2H), 1.53 (dd, J=7.0, 13.6 Hz, 7H), 1.42-1.28 (m, 1H), 1.10 (t, J=7.3 Hz, 3H), 0.96-0.76 (m, 3H).

MS (ESI) m/z: 812.5 [M+H$^+$]

Process for preparing embodiment 14-17 can refer to the process for preparing embodiment 13.

Embodiment 14

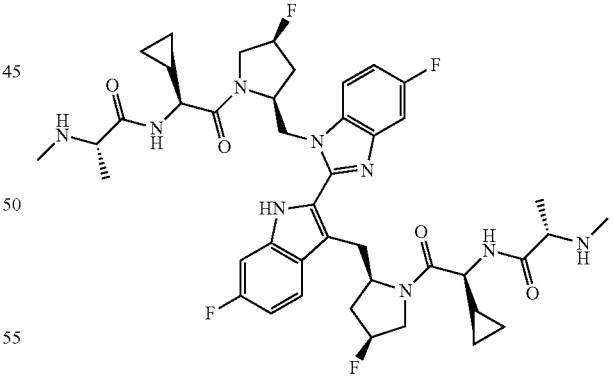

$^1$HNMR (MeOD, 400 MHz): δ 8.10 (dd, J=4.0, 12.0 Hz, 1H), 7.93 (dd, J=4.0, 12.0 Hz, 1H), 7.82 (dd, J=4.0, 12.0 Hz, 1H), 7.56 (td, J=4.0, 8.0 Hz, 1H), 7.43 (dd, J=4.0, 12.0 Hz, 1H), 7.11 (dt, J=2.0, 8.0 Hz, 1H), 5.47 (d, J=12.0 Hz, 1H), 5.33 (d, J=12.0 Hz, 1H), 4.91-4.77 (m, 2H),4.73-4.58 (m, 1H),4.52-4.46 (m, 1H),4.28-3.73 (m, 8H),3.70-3.59 (m, 1H), 3.27-3.13 (m, 1H), 2.66 (d, J=16.0 Hz, 6H), 2.24-1.88 (m, 4H), 1.59-1.39 (m, 6H), 1.38-1.25 (m, 1H), 0.93-0.79 (m, 1H), 0.77-0.12 (m, 4H).

MS (ESI) m/z: 836.4 [M+H$^+$]

Embodiment 15

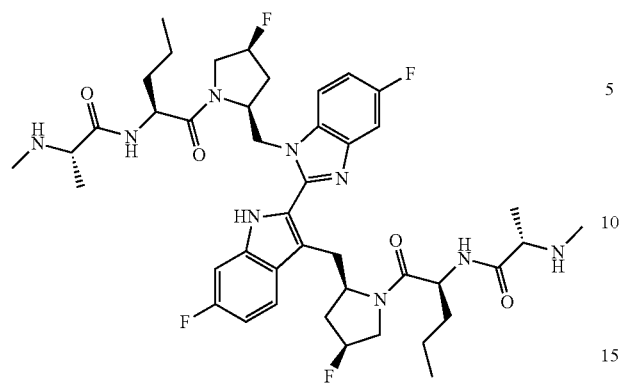

¹HNMR (MeOD, 400 MHz): δ 8.84 (d, J=8.0 Hz, 1H), 8.68 (d, J=8.0 Hz, 1H), 8.05 (dd, J =4.0, 8.0 Hz, 1H), 7.94 (dd, J=4.0, 8.0 Hz, 1H), 7.80 (dd, J=4.0, 8.0 Hz, 1H), 7.55 (dt, J=2.4, 8.0 Hz, 1H), 7.42 (dd, J=2.0, 8.0 Hz, 1H), 7.11 (dt, J=2.0, 8.0 Hz, 1H), 5.57-5.28 (m, 2H), 4.82-4.64 (m, 3H), 4.60-4.47 (m, 2H), 4.43-4.35 (m, 1H), 4.22-3.85 (m, 6H), 3.63 (dd, J=4.0, 16.0 Hz, 1H), 3.21-3.11 (m, 1H), 2.71-2.62 (m, 6H), 2.25-1.90 (m, 5H), 1.83-1.66 (m, 2H), 1.52 (dd, J=4.0, 16.0 Hz, 6H), 1.38-1.16 (m, 5H), 1.03 (t, J=8.0 Hz, 3H), 0.93-0.89 (m, 3H).
MS (ESI) m/z: 840.3 [M+H⁺]

Embodiment 16

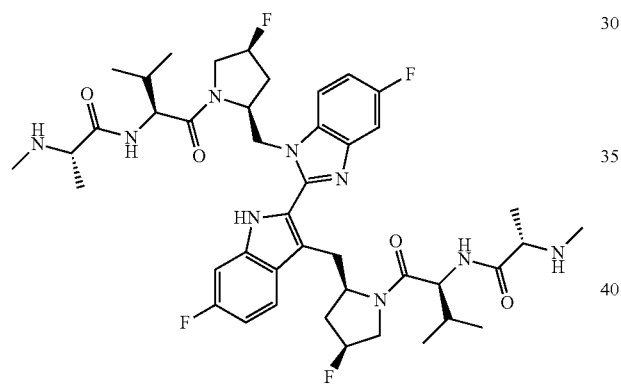

¹HNMR (MeOD, 400 MHz): δ 9.01-8.78 (m, 1H), 8.74-8.54 (m, 1H), 8.14-8.11 (m, 1H), 8.06-7.78 (m, 2H), 7.57-7.52 (m, 1H), 7.45 (d, J=8.0 Hz, 1H), 7.12-7.08 (m, 1H), 5.56-5.42 (m, 1H), 5.18-4.95 (m, 3H), 4.79-4.64 (m, 1H), 4.61-4.27 (m, 3H),4.27-3.84 (m, 6H),3.70-3.50 (m, 1H),2.67 (d, J=16.0 Hz, 6H), 2.32-1.78 (m, 6H), 1.64-1.36 (m, 6H), 1.11 (d, J=4.0, 6H), 0.91 (d, J=4.0 Hz, 6H).
MS (ESI) m/z: 840.5 [M+H⁺]

Embodiment 17

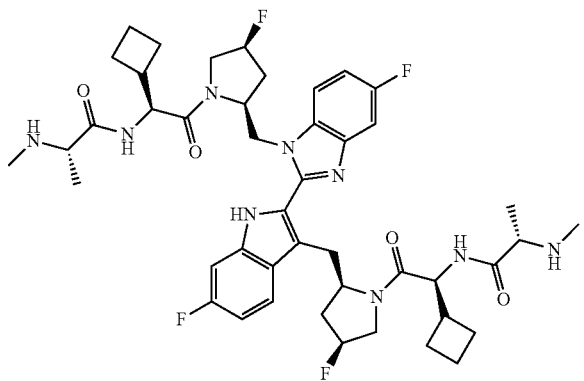

¹HNMR (MeOD, 400 MHz): δ 8.86-8.68 (m, 1H), 8.14 (d, J=4.0 Hz, 1H),7.93 (dd, J=4.0, 8.0 Hz, 1H), 7.86 (d, J=8.0 Hz, 1H), 7.58 (t, J=8.0 Hz, 1H), 7.45 (d, J=8.0 Hz, 1H), 7.13 (t, J =8.0 Hz, 1H), 5.53-5.33 (m, 2H), 4.80-4.60 (m, 4H), 4.58-4.48 (m, 2H),4.26-4.07 (m, 3H),4.06-3.88 (m, 3H), 3.63-3.51 (m, 1H), 2.95-2.79 (m, 1H), 2.69 (d, J=12.0 Hz, 1H), 2.62-2.50 (m, 1H), 1.90 (d, J=4.0 Hz, 16H), 1.52 (dd, J=4.0, 12.0 Hz, 6H).
MS (ESI) m/z: 864.3 [M+H⁺]

Embodiment 18

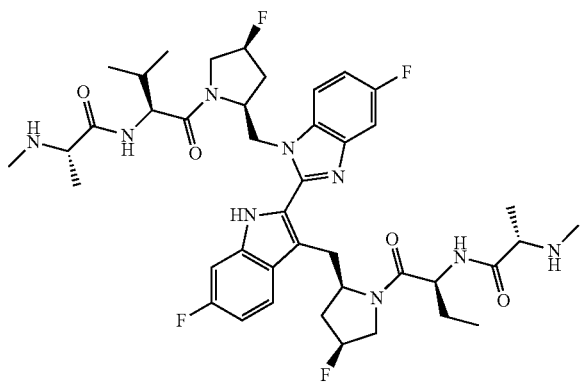

Synthetic process: preparation for embodiment 18

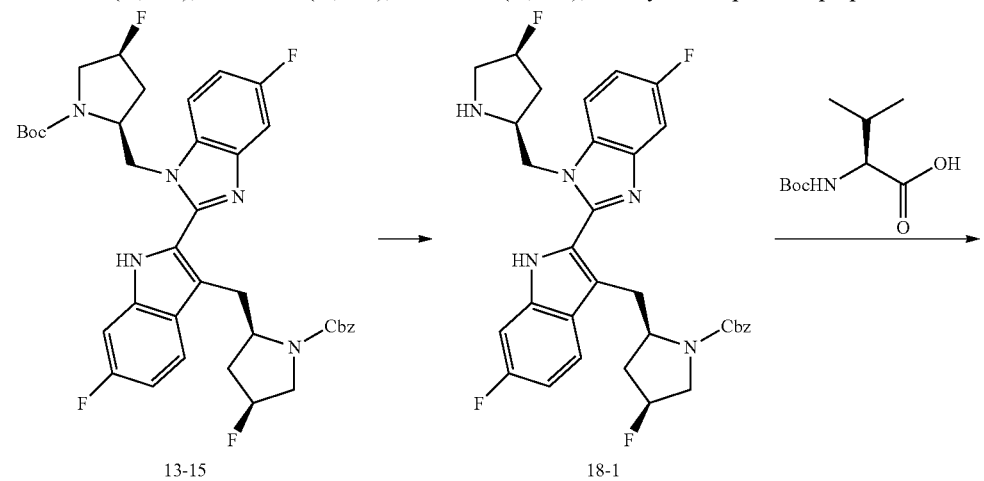

83
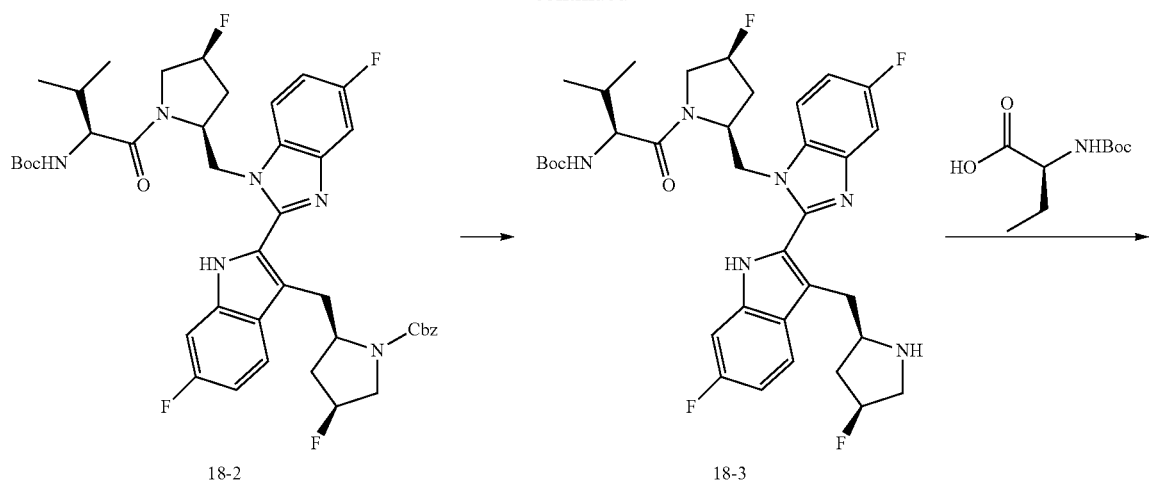
18-2 → 18-3
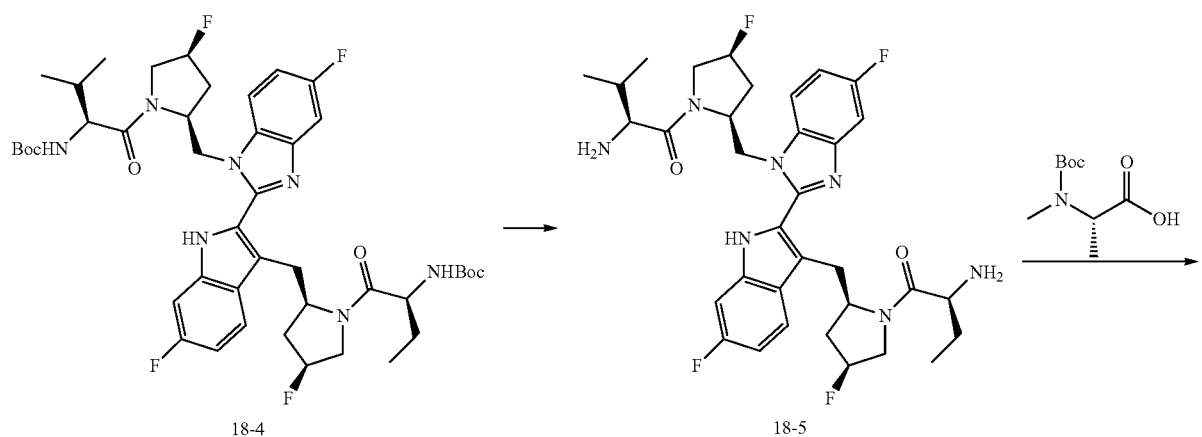
18-4 → 18-5
84
-continued
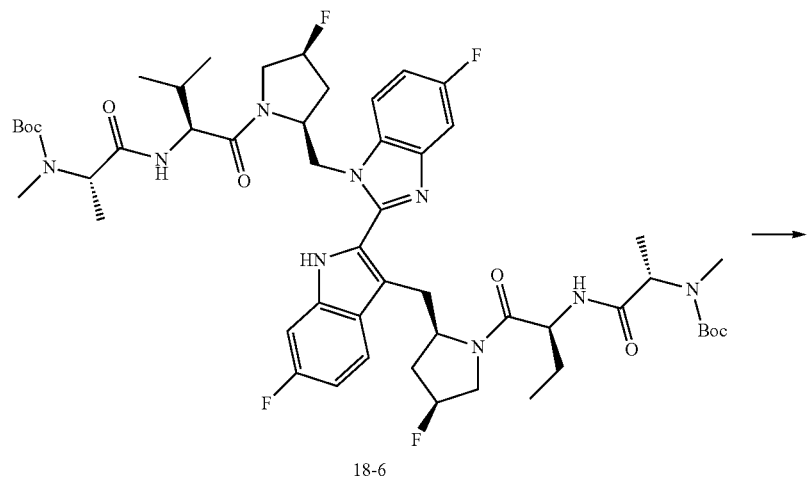
18-6

-continued

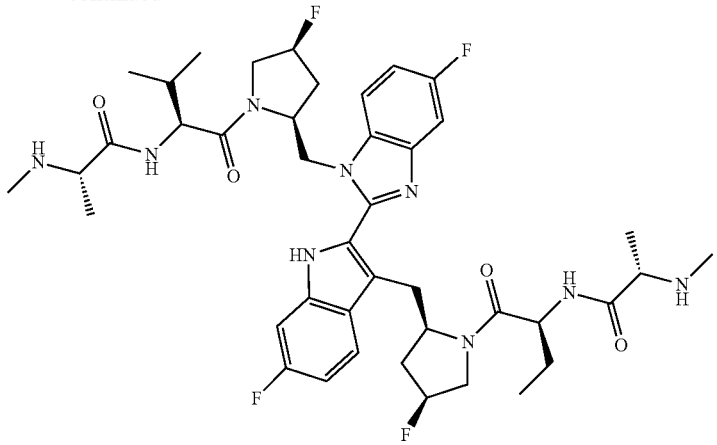

example 18

Step A: To a solution of benzyl (2R,4S)-2-((2-(1-(((2S,4S)-1-(tert-butoxycarbonyl)-4-fluoropyrrolidin-2-yl)methyl)-5-fluoro-1H-benzo[d]imidazol-2-yl)-6-fluoro-1H-indol-3-yl)methyl)-4-fluoropyrrolidine-1-carboxylate (400.00 mg, 510.10 µmol) in EtOAc (1.00 mg) was added HCl/EtOAc (4 mol/L, 1.00 mL) at 20° C. After stiring for 30 min at the same temperature, the mixture was concentrated in vacuo to remove the solvent and give benzyl (2R,4S)-4-fluoro-2-((6-fluoro-2-(5-fluoro-14(2S,4S)-4-fluoropyrrolidin-2-yl)methyl)-1H-benzo[d]imidazol-2-yl)-1H-indol-3-yl)methyppyrrolidine-1-carboxylate (332.00 mg, crude product, hydrochloride) as a brown solid.

Step B: To a solution of N-Boc-L-valine (206.03 mg, 948.30 µmol) in DMF (2.00 mL) were added N-methylmorpholine (239.80 mg, 2.37 mmol, 260.65 mL) and HATU (396.63 mg, 1.04 mmol) and the mixture was stirred for 30 min at 20° C. Then a solution of benzyl (2R,4S)-4-fluoro-2-((6-fluoro-2-(5-fluoro-1-(((2S,4S)-4-fluoropyrrolidin-2-yl)methyl)-1H-benzo[d]imidazol-2-yl)-1H-indol-3-yl)methyppyrrolidine-1-carboxylate (304.44 mg, crude product, hydrochloride) in DMF (1.00 mL) was added to the mixture at 20° C. and the mixture was stirred for further 1 h at the same temperature. The mixture was diluted with water (200 mL) and EtOAc (200 mL) and the organic phase was separated, washed with sat.aq. NaCl (100 mL×3) and concentrated in vacuo. The residue was purified by flash column chromatography eluted with Pet. Ether/EtOAc (3/1 to 2/3) to give benzyl (2R,4S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-6-fluoro-1H-indol-3-yl)methyl)-4-fluoropyrrolidine-1-carboxylate (400 mg, 455.73 µmol, 96.12%).

$^1$HNMR (DMSO, 400 MHz): δ 12.05-11.67 (m, 1H),8.08-7.47 (m, 1H),7.47-7.36 (m, 1H),7.27 (br.s., 5H),7.01 (br.s., 3H), 6.53 (d, J=9.2 Hz, 1H), 5.28-4.90 (m, 3H), 4.62-4.09 (m, 2H),3.98-3.79 (m, 2H),3.78-3.68 (m, 2H),3.66-3.47 (m, 2H),2.96-2.80 (m, 1H), 2.70 (s, 7H), 1.92 (s, 4H), 1.39 (s, 9H), 0.85-0.80 (m, 6H).

MS (ESI) m/z: 805.5 [M+H$^+$]

Step C: A solution of benzyl (2R,4S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-6-fluoro-1H-indol-3-yl)methyl)-4-fluoropyrrolidine-1-carboxylate (400.00 mg, 455.73 µmol) in EtOAc (20.00 mL) and MeOH (5.00 mL) was added Pd/C (100.00 mg, 10%) at 25° C. and under N$_2$, the resultant suspension was degassed in vacuo and charged with H$_2$ for couple times, and then was stirred for 3 h under the atmosphere of H$_2$ at 25° C. The mixture was filtered with kieselguhr, washed with MeOH (about 200 ml) and concentrated in vacuo to give tert-butyl ((S)-1-((2S,4S)-4-fluoro-2-((5-fluoro-2-(6-fluoro-3-(((2R,4S)-4-fluoropyrrolidin-2-yl)methyl)-1 H-indol-2-yl)-1H-benzo[d]imidazol-1-yl)methyl)pyrrolidin-1-yl)-3-methyl-1-oxobutan-2-yl)carbamate (320.00 mg, 395.98 µmol 86.89%).

MS (ESI) m/z: 671.5 [M+H$^+$]

Step D: To a solution of N-Boc-L-n-butyric acid(160.95 mg, 791.96 µmol) in DMF (1.00 mL) were added N-methylmorpholine (120.16 mg, 1.19 mmol, 130.61 µL) and HATU (376.41 mg, 989.95 µmol) and the mixture was stirred for 30 min at 20° C. Then the mixture was added with tert-butyl ((S)-1-((2S,4S)-4-fluoro-2-((5-fluoro-2-(6-fluoro-3-(((2R,4S)-4-fluoropyrrolidin-2-yl)methyl)-1-H-indol-2-yl)-1H-benzo[d]imidazol-1-yl)methyl)pyrrolidin-1-yl)-3-methyl-1-oxobutan-2-yl)carbamate (320.00 mg, 395.98 µmol) in DMF (1.00 mL) at 20° C. and stirred for further 1 h at the same temperature. The mixture was diluted with water (150 mL) and EtOAc (200 mL), then the organic phase was separated, washed with sat.aq. NaCl (100 mL×3) and concentrated in vacuo at 45° C. The residue was purified by flash column chromatography eluted with Pet. Ether/EtOAc (3/1 to 2/1) to give tert-butyl ((S)-1-((2S,4S)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)-4-fluoro pyrrolidin-1-yl)-3-methyl-1-oxobutan-2-yl)carbamate (320.00 mg, 321.51 µmol, 81.19%).

MS (ESI) m/z: 856.4 [M+H$^+$]

Step E: A solution of tert-butyl ((S)-1-((2S,4S)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)-4-fluoropyrrolidin-1-yl)-3-methyl-1-oxobutan-2-yl)carbamate (320.00 mg, 321.51 µmol) indioxane (2.00 mL) was added HCl/dioxane (4 mol/L, 2.00 mL) dropwise at 25° C. After stirring for 30 min at 25° C., the mixture was concentrated in vacuo to give (S)-2-amino-1-((2S,4S)-2-((2-(3-(((2R,4S)-1-((S)-2-aminobutanoyl)-4-fluoropyrrolidin-2-yl)methyl)-6-fluoro-1H-indol-2-yl)-5-fluoro-1H-benzo[d]imidazol-1-yl)methyl)-4-fluoropyrrolidin-1-yl)-3-methylbutan-1-one (260.00 mg, 321.14 99.89%, hydrochloride).

MS (ESI) m/z: 656.5 [M+H$^+$]

Step F: To a stirring solution of N-Boc-N-methyl-L-alanine (228.43 mg, 1.12 mmol) in DMF (1.00 mL) were added N-methylmorpholine (194.90 mg, 1.93 mmol, 211.85 μL) and HATU (451.80 mg, 1.19 mmol), the mixture was stirred for 30 min at 25° C., and a solution of (S)-2-amino-1-((2S,4S)-2-((2-(3-(((2R,4S)-1-((S)-2-aminobutanoyl)-4-fluoropyrrolidin-2-yl)methyl)-6-fluoro-1H-indol-2-yl)-5-fluoro-1H-benzo[d]imidazol-1-yl)methyl)-4-fluoropyrrolidin-1-yl)-3-methylbutan-1-one (260.00 mg, 321.14 hydrochloride) in DMF (1.00 mL) was added to the mixture. After stirring for 1 h at 25° C., the mixture was diluted with water (100 mL) and EtOAc (200 mL). The organic phase was separated, washed with sat.aq. NaCl (100 mL×3) and concentrated at 45° C. in vacuo. The residue was purified by flash column chromatography eluted with Pet. Ether/EtOAc (3/1 to 2/3) to give tert-butyl ((S)-1-(((S)-1-((2R,4S)-2-((2-(1-(((2S,4S)-1-(N-(tert-butoxycarbonyl)-N-methyl-L-alanyl-L-valyl)-4-fluoropyrrolidin-2-yl)methyl)-5-fluoro-1H-benzo[d]imidazol-2-yl)-6-fluoro-1H-indol-3-yl) methyl)-4-fluoropyrrolidin-1-yl)-1-oxobutan-2-yl) amino)-1-oxopropan-2-yl)(methyl)carbamate (260.00 mg, 222.97 μmol 69.43%) as yellow solid.

MS (ESI) m/z: 1026.3 [M+H⁺]

Step G: To a solution of tert-butyl ((S)-1-(((S)-1-((2R,4S)-2-((2-(1-(((2S,4S)-1-(N-(tert-butoxycarbonyl)-N-methyl-L-alanyl-L-valyl)-4-fluoropyrrolidin-2-yl)methyl)-5-fluoro-1H-benzo[d]imidazol-2-yl)-6-fluoro-1H-indol-3-yl) methyl)-4-fluoropyrrolidin-1-yl)-1-oxobutan-2-yl) amino)-1-oxopropan-2-yl)(methyl)carbamate (260.00 mg, 222.97 μmol) in dichloromethane (1.00 mL) was added trifluoroacetic acid (1.54 g, 13.51 mmol, 1.00 mL) dropwise at 25° C. After stirring for 30 min at 25° C., the mixture was concentrated in vacuo. The residue was purified by prep HPLC to give embodiment 18 (85.00 mg, 94.00 μmol, 42.16% hydrochloride).

¹HNMR (DMSO, 400 MHz): δ 8.30-8.05 (m, 1H), 7.98-7.76 (m, 2H), 7.62-7.36 (m, 2H), 7.18-6.99 (m, 1H), 5.53-5.43 (m, 1H), 5.38-5.30 (m, 1H), 5.08-4.96 (m, 3H), 4.76-4.67 (m, 1H), 4.64-4.44 (m, 2H), 4.41-4.25 (m, 1H), 4.23-3.86 (m, 6H), 3.70-3.52 (m, 1H), 2.67 (d, J=12.8 Hz, 6H), 2.29-1.73 (m, 7H), 1.60-1.42 (m, 6H), 1.15-1.03 (m, 3H), 0.98-0.85 (m, 6H).

MS (ESI) m/z: 826.5 [M+H⁺]

Process for preparing embodiment 19-36 can refer to the process for preparing embodiment 18.

Embodiment 19

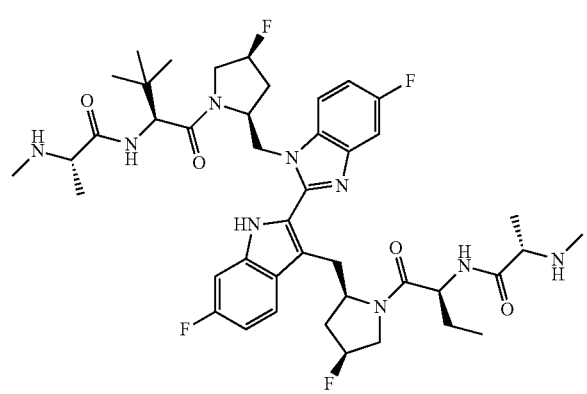

¹HNMR (MeOD, 400 MHz): δ 9.01-8.87 (m, 1H), 8.62-8.46 (m, 1H), 8.15 (dd, J=4.0, 12.0 Hz, 1H), 7.92 (dd, J=4.0, 8.0 Hz, 1H), 7.87 (dd, J=4.0, 8.0 Hz, 1H), 7.56 (td, J=4.0, 8.0 Hz, 1H), 7.48 (dd, J=4.0, 12.0 Hz, 1H), 7.12 (td, J=4.0, 8.0 Hz, 1H), 5.52 (d, J=16.0 Hz, 1H), 5.38 (d, J=16.0 Hz, 1H), 5.08-4.97 (m, 1H), 4.76-4.63 (m, 1H), 4.61-4.50 (m, 2H), 4.48-4.42 (m, 1H), 4.24-3.94 (m, 1H), 3.70-3.55 (m, 1H), 2.74-2.63 (m, 6H), 2.32-1.78 (m, 7H), 1.58 (d, J=8.0 Hz, 3H), 1.46 (d, J=8.0 Hz, 3H), 1.13 (t, J=8.0 Hz, 3H), 1.01 (s, 9H), 0.98-0.93 (m, 1H).

MS (ESI) m/z: 840.3 [M+H⁺]

Embodiment 20

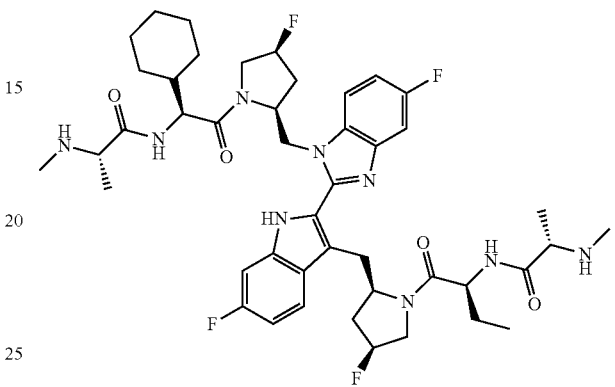

¹HNMR (MeOD, 400 MHz): δ 8.97-8.84 (m, 1H), 8.74-8.59 (m, 1H), 8.12 (dd, J=4.0, 8.0 Hz, 1H), 7.93 (dd, J=4.0, 12.0 Hz, 1H), 7.85 (dd, J=4.0, 12.0 Hz, 1H), 7.57 (td, J=4.0, 8.0 Hz, 1H), 7.46 (dd, J=4.0, 12.0 Hz, 1H), 7.12 (td, J=4.0, 8.0 Hz, 1H), 5.50 (d, J=16.0 Hz, 1H), 5.37 (d, J=16.0 Hz, 1H), 5.09-5.00 (m, 1H), 4.77-4.62 (m, 1H), 4.61-4.46 (m, 2H), 4.39-4.31 (m, 1H), 4.24-3.91 (m, 6H), 3.69-3.56 (m, 1H), 3.29-3.23 (m, 1H), 2.69 (d, J=16.0 Hz, 6H), 2.27-1.82 (m, 6H), 1.80-1.62 (m, 5H), 1.60-1.44 (m, 7H), 1.43-1.33 (m, 1H), 1.31-0.96 (m, 9H).

MS (ESI) m/z: 866.3 [M+H⁺]

Embodiment 21

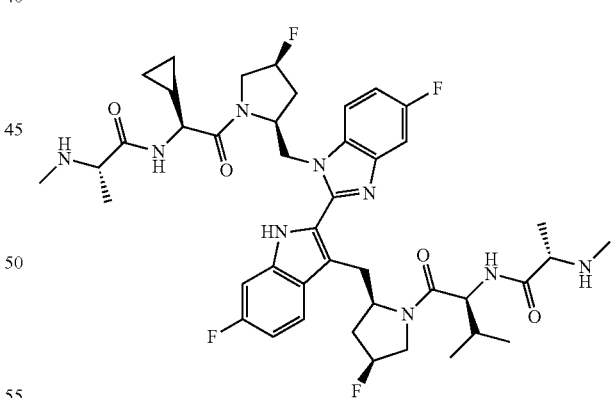

¹HNMR (MeOD, 400 MHz): δ 8.97-8.89 (m, 1H), 8.86-8.79 (m, 1H), 8.10 (dd, J=4.0, 8.0 Hz, 1H), 7.94 (dd, J=4.0, 8.0 Hz, 1H), 7.84 (dd, J=4.0, 8.0 Hz, 1H), 7.57 (td, J=4.0, 8.0 Hz, 1H), 7.43 (dd, J=4.0, 8.0 Hz, 1H), 7.12 (td, J=4.0, 8.0 Hz, 1H), 5.52 (d, J=16.0 Hz, 1H), 5.37 (d, J=16.0 Hz, 1H), 5.02-4.95 (m, 1H), 4.73-4.64 (m, 1H), 4.59-4.48 (m, 1H), 4.47-4.39 (m, 5H), 4.27-3.97 (m, 5H), 3.95-3.89 (m, 2H), 3.71-3.62 (m, 1H), 3.30-3.20 (m, 1H), 2.68 (d, J=16.0 Hz, 6H), 2.28-1.99 (m, 5H), 1.53-1.50 (m, 6H), 1.13 (d, J=4.0 Hz, 6H), 1.03-0.82 (m, 2H), 0.64-0.52 (m, 1H), 0.48-0.30 (m, 3H).

MS (ESI) m/z: 838.4 [M+H⁺]

Embodiment 22

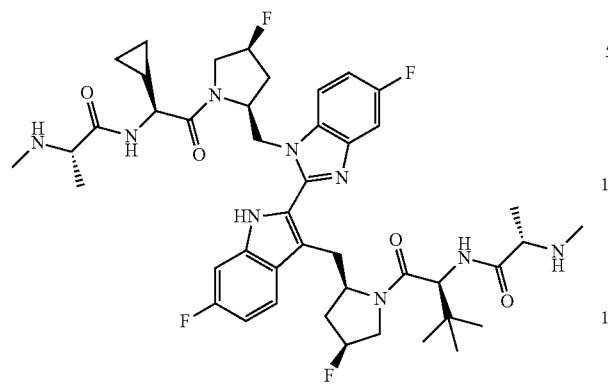

$^1$HNMR (MeOD, 400 MHz): δ 8.93-8.81 (m, 1H), 8.69-8.58 (m, 1H), 8.07 (dd, J=4.0, 8.0 Hz, 1H), 7.92 (dd, J=4.0, 8.0 Hz, 1H), 7.87 (dd, J=4.0, 8.0 Hz, 1H), 7.54 (td, J=4.0, 8.0 Hz, 1H), 7.42 (dd, J=4.0, 8.0 Hz, 1H), 7.10 (td, J=4.0, 8.0 Hz, 1H), 5.49 (d, J=16.0 Hz, 1H), 5.36 (d, J=16.0 Hz, 1H), 5.04-4.95 (m, 1H), 4.71-4.46 (m, 1H), 4.23-3.94 (m, 5H), 3.92-3.82 (m, 2H), 3.66-3.54 (m, 1H), 2.66 (d, J=16.0 Hz, 6H), 2.25-1.92 (m, 4H), 1.59-1.52 (m, 1H), 1.52-1.43 (m, 6H), 1.17 (s, 9H), 1.05-0.98 (m, 1H), 0.92-0.82 (m, 1H), 0.60-0.50 (m, 1H), 0.41-0.27 (m, 3H).

MS (ESI) m/z: 852.4 [M+H$^+$]

Embodiment 23

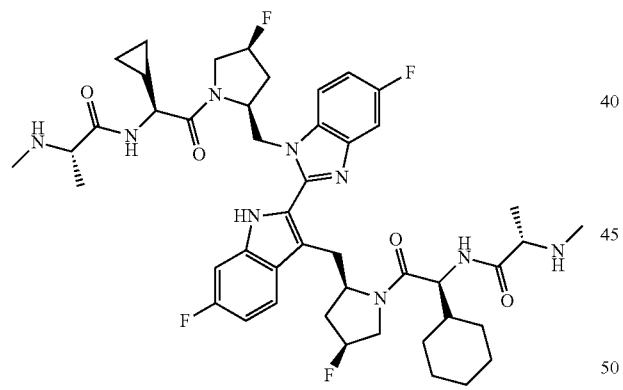

$^1$HNMR (MeOD, 400 MHz): δ 8.99-8.87 (m, 1H), 8.86-8.75 (m, 1H), 8.10 (dd, J=4.0, 12.0 Hz, 1H), 7.92 (dd, J=4.0, 8.0 Hz, 1H), 7.83 (dd, J=4.0, 8.0 Hz, 1H), 7.55 (td, J=4.0, 12.0 Hz, 1H), 7.42 (dd, J=4.0, 8.0 Hz, 1H), 7.10 (td, J=4.0, 8.0 Hz, 1H), 5.48 (d, J=16.0 Hz, 1H), 5.34 (d, J=16.0 Hz, 1H), 4.75-4.62 (m, 1H), 4.57-4.46 (m, 1H), 4.45-4.39 (m, 1H), 4.30-3.79 (m, 8H), 3.70-3.59 (m, 1H), 3.29-3.19 (m, 1H), 2.66 (d, J=16 Hz, 6H), 2.25-1.63 (m, 11H), 1.51-1.48 (m, 7H), 1.34-1.15 (m, 5H), 0.99-0.82 (m, 1H), 0.61-0.48 (m, 1H), 0.46-0.27 (m, 3H).

MS (ESI) m/z: 878.4 [M+H$^+$]

Embodiment 24

$^1$HNMR (MeOD, 400 MHz): δ 8.09 (d, J=8.0 Hz, 1H), 7.94 (dd, J=4.0, 8.0 Hz, 1H), 7.85 (d, J=8.0 Hz, 1H), 7.56 (t, J=8.0 Hz, 1H), 7.44 (d, J=8.0 Hz, 1H), 7.12 (t, J=8.0 Hz, 1H), 5.49 (d, J=20.0 Hz, 1H), 5.36 (d, J=16.0 Hz, 1H), 4.75-4.65 (m, 1H), 4.63-4.33 (m, 4H), 4.01 (m, 7H), 3.66 (d, J=8.0 Hz, 1H), 3.29-3.13 (m, 1H), 2.68 (d, J=12.0 Hz, 6H), 2.33-1.92 (m, 6H), 1.52 (d, J=8.0 Hz, 6H), 1.43-1.33 (m, 1H), 1.13 (d, J=4.0 Hz, 6H), 0.92 (t, J=4.0 Hz, 3H).

MS (ESI) m/z: 826.4 [M+H$^+$]

Embodiment 25

$^1$HNMR (MeOD, 400 MHz): δ 8.93-8.49 (m, 1H), 7.92 (d, J=8.0 Hz, 1H), 7.76 (dd, J=4.0, 8.0 Hz, 1H), 7.66 (t, J=8.0 Hz, 1H), 7.39 (d, J=8.0 Hz, 1H), 7.27 (t, J=8.0 Hz, 1H), 6.94 (t, J =8.0 Hz, 1H), 5.37-5.12 (m, 2H), 4.59-4.47 (m, 1H), 4.41-4.27 (m, 1H), 4.24-4.15 (m, 1H), 4.08-3.72 (m, 7H), 3.48 (d, J=12.0 Hz, 1H), 3.06 (br.s., 1H), 2.51 (d, J=12.0 Hz, 6H), 2.07-1.85 (m, 4H), 1.36 (dd, J=4.0, 12.0 Hz, 10H), 0.73 (t, J=8.0 Hz, 3H), 0.61-0.14 (m, 4H).

MS (ESI) m/z: 824.3 [M+H$^+$]

Embodiment 26

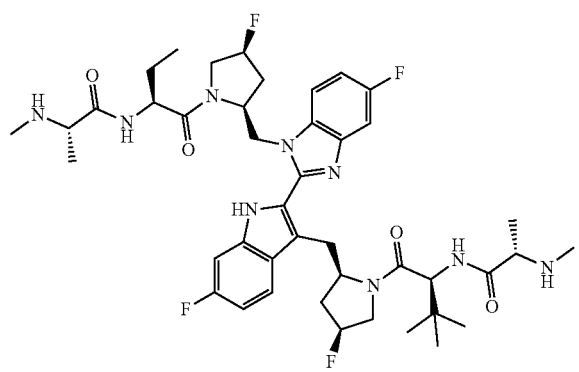

¹HNMR (MeOD, 400 MHz): δ 8.56 (br.s., 1H), 7.97 (d, J=8.0 Hz, 1H), 7.86-7.76 (m, 2H), 7.44 (br.s., 1H), 7.34 (d, J=8.0 Hz, 1H), 7.01 (t, J=8.0 Hz, 1H), 5.40 (d, J=8.0 Hz, 1H), 5.26 (d, J=12.0 Hz, 1H), 4.49 (br.s., 4H), 4.31-4.16 (m, 1H), 4.14-3.73 (m, 6H), 3.51 (d, J=12.0 Hz, 1H), 2.56 (d, J=12.0 Hz, 6H), 2.16-1.84 (m, 4H), 1.40 (d, J=8.0 Hz, 9H), 1.07 (s, 8H), 0.94-0.87 (m, 1H), 0.77 (t, J=8.0 Hz, 3H).
MS (ESI) m/z: 840.3 [M+H⁺]

Embodiment 27

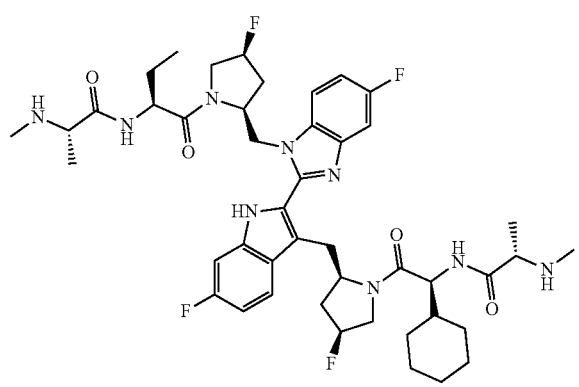

¹HNMR (MeOD, 400 MHz): δ 8.88-8.72 (m, 1H), 8.10 (dd, J=4.0, 8.0 Hz, 1H), 7.95 (dd, J=4.0, 8.0 Hz, 1H), 7.87-7.82 (m, 1H), 7.61-7.52 (m, 1H), 7.44 (dd, J=4.0, 12.0 Hz, 1H), 7.12 (d, J=4.0 Hz, 1H), 5.54-5.30 (m, 2H), 5.01-4.92 (m, 1H), 4.85-4.69 (m, 2H), 4.42 (td, J=4.0, 4.0 Hz, 3H), 4.01 (br.s., 6H), 3.66 (d, J=12.0 Hz, 1H), 3.29-3.18 (m, 1H), 2.70-2.64 (m, 6H), 2.19-1.70 (m, 10H), 1.52 (dd, J=8.0, 12.0 Hz, 6H), 1.47-1.18 (m, 7H), 0.93 ppm (t, J=8.0 Hz, 3H).
MS (ESI) m/z: 866.4 [M+H⁺]

Embodiment 28

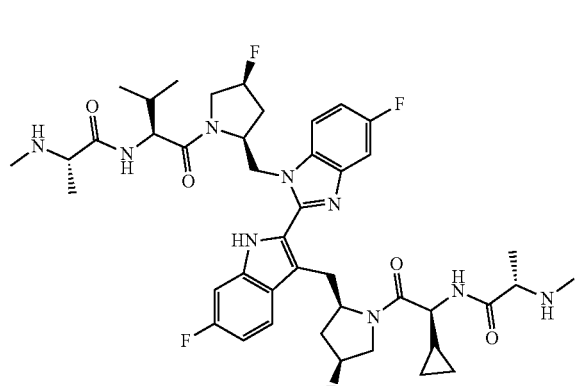

¹HNMR (MeOD, 400 MHz): δ 8.59-8.44 (d, J=8.0 Hz, 1H), 8.04-7.88 (m, 1H), 7.73 (dd, J=4.0, 8.0 Hz, 1H), 7.64 (d, J=8.0 Hz, 1H), 7.40-7.32 (m, 1H), 7.26 (d, J=8.0 Hz, 1H), 6.91 (t, J=8.0 Hz, 1H), 5.35-5.08 (m, 2H), 4.88-4.76 (m, 1H), 4.61-4.43 (m, 1H), 4.39-4.13 (m, 2H), 4.06-3.67 (m, 8H), 3.44 (d, J=12.0 Hz, 1H), 3.09-3.02 (m, 1H), 2.51-2.45 (m, 6H), 2.02-1.73 (m, 5H), 1.42-1.26 (m, 6H), 1.21-1.05 (m, 1H), 0.81-0.62 (m, 6H), 0.60-0.37 (m, 3H), 0.36-0.25 (m, 1H).
MS (ESI) m/z: 838.3 [M+H⁺]

Embodiment 29

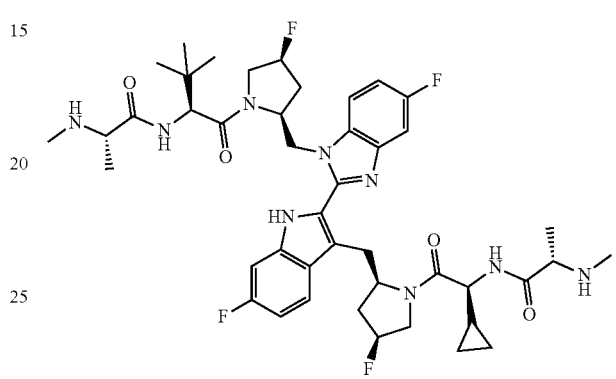

¹HNMR (MeOD, 400 MHz): δ 8.04 (dd, J=4.0, 8.0 Hz, 1H), 7.83 (dd, J=4.0, 8.0 Hz, 1H), 7.69 (d, J=4.0 Hz, 1H), 7.40 (t, J=8.0 Hz, 1H), 7.35-7.28 (m, 1H), 6.99 (t, J=8.0 Hz, 1H), 5.33 (br.s., 1H), 4.35 (m, 4H), 4.18-4.09 (m, 1H), 4.06-3.81 (m, 7H), 3.60-3.45 (m, 1H), 3.17-3.07 (m, 1H), 2.57 (d, J=20.0 Hz, 6H), 2.09-1.85 (m, 4H), 1.94 (s, 3H), 1.45 (d, J=8.0 Hz, 3H), 1.29-1.18 (m, 1H), 0.92 (s, 9H), 0.69-0.49 (m, 3H), 0.45-0.36 (m, 1H).
MS (ESI) m/z: 852.4 [M+H⁺]

Embodiment 30

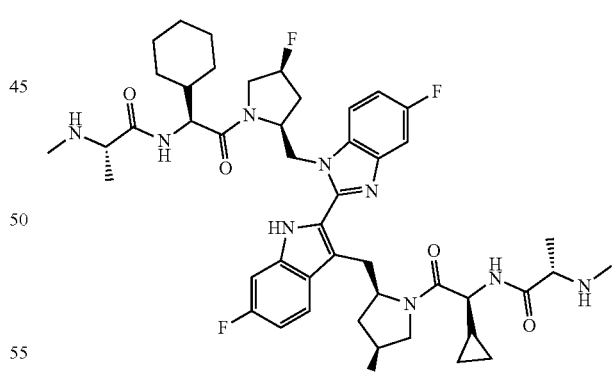

¹HNMR (MeOD, 400 MHz): δ 8.58 (d, J=8.0 Hz, 1H), 8.01 (d, J=4.0 Hz, 1H), 7.82 (dd, J=4.0, 8.0 Hz, 1H), 7.73 (d, J=8.0 Hz, 1H), 7.45 (t, J=8.0 Hz, 1H), 7.35 (d, J=8.0 Hz, 1H), 7.01 (t, J=8.0 Hz, 1H), 5.47-5.20 (m, 2H), 4.87 (br.s., 2H), 4.66-4.34 (m, 2H), 4.29-3.78 (m, 8H), 3.58-3.44 (m, 1H), 3.19-3.11 (m, 1H), 2.57 (d, J=20.0 Hz, 6H), 2.18-1.77 (m, 4H), 1.69-1.48 (m, 5H), 1.47-1.35 (m, 6H), 1.34-1.15 (m, 3H), 1.14-0.87 (m, 4H), 0.56 (br.s., 4H).
MS (ESI) m/z: 878.4 [M+H⁺]

Embodiment 31

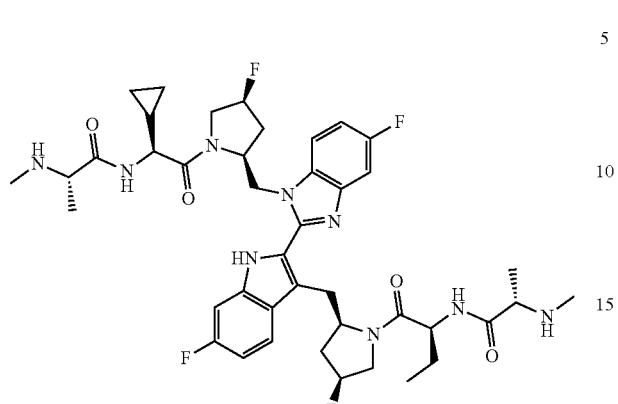

¹HNMR (MeOD, 400 MHz): δ 8.17-8.06 (m, 1H), 7.94 (dd, J=4.0, 8.0 Hz, 1H), 7.84 (d, J=4.0 Hz, 1H), 7.57 (t, J=8.0 Hz, 1H), 7.44 (d, J=8.0 Hz, 1H), 7.16-7.08 (m, 1H), 5.49 (br.s., 1H), 5.36 (d, J=4.0 Hz, 1H), 4.78-4.63 (m, 2H), 4.53 (br.s., 2H), 4.22-3.85 (m, 8H), 3.65 (d, J=12.0 Hz, 1H), 3.29-3.10 (m, 1H), 2.94-2.76 (m, 1H), 2.68 (d, J=16.0 Hz, 6H), 2.25-2.03 (m, 4H), 2.03-1.75 (m, 3H), 1.53 (dd, J=4.0, 16.0 Hz, 6H), 1.11 (t, J=8.0 Hz, 3H), 0.94-0.83 (m, 1H), 0.62-0.53 (m, 1H), 0.43 (q, J=8.0 Hz, 3H).

MS (ESI) m/z: 824.4 [M+H⁺]

Embodiment 32

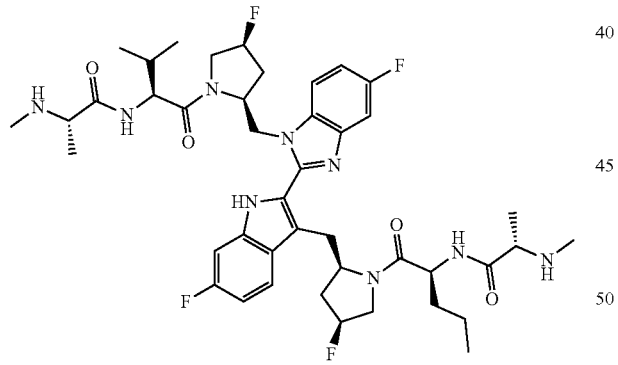

¹HNMR (MeOD, 400 MHz): δ 8.90 (d, J=8.0 Hz, 1H), 8.72 (d, J=8.0 Hz, 1H), 8.15 (dd, J =4.0, 12.0 Hz, 1H), 7.93 (dd, J=4.0, 8.0 Hz, 1H), 7.85 (d, J=8.0 Hz, 1H), 7.61-7.52 (m, 1H), 7.49-7.42 (m, 1H), 7.12 (dt, J=8.0, 12.0 Hz, 1H), 5.54-5.32 (m, 2H), 4.79 (m, 2H), 4.65-4.48 (m, 3H), 4.40 (t, J=8.0 Hz, 1H), 4.24-3.90 (m, 7H), 3.62 (d, J=16.0 Hz, 1H), 2.69 (d, J=12.0 Hz, 6H), 2.19-1.97 (m, 5H), 1.84-1.76 (m, 2H), 1.57-1.48 (m, 8H), 1.03 (t, J=8.0 Hz, 3H), 0.97 (d, J=8.0 Hz, 3H), 0.92 (d, J=8.0 Hz, 3H).

MS (ESI) m/z: 840.2 [M+H⁺]

Embodiment 33

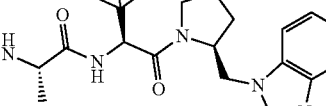

¹HNMR (MeOD, 400 MHz): δ 8.94 (d, J=8.0 Hz, 1H), 8.58 (d, J=8.0 Hz, 1H), 8.16 (dd, J =4.0, 8.0 Hz, 1H), 7.93 (dd, J=8.0, 12.0 Hz, 1H), 7.87 (d, J=8.0 Hz, 1H), 7.55 (t, J=12.0 Hz, 1H), 7.48 (d, J=8.0 Hz, 1H), 7.12 (t, J=8.0 Hz, 1H), 5.58-5.31 (m, 2H), 4.78-4.52 (m, 5H), 4.47 (d, J=8.0 Hz, 1H), 4.28-3.89 (m, 7H), 3.62 (d, J=12.0 Hz, 1H), 2.69 (d, J=20.0 Hz, 6H), 2.28-1.95 (m, 4H), 1.83 (d, J=8.0 Hz, 2H), 1.67-1.40 (m, 8H), 1.12-0.91 (m, 12H).

MS (ESI) m/z: 854.3 [M+H⁺]

Embodiment 34

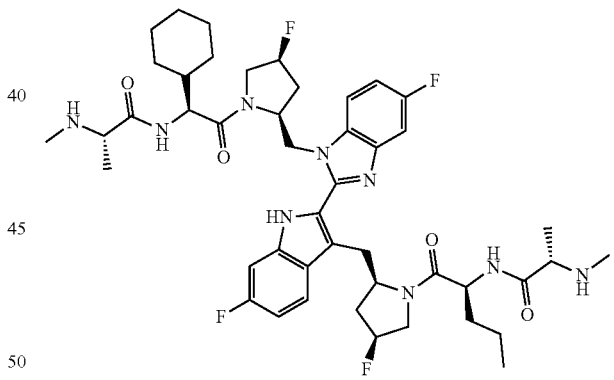

¹HNMR (MeOD, 400 MHz): δ 8.13-8.05 (m, 1H), 7.95 (dd, J=4.0, 8.0 Hz, 1H), 7.75 (d, J=4.0 Hz, 1H), 7.49 (t, J=8.0 Hz, 1H), 7.39 (d, J=12.0 Hz, 1H), 7.09 (t, J=12.0 Hz, 1H), 5.46-5.26 (m, 2H), 4.70 (m, J=6.8 Hz, 3H), 5.58 (br.s., 1H), 4.36 (br d, J=8.0 Hz, 1H), 4.11-3.84 (m, 7H), 3.60 (br d, J=13.2 Hz, 1H), 3.22-3.12 (m, 1H), 2.68 (d, J=16.0 Hz, 6H), 2.17-1.92 (m, 6H), 1.83-1.66 (m, 11H), 1.22 (d, J=8.0 Hz, 4H), 1.03 (t, J=8.0 Hz, 3H).

MS (ESI) m/z: 880.4 [M+H⁺]

Embodiment 35

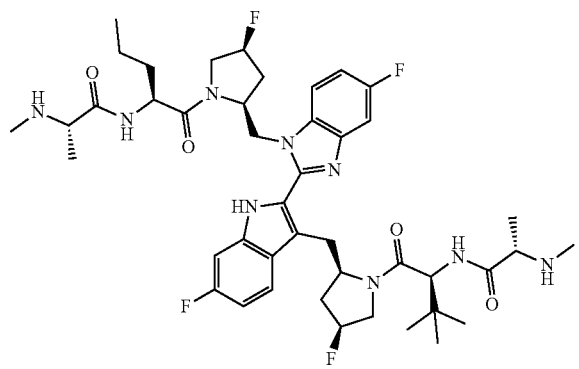

¹HNMR (MeOD, 400 MHz): δ 8.64 (d, J=5.77 Hz, 1H), 8.05 (dd, J=3.95, 8.97 Hz, 1H), 7.94 (dd, J=5.14, 8.91 Hz, 1H), 7.87 (d, J=7.28 Hz, 1H), 7.56 (t, J=8.41 Hz, 1H), 7.44 (d, J=7.78 Hz, 1H), 7.12 (t, J=8.16 Hz, 1H), 5.44-5.58 (m, 1H), 5.31-5.43 (m, 1H), 4.57-4.68 (m, 3H), 4.53 (br.s., 1H), 4.37 (br.s., 1H), 3.83-4.24 (m, 6H), 3.62 (d, J=13.55 Hz, 1H), 3.18-3.30 (m, 2H), 2.67 (d, J=17.57 Hz, 6H), 1.94-2.27 (m, 4H), 1.49 (d, J=6.65 Hz, 6H), 1.30 (d, J=7.15 Hz, 3H), 1.18 (s, 9H), 0.99 (s, 1H), 0.90 (t, J=5.52 Hz, 3H).

MS (ESI) m/z: 854.4 [M+H⁺]

Embodiment 36

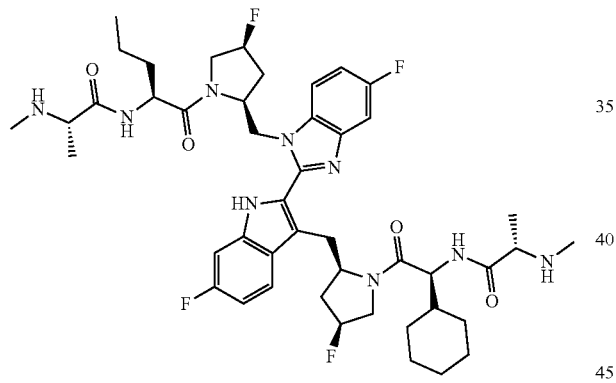

¹HNMR (MeOD, 400 MHz): δ 8.79 (d, J=7.28 Hz, 1H), 8.69 (d, J=6.65 Hz, 1H), 8.06 (dd, J=3.64, 8.91 Hz, 1H), 7.93 (dd, J=5.08, 8.85 Hz, 1H), 7.83 (d, J=6.27 Hz, 1H), 7.55 (t, J=8.47 Hz, 1H), 7.42 (d, J=7.53 Hz, 1H), 7.10 (t, J=9.10 Hz, 1H), 5.27-5.55 (m, 2H), 4.50 (br.s., 1H), 4.40 (d, J=7.28 Hz, 2H), 4.01-4.25 (m, 3H), 3.82-4.01 (m, 4H), 3.64 (d, J=13.93 Hz, 1H), 3.11-3.23 (m, 1H), 2.65 (d, J=11.92 Hz, 6H), 2.00-2.28 (m, 4H), 1.79 (br.s., 7H), 1.48 (t, J=6.21 Hz, 6H), 1.09-1.40 (m, 10H), 0.90 (t, J=6.09 Hz, 3H).

MS (ESI) m/z: 880.4 [M+H⁺]

Embodiment 37

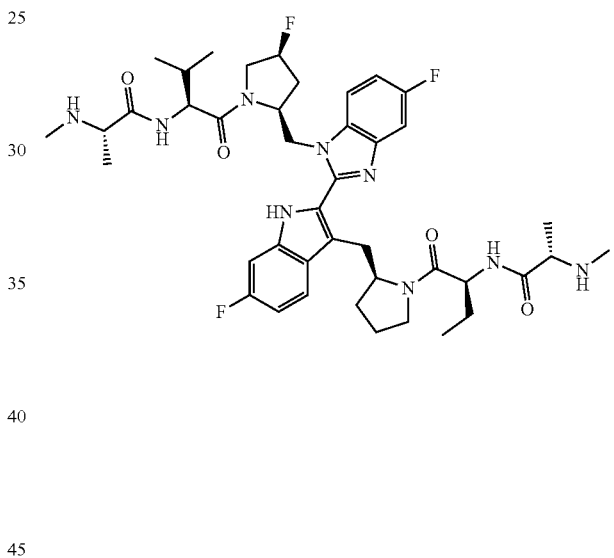

Reaction Process: Preparation of Embodiment 37

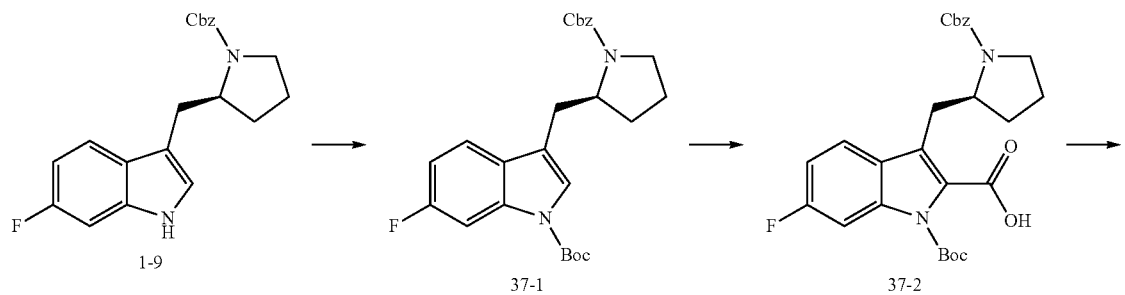

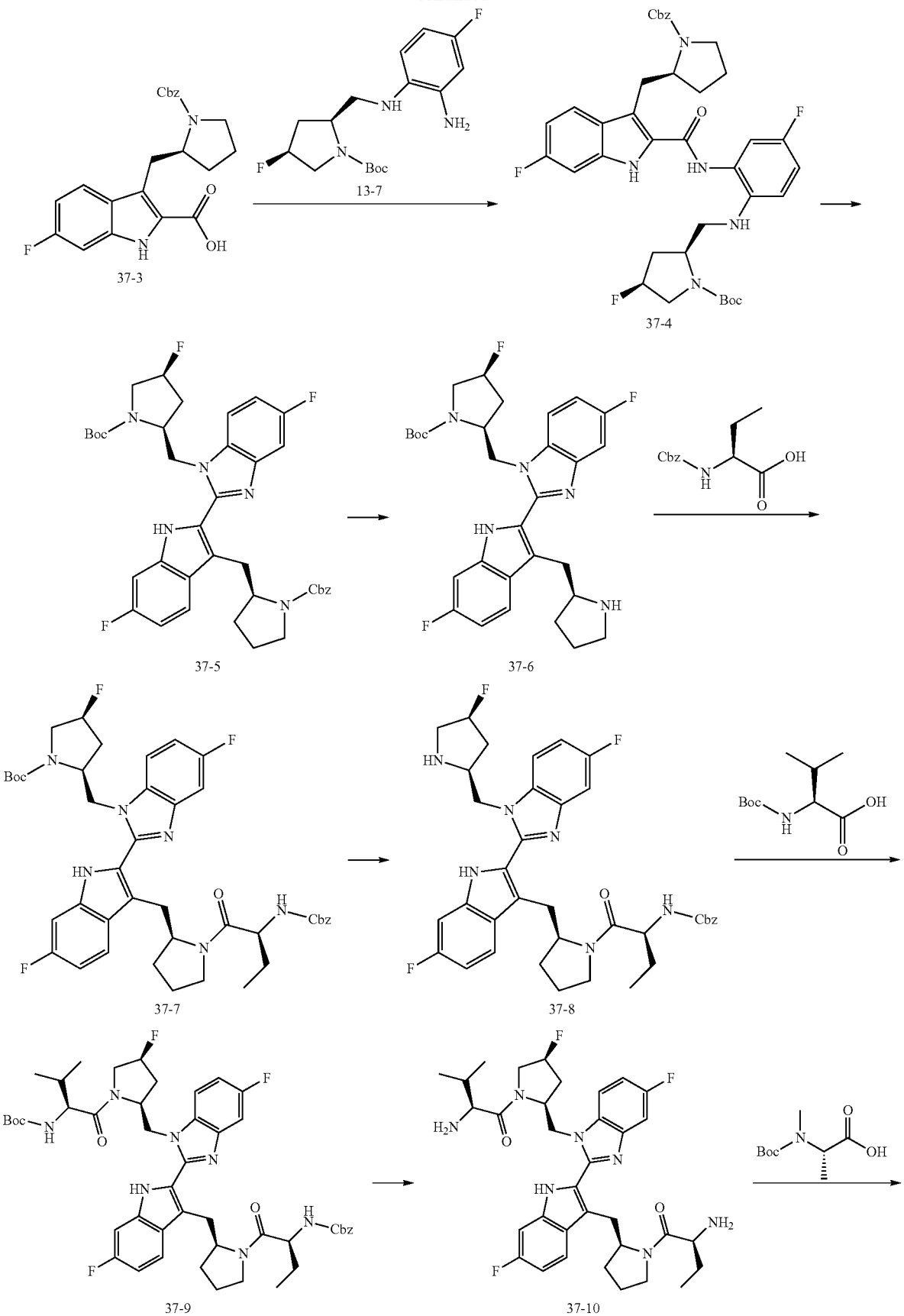

-continued

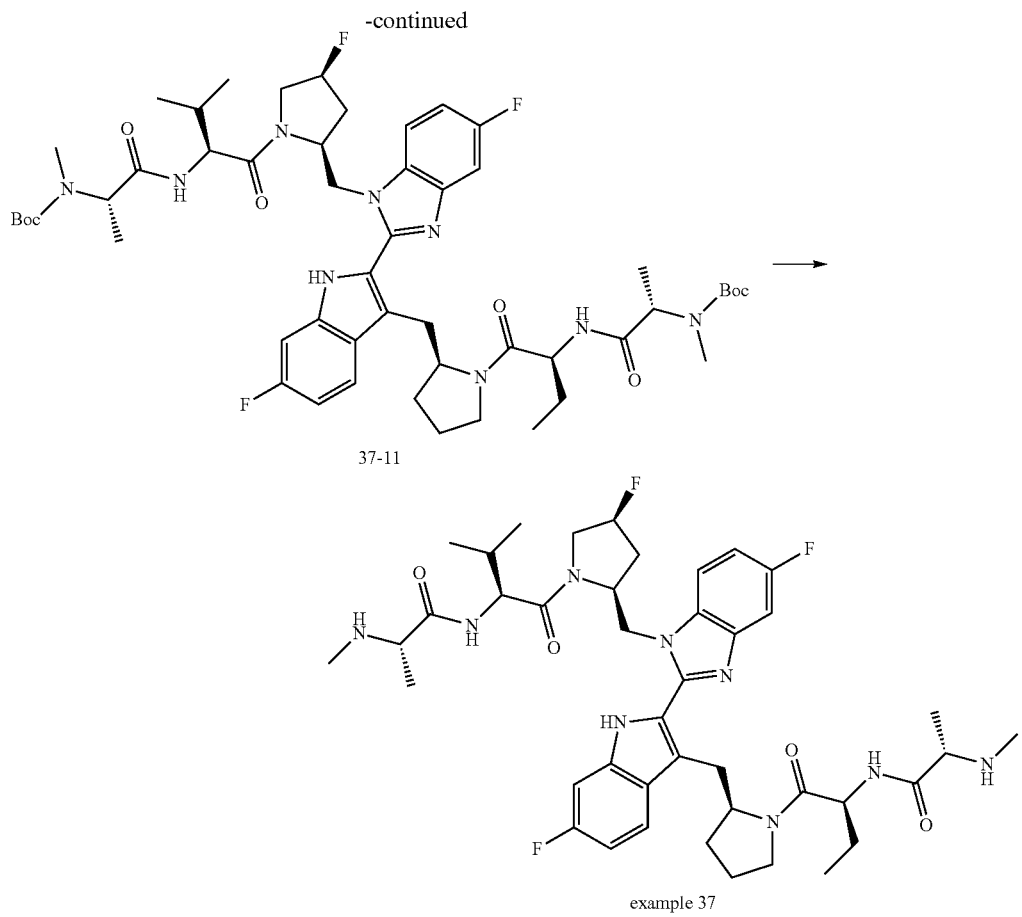

37-11 example 37

Step A: To a solution of benzyl (S)-2-((6-fluoro-1H-indol-3-yl)methyl)pyrrolidine-1-carboxylate (5 g, 14.19 mmol) in dichloromethane (30 mL) was added DMAP (34.67 mg, 283.77 μmol), followed by adding a solution of (Boc)$_2$O (3.25 g, 14.90 mmol) in dichlorometane (20 mL) dropwise. After the addition, the mixture was stirred for 16 h at 10-20° C. When the reaction was complete, the mixture was concentrated in vacuo. The residue was purified by flash column chromatography eluted with Pet. Ether/EtOAc (30:1 to 20:1) to give tert-butyl (S)-3-((1-((benzyloxy)carbonyl)pyrrolidin-2-yl)methyl)-6-fluoro-1H-indole-1-carboxylate (6.5 g, 97.18%).

$^1$HNMR (CDCl$_3$, 400 MHz): δ 7.80-7.60 (m, 1H), 7.40-7.20 (m, 6H), 7.08-6.84 (m, 1H), 6.61 (t, J=8.2 Hz, 1H), 5.13 (s, 2H), 4.17-3.98 (m, 1H), 3.47-3.29 (m, 2H), 2.57-2.40 (m, 1H), 1.85-1.65 (m, 4H), 1.59 (s, 9H).

MS (ESI) m/z: 475.2 [M+H$^+$]

Step B: To a solution of tert-butyl-(S)-3-((1-((benzyloxy)carbonyl)pyrrolidin-2-yl)methyl)-6-fluoro-1H-indole-1-carboxylate (6.5 g, 13.79 mmol) in THF (120 mL) was added LDA (2 mol/L, 13.79 mL) dropwise at −70° C. under the atmosphere of N$_2$ and the mixture was stirred for 15 min at the same temperature, and then dry ice (13.79 mmol)was added. While stirring, the mixture was warmed to 20° C. in 105 min, and then was quenched with water (50 mL), and extracted with EtOAc (100 mL). The organic phase was washed with sat.aq NaCl (100 mL), dried over anhydrous Na$_2$SO$_4$, filtered and the filtrate was concentrated in vacuo. The residue was purified by flash column chromatography eluted with DCM/MeOH (100:1 to 33:1) to give (S)-3-((1-((benziloxy)carbonyl)pyrrolidin-2-yl)methyl)-1-(tert-butoxycarbonyl)-6-fluoro-1H-indole-2-carboxylic acid (3.9 g, 44.09%).

$^1$HNMR (DMSO, 400 MHz): δ 13.56 (br.s., 1H), 7.51-7.19 (m, 8H), 5.21-4.97 (m, 2H), 4.11-3.98 (m, 1H), 3.00-2.79 (m, 1H), 1.89-1.61 (m, 5H), 1.56 (d, J=6.1 Hz, 9H).

MS (ESI) m/z: 497.3 [M+H$^+$]

Step C: To a solution of (S)-3-((1-((benzyloxy)carbonyl)pyrrolidin-2-yl)methyl)-1-(tert-butoxycarbonyl)-6-fluoro-1H-indole-2-carboxylic acid (2.5 g, 5.03 mmol) in dichloromethane (20 mL) was added trifluoroacetic acid (135.06 mmol, 10 mL) at 5-20° C. The mixture was stirred for 16 h at 5-20° C. After the reaction was complete, the mixture was concentrated to remove dichloromethane and most of trifluoroacetic acid. The residue was diluted with dichloromethane and washed with 10% aq NaOH. The organic phase was concentrated in vacuo to give crude product, (S)-3-((1-((benzyloxy)carbonyl)pyrrolidin-2-yl)methyl)-6-fluoro-1H-indole-2-carboxylic acid (1.5 g, 75.23%) which was used for next step.

MS (ESI) m/z: 397.3 [M+H$^+$]

Step D: To a solution of (S)-3-((1-((benzyloxy)carbonyl)pyrrolidin-2-yl)methyl)-6-fluoro-1H-indole-2-carboxylic acid (1.5 g, 3.78 mmol) in dichloromethane (15mL) were added pyridine (61.95 mmol, 5 mL), tert-butyl (2 S,4 S)-2-(((2-amino-4-fluorophenyl)amino)methyl)-4-fluoropyrrolidine-1-carboxylate (1.11 g, 3.40mmol) and EDCI (1.09 g, 5.67 mmol). The mixture was stirred for 16 h at 10-25° C. After the reaction was complete, the mixture was quenched with hydrochloric acid (1 mol/L, 50 mL) and extracted with dichloromethane (50 mL). The organic phase was separated and washed with sat.aq. NaCl (50 mL), dried over anhydrous Na₂SO₄, filtered and the filtrate was concentrated in vacuo to give crude product. The residue was purified by flash column chromatography eluted with Pet. Ether/EtOAc (10:1 to 5:1) to give tert-butyl (2S,4S)-2-(((2-(3-(((S)-1-((benzyloxy)carbonyl)pyrrolidin-2-yl)methyl)-6-fluoro-1H-indole-2-carboxamido)-4-fluorophenyl)amino)methyl)-4-fluoropyrrolidine-1-carboxylate (800.00 mg, 20.39%).

MS (ESI) m/z: 706.2 [M+H⁺]

Step E: Tert-butyl (2S,4S)-2-(((2-(3-(((S)-1-((benzyloxy)carbonyl)pyrrolidin-2-yl)methyl)-6-fluoro-1H-indole-2-carboxamido)-4-fluorophenyl)amino)methyl)-4-fluoropyrrolidine-1-carboxylate (500.00 mg, 708.46 μmol) was dissolved in acetic acid (5 mL) and the mixture was stirred for 4 h at 85° C. After the reaction was complete, the mixture was concentrated in vacuo to remove the solvent. The crude product was purified by flash column chromatography eluted with EtOAc/Pet. Ether (10-20%) to give tert-butyl (2S,4S)-2-((2-(3-(((S)-1-((benzyloxy)carbonyl)pyrrolidin-2-yl)methyl)-6-fluoro-1H-indol-2-yl)-5-fluoro-1H-benzo[d]imidazol-1-yl)methyl)-4-fluoropyrrolidine-1-carboxylate (300.00 mg, 56.03%).

MS (ESI) m/z: 688.1 [M+H⁺]

Step E: To a solution of tert-butyl (2S,4S)-2-((2-(3-(((S)-1-((benzyloxy)carbonyl)pyrrolidin-2-yl)methyl)-6-fluoro-1H-indol-2-yl)-5-fluoro-1H-benzo[d]imidazol-1-yl)methyl)-4-fluoropyrrolidine-1-carboxylate (300.00 mg, 436.21 μmol) in MeOH (5 mL) was added Pd/C (0.1 g, 10%) at the atmosphere of N₂. The mixture was charged with H₂ for 3 times and stirred for 16 h at 30-35° C. under anatmosphere of 15 psi H₂. The mixture was cooled to room temperature, filtered with kieselguhr and the filtrate was concentrated in vacuo to give crude product, tert-butyl (2S,4S)-4-fluoro-2-((5-fluoro-2-(6-fluoro-3-(((S)-pyrrolidin-2-yl)methyl)-1H-indol-2-yl)-1H-benzo[d]imidazol-1-yl)methyl)pyrrolidine-1-carboxylate (190.00 mg, 322.60 μmol, 73.96%).

MS (ESI) m/z: 554.3 [M+H⁺]

Step G: To a solution of N-Boc-L-n-butyric acid(122.13 mg, 514.8 μmol) in DMF (1 mL) were added HATU (195.74 mg, 514.8 μmol) and N-methylmorpholine (1.03 mmol, 113.20 μL), the mixture was stirred for 15 min at 10-20° C., and then added with a solution of tert-butyl (2S,4S)-4-fluoro-2-((5-fluoro-2-(6-fluoro-3-(((S)-pyrrolidin-2-yl)methyl)-1H-indol-2-yl)-1H-benzo[d]imidazol-1-yl)methyl)pyrrolidine-1-carboxylate (crude product, 190.00 mg, 343.20 μmol) in DMF (2 mL). After stirring for 16 h at 10-20° C., the mixture was added with water (30 mL) and extracted with EtOAc (50 mL). The organic phase was separated, washed with sat.aq. NaCl (50 mL), dried over anhydrous Na₂SO₄, filtered and the filtrate was concentrated in vacuo to give crude product, tert-butyl (2S,4S)-2-((2-(3-(((S)-1-((S)-2-(((benzyloxy)carbonyl)amino)butanoyl)pyrrolidin-2-yl)methyl)-6-fluoro-1H-indol-2-yl)-5-fluoro-1H-benzo[d]imidazol-1-yl)methyl)-4-fluoropyrrolidine-1-carboxylate (300.00 mg).

MS (ESI) m/z: 773.2 [M+H⁺]

Step H: To a solution of tert-butyl (2S,4S)-2-((2-(3-(((S)-1-((S)-2-(((benzyloxy)carbonyl)amino)butanoyl)pyrrolidin-2-yl)methyl)-6-fluoro-1H-indol-2-yl)-5-fluoro-1H-benzo[d]imidazol-1-yl)methyl)-4-fluoropyrrolidine-1-carboxylate (300.00 mg, crude product) in dichloromethane (2 mL) was added TFA (13.15 mmol, 1 mL). After stirring for 2 h at 10-20° C., the mixture was concentrated in vacuo to remove the solvent and most of TFA to give crude product benzyl ((S)-1-((S)-2-((6-fluoro-2-(5-fluoro-1-(((2S,4S)-4-fluoropyrrolidin-2-yl)methyl)-1H-benzo[d]imidazol-2-yl)-1H-indol-3-yl)methyl)pyrrolidin-1-yl)-1-oxobutan-2-yl)carbamate (500.00 mg, trifluoroacetate) which can be used without any further purification for next step.

MS (ESI) m/z: 673.3 [M+H⁺]

Step I: To a solution of N-Boc-L-valine (103.55 mg, 476.64 μmol) in DMF (1 mL) were added NMM (953.28 μmol, 104.80 μL) and HATU (181.23 mg, 476.64 μmol). After stirring for 15 min at 10-20° C., the mixture was added with benzyl ((S)-1-((S)-2-((6-fluoro-2-(5-fluoro-1-(((2S,4S)-4-fluoropyrrolidin-2-yl)methyl)-1H-benzo[d]imidazol-2-yl)-1H-indol-3-yl)methyl)pyrrolidin-1-yl)-1-oxobutan-2-yl)carbamate (250.00 mg, 317.76 μmol, crude product, trifluoroacetate) in DMF (1 mL). After stirring for 4 h at 10-20° C., the mixture was added with water (30 mL) and extracted with EtOAc (50 mL). The organic phase was separated, washed with sat.aq. NaCl (50 mL), dried over Na₂SO₄, filtered and the filtrate was concentrated in vacuo to give crude product. The crude product was purified by flash column chromatography eluted with Pet. Ether/EtOAc (1:1) to give benzyl ((S)-1-((S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-6-fluoro-1H-indol-3-yl)methyl)pyrrolidin-1-yl)-1-oxobutan-2-yl)carbamate (200.00 mg, crude product).

MS (ESI) m/z: 872.4 [M+H⁺]

Step J: To a solution of benzyl ((S)-1-((S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-6-fluoro-1H-indol-3-yl)methyl)pyrrolidin-1-yl)-1-oxobutan-2-yl)carbamate (200.00 mg, 229.36 μmol, crude product) in dichloromethane (1 mL) was added HBr/AcOH (229.36 μmol, 1.00 mL). After stirring for 1 h at 10-20° C., the mixture was concentrated in vacuo to remove the solvent. The crude product was diluted with water (30 mL), extracted with methyl tert-butyl ether (30 mL). The aqueous was separated, adjusted pH to 8-9, extracted with EtOAc (50 mL). The organic phase was separated, washed with sat.aq. NaCl (50 mL), dried over anhydrous Na₂SO₄, filtered and the filtrate was concentrated in vacuo to give crude product, (S)-2-amino-1-((2S,4S)-2-((2-(3-(((S)-1-((S)-2-aminobutanoyl)pyrrolidin-2-yl)methyl)-6-fluoro-1H-indol-2-yl)-5-fluoro-1H-benzo[d]imidazol-1-yl)methyl)-4-fluoropyrrolidin-1-yl)-3-methylbutan-1-one (100.00 mg, crude product).

MS (ESI) m/z: 638.2 [M+H⁺]

Step K: To a solution of N-Boc-N-methyl-L-alanine (95.60 mg, 470.40 μmol) in DMF (1 mL) were added N-methylmorpholine (103.43 mg, 940.80 μmol) and HATU (178.86 mg, 470.40 μmol) and the mixture was stirred for 15 min at 25° C. Then the mixture was added with a solution of (S)-2-amino-1-((2S,4S)-2-((2-(3-((S)-1-((S)-2-aminobutanoyl)pyrrolidin-2-yl)methyl)-6-fluoro-1H-indol-2-yl)-5-fluoro-1H-benzo[d]imidazol-1-yl)methyl)-4-fluoropyrrolidin-1-yl)-3-methylbutan-1-one (crude product) in DMF (1 mL)and the mixture was stirred for further 16 h at 25° C. The mixture was added with water (20 mL) and extracted with EtOAc (60 mL) twice. The combinated organic phase was washed with sat.aq. NaCl (50 mL), dried over anhydrous Na₂SO₄, filtered and concentrated in vacuo to give crude product. The crude product was purified by flash column chromatography eluted with Pet. Ether/EtOAc (1:2) to give tert-butyl ((S)-1-(((S)-1-((2S,4S)-2-((2-(3-(((S)-1-((S)-2-((S)-2-((tert-butoxycarbonyl)(methyl)amino)propanamido)butanoyl)pyrrolidin-2-yl)methyl)-6-fluoro-1H-indol-2-yl)-5-fluoro-1H-benzo[d]imidazol-1-yl)methyl)-4- fluoropyrrolidin-1-yl)-3-methyl-1-oxobutan-2-yl)amino)-1-oxopropan-2-yl)(methyl)carbamate (80.00 mg, 78.56 μmol 50.10%) as white solid.

MS (ESI) m/z: 1008.5 [M+H$^+$]

Step L: To a solution of tert-butyl ((S)-1-(((S)-1-((2S,4S)-2-((2-(3-(((S)-1-((S)-2-((S)-2-((tert-butoxycarbonyl)(methyl)amino)propanamido)butanoyl)pyrrolidin-2-yl)methyl)-6-fluoro-1H-indol-2-yl)-5-fluoro-1H-benzo[d]imidazol-1-yl)methyl)-4-fluoropyrrolidin-1-yl)-3-methyl-1-oxobutan-2-yl)amino)-1-oxopropan-2-yl)(methyl)carbamate (80.00 mg, 78.56 μmol) in dichloromethane (2 mL) was added TFA (1 mL). After stirring for 1 h at 10-20° C., the mixture was concentrated in vacuo to remove the solvent and TFA. The crude product was purified by prep HPLC to give embodiment 37 (38.22 mg, 43.39 μmol 54.68%, hydrochloride).

$^1$HNMR (MeOD, 400 MHz): δ 12.34 (s, 1H), 8.93 (d, J=6.8 Hz, 1H), 8.58 (d, J=7.2 Hz, 1H), 8.12 (dd, J=3.9, 9.0 Hz, 1H), 7.99-7.90 (m, 2H), 7.59-7.47 (m, 2H), 7.16-7.07 (m, 1H), 5.56-5.35 (m, 1H), 5.07-5.01 (m, 1H), 4.96 (d, J=8.8 Hz, 1H), 4.69 (d, J=6.8 Hz, 2H), 4.50-4.43 (m, 1H), 4.35 (br.s., 1H), 4.20-3.97 (m, 4H), 3.88 (dd, J=7.8, 16.2 Hz, 2H), 3.52 (d, J=13.9 Hz, 1H), 3.26-3.15 (m, 1H), 2.73 (s, 3H), 2.67 (s, 3H), 2.35 (br,s 1H), 2.70-1.79 (m, 7H), 1.60 (d, J=6.8 Hz, 3H), 1.47 (d, J=6.6 Hz, 3H), 1.12 (t, J=7.2 Hz, 3H), 1.03 (s, 9H).

MS (ESI) m/z: 808.4 [M+H$^+$]

Embodiment 38

Embodiment 38 was prepared according to the process for preparing embodiment 37

$^1$HNMR (MeOD, 400 MHz): δ 6 8.88 (d, J=7.0 Hz, 1H), 8.73 (d, J=7.1 Hz, 1H), 8.11 (dd, J =3.9, 9.1 Hz, 1H), 7.99-7.86 (m, 2H), 7.59-7.44 (m, 2H), 7.11 (dt, J=2.1,9.2 Hz, 1H), 5.56-5.35 (m, 1H), 5.10-4.99 (m, 1H), 4.77 (br.s., 1H), 4.66 (d, J=5.1 Hz, 1H), 4.45-4.38 (m, 1H), 4.33 (br.s., 1H), 4.19-3.94 (m,1H), 3.92-3.78 (m, 2H), 3.53 (d, J=14.2 Hz, 1H), 3.24-3.12 (m, 1H),2.67-2.60 (m, 7H), 2.31 (br.s., 1H), 2.24-1.76 (m, 9H), 1.58 (d, J=6.8 Hz, 3H), 1.51 (d, J=7.0 Hz, 3H), 1.10 (t, J=7.3 Hz, 3H), 0.97 (dd, J=6.7,19.2 Hz, 6H).

MS (ESI) m/z: 822.3 [M+H$^+$]

Embodiment 39

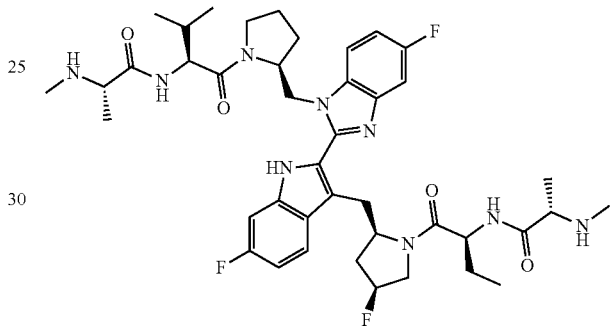

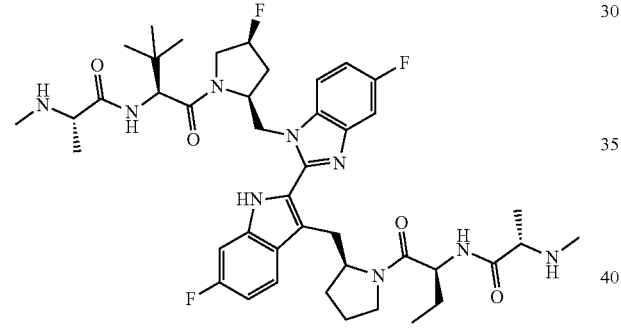

Reaction process: the preparation of embodiment 39

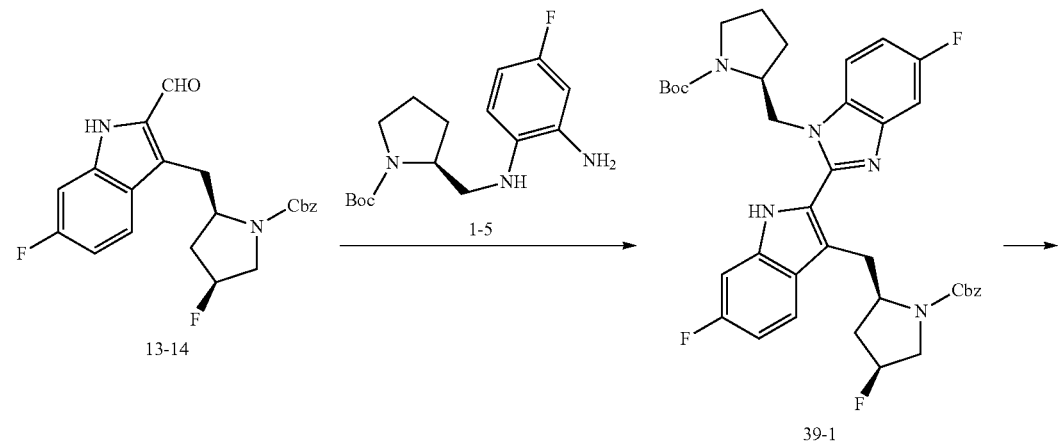

105                                106
-continued
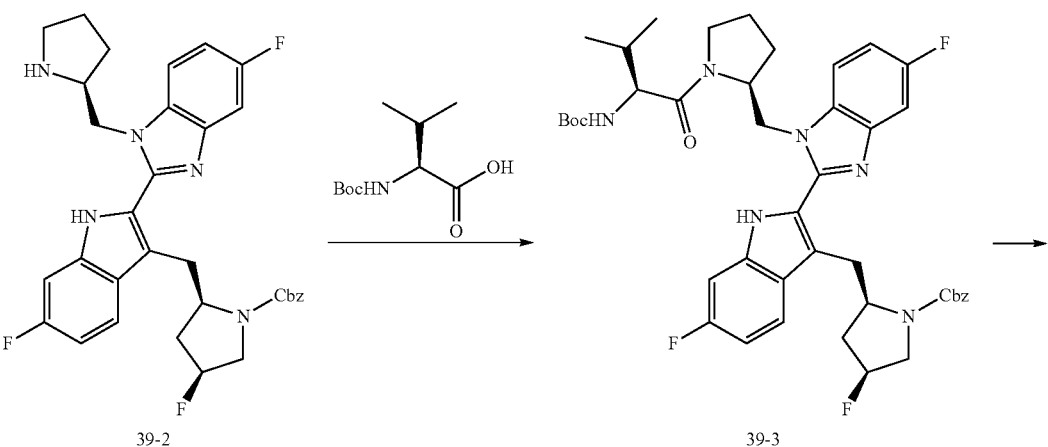
39-2                                39-3
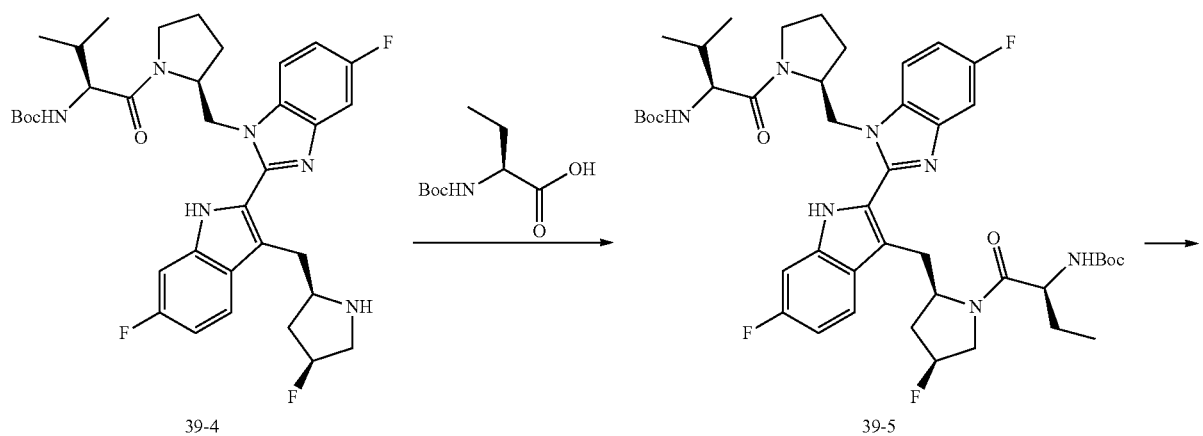
39-4                                39-5
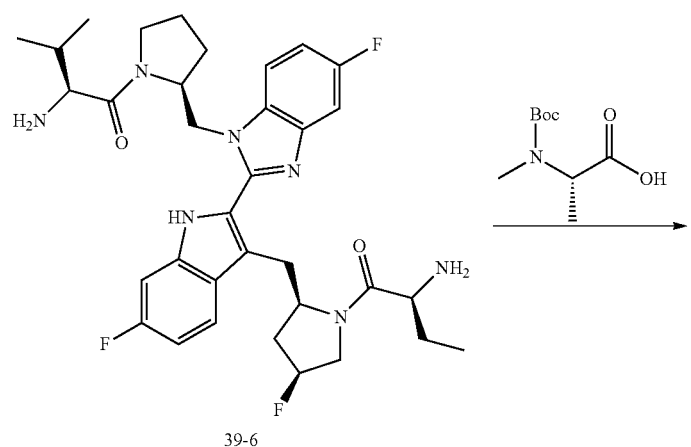
39-6

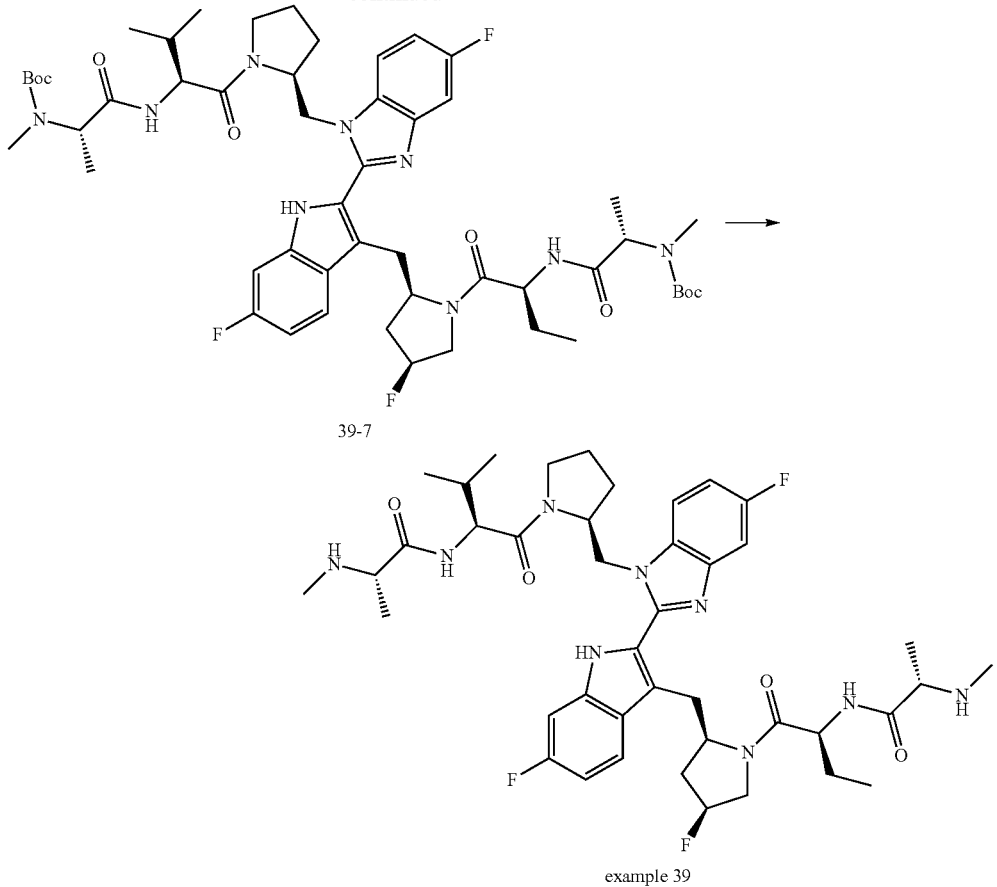

39-7 example 39

Step A: To a solution of tert-butyl (S)-2-(((2-amino-4-fluorophenyl)amino)methyl)pyrrolidine-1-carboxylate (4.13 g, 13.36 mmol) in DMF (30.00 mL) and H₂O (2.00 mL) was added benzyl (2R,4S)-4-fluoro-2-((6-fluoro-2-formyl-1H-indol-3-yl)methyl)pyrrolidine-1-carboxylate (3.80 g, 6.68 mmol) at 0° C. After stirring for 30 min, the mixture was added with Oxone (3.05 g, 20.03 mmol) at 0° C. After stirring for 16 h at 15° C., the mixture was diluted with EtOAc (300 mL) and water (300 mL). The organic phase was separated, washed with sat.aq. NaCl, dried over anhydrous $Na_2SO_4$, filtered and the filtrate was concentrated in vacuo. The residue was purified by flash column chromatography eluted with Pet. Ether/EtOAc (10/1 to 2/1) to give benzyl (2R,4S)-2-((2-(1-(((S)-1-(tert-butoxycarbonyl)pyrrolidin-2-yl)methyl)-5-fluoro-1H-benzo[d]imidazol-2-yl)-6-fluoro-1H-indol-3-yl)methyl)-4-fluoropyrrolidine-1-carboxylate (2.30 g, 2.71 mmol, 40.55%).

¹HNMR (MeOD, 400 MHz): δ 11.52-11.78 (m, 1H), 7.58-7.86 (m, 1H), 7.45-7.54 (m, 1H), 7.26-7.44 (m, 6H), 7.11-7.26 (m, 2H), 6.63-7.05 (m, 1H), 4.90-5.21 (m, 4H), 4.30-4.58 (m, 1H), 3.89-4.26 (m, 3H), 3.37-3.77 (m, 3H), 2.64-3.15 (m, 3H), 2.01-2.30 (m, 1H), 2.00 (s, 2H), 1.41-1.61 (m, 2H), 1.13-1.40 (m, 9H).

MS (ESI) m/z: 688.3 [M+H⁺]

Step B: To a solution of benzyl (2R,4S)-2-((2-(1-(((S)-1-(tert-butoxycarbonyl)pyrrolidin-2-yl)methyl)-5-fluoro-1H-benzo[d]imidazol-2-yl)-6-fluoro-1H-indol-3-yl)methyl)-4-fluoropyrrolidine-1-carboxylate (600.00 mg, 706.65) in dioxane (6.00 mL) was added HCl/dioxane (4 mol/L, 6.00 mL) at 15° C. After stirring for 1 h at 15° C., the mixture was concentrated at 45° C. in vacuo to remove the solvent and give benzyl (2R,4S)-4-fluoro-2-((6-fluoro-2-(5-fluoro-14 (S)-pyrrolidin-2-yl)methyl)-1H-benzo[d]imidazol-2-yl)-1H-indol-3-yl)methyl)pyrrolidine-1-carboxylate (540.00 mg, crude product, hydrochloride).

Step C: To a solution of N-Boc-L-valine (140.99 mg, 648.95 μmol) in DMF (2.00 mL) were added N-methylmorpholine (131.28 mg, 1.30 mmol, 142.70 μL) and HATU (263.20 mg, 692.21 μmol) at 15° C. After stirring for 30 min at 15° C., the mixture was added with a solution of benzyl (2R,4S)-4-fluoro-2-((6-fluoro-2-(5-fluoro-1-(((S)-pyrrolidin-2-yl)methyl)-1H-benzo[d]imidazol-2-yl)-1H-indol-3-yl)methyl)pyrrolidine-1-carboxylate (270.00 mg, crude product, hydrochloride) in DMF (2.00 mL)and stirred for further 1 h at 15° C. The mixture was added to water (100 mL) and solids was precipitated. After stirring for further 10 min, the mixture was filtered and dried to give benzyl (2R,4S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)-4-fluoropyrrolidine-1-carboxylate (335.00 mg, 357.61 μmol, 82.66%).

MS (ESI) m/z: 787.3 [M+H⁺]

Step D: To a solution of benzyl (2R,4S)-2-((2-(1-(((S)-1-((tert-butoxycarbonyl)-L-valyl)pyrrolidin-2-yl)methyl)-5-fluoro-1H-benzo[d]imidazol-2-yl)-6-fluoro-1H-indol-3-yl)methyl)-4-fluoropyrrolidine-1-carboxylate (335.00 mg, 357.61 μmol) in EtOAc (20.00 mL) and MeOH (4.00 mL) was added Pd/C (100 mg, 10%) at 15° C. under the atmosphere of $N_2$. The mixture was degassed in vacuo and charged with $H_2$ for couple times and stirred for 24 h at 25°

C. under the atmosphere of 15 psi H₂. The mixture was filtered with kieselguhr, washed with MeOH (about 100 mL) and the filtrate was concentrated in vacuo to give tert-butyl ((S)-1-((S)-2-((5-fluoro-2-(6-fluoro-3-(((2R,4S)-4-fluoropyrrolidin-2-yl)methyl)-1H-indol-2-yl)-1H-benzo[d]imidazol-1-yl)methyl)pyrrolidin-1-yl)-3-methyl-1-oxobutan-2-yl) carbamate (309.00 mg, crude product).

MS (ESI) m/z: 653.3 [M+H⁺]

Step E: To a solution of N-Boc-L-n-butyric acid(129.88 mg, 639.07 μmol) in DMF (3.00 mL) were added N-methylmorpholine (129.28 mg, 1.28 mmol, 140.52 μL) and HATU (259.19 mg, 681.67 μmol) at 18° C. and the mixture was stirred for 30 min at 18° C., and then a solution of tert-butyl ((S)-1-((S)-2-((5-fluoro-2-(6-fluoro-3-(((2R,4S)-4-fluoropyrrolidin-2-yl)methyl)-1H-indol-2-yl)-1H-benzo[d]imidazol-1-yl)methyl)pyrrolidin-1-yl)-3-methyl-1-oxobutan-2-yl)carbamate (309.00 mg, crude product) in DMF (3.00 mL) was added to the mixture. After stirring for 1 h at 18° C., the mixture was poured into water (100 mL) and solid was precipitated. After stirring for further 10 min, the mixture was filtered and dried to give tert-butyl ((S)-1-((S)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)pyrrolidin-1-yl)-3-methyl-1-oxobutan-2-yl)carbamate (346.00 mg, 334.45 μmol, 78.50%).

MS (ESI) m/z: 838.4 [M+H⁺]

Step F: To a solution of tert-butyl ((S)-1-((S)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)pyrrolidin-1-yl)-3-methyl-1-oxobutan-2-yl)carbamate (346.00 mg, 412.90 μmol) in dichloromethane (3.00 mL) was added TFA dropwise (4.62 g, 40.52 mmol, 3.00 mL) at 18° C. After stirring for 30 min at 18° C., the mixture was concentrated in vacuo at 45° C. to remove the solvent and give (S)-2-amino-1((S)-2-((2-(3-(((2R,4S)-1-((S)-2-aminobutanoyl)-4-fluoropyrrolidin-2-yl)methyl)-6-fluoro-1H-indol-2-yl)-5-fluoro-1H-benzo[d]imidazol-1-yl)methyl)pyrrolidin-1-yl)-3-methylbutan-1-one (357.00 mg, 412.34 μmol, 99.87%, trifluoroacetate).

Step G: To a solution of N-Boc-N-methyl-L-alanine (209.50 mg, 1.03 mmol) in DMF (3.00 mL) were added N-methylmorpholine (250.25 mg, 2.47 mmol, 272.01 μL) and HATU (407.64 mg, 1.07 mmol) at 18° C. and the mixture was stirred for 30 min at 18° C. Then a solution of (S)-2-amino-1-((S)-2-((2-(3-(((2R,4S)-1-((S)-2-aminobutanoyl)-4-fluoropyrrolidin-2-yl)methyl)-6-fluoro-1H-indol-2-yl)-5-fluoro-1H-benzo[d]imidazol-1-yl)methyl)pyrrolidin-1-yl)-3-methylbutan-1-one (357.00 mg, 412.34 μmol, trifluoroacetate) in DMF (3.00 mL)was added and the mixture was stirred for further 1 h at 18° C. The mixture was poured into water (100 mL) and solid was precipitated. After stirring for further 10 min, the mixture was filtered and dried to give light yellow solid. The light yellow solid was purified by flash column chromatography eluted with Pet. Ether/ EtOAc (1/3) to give tert-butyl ((S)-1-(((S)-1-((S)-2-((2-(3-(((2R,4S)-1-((S)-2-((S)-2-((tert-butoxycarbonyl)(methyl) amino)propanamido)butanoyl)-4-fluoropyrrolidin-2-yl) methyl)-6-fluoro-1H-indol-2-yl)-5-fluoro-1H-benzo[d] imidazol-1-yl)methyl)pyrrolidin-1-yl)-3-methyl-1-oxobutan-2-yl)amino)-1-oxopropan-2-yl)(methyl) carbamate (200.00 mg, 168.62 μmol 40.89%).

MS (ESI) m/z: 1008.5 [M+H⁺]

Step H: To a solution of tert-butyl ((S)-1-(((S)-1-((S)-2-((2-(3-(((2R,4S)-1-((S)-2-((S)-2-((tert-butoxycarbonyl) (methyl)amino)propanamido)butanoyl)-4-fluoropyrrolidin-2-yl)methyl)-6-fluoro-1H-indol-2-yl)-5-fluoro-1H-benzo[d] imidazol-1-yl)methyl)pyrrolidin-1-yl)-3-methyl-1-oxobutan-2-yl)amino)-1-oxopropan-2-yl)(methyl) carbamate (200.00 mg, 168.62 μmol) in dichloromethane (3.00 mL) was added TFA dropwise (4.62 g, 40.52 mmol, 3.00 mL) at 18° C. After stirring for 30 min at 18° C., the mixture was concentrated in vacuo to remove the solvent and give residue. The residue was purified by prep HPLC to give embodiment 39 (120.00 mg, 136.23 μmol 80.79%, hydrochloride).

¹HNMR (MeOD, 400 MHz): δ 12.34 (s, 1H), 8.93 (d, J=6.8 Hz, 1H), 8.58 (d, J=7.2 Hz, 1H), 8.12 (dd, J=3.6,9.0 Hz, 1H), 7.99-7.90 (m, 2H), 7.59-7.47 (m, 2H), 7.16-7.07 (m, 1H), 5.56-5.35 (m, 1H), 5.07-5.01 (m, 1H), 4.96 (d, J=8.8 Hz, 1H), 4.69 (d, J=6.8 Hz, 2H), 4.50-4.43 (m, 1H), 4.35 (br.s., 1H), 4.20-3.97 (m,4H), 3.88(dd, J=7.8, 16.2 Hz, 2H), 3.52 (d, J=13.9 Hz, 1H), 3.26-3.15 (m, 1H),2.73 (s, 3H), 2.67 (s, 3H), 2.35 (br.s., 1H), 2.20-1.79 (m, 7H), 1.60 (d, J=6.8 Hz, 3H), 1.47 (d, J=6.6 Hz, 3H), 1.12 (t, J=7.2 Hz, 3H), 1.03 (s, 9H).

MS (ESI) m/z: 808.3 [M+H⁺]

Process for preparing embodiment 40, 41, 42 can refer to the process for preparing embodiment 39

Embodiment 40

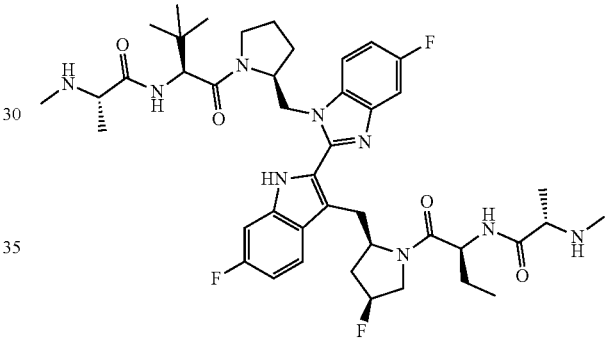

¹HNMR (MeOD, 400 MHz): δ 8.88 (d, J=7.0 Hz, 1H), 8.73 (d, J=7.1 Hz, 1H), 8.11 (dd, J=3.9,9.1 Hz, 1H), 7.99-7.86 (m, 2H), 7.59-7.44 (m, 2H), 7.11 (dt, J=2.1,9.2 Hz, 1H), 5.56-5.35 (m, 1H), 5.10-4.99 (m, 1H), 4.77 (br.s., 1H), 4.66 (d, J=5.1 Hz, 1H), 4.45-4.38 (m, 1H), 4.33 (br.s., 1H), 4.19-3.94 (m,4H), 3.92-3.78 (m, 2H), 3.53 (d, J=14.2 Hz, 1H), 3.24-3.12 (m, 1H),2.67-2.60 (m, 7H), 2.31 (br.s., 1H), 2.24-1.76 (m, 9H), 1.58 (d, J=6.8 Hz, 3H), 1.51 (d, J=7.0 Hz, 3H), 1.10 (t, J=7.3 Hz, 3H), 0.97 (dd, J=6.7,19.2 Hz, 6H).

MS (ESI) m/z: 822.3 [M+H⁺]

Embodiment 41

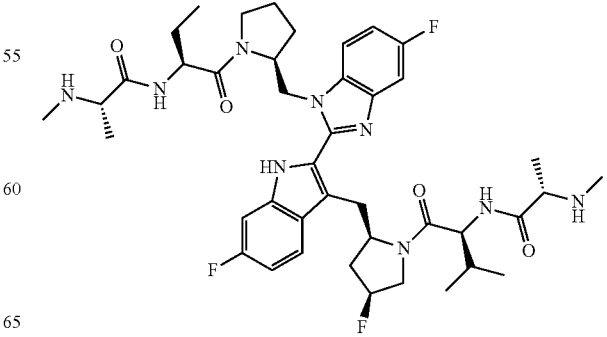

¹HNMR (MeOD, 400 MHz): δ 8.20 (Dd, J=9.03, 3.89 Hz, 1H), 7.95 (dd, J=8.91, 5.14 Hz, 1H), 7.86 (dd, J=7.78, 2.01 Hz, 1H), 7.51-7.59 (m, 1H), 7.47 (dd, J=9.41, 2.13 Hz, 1H), 7.12 (td, J=9.16, 2.13 Hz, 1H), 5.29-5.56 (m, 1H), 4.74 (dd, J=14.81, 7.65 Hz, 2H), 4.40-4.61 (m, 4H), 4.08-4.26 (m,1H), 3.89-4.04(m, 2H), 3.58-3.80 (m, 3H), 3.21-3.30 (m, 1H),2.63-2.74 (m, 6H), 2.16-2.28 (m, 9H), 2.11 (d, J=18.32 Hz, 1H), 1.96-2.06 (m, 2H), 1.83-1.90 (m, 1H), 1.68-1.79 (m, 1H), 1.49-1.59 (m, 7H), 1.42 (dd, J=14.81, 7.40 Hz, 1H), 1.08-1.20 (m, 6H), 0.87-0.96 (m, 3H).

MS (ESI) m/z: 808 [M+H⁺]

Embodiment 42

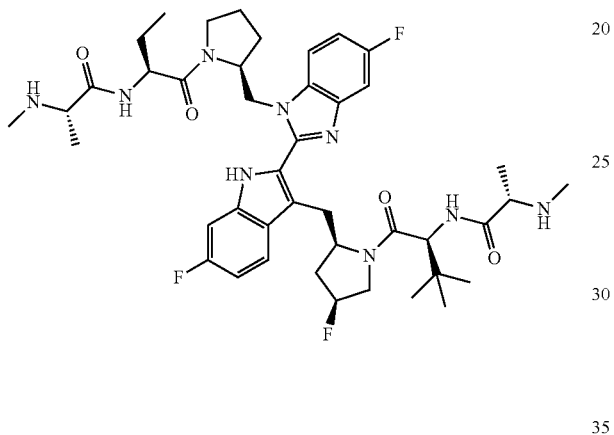

¹HNMR (MeOD, 400 MHz): δ8.20 (dd, J=9.16, 4.02 Hz, 1H), 7.94 (dd, J=8.91, 5.14 Hz, 1H), 7.89 (dd, J=7.84, 2.20 Hz, 1H), 7.55 (td, J=9.16, 2.13 Hz, 1H), 7.48 (dd, J=9.29, 2.13 Hz, 1H), 7.13 (td, J=9.16, 2.13 Hz, 1H), 5.32-5.53 (m, 1H), 4.78 (dd, J=14.74, 7.84 Hz, 2H), 4.40-4.66 (m, 5H), 4.04-4.24 (m,3H), 3.94 (q, J=7.03 Hz, 1H), 3.69-3.81 (m, 2H), 3.64 (d, J=13.18 Hz, 1H), 2.61-2.76 (m, 7H), 2.10-2.25 (m, 2H), 2.02 (m, 1H), 1.81-1.93 (m, 1H), 1.68-1.78 (m, 1H), 1.48-1.60 (m, 7H), 1.39-1.46 (m, 1H), 1.20 (s, 9H), 0.90 (t, J=7.34 Hz, 3H).

MS (ESI) m/z: 822 [M+H⁺]

Embodiment 43

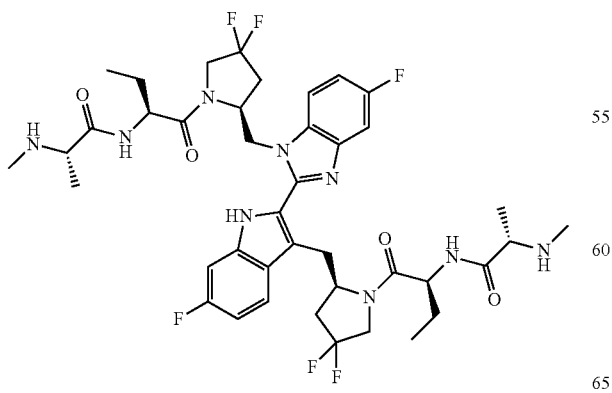

Reaction process: preparation of intermediate 43-8

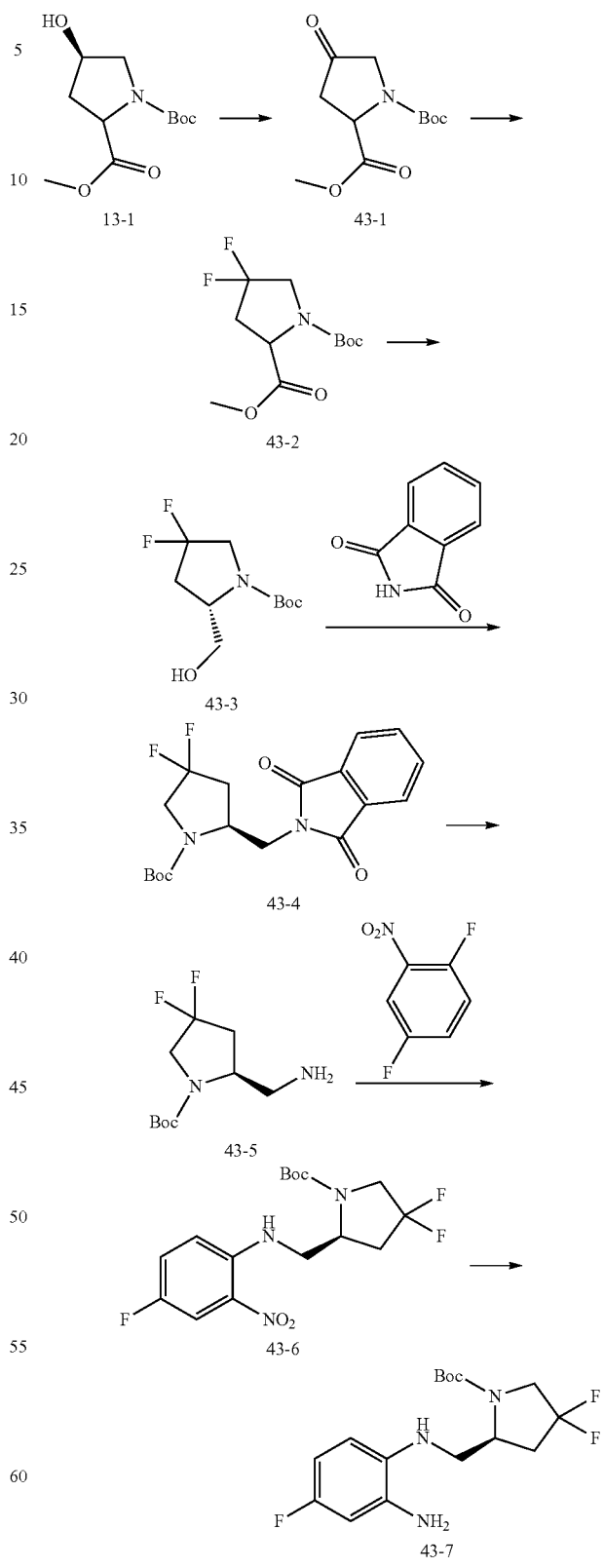

Step A: To a solution of N-Boc-trans-4-hydroxyl-L-methyl prolinate (114.00 g, 464.79 mmol) in dichloromethane (1.2 L) was added trichloroisocyanuric acid(113.42 g, 488.03 mmol) and then TEMPO (1.46 g, 9.30 mmol) was added at 0° C. After stirring for 0.5 h at 10-20° C., the mixture was filtered with kieselguhr. The dichloromethane phase was washed with sat. aq $K_2CO_3$ (1000 mL) twice, then with sat.aq NaCl (800 mL), dried over anhydrous $Na_2SO_4$, filtered and the filtrate was concentrated in vacuo to give N-Boc-4-oxo-L-methyl prolinate (111.00 g, 456.30 mmol, 98.17%).

$^1$H NMR (CDCl$_3$, 400 MHz): δ 4.81-4.64 (m, 1H), 3.84 (d, J=7.8 Hz, 2H), 3.73 (s, 3H), 2.99-2.84 (m, 1H), 2.55 (d, J=20.0 Hz, 1H), 1.43 (d, J=8.0 Hz, 9H).

Step B: To a solution of N-Boc-4-oxo-L-methyl prolinate (106.00 g, 435.75 mmol) in dichloromethane (500 mL) was added DAST (119.40 g, 740.78 mmol) in dichloromethane (500 mL) dropwise at 0° C. After the addition, the mixture was added with EtOH (4.02 g, 87.15 mmol) and the mixture was stirred for 18 h at 0-20° C. The mixture was poured into icy sat.aq NaHCO$_3$ slowly. After CO$_2$ overflowed totally, the mixture was extracted with dichloromethane (2000 mL) twice, and the dichloromethane was dried over anhydrous Na$_2$SO$_4$, filtered and the filtrate was concentrated in vacuo to give crude product. The crude product was purified by flash column chromatography eluted with Pet. Ether/EtOAc (50:1 to 10:1) to give N-Boc-4,4-fluor-L-methyl prolinate (70.00 g, 263.90 mmol, 60.56%).

$^1$H NMR (CDCl$_3$, 400 MHz): δ 4.57-4.40 (m, 1H), 3.89-3.72 (m, 5H), 2.78-2.60 (m, 1H), 2.45 (m, 1H), 1.44 (d, J=20.0 Hz, 9H).

Step C: To a stirring solution of N-Boc-4,4-fluor-L-methyl prolinate (50.00 g, 188.50 mmol) in THF (500 mL) were added LiCl (17.58 g, 414.70 mmol) and NaBH$_4$ (17.83 g, 471.25 mmol) at 10-20° C. The mixture was cooled to 0° C. and EtOH (1 L) was added. The mixture was stirred for 1 h at 0° C., and then was stirred for 17 h at 10-20° C. Then the mixture was cooled to 0° C. and 10% aq. NaHSO$_4$ was added to adjust pH to 3. The mixture was concentrated to remove the solvent, added with water (500 mL) and extracted with dichloromethane (1500 mL) for 3 times. The organic phase was dried over anhydrous Na$_2$SO$_4$, filtered and the filtrate was concentrated to give N-Boc-4,4-fluor-L-methyl prolinol (44.00 g, crude product).

$^1$H NMR (CDCl$_3$, 400 MHz): δ 4.19-3.95 (m, 2H), 3.84-3.40 (m, 4H), 2.42 (dq, J=9.0, 13.1 Hz, 9H), 2.11 (br.s., 1H), 1.46-1.37 (m, 9H).

Step D: To a solution of N-Boc-4,4-difluor-L-prolinol (44 g, crude product) in THF (440 mL) were added phthalimide (28.65 g, 194.74 mmol) and triphenylphosphine (51.08 g, 194.74 mmol) at 10-20° C. Then the mixture was added with DIAD (39.38 g, 194.74 mmol). After the addition,the mixture was stirred for 16 h at 10-20° C., then concentrated to remove the solvent, water (500 mL) was added and then the mixture was extracted with dichloromethane twice (1000 mL). The combined organic phase was washed with sat.aq NaCl (500 mL), dried over Na$_2$SO$_4$, filtered and the filtrate was concentrated in vacuo to give crude product. The crude product was purified by flash column chromatography eluted with Pet. Ether/EtOAc (20:1 to 10:1) to give tert-butyl (S)-2-((1,3-dioxoisoindolin-2-yl)methyl)-4,4-difluoropyrrolidine-1-carboxylate (65.00 g,170.32 mmol, 91.83%).

$^1$H NMR (CDCl$_3$, 400 MHz): δ 7.88-7.62 (m, 4H), 4.62-4.37 (m, 1H), 4.01-3.62 (m, 4H), 2.61-2.42 (m, 1H), 2.28(d, J=16.0 Hz, 1H), 1.35-1.17 (m, 9H).

Step E: To a solution of tert-butyl (S)-2-((1,3-dioxoisoindolin-2-yl)methyl)-4,4-difluoropyrrolidine-1-carboxylate (69.00 g, 188.34 mmol) in ethanol (1 L) was added hydrazine hydrate (24.05 g, 470.85 mmol). After reacting for 2 h at 60° C., the mixture was cooled to room temperature, then diluted with dichloromethane (1000 mL), filtered, and filter cake was washed with dichloromethane. The combined organic phase was concentrated in vacuo to give crude product. The residue was dulited with dichloromethane (200 mL), filtered, and filter cake was washed with dichloromethane. The combined organic phase was concentrated in vacuo to give tert-butyl (S)-2-(aminomethyl)-4,4-difluoropyrrolidine-1-carboxylate (50.00 g, crude product).

$^1$HNMR (CDCl3, 400 MHz): δ 3.90-3.68 (m, 2H), 3.45 (m, 4H), 2.83-2.56 (m, 2H), 1.41 (s, 9H).

Step F: To a solution of tert-butyl (S)-2-(aminomethyl)-4,4-difluoropyrrolidine-1-carboxylate (44.50 g, 188.35 mmol) in acetonitrile (500 mL) were added 1,4-difluoro-2-nitrobenzene (29.96 g, 188.35 mmol) and potassium carbonate (52.06 g, 376.70 mmol) at 10-20° C. After reacting for 2 h at 80° C., the mixture was cooled to 10-20° C., filtered and then the filtrate was concentrated in vacuo to give crude product. The crude product was purified by flash column chromatography eluted with Pet. Ether/EtOAc (20:1 to 10:1) to give tert-butyl (S)-4,4-difluoro-2-(((4-fluoro-2-nitrophenyl)amino)methyl)pyrrolidine-1-carboxylate (31.00 g, 78.30 mmol, 41.57%).

$^1$HNMR (CDCl3, 400 MHz): δ 8.21 (br.s., 1H), 7.92 (d, J=8.0 Hz, 1H), 7.36-7.30 (m, 1H), 7.24 (br.s., 1H), 4.37 (br.s., 1H), 3.88-3.65 (m, 3H), 3.41 (td, m, 1H), 2.65-2.47 (m, 1H), 2.36 (br.s., 1H), 1.52 (br.s., 9H).

Step G: To a solution of tert-butyl (S)-4,4-difluoro-2-(((4-fluoro-2-nitrophenyl)amino)methyl)pyrrolidine-1-carboxylate (10.00 g, 26.64 mmol) in methanol (300 mL) was added Pd/C (10%, 1 g) at the atmosphere of N$_2$. The mixture was charged with H$_2$ for 3 times, then stirred for 2 h at 25-30° C. under the atmosphere of 30-40 psi H$_2$. The mixture was filtered and the filtrate was concentrated in vacuo to give tert-butyl (S)-2-(((2-amino-4-fluorophenyl)amino)methyl)-4,4-difluoropyrrolidine-1-carboxylate (9.00 g, 17.98 mmol, 67.50%).

Reaction Process: Preparation of Intermediates 43-16

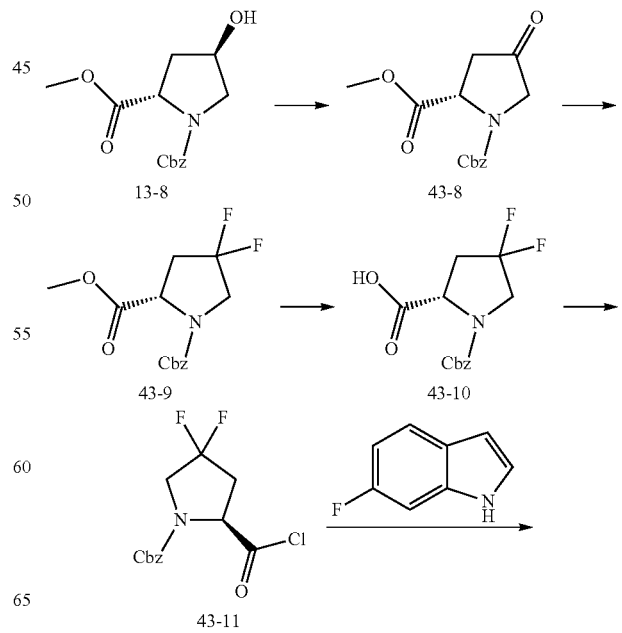

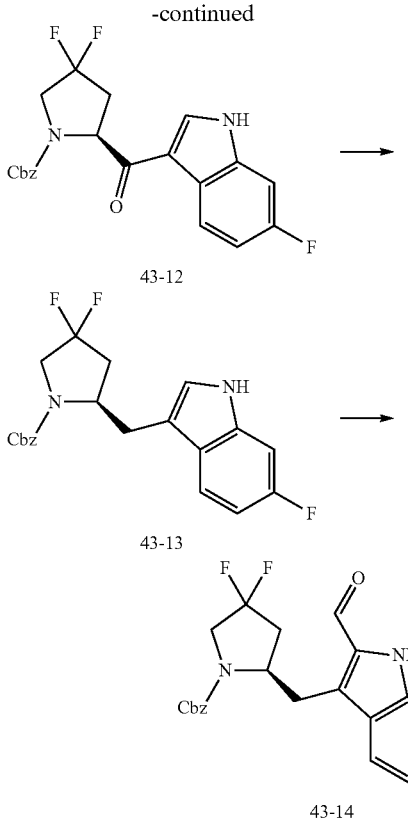

43-12

43-13

43-14

Step A: To a stirring solution of N-Cbz-cis-4-hydroxyl-L-methylprolinate (150.00 g, 537.08 mmol) in dichloromethane (1.5 L) was added trichloroisocyanuric acid (131.06 g, 563.93 mmol) and then TEMPO (8.45 g, 53.71 mmol) was added at 0° C. After stirring for 30 min at 15° C., the mixture was filtered, then quenched with aq $Na_2S_2SO_3$ (300 mL), diluted with water (500 mL) and then was extracted with dichloromethane (200 mL×2). The combinated organic phase was washed with sat.aq NaCl (300 mL), dried over anhydrous $Na_2SO_4$, and concentrated in vacuo. The residue was purified by flash column chromatography eluted with Pet. Ether/EtOAc (2/1 to 1/0) to give N-Cbz-4-oxo-L-methylprolinate (90.00 g, 324.59 mmol, 60.44%).

$^1$HNMR (CDCl3, 400 MHz): δ 7.15-7.47 (m, 5H), 5.07-5.29 (m, 2H), 4.86 (dd, J=18.36, 10.48 Hz, 1H), 3.88-4.05 (m, 2H), 3.53-3.86 (m, 3H), 2.88-3.03 (m, 1H), 2.61 (dd, J=18.89, 2.57 Hz, 1H).

Step B: To a stirring solution of N-Cbz-4-oxo-L-methylprolinate (75.00 g, 270.49 mmol) in anhydrous dichloromethane (650 mL) was added DAST (74.12 g, 459.83 mmol, 60.75 mL) in dichloromethane at 0° C. and then EtOH (249.23 mg, 5.41 mmol, 315.48 mL) was added to the mixture. After stirring for 12 h at 15° C., the mixture was quenched with water (300 mL), diluted with water (150 mL) and extracted with EtOAc (500 mL×3). The combined organic phase was washed with sat.aq NaCl, dried over anhydrous $Na_2SO_4$ and the filtrate was concentrated in vacuo to give N-Cbz-4,4-difluoro-L-methylprolinate (78 g, crude product).

$^1$HNMR (CDCl3, 400 MHz): δ 7.29-7.45 (m, 5H), 5.05-5.29 (m, 2H), 4.54-4.70 (m, 1H), 3.91 (t, J=12.92 Hz, 2H), 3.59-3.84 (m, 3H), 2.64-2.85 (m, 1H), 2.52 (qd, J=13.18, 4.89 Hz, 1H).

Step C: To a solution of N-Cbz-4,4-difluoro-L-methylprolinate (78 g, crude product) in THF (500 mL) was added aq. LiOH.H2O (32.81 g, 781.89 mmol) solution (100 mL) and the mixture was stirred for 2 h at 15° C. The mixture was concentrated in vacuo to remove THF and the aqueous phase was washed with dichloromethane (200 ml X2), then adjusted pH to 1 with hydrochloric acid solution (1 mol/L, about 40 mL), extracted with dichloromethane (400 mL×3). The organic phase was washed with sat.aq NaCl, dried over anhydrous $Na_2SO_4$ and concentrated in vacuo. The residue was purified by flash column chromatography eluted with DCM/MeOH (1/0 to 20:1) to give N-Cbz-4,4-difluoro-L-proline (50.00 g, 152.50mmol, 58.51%).

$^1$HNMR (CDCl3, 400 MHz): δ 8.77 (br.s., 1H), 7.29-7.46 (m, 5H), 5.09-5.30 (m, 2H), 4.55-4.71 (m, 1H), 3.78-4.04 (m, 2H), 2.50-2.93 (m, 2H).

Step D: To a stirring solution of oxalyl chloride (26.70 g, 210.35 mmol, 18.41 mL) in anhydrous toluene (50 mL) was added DMF (768.72 mg, 10.52 mmol, 809.18 μL, 0.10 eq) at 0° C. After the addition, the mixture was stirred for 30 min and N-Cbz-4,4-difluoro-L-proline was added at 0° C. The mixture was stirred for 5 h at 25° C., and concentrated to give N-Cbz-4,4-difluoro-L-proline chloride which was dissolved in toluene and used for next step directly.

Step E: To a stirring solution of 6-fluoro-1H-indole (21.32 g, 157.76 mmol) in toluene (100 mL) and chlorobenzene (80 mL) was added ethyl Grignard reagent (3 mol/L, 54.34 mL) dropwise at 0° C. in 30 min. After stirring for 30 min at the same temperature, the mixture was added with N-Cbz-4,4-difluoro-L-proline chloride in toluene at 0° C. and stirred for another 5 h at 25° C. The mixture was quenched with aq $NH_4Cl$ (300 mL) at 25° C., diluted with water (100 mL) and extracted with EtOAc (200 mL×2). The combined organic phase was washed with aq NaCl (50 mL×1), dried over anhydrous $Na_2SO_4$ and concentrated in vacuo. The residue was purified by flash column chromatography eluted with DCM/EtOAc (1:0 to 10:1) to give benzyl (S)-4,4-difluoro-2-(6-fluoro-1H-indole-3-carbonyl)pyrrolidine-1-carboxylate (30.00 g, 64.87 mmol, 61.68%) as buff yellow.

$^1$HNMR (DMSO, 400 MHz): δ 12.20 (d, J=9.29 Hz, 1H), 8.52 (dd, J=16.12, 2.20 Hz, 1H), 8.16 (ddd, J=16.91, 8.75, 5.71 Hz, 1H), 7.28-7.46 (m, 4H), 7.00-7.18 (m, 3H), 5.40-5.54 (m, 1H), 4.92-5.17 (m, 2H), 3.80-4.13 (m, 2H), 2.93-3.18 (m, 1H), 2.38-2.49 (m, 1H).

Step F: To a stirring solution of benzyl (S)-4,4-difluoro-2-(6-fluoro-1H-indole-3-carbonyl)pyrrolidine-1-carboxylate (30.00 g, 64.87 mmol) in THF (200 mL) was added $LiBH_4$ (2 M, 64.87 mL). The mixture was stirred for 4 h at 15° C., and then methylsulphonic acid (11.53 g, 120.00 mmol, 8.54 mL)was added, and the mixture was further stirred for 12 h at 15° C. Then the mixture was quenched with aq. $NH_4Cl$ (200 mL), and extracted with EtOAc (200 mL×2). The combined organic phase was washed with aq NaCl (50 mL), dried over $Na_2SO_4$ and concentrated in vacuo. The residue was purified by flash column chromatography eluted with Pet. Ether/EtOAc (1:0/7:1) to give benzyl (R)-4,4-difluoro-2-((6-fluoro-1H-indol-3-yl)methyl) pyrrolidine-1-carboxylate (17 g, 40.27 mmol, 62.08%).

$^1$HNMR (CDCl$_3$, 400 MHz): δ 8.13 (s, 1H), 7.36-7.54 (m, 6H), 6.83-7.10 (m, 3H), 5.24 (s, 2H), 4.30-4.52 (m, 1H), 3.65-4.07 (m, 2H), 3.22-2.52 (m, 1H), 2.75-3.00 (m, 1H), 2.16-2.44 (m, 2H).

Step G: To a stirring solution of DMF (3.76 g, 51.50 mmol, 3.96 mL) was added phosphorusoxychloride(8.15 g, 51.50 mmol, 3.96 mL) at 0° C. under $N_2$, and the mixture was stirred for 1 h at 0° C. Then the mixture was added with a solution of benzyl (R)-4,4-di fluoro-2-((6-fluoro-1H-indol-3-yl)m ethyl)pyrrolidine-1-carboxylate (10 g, 25.75 mmol,) in 1,2-dichloroethane (20 mL) dropwise at 0° C. After stirring for 11 h at 15° C., the mixture was quenched with sat.aq Na₂CO₃ (100 mL) at 0° C. and extracted with dichloromethane (60 mL×3). The combined organic phase was washed with sat.aq NaCl (60 mL×1), dried over Na₂SO₄ and concentrated in vacuo to give benzyl (R)-4,4-difluoro-2-((6-fluoro-2-formyl-1H-indol-3-yl)methyl)pyrrolidine-1-carboxyl ate (9.2 g).

Reaction process: preparation of embodiment 43

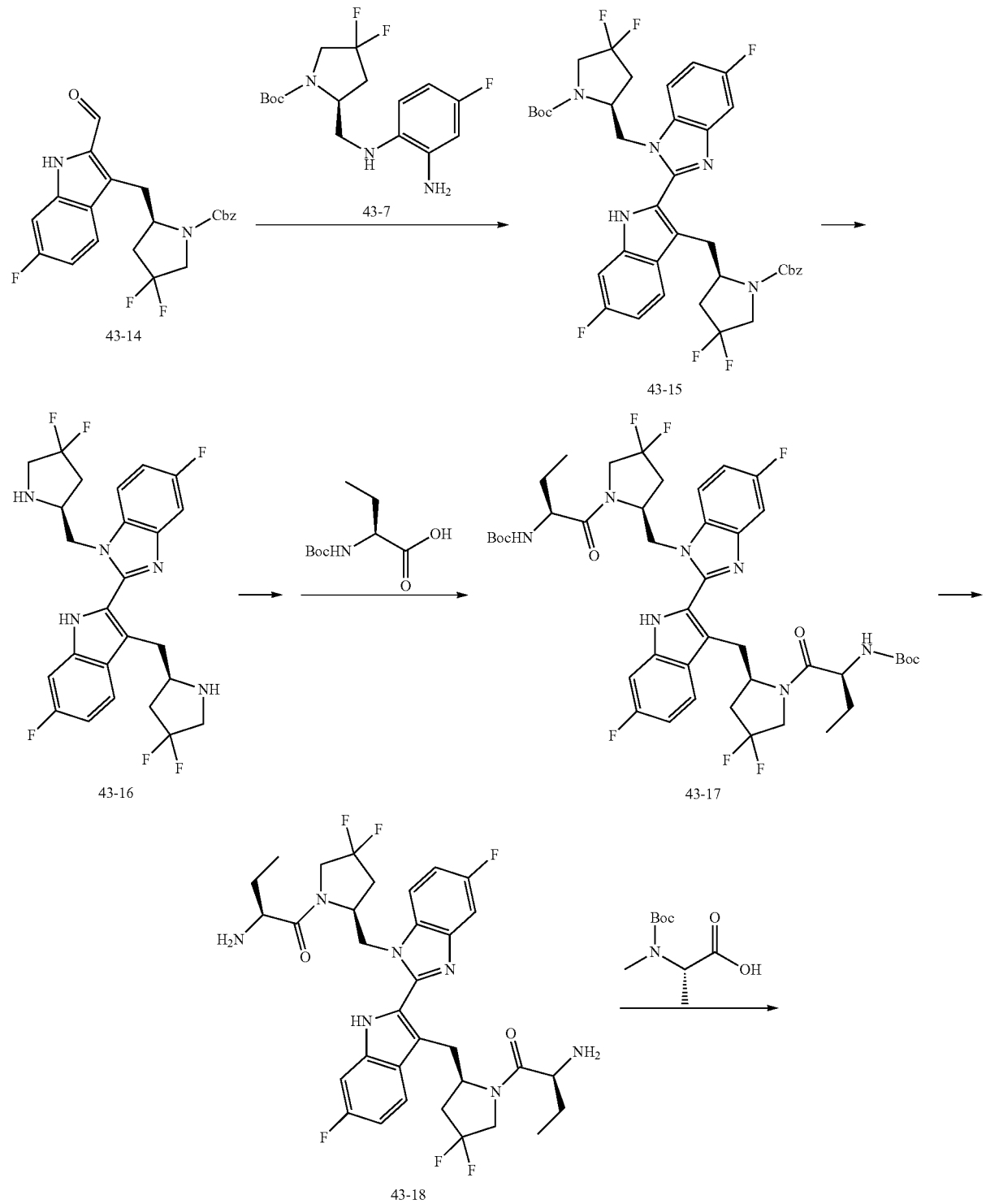

-continued

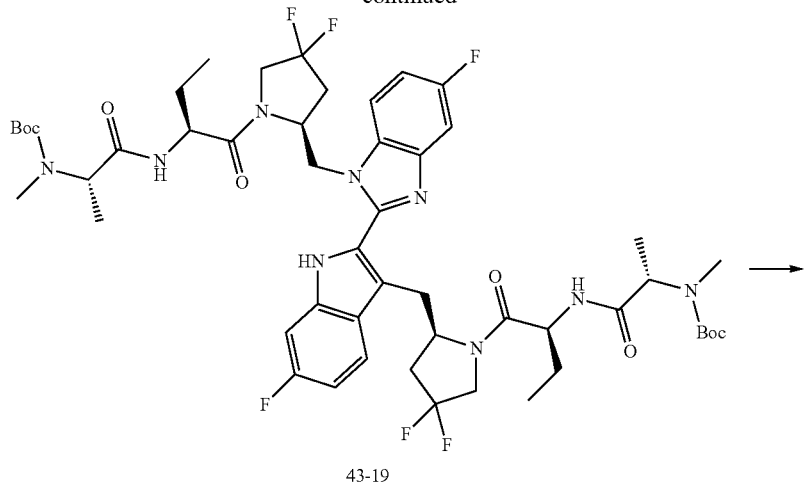

43-19

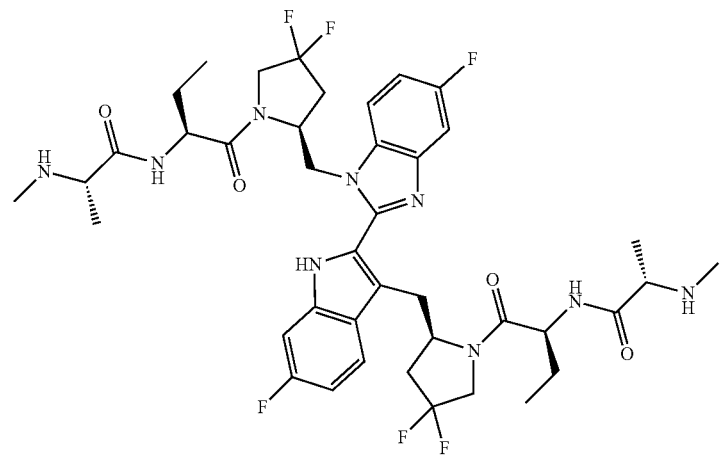

example 43

Step A: To a solution of benzyl (R)-4,4-difluoro-2-((6-fluoro-2-formyl-1H-indol-3-yl)methyl)pyrrolidine-1-carboxylate (9.04 g,8.69 mmol) in DMF (20 mL) and water (0.2 mL) was added tert-butyl (S)-2-(((2-amino-4-fluorophenyl)amino)methyl)-4,4-difluoropyrrolidine-1-carboxylate (3.00 g, 8.69 mmol) and potassium peroxymonosulfate (2.64 g, 17.38 mmol) at 10-20° C. After stirring for 16 h at the same temperature, the mixture was quenched with water (100 mL) and extracted with EtOAc (300 mL) for 3 times. The combined organic phase was washed with aq. NaCl (300 mL), dried over $Na_2SO_4$, filtered and the filtrate was concentrated in vacuo to give crude product. The crude product was purified by flash column chromatography eluted with Pet. Ether/EtOAc (10:1) to give benzyl (R)-2-((2-(1-(((S)-1-(tert-butoxycarbonyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidine-1-carboxylate (2 g, 2.56 mmol, 29.48%).

Step B: To a solution of benzyl (R)-2-((2-(1-(((S)-1-(tert-butoxycarbonyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidine-1-carboxylate (600.00 mg, 808.93 μmol) in DCM (5 mL) was added HBr/AcOH (89.74 mg, 808.93 μmol) at 10-20° C. and the mixture was stirred for 1 h at 10-20° C. The mixture was concentrated in vacuo to remove the solvent and acetic acid. The crude product was washed for 3 times with methyl tert-butyl ether (30 mL) to give 1-(((S)-4,4-difluoropyrrolidin-2-yl)methyl)-2-(3-(((R)-4,4-difluoropyrrolidin-2-yl)methyl)-6-fluoro-1H-indol-2-yl)-5-fluoro-1H-benzo[d]imidazole (500 mg, 672.34 μmol, 83.12%).

MS (ESI) m/z: 508.2 [M+H$^+$]

Step C: To a stirring solution of N-Boc-L-n-butyric acid (227.73 mg, 1.12 mmol) in DMF (2 mL) were added N-methylmorpholine (226.69 mg, 2.24 mmol) and HATU (426.08 mg, 1.12 mmol) and the mixture was stirred for 30 min at 10-20° C. Then the mixture was added with 1-(((S)-4,4-difluoropyrrolidin-2-yl)methyl)-2-(3-(((R)-4,4-difluoropyrrolidin-2-yl)methyl)-6-fluoro-1H-indol-2-yl)-5-fluoro-1H-benzo[d]imidazole (250.00 mg, 373.52 mmol) and stirred for 16 h at 10-20° C. The mixture was quenched with water (30 mL) and extracted with EtOAc (50 mL). The organic phase was washed with sat. aq. NaCl (50mL), dried over anhydrous $Na_2SO_4$, filtered and concentrated in vacuo to give crude product. The crude product was purified by thin-layer preparative chromatography with a developing agent of Pet. Ether/EtOAc (1:1) to give tert-butyl ((S)-1-((S)-2-((2-(3-(((R)-1-((S)-2-((tert-butoxycarbonyl)amino)butanoyl)-4,4-difluoropyrrolidin-2-yl)methyl)-6-fluoro-1H-indol-2-yl)-5-fluoro-1H-benzo[d]imidazol-1-yl)methyl)-4,4-difluoropyrrolidin-1-yl)-1-oxobutan-2-yl)carbamate (100 mg, 100.24 μmol, 26.84%).

MS (ESI) m/z: 878.3 [M+H$^+$]

Step D: Tert-butyl ((S)-1-((S)-2-((2-(3-(((R)-1-((S)-2-((tert-butoxycarbonyl)amino)butanoyl)-4,4-difluoropyrrolidin-2-yl)methyl)-6-fluoro-1H-indol-2-yl)-5-fluoro-1H-benzo[d]imidazol-1-yl)methyl)-4,4-difluoropyrrolidin-1-yl)-1-oxobutan-2-yl)carbamate (100 mg, 113.91 μmol) was dissolved in HCl/dioxane (113.91 μmol, 5 mL) and the mixture was stirred for 5 h at 10-20° C. The mixture was concentrated in vacuo to give (S)-2-amino-1-((R)-2-((2-(1-(((S)-1(S)-2-aminobutanoyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidin-1-yl) butan-1-one (85.00 mg, 98.52 μmol, 86.49%, hydrochloride).

MS (ESI) m/z: 678.3 [M+H$^+$]

Step E: To a solution of N-Boc-N-methyl-L-alanine (69.86 mg, 343.74 μmol) in DMF (2 mL) were added N-methylmorpholine (69.54 mg, 687.48 μmol) and HATU (130.70 mg, 343.74 μmol). The mixture was stirred for 30 min at 10-20° C., and then (S)-2-amino-1-((R)-2-((2-(1-(((S)-1-(((S)-2-aminobutanoyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidin-1-yl) butan-1-one (85.00 mg, 114.58 μmol, hydrochloride)was added. After stirring for 1.5 h at 10-20° C., the mixture was added with water (30 mL) and extracted with EtOAc (50 mL).The organic phase was washed with sat aq. NaCl (50 mL), dried over anhydrous Na$_2$SO$_4$, filtered and concentrated in vacuo to give crude product. The crude product was purified by thin-layer preparative chromatography with a developing agent of Pet. Ether/EtOAc (1:1) to give tert-butyl ((S)-1-(((S)-1-((R)-2-((2-(1-(((S)-1-((S)-2-((S)-2-((tert-butoxycarbonyl)(methyl)amino)propanamido)butanoyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidin-1-yl)-1-oxobutan-2-yl)amino)-1-oxopropan-2-yl)(methyl) carbamate (100.00 mg, 87.78 μmol 76.61%).

MS (ESI) m/z: 1048.4 [M+H$^+$]

Step F: To a solution of tert-butyl ((S)-1-(((S)-1-((R)-2-((2-(1-(((S)-1-((S)-2-((S)-2-((tert-butoxycarbonyl)(methyl)amino)propanamido)butanoyl)-4,4-difluoropyrrolidin-2-yl)methyl)-5-fluoro-1H-benzo[d]imidazol-2-yl)-6-fluoro-1H-indol-3-yl)methyl)-4,4-difluoropyrrolidin-1-yl)-1-oxobutan-2-yl)amino)-1-oxopropan-2-yl)(methyl) carbamate (100.00 mg, 95.41 μmol) in dichloromethane (4 mL) was added TFA (3.00 g, 26.29 mmol). After stirring for 2 h at 10-20° C., the mixture was concentrated in vacuo to remove the solvent. The residue was purified by prep HPLC to give embodiment 43 (30.00 mg, 32.58 μmol, 34.15%, hydrochloride).

$^1$HNMR (MeOH, 400 MHz): δ 8.83 (d, J=6.0 Hz, 1H), 8.68 (d, J=6.4 Hz, 1H), 8.18 (d, J=5.6 Hz, 1H), 7.96 (dd, J=5.0, 8.8 Hz, 1H), 7.78 (d, J=6.8 Hz, 1H), 7.58 (t, J=8.7 Hz, 1H), 7.40 (d, J=8.4 Hz, 1H), 7.12 (t, J=8.4 Hz, 1H), 4.85-4.06 (m, 10H), 3.94 (dd, J=6.8, 16.9 Hz, 2H), 3.67 (d, J=12.5 Hz, 1H), 3.10 (t, J=11.2 Hz, 2H), 2.74-2.14 (m, 11H), 1.84-1.68 (m, 2H), 1.60-1.44 (m, 7H), 1.43-1.21 (m, 2H), 1.04 (t, J=6.4 Hz, 3H), 0.90-0.78 (m, 3H).

MS (ESI) m/z: 870.3 [M+Na$^+$]

Process for preparing embodiments 44-47 can refer to the process for preparing embodiment 43

Embodiment 44

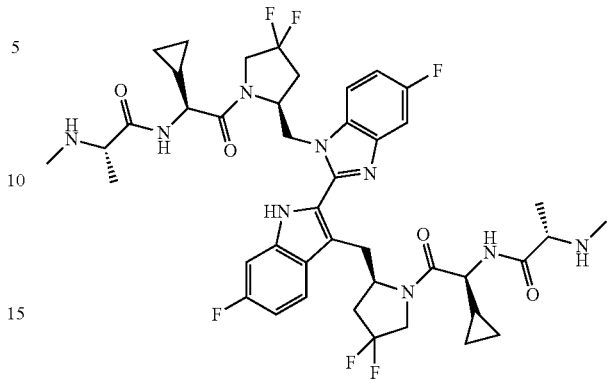

$^1$HNMR (MeOH, 400 MHz): δ 8.89 (d, J=5.0 Hz, 1H), 8.73 (d, J=5.5 Hz, 1H), 8.03 (d, J=5.9 Hz, 1H), 7.81 (dd, J=5.1, 8.6 Hz, 1H), 7.62 (d, J=6.7 Hz, 1H), 7.42 (t, J=8.2 Hz, 1H), 7.24 (d, J=9.0 Hz, 1H), 6.96 (t, J=8.8 Hz, 1H), 4.84 (br.s., 1H), 4.60-4.36 (m, 2H), 4.22-3.89 (m, 5H), 3.87-3.69 (m, 3H), 3.65-3.46 (m, 2H), 2.98 (br.s., 1H), 2.57-2.01 (m, 11H), 1.33 (dd, J=6.5, 19.4 Hz, 6H), 1.24-1.01 (m, 2H), 0.66-0.10 (m, 10H).

MS (ESI) m/z: 872.3 [M+H$^+$]

Embodiment 45

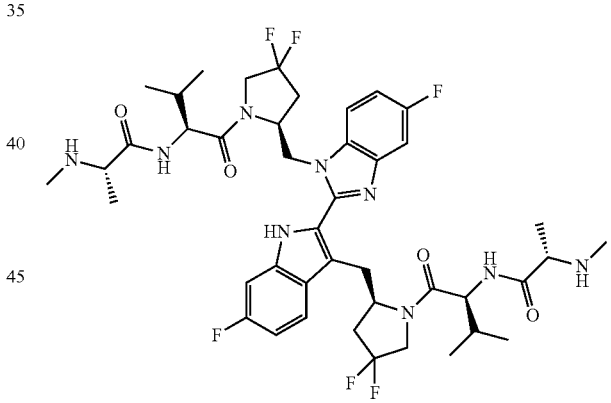

$^1$HNMR (MeOD, 400 MHz): δ 8.82 (d, J=6.9 Hz, 0.5H), 8.66 (d, J=7.5 Hz, 0.5H), 8.23 (d, J=5.5 Hz, 1H), 7.94 (dd, J=5.1, 8.8 Hz, 1H), 7.80 (d, J=6.7 Hz, 1H), 7.57 (t, J=9.0 Hz, 1H), 7.44-7.36 (m, 1H), 7.12 (t, J=8.3 Hz, 1H), 5.12-5.01 (m, 1H), 4.83 (dd, J=7.7, 14.2 Hz, 2H), 4.66 (br.s., 2H), 4.55 (br.s., 1H), 4.45-4.06 (m, 5H), 4.01-3.90 (m, 2H), 3.67 (d, J=13.4 Hz, 1H), 3.21-3.09 (m, 1H), 2.70-2.61 (m, 6H), 2.47 (d, J=13.9 Hz, 1H), 2.42-2.26 (m, 2H), 2.24-2.08 (m, 2H), 1.91 (dd, J=6.5, 13.1 Hz, 1H), 1.45 (dd, J=6.8, 16.6 Hz, 6H), 1.05 (t, J=6.8 Hz, 6H), 0.86-0.75 (m, 6H).

MS (ESI) m/z: 876.3 [M+H$^+$]

Embodiment 46

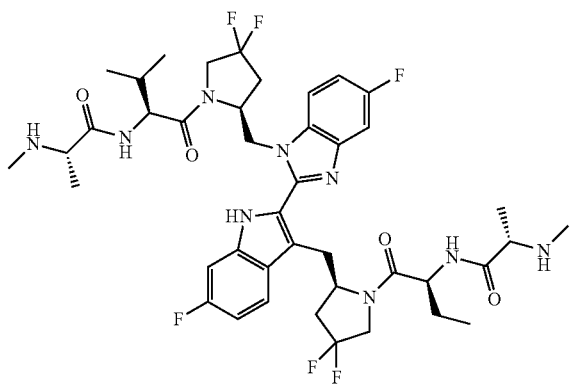

¹HNMR (MeOD, 400 MHz): δ 8.71 (d, J=4.0 Hz, 1H), 8.55 (d, J=8.0 Hz, 1H), 8.13 (d, J=4.0 Hz, 1H), 7.84 (dd, J=8.0, 4.0 Hz, 1H), 7.68 (d, J=8.0 Hz, 1H), 7.47 (t, J=8.0 Hz, 1H), 7.30 (d, J=8.0 Hz, 1H), 7.01 (t, J=8.0 Hz, 1H), 4.94 (d, J=12.0 Hz, 1H), 4.30-4.64 (m, 3H), 3.97-4.29 (m, 5H), 3.83 (d, J=4.0 Hz, 2H), 3.55 (d, J=12.0 Hz, 1H), 3.03 (br.s., 1H), 2.50-2.61 (m, 6H), 1.98-2.49 (m, 5H), 1.81 (d, J=4.0 Hz, 1H), 1.56-1.76 (m, 2H), 1.28-1.43 (m, 6H), 0.93 (t, J=8.0 Hz, 3H), 0.72 ppm (dd, J=12.0, 8.0 Hz, 6H).

MS (ESI) m/z: 862.2 [M+H⁺]

Embodiment 47

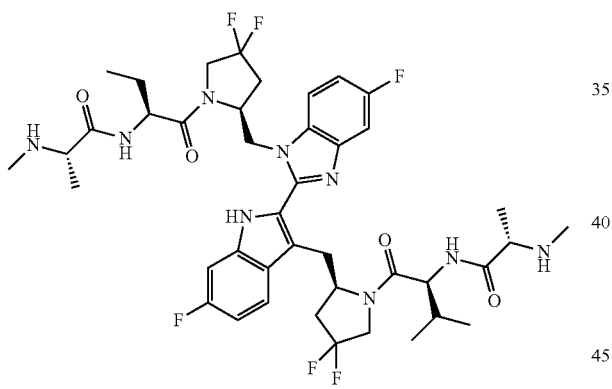

¹HNMR (MeOD, 400 MHz): δ 8.79 (d, J=8.0 Hz, 1H), 8.67 (d, J=8.0 Hz, 1H), 8.18 (d, J=8.0 Hz, 1H), 7.98 (dd, J=4.0, 8.0 Hz, 1H), 7.80 (d, J=8.0 Hz, 1H), 7.59 (t, J=8.0 Hz, 1H), 7.41 (dd, J=4.0, 8.0 Hz, 1H), 7.13 (t, J=8.0 Hz, 1H), 5.06-4.94 (m, 2H), 4.81 (br.s., 1H), 4.70 (br.s., 1H), 4.58 (br.s., 1H), 4.46-4.08 (m, 6H), 4.02-3.86 (m, 2H), 3.70 (d, J=16.0 Hz, 1H), 3.18-3.07 (m, 1H), 2.67 (d, J=12.0 Hz, 6H), 2.52 (d, J=12.0 Hz, 1H), 2.43-2.08 (m, 4H), 1.53-1.42 (m, 6H), 1.40-1.27 (m, 2H), 1.06 (t, J=8.0 Hz, 6H), 0.83 (t, J=8.0 Hz, 3H).

MS (ESI) m/z: 862.2 [M+H⁺]

Embodiment 48

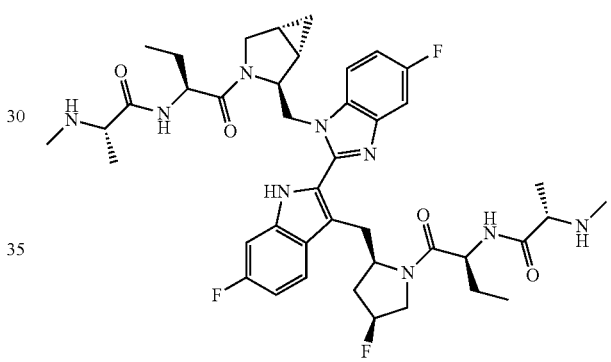

Reaction Process: the Preparation of Embodiment 48

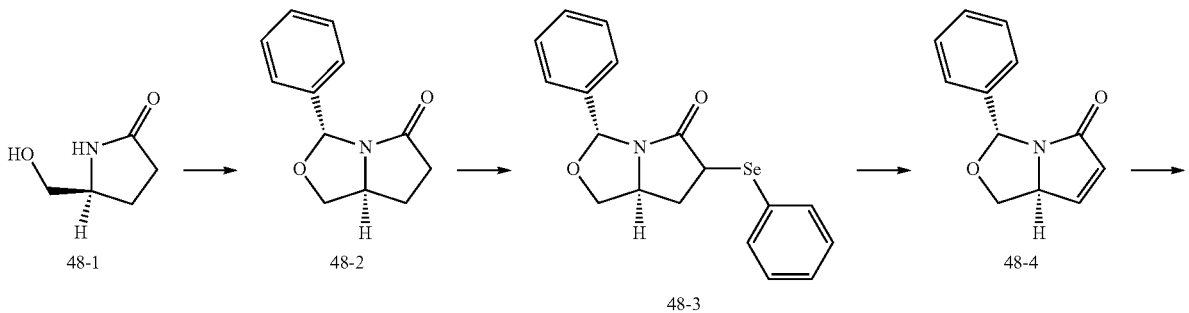

-continued
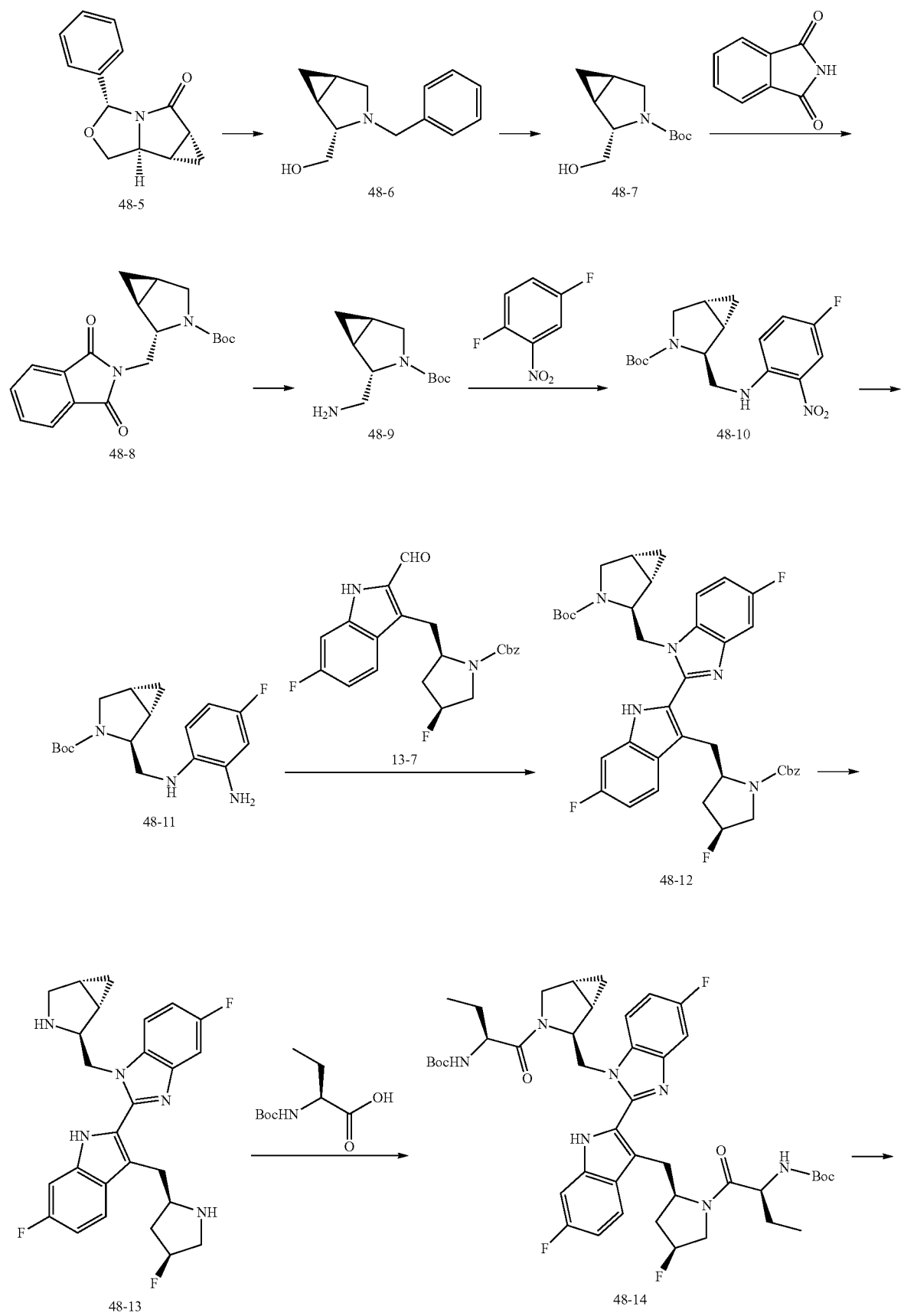

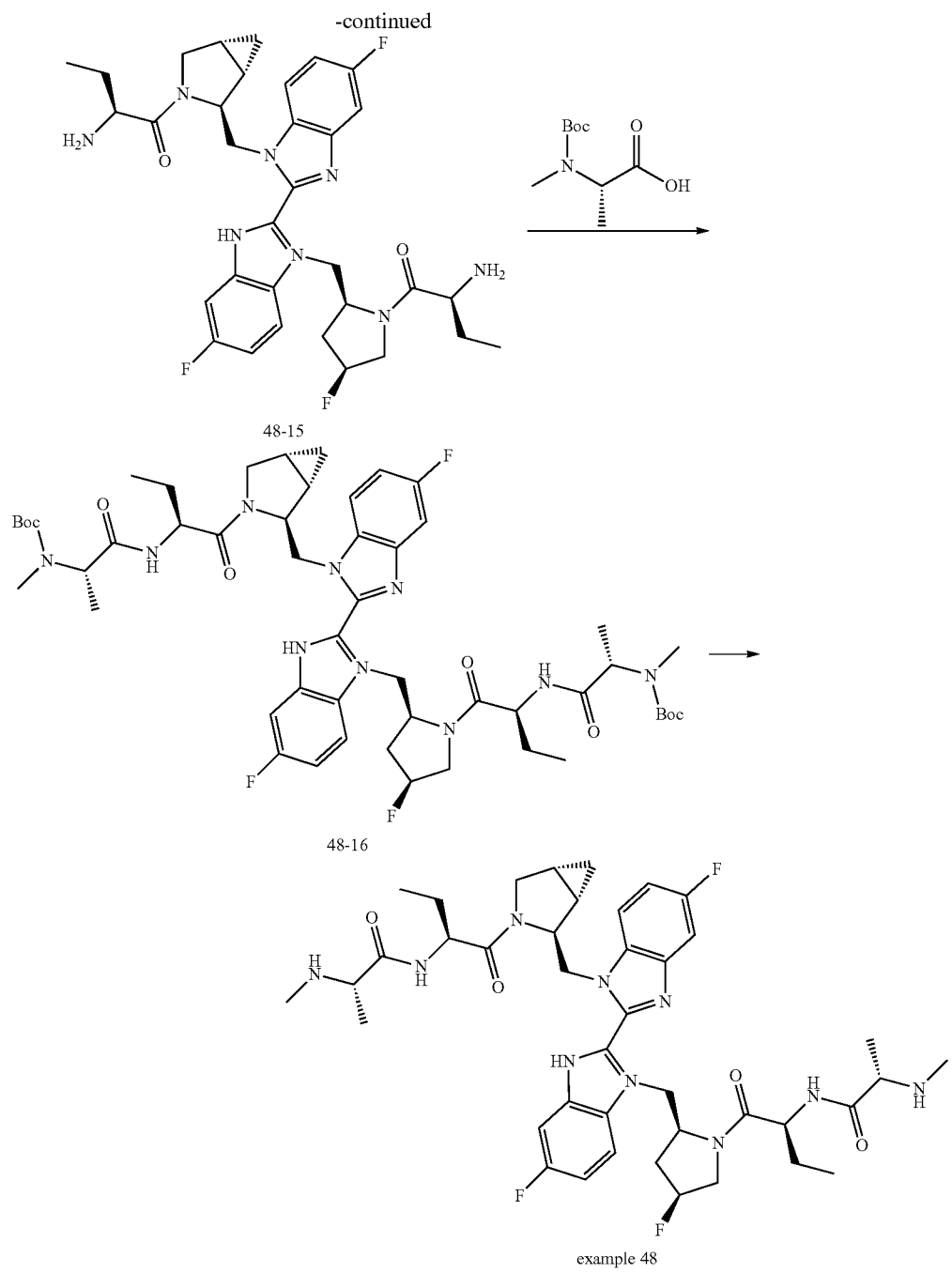

example 48

Step A: A stirring solution of L-pyroglutaminol (15 g, 130.29 mmol), benzaldehyde (15.90 g, 149.83 mmol, 15.14 mL) and p-toluenesulfonic acid monohydrate (1.24 g, 6.51 mmol) in toluene (250 mL) was refluxed for 5 h, and then cooled to room temperature, quenched with sat.aq Na₂CO₃ (300 mL) and extracted with EtOAc (200 mL×3). The combined organic phase was washed with aq. NaCl (100 mL×1), dried over Na₂SO₄ and concentrated in vacuo. The residue was purified by flash column chromatography eluted with Pet. Ether/EtOAc (2/1 to 2/3) to give (3R,7aS)-3-phenyltetrahydro-3H,5H-pyrrolo [1,2-c]oxazol-5-one (11 g, 47.09 mmol, 36.14%).

¹HNMR (CDCl₃, 400 MHz): δ 7.52-7.29 (m, 5H), 6.34 (s, 1H), 4.27-4.21 (m, 1H), 4.20-4.10 (m, 1H), 3.49 (t, J=8.03 Hz, 1H), 2.82 (dt, J=17.38, 9.57 Hz, 1H), 2.56 (ddd, J=17.35, 9.94, 3.70 Hz, 1H), 2.44-2.33 (m, 1H), 2.04-1.87 (m, 1H).

Step B: To a solution of (3R,7aS)-3-phenyltetrahydro-3H, 5H-pyrrolo[1,2-c]oxazol-5-one (14 g, 68.88 mmol) in anhydrous THF (28 mL) was added KHMDS (1 M, 68.88 mL)at −78° C. After the addition, the mixture was stirred for 30 min at −78° C. Then the mixture was added with trimethylsilyl chloride (9.73 g, 89.54 mmol, 11.31 mL) in anhydrous THF (20 mL), warmed to 0° C. in 1 h, and stirred for 3 h at 0° C. Then the mixture was added with a solution of bromoselenobenzene(18.04 g, 76.46 mmol)in anhydrous THF (20 mL) while the temperature was maintained at 0° C., and the mixture was stirred for 7.5 h at 17° C., then quenched with sat.aq NaHCO₃ (250 mL) and extracted with EtOAc (250 mL×3). The combined organic phase was washed with aq. NaCl (100 mL×1), dried over Na₂SO₄ and concentrated in vacuo. The residue was purified by flash column chromatography eluted with Pet. Ether/EtOAc (4:1) to give (3R,7aS)-3-phenyl-6-(phenylselanyl)tetrahydro-3H,5H-pyrrolo[1,2-c]oxazol-5-one (20 g).

Step C: To a solution of (3R,7aS)-3-phenyl-6-(phenylselanyl)tetrahydro-3H,5H-pyrrolo[1,2-c]oxazol-5-one (19 g, 53.03 mmol) in EtOAc (190 mL) was added aq. H₂O₂ (30%, 23.90 mL) at 0° C. After stirring for 30 min at 0° C., the mixture was added with methanesulfonic acid (11.53 g, 120.00 mmol, 8.54 mL) and stirred for 12 h at 15° C. The mixture was added with water (100 mL) and extracted with EtOAc (200 mL×1). The combined organic phase was washed with aq. NaCl (100 mL×1), dried over Na₂SO₄ and concentrated in vacuo. The residue was purified by flash column chromatography eluted with Pet. Ether/EtOAc (4:1 to 0:1) to give (3R,7aS)-3-phenyl-1,7a-dihydro-3H,5H-pyrrolo[1,2-c]oxazol-5-one (7.4 g, 36.78 mmol, 69.35%).

¹HNMR (CDCl₃, 400 MHz): δ 7.40-7.32 (m, 2H), 7.25-7.13 (m, 3H), 7.09 (dd, J=5.93, 1.65 Hz, 1H), 6.04-5.96 (m, 2H), 4.48-4.40 (m, 1H), 4.13-4.06 (m, 1H), 3.25 (t, J=8.31 Hz, 1H).

Step D: To a solution of dimethyl sulfoxide (160 mL) was added NaH (3.05 g, 76.33 mmol, 60%) at 15° C., and then was added trimethylsulfoxonium iodide (18.90 g, 85.88 mmol, 11.31 mL) in batches and the mixture was stirred for 30 min at the same temperature. The mixture was warmed to 55° C. and stirred for 30 min, and then (3R,7aS)-3-phenyl-1,7a-dihydro-3H,5H-pyrrolo[1,2-c]oxazol-5-one (6.40 g, 31.81 mmol) in dimethyl sulfoxide (64 mL) was added and the mixture was stirred for 2 h at 55° C., then cooled to 4° C., quenched with water (500 mL) and extracted with methyl tert-butyl ester (200 mL×2). The combined organic phase was washed with aq. NaCl (100 mL×1), dried over Na₂SO₄ and concentrated in vacuo. The residue was purified by flash column chromatography eluted with EtOAc/Pet. Ether (20/1 to 10/1) to give (3R,5aR,6aS,6bS)-3-phenyltetrahydro-3H-cyclopropa[3,4]pyrrolo[1,2-c]oxazol-5(1H)-one (4,7 g, 20.09 mmol, 63.15%).

¹HNMR (CDCl₃, 400 MHz): δ 7.42-7.29 (m, 5H), 6.39-6.30 (m, 1H), 4.23 (dd, J=7.78, 6.15 Hz, 1H), 3.91 (dd, J=9.16, 6.27 Hz, 1H), 3.48 (dd, J=9.47, 7.97 Hz, 1H), 2.21-1.99 (m, 2H), 1.38-1.30 (m, 1H), 1.20-1.13 (m, 1H).

Step E: To a solution of (3R,5aR,6aS,6bS)-3-phenyltetrahydro-3H-cyclopropa[3,4]pyrrolo[1,2-c]oxazol-5(1H)-one (5 g, 23.23 mmol) in anhydrous THF (30 mL) was added a suspension of LiAlH₄ (1.5 g, 39.49 mmol) in anhydrous THF (30 mL) at 0° C. The mixture was warmed to reflux and stirred for 1 h, and then cooled to 0° C. and water (1.5 mL)was added dropwise slowly. The mixture was added with aq 15% aq. NaOH (1.5 mL), THF (15 mL) and water (5 mL) successively and stirred strongly for 0.5 h. The mixture was dried over Na₂SO₄, filtered and concentrated in vacuo to give ((1S,2S,5R)-3-benzyl-3-azabicyclo[3.1.0]hexan-2-yl)methanol (4.5 g, 22.14 mmol, 95.31%).

¹HNMR (CDCl₃, 400 MHz): δ 7.42-7.29 (m, 5H), 6.39-6.30 (m, 1H), 4.23 (dd, J=7.78, 6.15 Hz, 1H), 3.91 (dd, J=9.16, 6.27 Hz, 1H), 3.48 (dd, J=9.47, 7.97 Hz, 1H), 2.21-1.99 (m, 2H), 1.38-1.30 (m, 1H), 1.20-1.13 (m, 1H).

Step F: To a solution of ((1S,2S,5R)-3-benzyl-3-azabicyclo[3.1.0]hexan-2-yl)methanol (4.5 g, 22.14 mmol) and Boc₂O (7.25 g, 33.21 mmol, 7.63 mL) in EtOAc (150 mL) was added Pd/C (788.08 mg, 442.74 μmol, 5%) at 15° C. The mixture was stirred for 12 h at the atmosphere of 15 psi H₂ and then filtered, the filtrate was concentrated in vacuo to give tert-butyl (1S,2S,5R)-2-(hydroxymethyl)-3-azabicyclo[3.1.0]hexane-3-carboxylate (3.8 g, 17.82 mmol, 80.50%).

¹HNMR (CDCl₃, 400 MHz): δ 4.12-3.30 (m, 6H), 1.48-1.43 (m, 9H), 1.41-1.21 (m, 2H), 0.77-0.67 (m, 1H), 0.17 (dt, J=8.16, 3.95 Hz, 1H).

Step G: To a solution of tert-butyl (1S,2S,5R)-2-(hydroxymethyl)-3-azabicyclo[3.1.0]hexane-3-carboxylate (3.80 g, 17.82 mmol), phthalimide (2.88 g, 19.60 mmol) and triphenylphosphine (5.14 g, 19.60 mmol) in anhydrous THF (40 mL) was added DIAD (3.96 g, 19.60 mmol, 3.81 mL) in anhydrous THF (5 mL) at 0° C. under N₂ and then the mixture was warmed to 15° C. and stirred for 11 h. The mixture was quenched with water (300 mL) and then extracted with EtOAc (300 mL×4). The combined organic phase was washed with aq NaCl (200 mL×1), dried over Na₂SO₄ and concentrated in vacuo. The residue was purified by flash column chromatography eluted with EtOAc/Pet. Ether (9.1-25%) to give tert-butyl (1S,2S,5R)-2-((1,3-dioxoisoindolin-2-yl)methyl)-3-azabicyclo[3.1.0]hexane-3-carboxylate (6 g, 15.85 mmol, 88.97%).

¹HNMR (CDCl3, 400 MHz): δ 7.90-7.81 (m, 2H), 7.76-7.63 (m, 2H), 4.37-4.16 (m, 1H), 3.92-3.74 (m, 2H), 3.73-3.47 (m, 1H), 3.35 (dd, J=10.98, 4.20 Hz, 1H), 1.50-1.35 (m, 2H), 1.22 (s, 9H), 0.65(td, J=7.69, 5.33 Hz, 1H), 0.23-0.05 (m, 1H).

MS (ESI) m/z: 744.1 [2M+Na⁺]

Step H: To a solution of tert-butyl (1S,2S,5R)-2-((1,3-dioxoisoindolin-2-yl)methyl)-3-azabicyclo[3.1.0]hexane-3-carboxylate (6 g, 15.85 mmol) in ethanol (40 mL) was added hydrazine hydrate (39.63 mmol, 2.27 mL, 85%) at 78° C. under N₂. After stirring for 2 h at 78° C., the mixture was filtered and the filtrate was concentrated in vacuo to give crude product, tert-butyl (1S,2S,5R)-2-(aminomethyl)-3-azabicyclo[3.1.0]hexane-3-carboxylate (3.7 g).

¹HNMR (CDCl3, 400 MHz): δ 3.83-3.26 (m, 3H), 2.87-2.72 (m, 2H), 1.44 (d, J=2.20 Hz, 9H), 1.41-1.38 (m, 1H), 1.36-1.29 (m, 1H), 0.73-0.62 (m, 1H), 0.12 (quin, J=4.46 Hz, 1H).

Step I: To a solution of tert-butyl (1S,2S,5R)-2-(aminomethyl)-3-azabicyclo[3.1.0]hexane-3-carboxylate (3.7 g) and potassium carbonate in acetonitrile (30 mL) was added 1,4-difluor-2-nitrobenzene (2.77 g, 17.43 mmol, 1.89 mL) at 15° C. under N₂.The mixture was warmed to 82° C. and stirred for 2 h. The mixture was added with water (100 mL) and then extracted with EtOAc (200 mL×1). The combined organic phase was washed with aq NaCl (100 mL×1), dried over Na₂SO₄ and concentrated in vacuo. The residue was purified by flash column chromatography eluted with Pet. Ether/EtOAc (20/1 to 10/1) to give tert-butyl (1S,2S,5R)-2-(((4-fluoro-2-nitrophenyl)amino)methyl)-3-azabicyclo[3.1.0]hexane-3-carboxylate (5.3 g, 15.05 mmol, 86.37%).

¹HNMR (CDCl3, 400 MHz): δ 8.38-8.14 (m, 1H), 7.90 (td, J=9.76, 2.95 Hz, 1H), 7.14-6.92 (m, 1H), 4.28-4.09 (m, 1H), 3.62-3.34 (m, 4H), 1.65-1.56 (m, 1H), 1.47 (d, J=14.81 Hz, 10H), 0.82-0.72 (m, 1H), 0.26-0.16 (m, 1H).

Step J: To a solution of tert-butyl (1S,2S,5R)-2-(((4-fluoro-2-nitrophenyl)amino)methyl)-3-azabicyclo[3.1.0]hexane-3-carboxylate (5.3 g, 15.05 mmol) in EtOAc (150 mL) and methanol (150 mL) was added Pd/C (826.59 mg, 779.80 μmol 10%) at 25° C. under the atmosphere of N₂. The mixture was stirred for 2 h at 25° C. under the atmosphere of 30 psi H₂. The mixture was filtered and the filtrate was concentrated in vacuo to give tert-butyl (1S,2S,5R)-2-(((2-amino-4-fluorophenyl)amino)methyl)-3-azabicyclo[3.1.0]hexane-3-carboxylate (4.5 g, 14.00 mmol, 93.03%).

¹HNMR (CDCl3, 400 MHz): δ 6.70-6.37 (m, 3H), 3.79-3.07 (m, 7H), 1.48-1.38 (m, 11H), 0.76-0.68 (m, 1H), 0.24-0.14 (m, 1H).

Step K: To a solution of tert-butyl (1S,2S,5R)-2-(((2-amino-4-fluorophenyl)amino)methyl)-3-azabicyclo[3.1.0]hexane-3-carboxylate (1 g, 3.11 mmol) and benzyl (2R,4S)-4-fluoro-2-((6-fluoro-2-formyl-1H-indol-3-yl)methyl)pyrrolidine-1-carboxylate (2.48 g, 3.11 mmol) in DMF (12 mL) and water (600 μL) was added Oxone (1.42 g, 9.33 mmol) at 25° C. After stirring for 2 h at the same temperature, the mixture was quenched with sat. aq NaHCO₃ (20 mL) and sat.aq sodium thiosulfate respectively and extracted with EtOAc (20 mL×3). The combined organic phase was washed with aq. NaCl (20 mL×1), dried over Na₂SO₄, and concentrated in vacuo. The residue was purified by flash column chromatography eluted with DCM/EtOAc (30:1 to 11:1) to give tert-butyl (1S,2S,5R)-2-((2-(3-(((2R,4S)-1-((benzyloxy)carbonyl)-4-fluoropyrrolidin-2-yl)methyl)-6-fluoro-1H-indol-2-yl)-5-fluoro-1H-benzo[d]imidazol-1-yl)methyl)-3-azabicyclo[3.1.0]hexane-3-carboxylate (1 g, 1.17 mmol, 37.68%).

¹HNMR (CDCl3, 400 MHz): δ 7.47-7.29 (m, 8H), 7.08 (d, J=8.93 Hz, 4H), 5.36-4.81 (m, 4H), 3.83-3.35 (m, 5H), 1.93-1.57 (m, 2H), 1.40-1.22 (m, 8H), 1.09-0.85 (m, 5H), 0.55-0.38 (m, 1H), −0.04 (d, J=15.16 Hz, 1H).

Step L: To a solution of tert-butyl (1S,2S,5R)-2-((2-(3-(((2R,4S)-1-((benzyloxy)carbonyl)-4-fluoropyrrolidin-2-yl)methyl)-6-fluoro-1H-indol-2-yl)-5-fluoro-1H-benzo[d]imidazol-1-yl)methyl)-3-azabicyclo[3.1.0]hexane-3-carboxylate (1 g, 1.17 mmol) was added HBr/AcOH (5 mL, 35%) at 15° C. and the mixture was stirred for 1 h at 15° C. The mixture was added with water (50 mL) and extracted with methyl tert-butyl ester (20 mL×3), and then the aqueous phase was adjust to pH to 10 with Na₂CO₃ and extracted with dichloromethane (50 mL×4). The combined organic phase was washed with aq. NaCl (50 mL×1), dried over Na₂SO₄, and concentrated in vacuo to give 1-(((1S,2S,5R)-3-azabicyclo[3.1.0]hexan-2-yl)methyl)-5-fluoro-2-(6-fluoro-3-(((2R,4S)-4-fluoropyrrolidin-2-yl)methyl)-1H-indol-2-yl)-1H-benzo[d]imidazole (600 mg, crude product).

¹HNMR (CDCl3, 400 MHz): δ 14.74 (br.s., 1H), 7.89 (ddd, J=17.82, 8.85, 5.08 Hz, 2H), 7.66 (dd, J=9.41, 2.38 Hz, 1H), 7.38-7.25 (m, 2H), 7.06 (td, J=9.22, 2.26 Hz, 1H), 5.67-5.46 (m, 1H), 4.43 (d, J=14.68 Hz, 1H), 4.20-3.95 (m, 4H), 3.52-3.33 (m, 5H), 3.08 (dd, J=11.42, 3.01 Hz, 1H), 2.31-2.16 (m, 1H), 1.74-1.64 (m, 1H), 1.61-1.53 (m, 1H), 0.62 (td, J=7.65, 4.64 Hz, 1H), 0.37 (q, J=4.02 Hz, 1H).

Step M: To a stirring solution of N-Boc-L-n-butyric acid (432.21 mg, 2.13 mmol) and N-methylmorpholine (286.82 mg, 2.84 mmol, 311.76 μL) in DMF (5 mL) was added HATU (808.64 mg, 2.13 mmol) at 15° C. and then was added 1-(((1S,2S,5R)-3-azabicyclo[3.1.0]hexan-2-yl)methyl)-5-fluoro-2-(6-fluoro-3-(((2R,4 S)-4-fluoropyrrolidin-2-yl)methyl)-1H-indol-2-yl)-1H-benzo[d]imidazole (330 mg, crude product) and the mixture was stirred for 2 h at 15° C. The mixture was purified by reversed-phase column eluted with acetonitrile and aq TFA (1‰) to give tert-butyl ((S)-1-((1S,2S,5R)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)-3-azabicyclo[3.1.0]hexan-3-yl)-1-oxobutan-2-yl)carbamate (390 mg, 452.54 mmol, 63.84%).

¹HNMR (CDCl3, 400 MHz): δ 7.56-7.38 (m, 3H), 7.22 (d, J=9.16 Hz, 2H), 7.15-6.95 (m, 5H), 5.33 (d, J=8.66 Hz, 1H), 4.74-4.52 (m, 4H), 4.41-4.06 (m, 7H), 4.01-3.71 (m, 8H), 3.66-3.55 (m, 3H), 1.82 (dt, J=13.43, 6.71 Hz, 4H), 1.73-1.59 (m, 6H), 1.47-1.41 (m, 30H), 1.04-0.96 (m, 5H), 0.93-0.79 (m, 3H), 0.73-0.52 (m, 6H), 0.43 (t, J=7.28 Hz, 1H), 0.14-0.07 (m, 1H).

Step N: To a solution of tert-butyl ((S)-1-((1S,2S,5R)-2-((2-(3-(((2R,4S)-1-((S)-2-((tert-butoxycarbonyl)amino)butanoyl)-4-fluoropyrrolidin-2-yl)methyl)-6-fluoro-1H-indol-2-yl)-5-fluoro-1H-benzo[d]imidazol-1-yl)methyl)-3-azabicyclo[3.1.0]hexan-3-yl)-1-oxobutan-2-yl)carbamate (390 mg, 452.54 μmol) in DCM (2 mL) was added TFA (2 mL) at 15° C. The mixture was stirred for 12 h at 15° C. and then concentrated in vacuo to give crude product (S)-2-amino-1-((2R,4S)-2-((2-(1-(((1S,2S,5R)-3-((S)-2-aminobutanoyl)-3-azabicyclo[3.1.0]hexan-2-yl)methyl)-5-fluoro-1H-benzo[d]imidazol-2-yl)-6-fluoro-1H-indol-3-yl)methyl)-4-fluoropyrrolidin-1-yl)butan-1-one (trifluoroacetate, 403 mg).

Step O: To a stirring solution of N-Boc-N-methyl-L-alanine (432.21 mg, 1.4 mmol) and N-methylmorpholine (283.15 mg, 2.80 mmol) in DMF (5 mL) was added HATU (532.20 mg, 1.4 mmol) at 15° C. and then added (S)-2-amino-1-((2R,4S)-2-((2-(1-(((1S,2S,5R)-3-((S)-2-aminobutanoyl)-3-azabicyclo[3.1.0]hexan-2-yl)methyl)-5-fluoro-1H-benzo[d]imidazol-2-yl)-6-fluoro-1H-indol-3-yl)methyl)-4-fluoropyrrolidin-1-yl)butan-1-one (403 mg). After stirred for 0.5 h at 15° C., the mixture was purified by reversed-phase column eluted with acetonitrile and aq TFA (1‰) to give tert-butyl ((S)-1-(((S)-1-((2R,4S)-2-((2-(1-(((1S,2S,5R)-3-((S)-2-((S)-2-((tert-butoxycarbonyl)(methyl)amino)propanamido)butanoyl)-3-azabicyclo[3.1.0]hexan-2-yl)methyl)-5-fluoro-1H-benzo[d]imidazol-2-yl)-6-fluoro-1H-indol-3-yl)methyl)-4-fluoropyrrolidin-1-yl)-1-oxobutan-2-yl)amino)-1-oxopropan-2-yl)(methyl)carbamate (350 mg, 347.86 μmol, 74.56%).

¹HNMR (CDCl3, 400 MHz): δ 8.07-7.97 (m, 1H), 7.30 (d, J=8.91 Hz, 1H), 7.10 (d, J=8.28 Hz, 1H), 7.04-6.96 (m, 2H), 6.94-6.85 (m, 2H), 5.14-4.90 (m, 2H), 4.60-4.39 (m, 7H), 3.89-3.69 (m, 5H), 6.67-3.46 (m, 4H), 2.78-2.65 (m, 11H), 1.84-1.52 (m, 8H), 1.50-1.35 (m, 35H), 1.11-0.97 (m, 3H), 0.96-0.67 (m, 7H), 0.60-0.42 (m, 5H), 0.06-0.06 (m, 1H).

Step P: To a solution of tert-butyl ((S)-1-(((S)-1-((2R,4S)-2-((2-(1-(((1S,2S,5R)-3-((S)-2-((S)-2-((tert-butoxycarbonyl)(methyl)amino)propanamido)butanoyl)-3-azabicyclo[3.1.0]hexan-2-yl)methyl)-5-fluoro-1H-benzo[d]imidazol-2-yl)-6-fluoro-1H-indol-3-yl)methyl)-4-fluoropyrrolidin-1-yl)-1-oxobutan-2-yl)amino)-1-oxopropan-2-yl)(methyl)carbamate (350 mg, 347.86 μmol) in dichloromethane (2 mL) was added TFA (2 mL) at 15° C. After stirring for 12 h at 15° C., the mixture was concentrated in vacuo to give crude product. The crude product was purified by prep HPLC to give embodiment 48 (hydrochloride, 170 mg, 193.43 μmol, 55.61%).

¹HNMR (MeOD, 400 MHz): δ 8.13 (dd, J=9.05, 3.79 Hz, 1H), 7.85 (dd, J=8.80, 5.14 Hz, 1H), 7.75 (dd, J=7.70, 1.96 Hz, 1H), 7.46 (t, J=9.11 Hz, 1H), 7.37 (dd, J=9.29, 1.83 Hz, 1H), 7.04 (td, J=9.17, 1.96 Hz, 1H), 5.47-5.22 (m, 1H), 4.89 (m, J=6.80 Hz, 1H), 4.79-4.70 (m, 2H), 4.46 (d, J=6.72 Hz, 2H), 4.31 (t, J=6.79 Hz, 1H), 4.19-4.06 (m, 1H), 4.04-3.66 (m, 6H), 3.56 (d, J=11.74 Hz, 1H), 3.20-3.09 (m, 1H), 2.63 (s, 3H), 2.55 (s, 3H), 2.14-1.60 (m, 5H), 1.49-1.42 (m, 3H), 1.38 (d, J=6.97 Hz, 4H), 1.33 (dd, J=17.73, 7.46 Hz, 1H), 1.03 (t, J=7.27 Hz, 3H), 0.71-0.62 (m, 3H), 0.60 (d, J=5.62 Hz, 1H), 0.00 (d, J=4.40 Hz, 1H).

MS (ESI) m/z: 806 [M+H⁺]

Process for preparing embodiment 49 can refer to the process for preparing embodiment 48

Embodiment 49
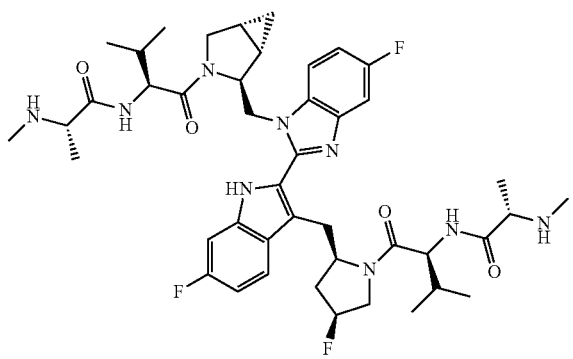
¹HNMR (MeOD, 400 MHz): δ 8.24 (dd, J=9.03, 3.76 Hz, 1H), 7.98-7.82 (m, 2H), 7.63-7.44 (m, 2H), 7.14 (td, J=9.13, 2.07 Hz, 1H), 5.60-5.35 (m, 1H), 5.03-4.96 (m, 1H), 4.60-4.51 (m, 1H), 4.49-4.39 (m, 2H), 4.30-4.10 (m, 4H), 4.08-3.98 (m, 2H), 3.95-3.79 (m, 3H), 3.71-3.60 (m, 1H), 2.71 (s, 3H), 2.65 (s, 3H), 2.31-2.18 (m, 2H), 2.09-1.96 (m, 1H), 1.90-1.72 (m, 1H), 1.53 (d, J=6.78 Hz, 3H), 1.45 (d, J=6.90 Hz, 4H), 1.14 (dd, J=6.46, 4.20 Hz, 6H), 0.78 (d, J=6.65 Hz, 3H), 0.69 (d, J=6.65 Hz, 4H), 0.12-0.02 (m, 1H).
MS (ESI) m/z: 834 [M+H⁺]
Embodiment 50
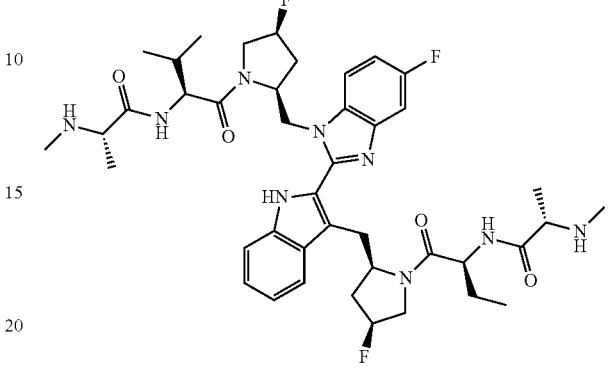
Synthetic process: preparation of embodiment 50
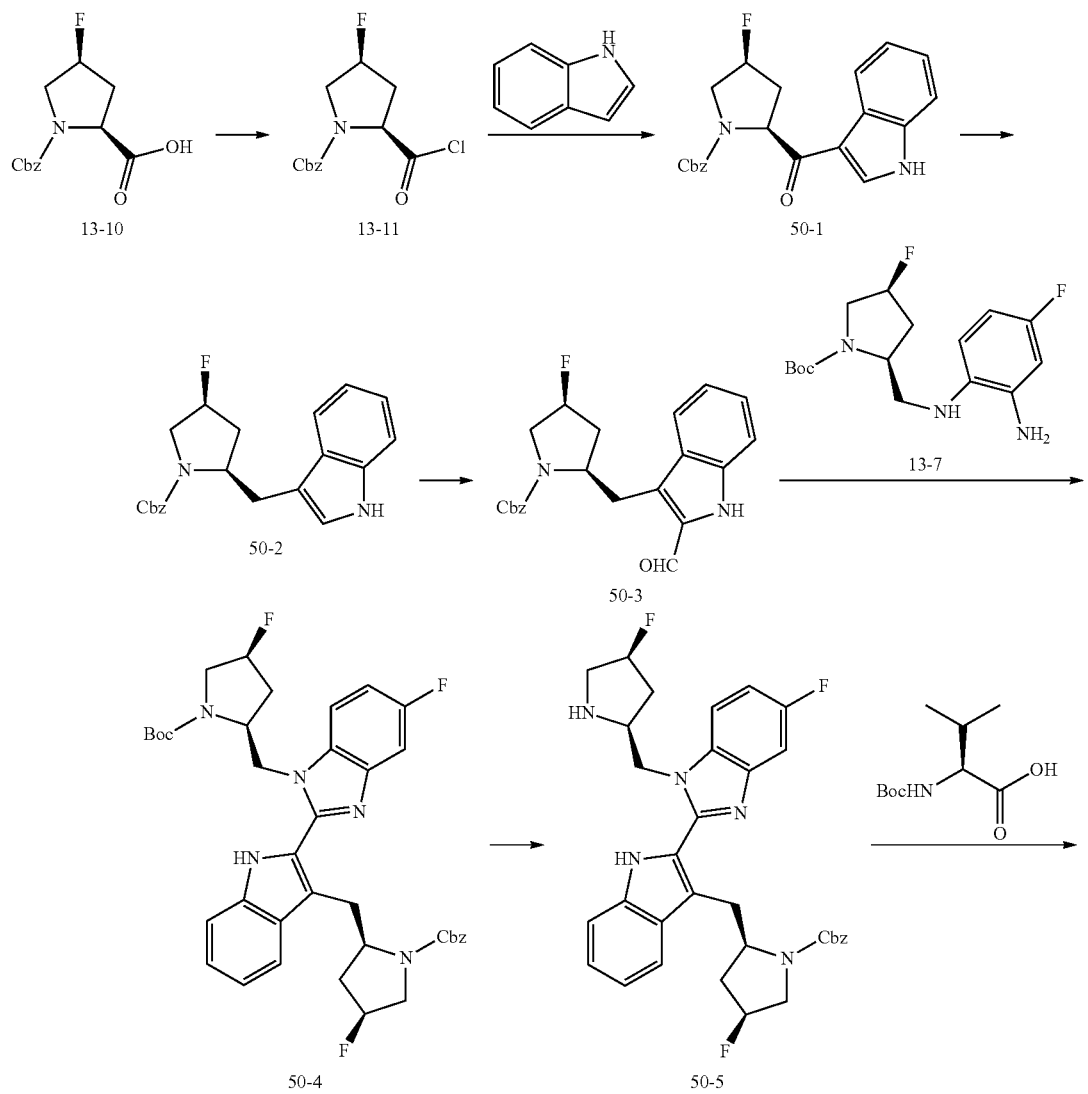

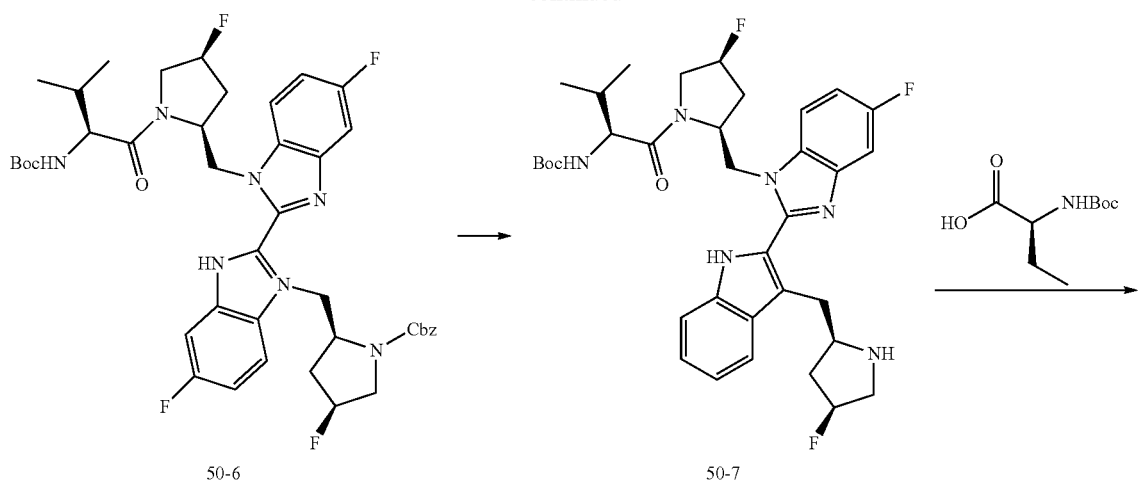
50-6 → 50-7
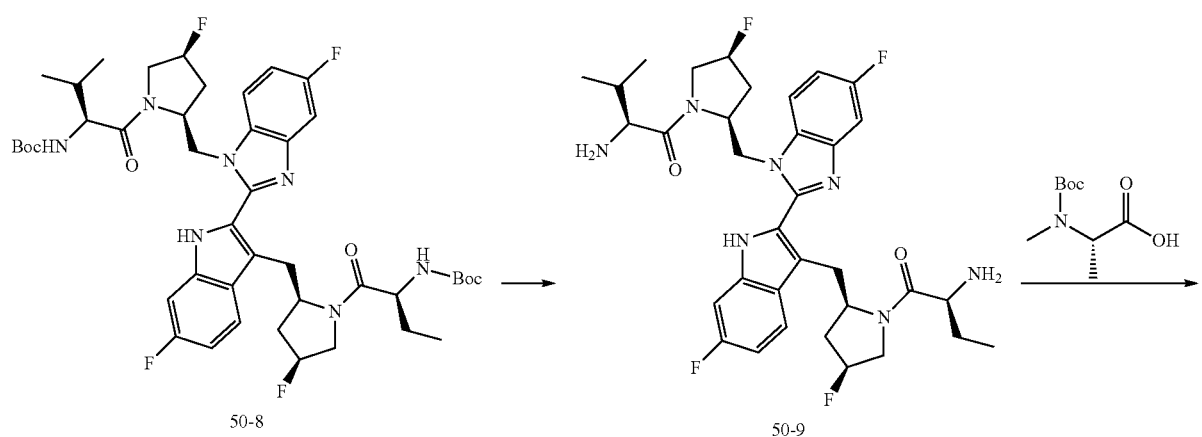
50-8 → 50-9
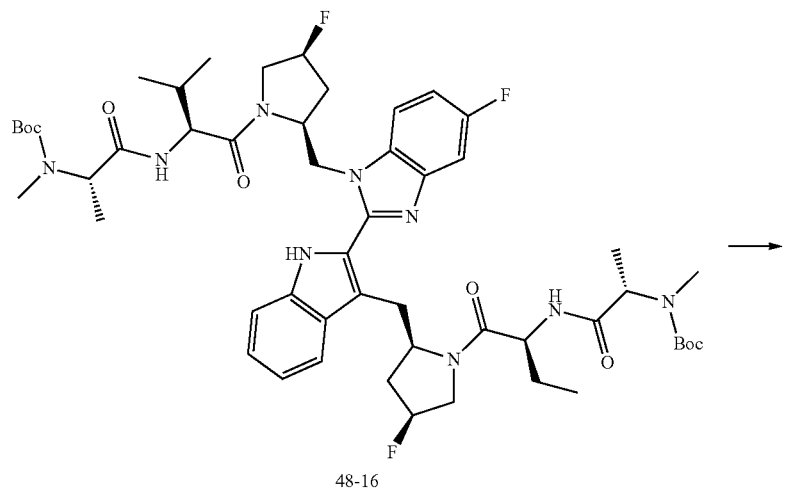
48-16

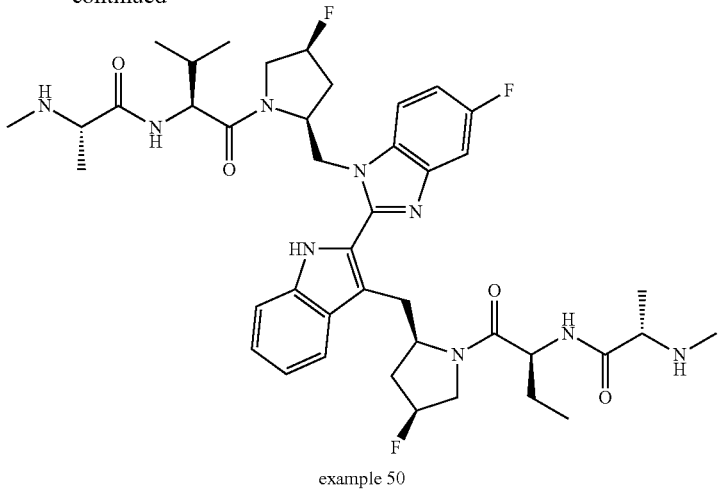

example 50

Step A: To a stirring solution of N-Cbz-cis-4-fluoro-L-proline (5.00 g, 18.71 mmol) in anhydrous toluene (50 mL) was added DMF (13.68 mg, 187.10 μmol, 14.40 μl) at 15° C. After the addition, the mixture was stirred for 15 min. And then the mixture was added with oxalyl chloride (3.56 g, 28.07 mmol, 2.46 mL) at 15° C., and stirred for 2 h at the same temperature. And then the mixture was concentrated to remove excess oxalyl chloride and the residue was dissolved in toluene and used for next step directly.

Step B: To a stirring solution of indole (3.29 g, 28.10 mmol) in toluene (25 mL) and chlorobenzene (25 mL) was added ethyl Grignard reagent (3 M, 9.68 mL) dropwise at 0° C. in 30 min. After the addition, the mixture was stirred for 30 min at the same temperature, N-Cbz-cis-4-fluor-L-proline chloride (5.35 g, 18.73 mmol) was added at 0° C. and the mixture was stirred for 2 h at 25° C., then quenched with aq NH$_4$Cl (300 mL) at 25° C., diluted with water (100 mL) and extracted with EtOAc (200 mL×2). The combined organic phase was washed with aq NaCl (200 mL×1), dried over anhydrous Na$_2$SO$_4$ and concentrated in vacuo. The residue was purified by flash column chromatography eluted with EtOAc/DCM (0%-10%) to giveb enzyl (2S,4S)-4-fluoro-2-(1H-indol e-3-carbonyl)pyrrolidine-1-carboxylate (3.80 g, 7.68 mmol, 40.98%).

$^1$HNMR (DMSO, 400 MHz): δ 12.07 (s, 1H), 8.43 (dd, J=7.64, 3.00 Hz, 1H), 8.30-8.17 (m, 1H), 7.55 (d, J=8.07 Hz, 1H), 7.50-7.34 (m, 3H), 7.33-5.11 (m, 5H), 5.47-5.25 (m, 2H), 5.17 (d, J=2.81 Hz, 1H), 5.06 (s, 1H), 4.00-3.72 (m, 2H), 2.98-2.69 (m, 1H), 2.47-2.26 (m, 1H).

MS (ESI) m/z: 367.0 [M+H$^+$]

Step C: To a stirring solution of benzyl (2S,4S)-4-fluoro-2-(1H-indole-3-carbonyl)pyrrolidine-1-carboxylate (3.80 g, 7.68 mmol) in THF (36 mL) was added LiBH$_4$ (2 M, 7.68 mL) and the mixture was stirred for 4 h at 15° C. The mixture was added withmethanesulfonic acid (1.36 g, 14.20 mmol, 1.01 mL) and stirred for 12 h at 15° C. And the mixture was quenched with aq NH$_4$Cl (200 mL), extracted with EtOAc (200 mL×2). The combined organic phase was washed with aq NaCl (50 mL), dried over Na$_2$SO$_4$ and concentrated in vacuo. The residue was purified by flash column chromatography eluted with EtOAc/Pet. Ether (0-14%) to give benzyl (2R,4S)-2-((1H-indol-3-yl)methyl)-4-fluoropyrrolidine-1-carboxylate (1.80 g, 4.60 mmol, 59.86%).

$^1$HNMR (DMSO, 400 MHz): δ 10.86 (d, J=8.31 Hz, 1H), 7.82-6.64 (m, 10H), 5.42-5.22 (m, 1H), 5.22-5.14 (m, 2H), 4.16 (m, J=8.30 Hz, 1H), 3.82-3.59 (m, 2H), 3.22 (d, J=11.62 Hz, 1H), 2.80-2.69 (m, 1H), 2.13-1.92 (m, 2H).

MS (ESI) m/z: 375.0 [M+Na$^+$]

Step D: To a stirring solution of DMF (672.00 mg, 9.19 mmol, 707.36 μL) was added phosphorusoxychloride (1.66 g, 10.83 mmol, 1.01 mL) at 0° C. under N$_2$. Then the mixture was stirred for 1 h at 0° C. and a solution of benzyl (2R,4S)-2-((1H-indol-3-yl)methyl)-4-fluoropyrrolidine-1-carboxylate (1.80 g, 4.60 mmol) in 1,2-dichloroethane was added dropwise to the mixture at 0° C. After stirring for 11 h at 15° C., the mixture was quenched with sat. aq NaHCO$_3$ (100 mL) at 0° C., diluted with dichloromethane (50 mL) and extracted with dichloromethane (100 mL×2). The combined organic phase was washed with aq NaCl (100 mL×1), dried over anhydrous Na$_2$SO$_4$ and concentrated in vacuo to give crude product benzyl (2R,4S)-4-fluoro-2-((2-formyl-1H-indol-3-yl)methyl)pyrrolidine-1-carboxylate (1.5 g).

Step E: To a solution of benzyl (2R,4S)-4-fluoro-2-((2-formyl-1H-indol-3-yl)methyl)pyrrolidine-1-carboxylate (1.5 g, 1.42 mmol) and tert-butyl (2S,4S)-2-(((2-amino-4-fluorophenyl)amino)methyl)-4-fluoropyrrolidine-1-carboxylate (464.71 mg, 1.42 mmol) in DMF (15 mL) and H$_2$O (1 mL) was added Oxone (648.03 mg, 4.26 mmol) at 15° C. After stirring for 12 h at 15° C., the mixture was quenched with sat. aq NaHCO$_3$ (20 mL) and sat. aq. Na$_2$S$_2$O$_3$(20 mL)and extracted with EtOAc (20 mL×3). The combinated organic phase was washed with sat.aq NaCl (20 mL×1), dried over Na$_2$SO$_4$ and concentrated in vacuo. The residue was purified by flash column chromatography eluted with EtOAc/Pet. Ether (3.2-50%) to give benzyl (2R,4S)-2-((2-(1-(((2S,4S)-1-(tert-butoxycarbonyl)-4-fluoropyrrolidin-2-yl)methyl)-5-fluoro-1H-benzo[d]imidazol-2-yl)-1H-indol-3-yl)methyl)-4-fluoropyrrolidine-1-carboxylate (450.00 mg, 615.05 μmol, 43.31%).

$^1$HNMR (CDCl$_3$, 400 MHz): δ 7.58-7.30 (m, 9H), 7.23 (d, J=7.65 Hz, 1H), 7.07 (td, J=9.16, 2.38 Hz, 1H), 5.28-4.89 (m, 4H), 4.68-4.22 (m, 3H), 3.84-3.42 (m, 5H), 3.17 (br.s., 1H), 2.20 (d, J=13.80 Hz, 1H), 1.94-1.66 (m, 3H), 1.28 (s, 9H).

MS (ESI) m/z: 688.2 [M+H$^+$]

Step F: To a solution of benzyl (2R,4S)-2-((2-(1-(((2S, 4S)-1-(tert-butoxycarbonyl)-4-fluoropyrrolidin-2-yl) methyl)-5-fluoro-1H-benzo[d]imidazol-2-yl)-1H-indol-3- yl)methyl)-4-fluoropyrrolidine-1-carboxylate (450.00 mg, 615.05 μmol) in DCM (3 mL) was added TFA (3 mL) at 15° C. After stirring for 12 h at 15° C., the mixture was concentrated to give crude product, benzyl (2R,4S)-4-fluoro-2-((2-(5-fluoro-1-(((2S,4S)-4-fluoropyrrolidin-2-yl)methyl)-1H-benzo[d]imidazol-2-yl)-1H-indol-3-yl)methyl)pyrrolidine-1-carboxylate (500 mg, trifluoroacetate).

Step G: To a stirring solution of (tert-butoxycarbonyl)-L-valine (232.23 mg, 1.07 mmol) and N-methylmorpholine (216.24 mg, 2.14 mmol, 235.04 μL) in DMF (3 mL) was added HATU (808.64 mg, 2.13 mmol) at 15° C. Then the mixture was added with benzyl (2R,4S)-4-fluoro-2-((2-(5-fluoro-1-(((2S,4S)-4-fluoropyrrolidin-2-yl)methyl)-1H-benzo[d]imidazol-2-yl)-1H-indol-3-yl)methyl)pyrrolidine-1-carboxylate (500 mg, trifluoroacetate) and stirred for 0.5 h at 15° C. The mixture was purified by reversed-phase column eluted with acetonitrile/aq TFA (1‰ to give benzyl (2R,4S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-1H-indol-3-yl)methyl)-4-fluoropyrrolidine-1-carboxylate (250.00 mg, 292.29 μmol, 41.02%).

¹HNMR (CDCl₃, 400 MHz): δ 7.63-6.79 (m, 12H), 5.18-4.80 (m, 5H), 4.70-4.21 (m, 3H), 4.04-3.39 (m, 6H), 3.10-2.85 (m, 1H), 1.81-1.47 (m, 4H), 1.34 (s, 9H), 0.84-0.67 (m, 4H), 0.54 (dd, J=18.13, 6.34 Hz, 3H).

MS (ESI) m/z: 787.2 [M+H⁺]

Step H: To a solution of benzyl (2R,4S)-2-((2-(1-(((2S,4S)-1-((tert-butoxycarbonyl)-L-valyl)-4-fluoropyrrolidin-2-yl)methyl)-5-fluoro-1H-benzo[d]imidazol-2-yl)-1H-indol-3-yl)methyl)-4-fluoropyrrolidine-1-carboxylate (250.00 mg, 292.29 μmol) in EtOAc (5 mL) and MeOH (5 mL) was added Pd/C (26.12 mg, 317.71 μmol, 10%) at 15° C. under the atmosphere of N₂. The mixture was stirred for 12 h at 15° C. under the atmosphere of 30 psi H₂. The mixture was filtered and concentrated in vacuo to give tert-butyl ((S)-1-((2S,4S)-4-fluoro-2-((5-fluoro-2-(3-(((2R,4S)-4-fluoropyrrolidin-2-yl)methyl)-1H-indol-2-yl)-1H-benzo[d]imidazol-1-yl)methyl)pyrrolidin-1-yl)-3-methyl-1-oxobutan-2-yl)carbamate (163.00 mg, 249.71 μmol, 78.60%).

MS (ESI) m/z: 653.3 [M+H⁺]

Step I: To a stirring solution of N-Boc-L-n-ethionin (76.13 mg, 374.57 μmol) and N-methylmorpholine (75.77 mg, 749.13 μmol, 82.36 μL) in DMF (3 mL) was added HATU (142.42 mg, 374.57 μmol) at 15, and then added tert-butyl ((S)-1-((2S,4S)-4-fluoro-2-((5-fluoro-2-(3-(((2R,4S)-4-fluoropyrrolidin-2-yl)methyl)-1H-indol-2-yl)-1H-benzo[d]imidazol-1-yl)methyl)pyrrolidin-1-yl)-3-methyl-1-oxobutan-2-yl)carbamate (163.00 mg, 249.71 μmol). After stirring for 0.5 h at 15° C., the mixture was purified by reversed-phase column eluted with acetonitrile/aq TFA (1‰) to give tert-butyl ((S)-1-((2S,4S)-2-((2-(3-(((2R,4S)-1-((S)-2-((tert-butoxycarbonyl)amino)butanoyl)-4-fluoropyrrolidin-2-yl)methyl)-1H-indol-2-yl)-5-fluoro-1H-benzo[d]imidazol-1-yl)methyl)-4-fluoropyrrolidin-1-yl)-3-methyl-1-oxobutan-2-yl)carbamate (100.00 mg, 119.34 μmol, 47.79%).

MS (ESI) m/z: 838.3 [M+H⁺]

Step J: To a solution of tert-butyl ((S)-1-((2S,4S)-2-((2-(3-(((2R,4S)-1-((S)-2-((tert-butoxycarbonyl)amino)butanoyl)-4-fluoropyrrolidin-2-yl)methyl)-1H-indol-2-yl)-5-fluoro-1H-benzo[d]imidazol-1-yl)methyl)-4-fluoropyrrolidin-1-yl)-3-methyl-1-oxobutan-2-yl)carbamate (100.00 mg, 119.34 μmol) in dichloromethane (2 mL) was added TFA (2 mL) at 15° C. After stirring for 0.5 h at 15° C., the mixture was concentrated in vacuo to give crude product (S)-2-amino-1-((2S,4S)-2-((2-(3-(((2R,4S)-1-((S)-2-aminobutanoyl)-4-fluoropyrrolidin-2-yl)methyl)-1H-indol-2-yl)-5-fluoro-1H-benzo[d]imidazol-1-yl)methyl)-4-fluoropyrrolidin-1-yl)-3-methylbutanylbutan-1-one (120 mg, trifluoroacetate).

MS (ESI) m/z: 638.2 [M+H⁺]

Step K: To a stirring solution of N-Boc-N-methyl-L-alanine (84.51 mg, 415.81 μmol) and N-methylmorpholine (84.12 mg, 831.62 μmol, 91.43 μL) in DMF (5 ml) was added HATU (158.10 mg, 415.81 μmol) at 15° C. and then added (S)-2-amino-1-((2S,4S)-2-((2-(3-(((2R,4S)-1-((S)-2-aminobutanoyl)-4-fluoropyrrolidin-2-yl)methyl)-1H-indol-2-yl)-5-fluoro-1H-benzo[d]imidazol-1-yl)methyl)-4-fluoropyrrolidin-1-yl)-3-methylbutan-1-one (120 mg, trifluoroacetate). The mixture was stirred for 12 h at 15° C. and purified directly by reversed-phase column eluted with acetonitrile/aq TFA (1‰) to give tert-butyl ((S)-1-(((S)-1-((2R,4S)-2-((2-(1-(((2S,4S)-1-(N-(tert-butoxycarbonyl)-N-methyl-L-alanyl-L-valyl)-4-fluoropyrrolidin-2-yl)methyl)-5-fluoro-1H-benzo[d]imidazol-2-yl)-1H-indol-3-yl)methyl)-4-fluoropyrrolidin-1-yl)-1-oxobutan-2-yl)amino)-1-oxopropan-2-yl)(methyl)carbamate (65.00 mg, 64.47 μmol, 46.51%).

MS (ESI) m/z: 1008.5 [M+H⁺]

Step L: To a solution of tert-butyl ((S)-1-(((S)-1-((2R,4S)-2-((2-(1-(((2S,4S)-1-(N-(tert-butoxycarbonyl)-N-methyl-L-alanyl-L-valyl)-4-fluoropyrrolidin-2-yl)methyl)-5-fluoro-1H-benzo[d]imidazol-2-yl)-1H-indol-3-yl)methyl)-4-fluoropyrrolidin-1-yl)-1-oxobutan-2-yl)amino)-1-oxopropan-2-yl)(methyl)carbamate (65.00 mg, 64.47 μmol) in dichloromethane (2 mL) was added TFA (2 mL) at 15° C. After stirring for 0.5 h at 15° C., the mixture was concentrated in vacuo to give crude product. The crude product was purified by reversed-phase column eluted with acetonitrile/aq hydrochloric acid (1‰) to give embodiment 50 (36.00 mg, 40.46 μmol, 62.76%, hydrochloride).

¹HNMR (MeOD, 400 MHz): δ 8.17 (dd, J=9.10, 4.08 Hz, 1H), 7.94(d, J=8.28 Hz, 1H), 7.85 (dd, J=7.84, 2.20 Hz, 1H), 7.75 (d, J=8.28 Hz, 1H), 7.56 (td, J=9.29, 2.38 Hz, 1H), 7.47 (t, J=7.59 Hz, 1H), 7.31 (t, J=7.65 Hz, 1H), 5.29-5.56 (m, 2H), 5.05-4.72 (m, 4H), 4.61-4.51 (m, 2H), 4.42-4.33 (m, 1H), 4.16-3.97 (m, 5H), 3.64(d, J=11.67 Hz, 1H), 3.32-3.23 (m, 1H), 2.71 (s, 3H), 2.67 (s, 3H), 2.21-1.84 (m, 7H), 1.56 (d, J=6.90 Hz, 3H), 1.49 (d, J=6.90 Hz, 3H), 1.12 (t, J=7.40 Hz, 3H), 0.94 (d, J=6.78 Hz, 3H), 0.89 (d, J=6.65 Hz, 3H).

MS (ESI) m/z: 808.3 [M+H⁺]

Embodiment 51

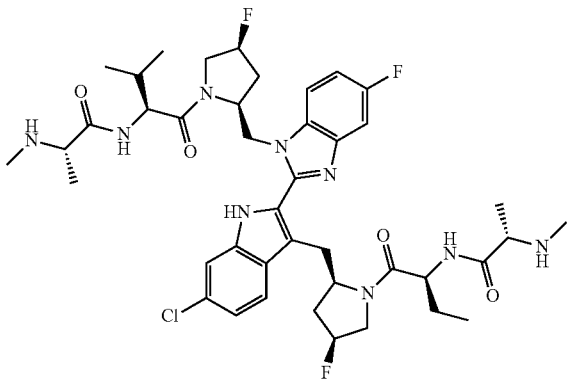

Process for preparing embodiment 51 can refer to the process for preparing embodiment 50

¹HNMR (MeOD, 400 MHz): δ 8.15 (br dd, J=9.17, 3.79 Hz, 1H), 7.96-7.84 (m, 2H), 7.79 (d, J=1.10 Hz, 1H), 7.57

(br t, J=8.93 Hz, 1H), 7.30 (dd, J=8.62, 1.28 Hz, 1H), 5.59-5.29 (m, 2H), 5.02 (m, 1H), 4.85-4.69 (m, 2H), 4.61-4.47 (m, 2H), 4.41-4.35 (m, 1H), 4.23-3.94 (m, 6H), 3.63(d, J=13.82 Hz, 1H), 3.26 (m, 1H),2.69 (d, J=12.72 Hz, 6H), 2.21-1.81 (m, 7H), 1.54 (dd, J=16.14, 6.85 Hz, 6H), 1.11 (t, J=7.72 Hz, 3H), 0.94 (dd, J=18.89, 6.66 Hz, 6H).

MS (ESI) m/z: 842.3 [M+H$^+$]

Biological Assay 1: affinity of compounds to cIAP1-BIR3, cIAP2-BIR3, XIAP-BIR3

1) Affinity of compounds listed in table to cIAP1-BIR3, Ciap2-BIR3, XIAP-BIR3 was tested referring to Nikolovska-Colesks, Z. et.Al. (Analytical Biochemistry, 2004,232:261-273) to obtain IC50 value. Generally speaking, in 10-dose IC50 mode, IAP antagonists with different concentrations were diluted in series by 3-fold and fluorescence labelled ARPFAQ-K (5-FAM)-NH$_2$ peptide was used as probe to test compounds binding to protein BIR3 domain.
2) Test condition: cIAP1-BIR3: 20 nM; cIAP2-BIR3: 60 nM; XIAP-BIR3: 30 nM; 5 nM probe in 100 mM tripotassium phosphate, pH 7.5, 0.1 mg/mL BSA, 0.005% Triton X100 and 0.5% DMSO.
3) Test procedure: compounds were added into protein with different concentrations by using ECHO (LabCyte), and then the mixture was preincubated for 15 min. The probe was added and the final concentration was 5 nM. After incubating for 60 min, FP was tested and mP was calculated. Experiment results were list in table 1.

TABLE 1

| | affinity to target protein in vitro (nM) | | |
|---|---|---|---|
| embodiment | cIAP1-BIR3 Protein | cIAP2-BIR3 Protein | XIAP-BIR3 Protein |
| 1 | <10 | 10-100 | 10-100 |
| 2 | <10 | 10-100 | 10-100 |
| 13 | 10-100 | 10-100 | 10-100 |
| 14 | <10 | 10-100 | 10-100 |
| 16 | <10 | 10-100 | 10-100 |
| 17 | <10 | 10-100 | <10 |
| 18 | <10 | 10-100 | 10-100 |
| 19 | <10 | 10-100 | 10-100 |
| 20 | <10 | 10-100 | 10-100 |
| 21 | <10 | 10-100 | 10-100 |
| 22 | <10 | 10-100 | 10-100 |
| 23 | <10 | <10 | 10-100 |
| 24 | <10 | 10-100 | 10-100 |
| 25 | <10 | 10-100 | 10-100 |
| 26 | <10 | <10 | <10 |
| 27 | <10 | <10 | <10 |

TABLE 1-continued

| | affinity to target protein in vitro (nM) | | |
|---|---|---|---|
| embodiment | cIAP1-BIR3 Protein | cIAP2-BIR3 Protein | XIAP-BIR3 Protein |
| 28 | <10 | 10-100 | <10 |
| 29 | <10 | 10-100 | 10-100 |
| 30 | <10 | 10-100 | 10-100 |
| 31 | <10 | 10-100 | 10-100 |
| 32 | <10 | 10-100 | 10-100 |
| 36 | <10 | 10-100 | 10-100 |
| 38 | <10 | 10-100 | <10 |
| 39 | <10 | 10-100 | <10 |
| 40 | <10 | 10-100 | 10-100 |
| 42 | <10 | 10-100 | <10 |
| 43 | 10-100 | 10-100 | 10-100 |
| 44 | <10 | 10-100 | <10 |
| 46 | <10 | 10-100 | 10-100 |

Conclusion: compounds in the present invention have higher cIAP1 inhibitory activity, medium XIAP inhibitory activity and better selectivity.

Biological Assay 2: TNF-α inducing NF-κB reporter

First day:

Dilution of Compounds:

1) tested compounds were added into DMSO to give parent liquor (10 mM);
2) reference compound Birinapant (32 μL, 10 mM) was added into DMSO (128 μL) to give a solution (2 mM);
3) 0.5 μL reference compound Birinapant (2 mM) and tested compounds (10 mM) were taken by Echo and added into Greiner 96 well black cell culture plate respectively. The initial concentration of the reference compound and tested compound was 10 μM and 50 μM, respectively. Then, the reference compound and tested compounds were diluted at 9 points in series by 5-fold; and every plate was repeated for 3 times.
4) the reference compound WXFL2012A001 (Birinapant) (final concentration: 10 μM) as HPE and DMSO (final concentration: 0.5%) as ZPE. Compounds arrangement as listed in table 2

TABLE 2

| | Compounds arrangement | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | HPE (WXFL2012A001 10 μM + 20 ng/mL TNF-α) | cpd1 (nM) | cpd1 (nM) | cpd1 (nM) | cpd1 (nM) | cpd1 (nM) | cpd1 (nM) | cpd1 (nM) | cpd1 (nM) | cpd1 (nM) | cpd1 (nM) | ZPE (DMSO + 20 ng/mL TNF-α) |
| B | | 10000.0 | 2000.00 | 400.00 | 80.00 | 16.00 | 3.20 | 0.64 | 0.13 | 0.03 | 0.01 | |
| C | | cpd2 (nM) | cpd2 (nM) | cpd2 (nM) | cpd2 (nM) | cpd2 (nM) | cpd2 (nM) | cpd2 (nM) | cpd2 (nM) | cpd2 (nM) | cpd2 (nM) | |
| D | | 50000.00 | 10000.00 | 2000.00 | 400.00 | 80.00 | 16.00 | 3.20 | 0.64 | 0.13 | 0.03 | |
| E | | cpd3 (nM) | cpd3 (nM) | cpd3 (nM) | cpd3 (nM) | cpd3 (nM) | cpd3 (nM) | cpd3 (nM) | cpd3 (nM) | cpd3 (nM) | cpd3 (nM) | |
| F | | 50000.00 | 10000.00 | 2000.00 | 400.00 | 80.00 | 16.00 | 3.20 | 0.64 | 0.13 | 0.03 | |
| G | | cpd4 (nM) | cpd4 (nM) | cpd4 (nM) | cpd4 (nM) | cpd4 (nM) | cpd4 (nM) | cpd4 (nM) | cpd4 (nM) | cpd4 (nM) | cpd4 (nM) | |
| H | | 50000.00 | 10000.00 | 2000.00 | 400.00 | 80.00 | 16.00 | 3.20 | 0.64 | 0.13 | 0.03 | |

5) purpose of the three repeated plates: the first plate was used for testing compounds' activity;
the second plate was used for testing cytotoxicity of the compounds; the third plate was used for solution replacement of the first and second plates: mixing inducer TNF-α and medium containing 0.1% FBS, and then being added to the third plate and the resultant mixture was transferred to the first plate where supernatants had been removed.

Cell Incubation
1) removing medium in NF-iBLuciferase Reporter Hela cell culture flask and washing cell once with PBS (10 mL)
2) adding 0.25% pancreatin (3 mL) to T150 cell culture flask, and placinginto cell incubator (37° C., 5%$CO_2$) and dissociating cell for 3 min, and then medium (10 mL) was added to end dissociation and blowing cells with electric pipette until cells were dispersed into single cell.
3) Calculating cell density with cell counter Countstar
4) Adjusting NF-κB Luciferase Reporter Hela density with medium to $2.0 \times 10^5$ cells/mL
5) Adding cells to two Greiner 96 well black cell culture plates containing compounds, (100 μL per well ($2.0 \times 10^4$ cells/well)), one plate was used for testing compounds' activity, another was used for testing cytotoxicity of the compounds.
6) Placing cell culture plates into cell incubator (37° C., 5%$CO_2$) and incubatingfor 24 h Second Day
TNF-α Inducing
1) TNF-α (100 μg/mL) was diluted into 20 ng/mL with 0.1% FBS medium and transferredto the third plate with 100 μL per well
2) Removing medium of the first 96 well black cell culture plate (compound activity testing plate) after 24 h, replacing with fresh medium containing the compound and 20 ng/mL TNF-α in the third plate
3) Placing cell culture plate into cell incubator (37° C., 5% $CO_2$) and incubatingfor 6 h
4) after 6 h, compound's activity in the first plate was tested according to Bright-Glo (Promega) manual method, luciferase signal in each well was tested by Envision plate reader
5) compound's cytotoxicity in the second plate was tested according to ATPlite 1Step (Perkin Elmer) manual method, luciferase signal in each well was tested by Envision plate reader
6) analyzing with software to obtain $EC_{50}$ of compound. Experiment results as listed in table 3

TABLE 3

| example | EC50 (nM) |
| --- | --- |
| 1 | <10 |
| 2 | 10-100 |
| 3 | <10 |
| 4 | 10-100 |
| 5 | 10-100 |
| 6 | 10-100 |
| 7 | 10-100 |
| 8 | <10 |
| 9 | 10-100 |
| 10 | 10-100 |
| 11 | 10-100 |
| 12 | 10-100 |
| 13 | >100 |
| 14 | 10-100 |
| 15 | 10-100 |
| 16 | <10 |
| 17 | <10 |
| 18 | <10 |

TABLE 3-continued

| example | EC50 (nM) |
| --- | --- |
| 19 | <10 |
| 20 | <10 |
| 21 | 10-100 |
| 22 | <10 |
| 23 | <10 |
| 24 | 10-100 |
| 25 | 10-100 |
| 26 | <10 |
| 27 | <10 |
| 28 | <10 |
| 29 | <10 |
| 30 | <10 |
| 31 | 10-100 |
| 32 | <10 |
| 33 | <10 |
| 34 | <10 |
| 35 | <10 |
| 36 | <10 |
| 37 | 10-100 |
| 38 | <10 |
| 39 | 10-100 |
| 40 | <10 |
| 41 | 10-100 |
| 42 | 10-100 |
| 43 | >100 |
| 44 | >100 |
| 45 | 10-100 |
| 46 | 10-100 |
| 47 | 10-100 |
| 48 | 10-100 |
| 49 | <10 |
| 50 | 10-100 |
| 51 | <10 |

Experiment results of compounds in the embodiments and control product IAP inhibitor Birinapant as listed in table 4

TABLE 4

| Samples (standard compounds) | EC50 (nM) |
| --- | --- |
| Birinapant | 7.05 |
| Example 1 | 7.11 |
| Example 16 | 0.66 |
| Example 18 | 6.05 |

Conclusion: representative compounds of the present invention contain equivalent or higher NF-κB inhibitory activity induced by TNF-αcompared to Birinapant.

What is claimed is:
1. A compound represented by formula (I) or a pharmaceutically acceptable salt thereof,

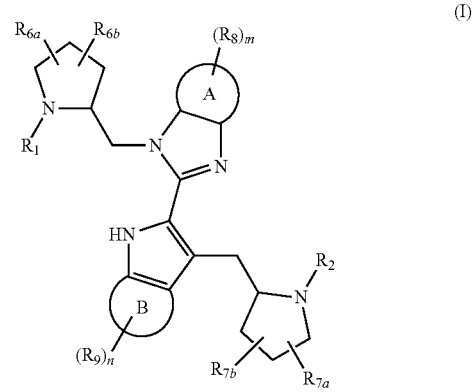

wherein,

R$_1$ and R$_2$ are independently selected from

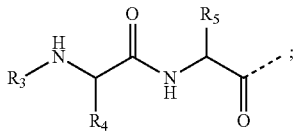

R$_3$, R$_4$ and R$_5$ are independently selected from the group consisting of C$_{1-6}$ alkyl, C$_{1-6}$ heteroalkyl, C$_{3-12}$ cycloalkyl, 3-12membered heterocycloalkyl, 5-12membered aryl or heteroaryl, 5-12membered aralkyl or heteroaralkyl; the C$_{1-6}$ alkyl, C$_{1-6}$ heteroalkyl, C$_{3-12}$ cycloalkyl, 3-12membered heterocycloalkyl, 5-12membered aryl or heteroaryl, 5-12membered aralkyl or heteroaralkyl are optionally substituted with 1, 2 or 3 of R, respectively;

R$_{6a}$ and R$_{6b}$ are independently selected from the group consisting of H, F, Cl, Br, I, OH, CN, NH$_2$, COOH, or C$_{1-6}$ alkyl, C$_{1-6}$ heteroalkyl, C$_{3-6}$ cycloalkyl, 3-6membered heterocycloalkyl, 5-6membered aryl or heteroaryl, 5-6membered aralkyl or heteroaralkyl; the C$_{1-6}$ alkyl, C$_{1-6}$ heteroalkyl, C$_{3-6}$ cycloalkyl, 3-6membered heterocycloalkyl, 5-6membered aryl or heteroaryl, 5-6membered aralkyl or heteroaralkyl are optionally substituted with 1, 2 or 3 of R, respectively;

or, optionally, R$_{6a}$ and R$_{6b}$ are linked together to form a 3-6membered ring optionally substituted with 1, 2 or 3 of R;

R$_{7a}$ and R$_{7b}$ are independently selected from the group consisting of H, F, Cl, Br, I, OH, CN, NH$_2$, COOH, or C$_{1-6}$ alkyl, C$_{1-6}$ heteroalkyl, C$_{3-6}$ cycloalkyl, 3-6membered heterocycloalkyl, 5-6memberedaryl or heteroaryl, 5-6membered aralkyl or heteroaralkyl; the C$_{1-6}$ alkyl, C$_{1-6}$ heteroalkyl, C$_{3-6}$ cycloalkyl, 3-6membered heterocycloalkyl, 5-6membered aryl or heteroaryl, 5-6membered aralkyl or heteroaralkyl are optically substituted with 1, 2 or 3 of R, respectively;

or, optionally, R$_{7a}$ and R$_{7b}$ are linked together to form a 3-6membered ring optionally substituted with 1, 2 or 3 of R;

ring A and ring B are independently selected from the group consisting of 5-6membered aryl or heteroaryl, 5-6membered aralkyl or heteroaralkyl, respectively;

R$_8$ and R$_9$ are independently selected from the group consisting of halogen, hydroxy or C$_{1-6}$ alkyl, C$_{1-6}$ heteroalkyl, C$_{3-6}$ cycloalkyl, 3-6membered heterocycloalkyl; the C$_{1-6}$ alkyl, C$_{1-6}$ heteroalkyl, C$_{3-6}$ cycloalkyl, 3-6membered heterocycloalkylare optionally substituted with 1, 2 or 3 of R, respectively;

m and n are selected from 0, 1, 2 or 3;

R is selected from the group consisting of F, Cl, Br, I, CN, OH, NH$_2$, COOH, or C$_{1-6}$ alkyl, C$_{1-6}$ heteroalkyl, C$_{3-6}$ cycloalkyl, 3-6membered heterocycloalkyl, phenyl and 5-6membered heteroaryl; the C$_{1-6}$ alkyl, C$_{1-6}$ heteroalkyl, C$_{3-6}$ cycloalkyl, 3-6membered heterocycloalkyl, phenyl and 5-6membered heteroaryl are optionally substituted with 1, 2 or 3 of R';

R' is selected from the group consisting of F, Cl, Br, I, OH, CN, NH$_2$, COOH, Me, Et, CF$_3$, CHF$_2$, CH$_2$F, NHCH$_3$ and N(CH$_3$)$_2$;

"hetero" means a hetero atom or a hetero group, is selected from the group consisting of —C(=O)N(R)—, —N(R)—, —C(=NR)—, —S(=O)$_2$N(R)—, —S(=O)N(R), —O—, —S—, =O, =S, —O—N=, —C(=O)O—, —C(=O)—, —C(=S)—, —S(=O)—, —S(=O)$_2$— and —N(R)C(=O)N(R)—;

In any case above, the number of hetero atom or hetero group is independently selected from 1, 2 or 3, respectively.

2. The compound or the pharmaceutically acceptable salt thereof of claim 1, wherein R is selected from the group consisting of F, Cl, Br, I, CN, OH, NH$_2$, COOH, or C$_{1-3}$ alkyl, C$_{1-3}$ alkoxy, C$_{1-3}$ alkylthio, C$_{1-3}$ alkylamino and N,N-di(C$_{1-2}$ alkyl)amino;

the C$_{1-3}$ alkyl, C$_{1-3}$ alkoxy, C$_{1-3}$ alkylthio, C$_{1-3}$ alkylamino and N,N-di(C$_{1-2}$ alkyl)amino are optionally substituted with 1, 2 or 3 R'.

3. The compound or the pharmaceutically acceptable salt thereof of claim 2, wherein R is selected from the group consisting of F, Cl, Br, I, CN, OH, NH$_2$, COOH, Me, Et, CF$_3$, CHF$_2$, CH$_2$F, NHCH$_3$, N(CH$_3$)$_2$,

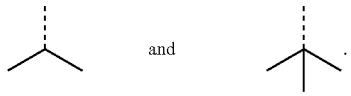

4. The compound or the pharmaceutically acceptable salt thereof of claim 1, wherein R$_3$ and R$_4$ are independently selected from the group consisting of C$_{1-4}$ alkyl, C$_{1-4}$ heteroalkyl, C$_{3-6}$ cycloalkyl, 3-6membered heterocycloalkyl, 5-6membered aryl or heteroaryl and 5-6membered aralkyl or heteroaralkyl; the C$_{1-4}$ alkyl, C$_{1-4}$ heteroalkyl, C$_{3-6}$ cycloalkyl, 3-6membered heterocycloalkyl, 5-6membered aryl or heteroaryl, 5-6membered aralkyl or heteroaralkyl are optionally substituted with 1, 2 or 3 of R, respectively.

5. The compound or the pharmaceutically acceptable salt thereof of claim 4, wherein R$_3$ and R$_4$ are independently selected from the group consisting of C$_{1-3}$ alkyl, C$_{1-3}$ heteroalkyl, phenyl, pyridinyl, pyrimidyl, pyrazinyl, pyridaziny, furyl, imidazolyl, oxazolyl, isoxazolyl, thienyl and pyrazolyl, respectively.

6. The compound or the pharmaceutically acceptable salt thereof of claim 5, wherein R$_3$ and R$_4$ are independently selected from Me, respectively.

7. The compound or the pharmaceutically acceptable salt thereof of claim 1, wherein R$_5$ is selected from the group consisting of C$_{1-4}$ alkyl, C$_{1-4}$ heteroalkyl, C$_{3-6}$ cycloalkyl, 3-6membered heterocycloalkyl, 5-6membered aryl or heteroaryl, and 5-6 membered aralkyl or heteroaralkyl; the C$_{1-4}$ alkyl, C$_{1-4}$ heteroalkyl, C$_{3-6}$ cycloalkyl, 3-6membered heterocycloalkyl, 5-6membered aryl or heteroaryl, and 5-6 membered aralkyl or heteroaralkyl are optionally substituted with 1, 2 or 3 of R.

8. The compound or the pharmaceutically acceptable salt thereof of claim 7, wherein R$_5$ is selected from the group consisting of C$_{1-4}$ alkyl, C$_{3-6}$ heteroalkyl, 3-6membered heterocycloalkyl, phenyl, pyridinyl, pyrimidyl, pyrazinyl, pyridaziny, furyl, imidazolyl, oxazolyl, isoxazolyl, thienyl and pyrazolyl.

9. The compound or the pharmaceutically acceptable salt thereof of claim 8, wherein R$_5$ is selected from

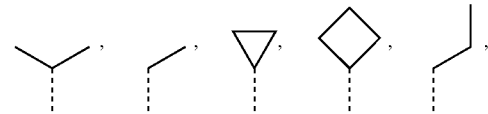

-continued

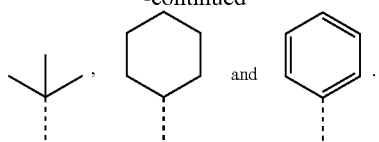

10. The compound or the pharmaceutically acceptable salt thereof of claim 1, wherein the structural unit

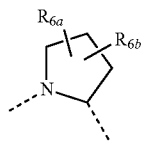

is selected from

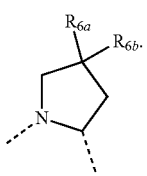

11. The compound or the pharmaceutically acceptable salt thereof of claim 10, wherein the structural unit

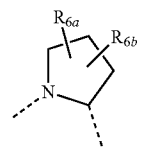

is selected from

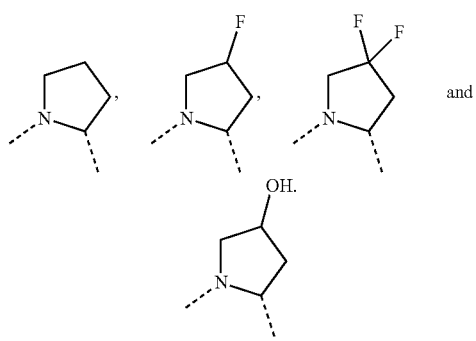

12. The compound or the pharmaceutically acceptable salt thereof of claim 1, wherein the structural unit

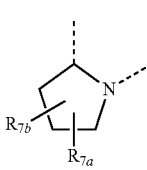

is selected from

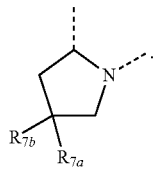

13. The compound or the pharmaceutically acceptable salt thereof of claim 12, wherein the structural unit

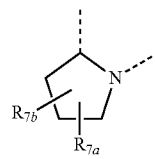

is selected from

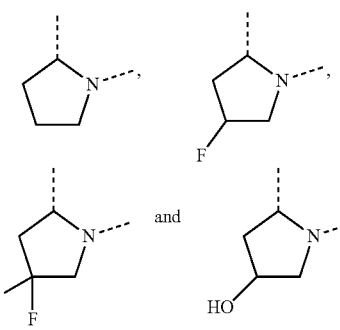

14. The compound or the pharmaceutically acceptable salt thereof of claim 1, wherein $R_{6a}$ and $R_{6b}$ are linked together to form a 3-6 membered cycloalkyl optionally substituted with 1, 2 or 3 of R.

15. The compound or the pharmaceutically acceptable salt thereof of claim 14, wherein $R_{6a}$ and $R_{6b}$ are linked together, the structural unit

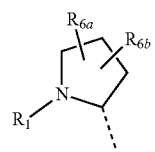

is selected from

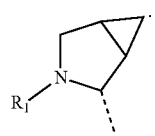

16. The compound or the pharmaceutically acceptable salt thereof of claim 15, wherein $R_{6a}$ and $R_{6b}$ are linked together, the structural unit is selected from

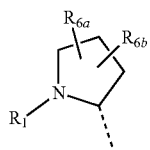

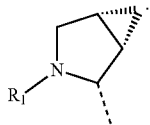

17. The compound or the pharmaceutically acceptable salt thereof of claim 1, wherein $R_{7a}$ and $R_{7b}$ are linked together to form a 3-6memberedcycloalkyl optionally substituted with 1, 2 or 3 of R.

18. The compound or the pharmaceutically acceptable salt thereof of claim 17, wherein $R_{7a}$ and $R_{7b}$ are linked together, the structural unit

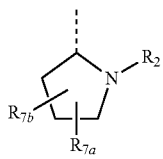

is selected from

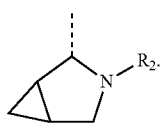

19. The compound or the pharmaceutically acceptable salt thereof of claim 1, wherein the structural unit

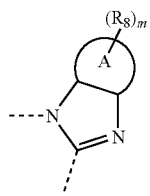

is selected from

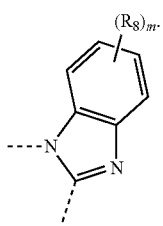

20. The compound or the pharmaceutically acceptable salt thereof of claim 19, wherein the structural unit

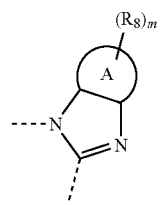

is selected from

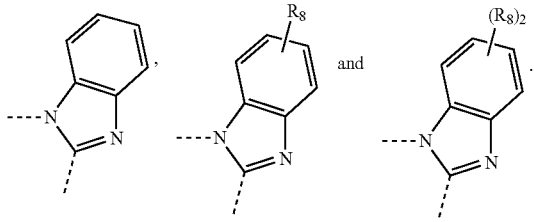

21. The compound or the pharmaceutically acceptable salt thereof of claim 20, wherein the structural unit

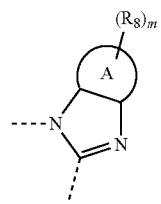

is selected from

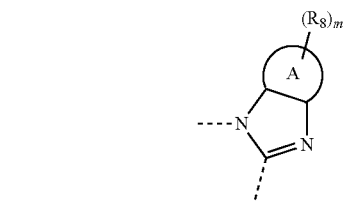

22. The compound or the pharmaceutically acceptable salt thereof of claim 21, wherein the structural unit is selected from

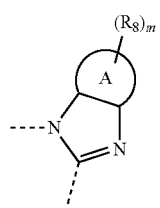

is selected from

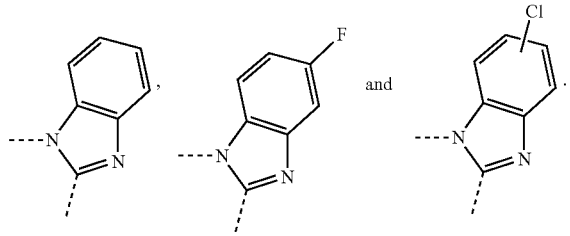

23. The compound or the pharmaceutically acceptable salt thereof of claim 1, wherein the structural unit

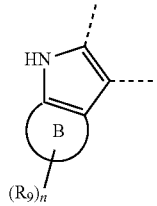

is selected from

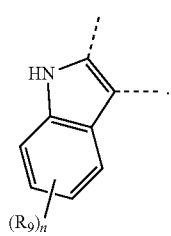

24. The compound or the pharmaceutically acceptable salt thereof of claim 23, wherein the structural unit

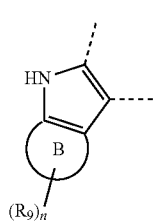

is selected from

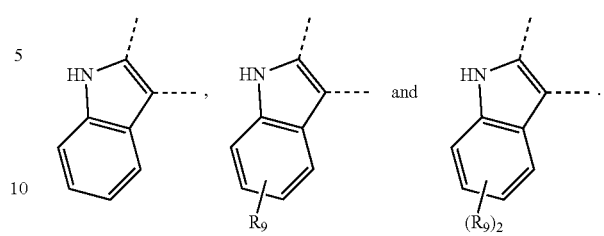

25. The compound or the pharmaceutically acceptable salt thereof of claim 24, wherein the structural unit

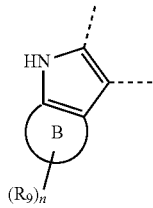

is selected from

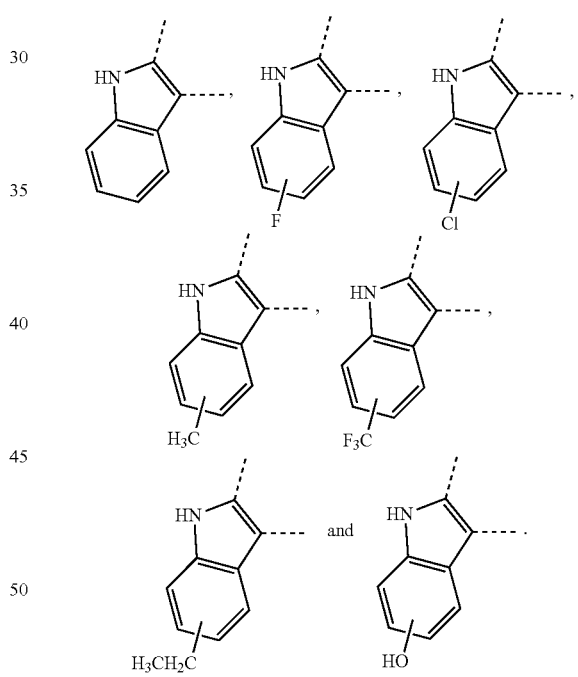

26. The compound or the pharmaceutically acceptable salt thereof of claim 25, wherein the structural unit

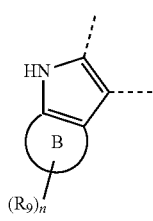

is selected from
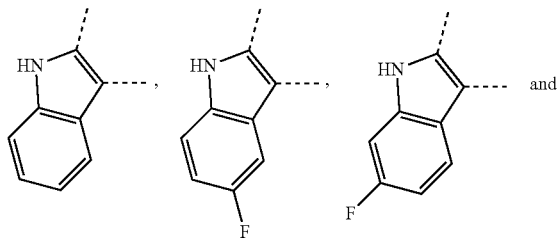
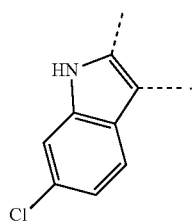
27. The compound or the pharmaceutically acceptable salt thereof of claim 1, wherein the compound is selected from
(II)
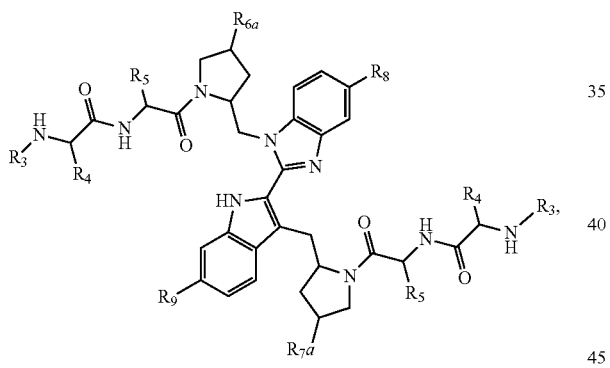
R$_3$, R$_4$, R$_5$, R$_{6a}$, R$_{7a}$, R$_8$, R$_9$ are as defined as claim 1.
28. The compound or the pharmaceutically acceptable salt thereof, which is selected from
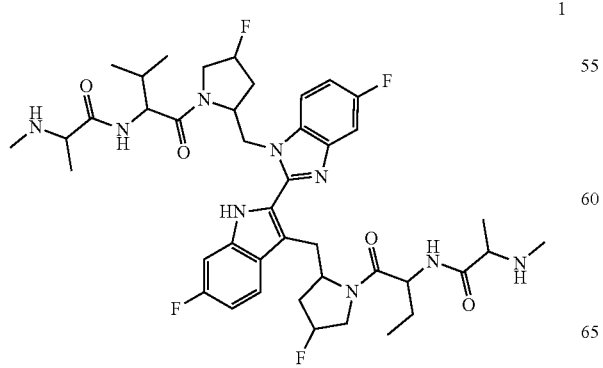
1
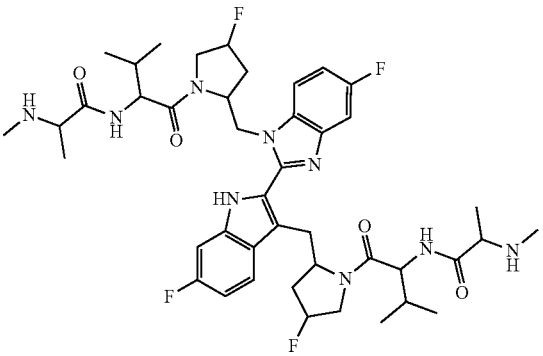
2
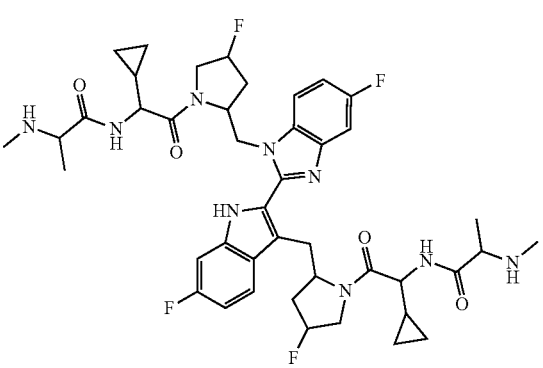
3
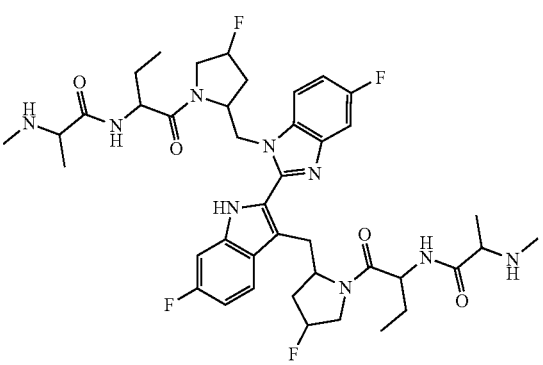
4
5

-continued

-continued
14
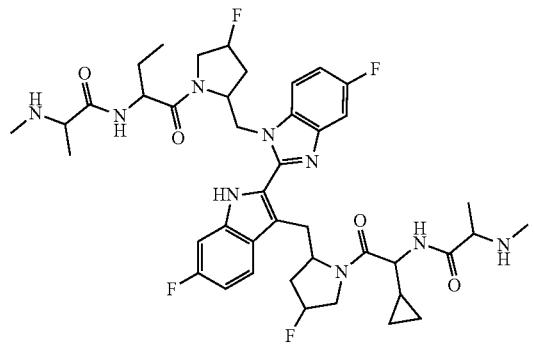
15
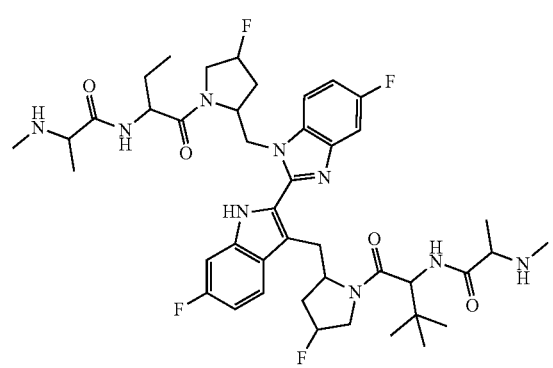
16
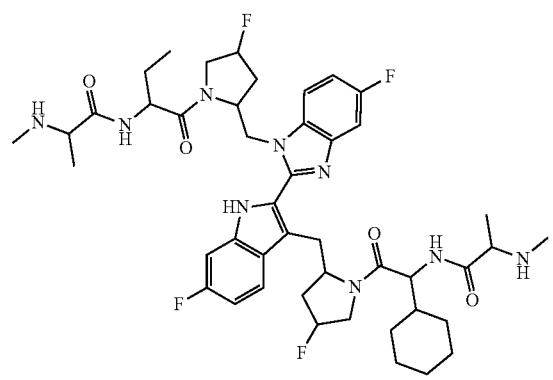
17
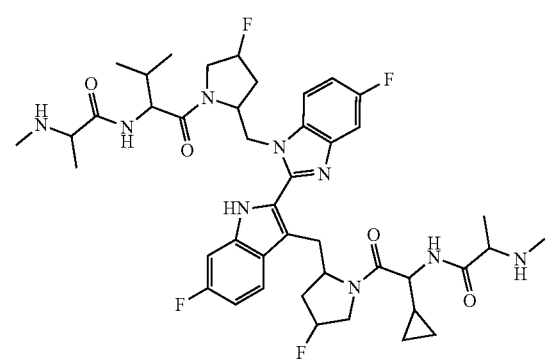
-continued
18
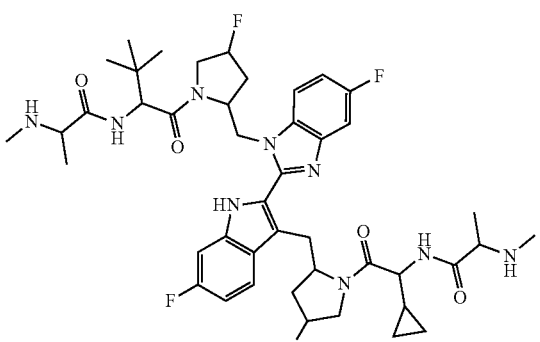
19
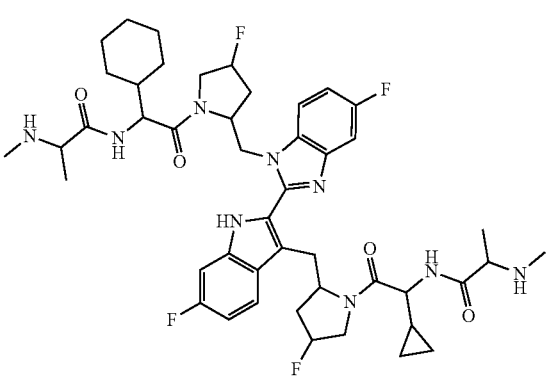
20
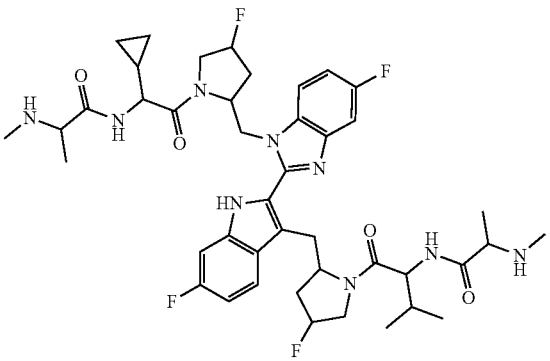
21
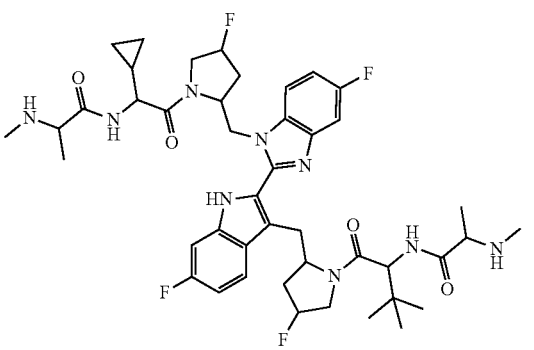

22
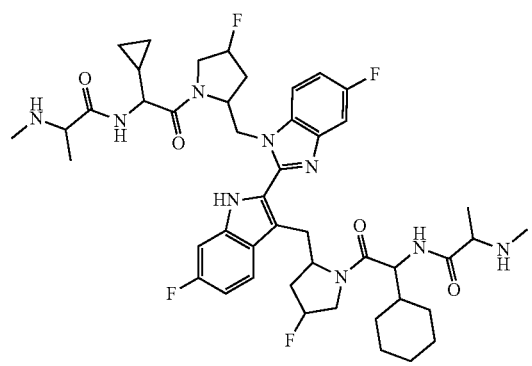
23
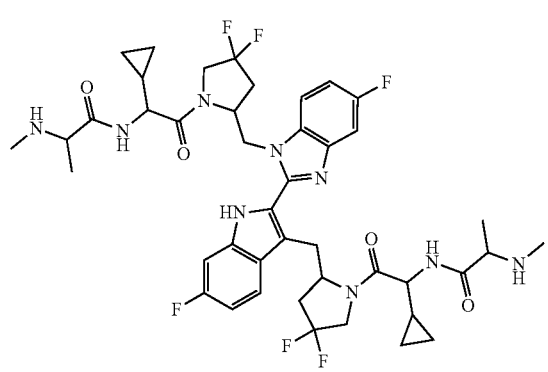
24
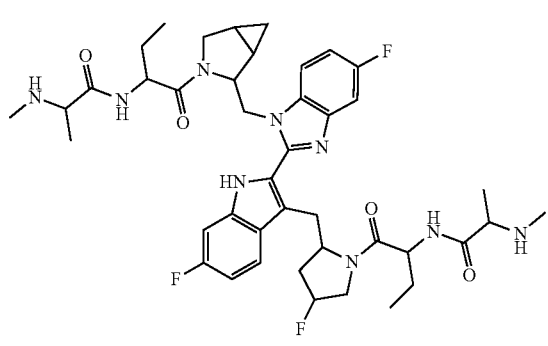
25
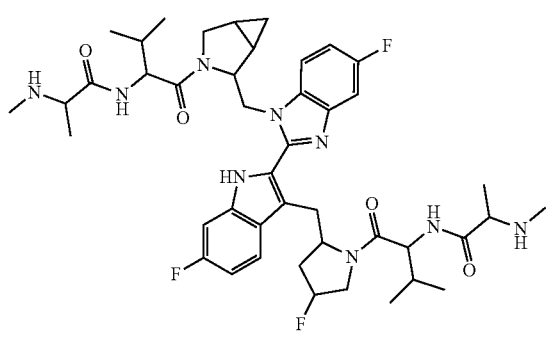
26
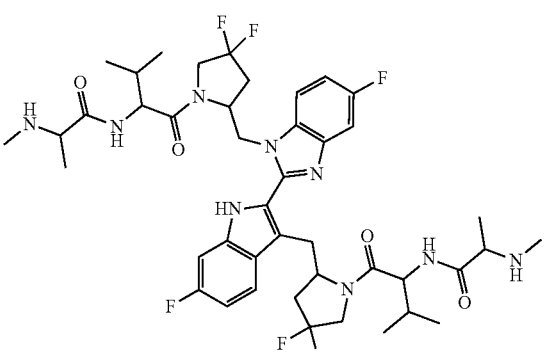
27
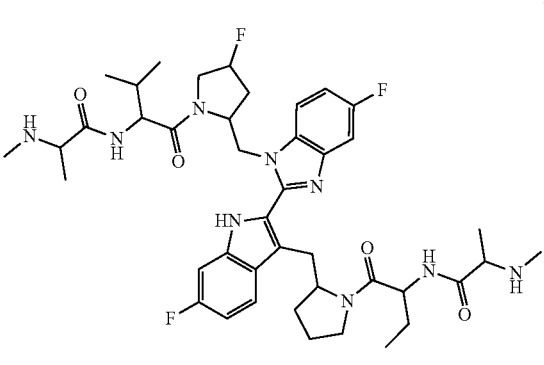
28
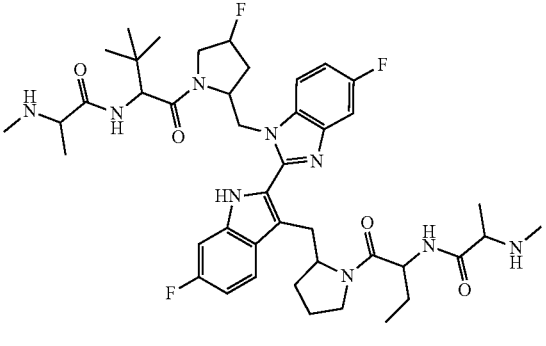
29
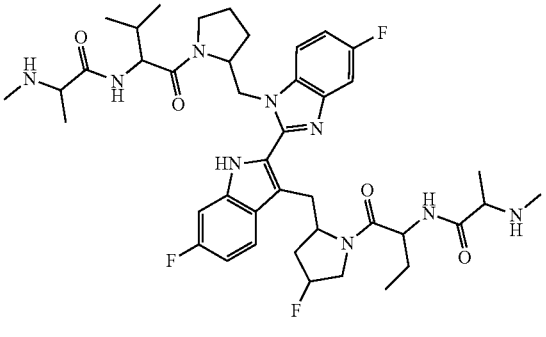

30
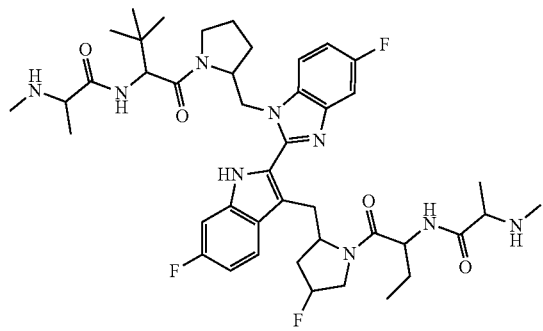
31
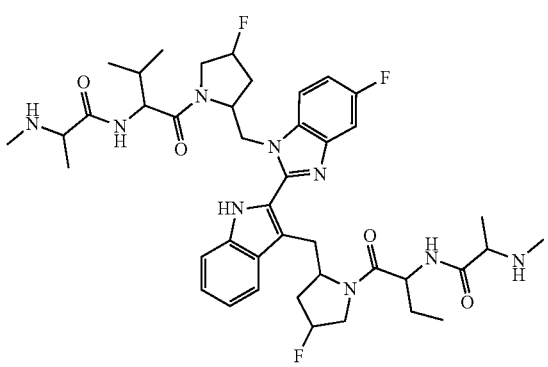
32
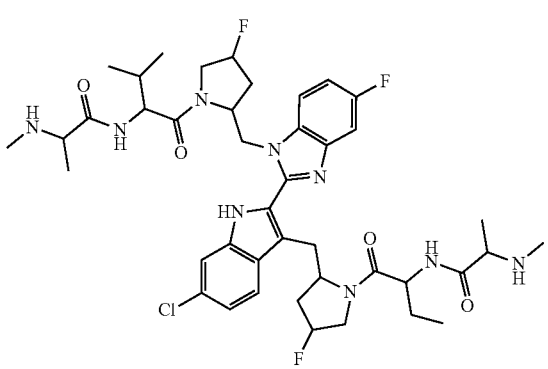
34
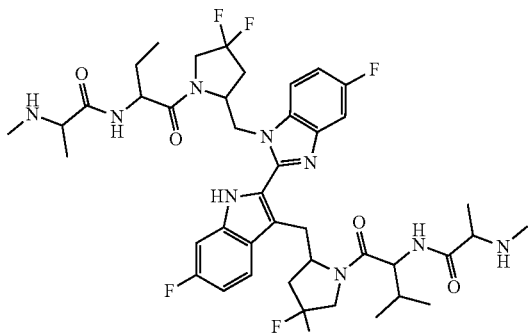
35
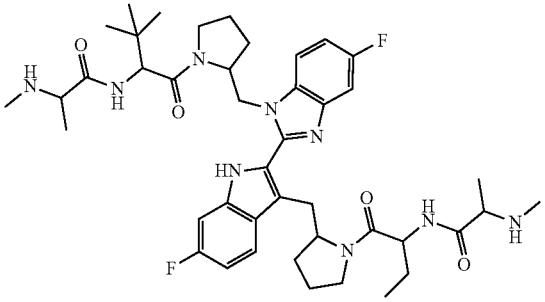
36
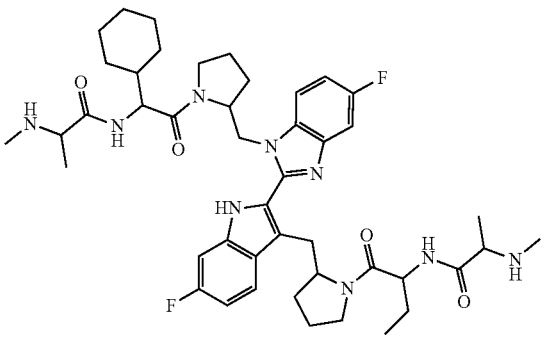

38
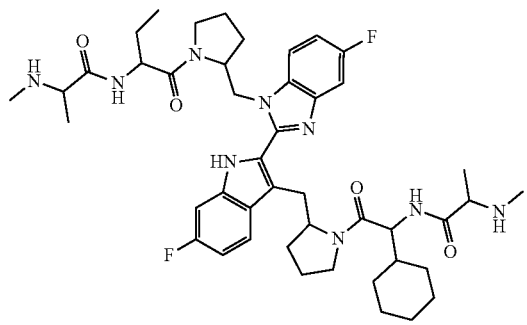
39
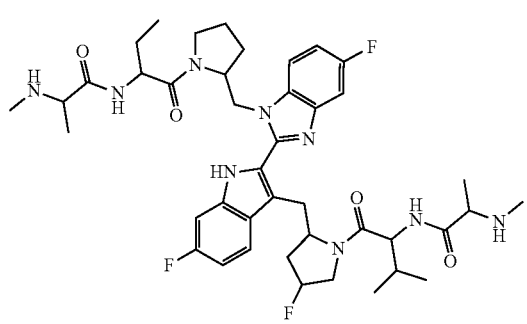
40
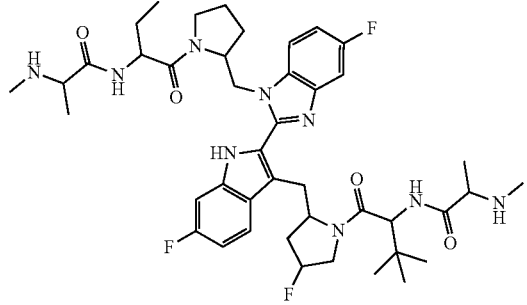
41
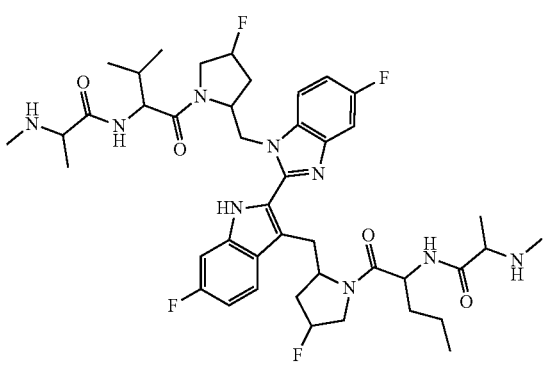
42
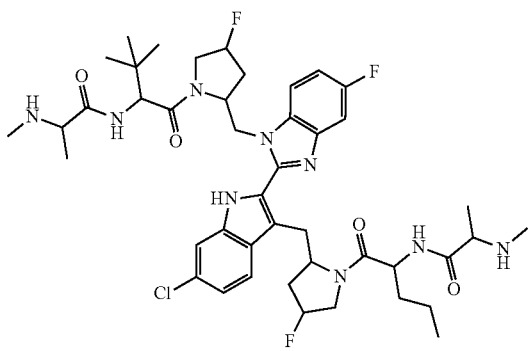
43
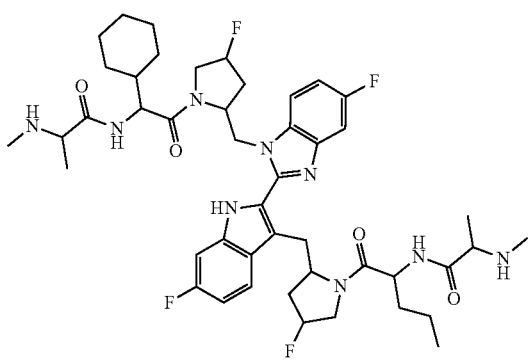
44
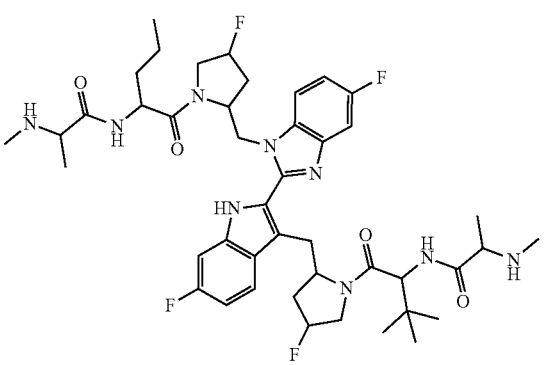
45
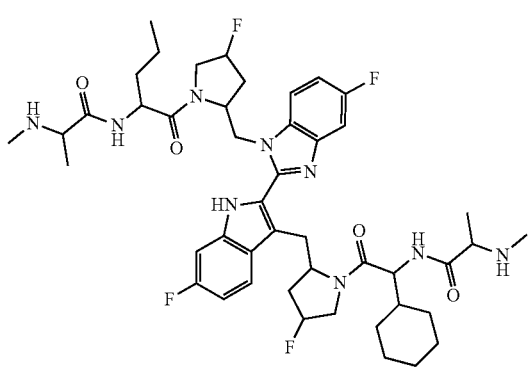

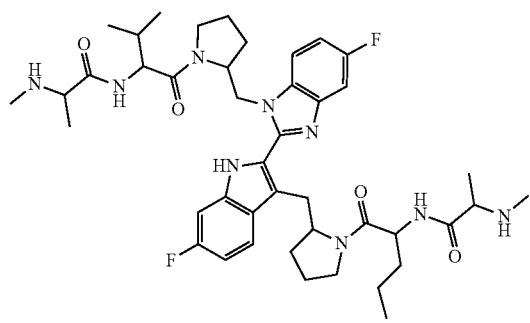
46
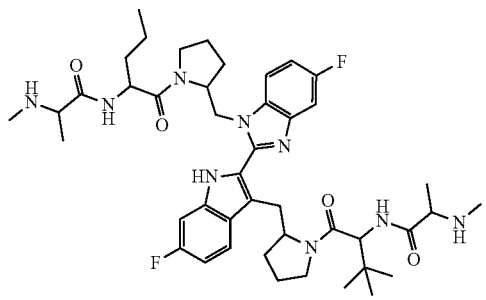
50
and
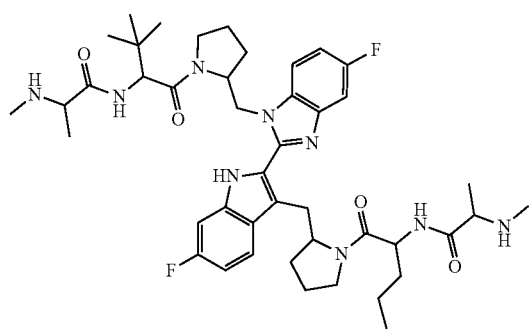
47
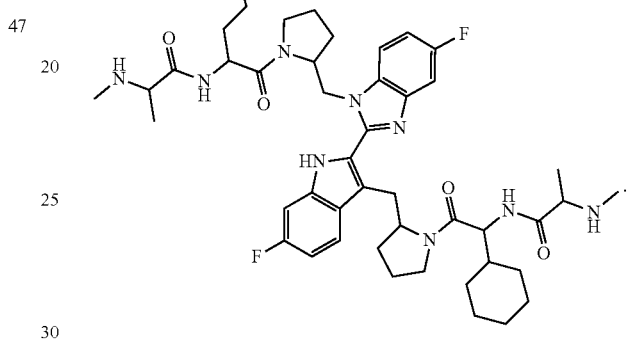
51
29. The compound or the pharmaceutically acceptable salt thereof of claim 28, which is selected from
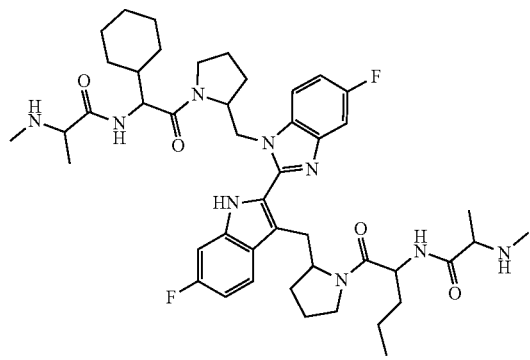
48
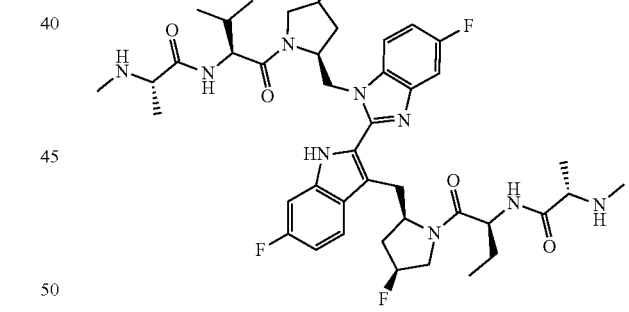
52
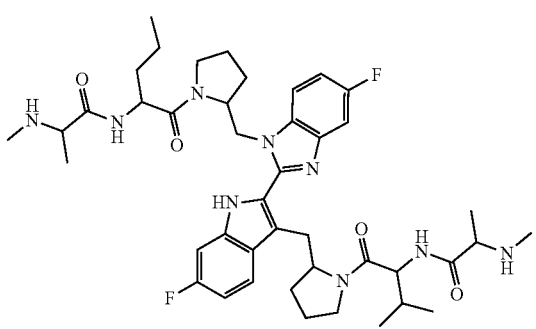
49
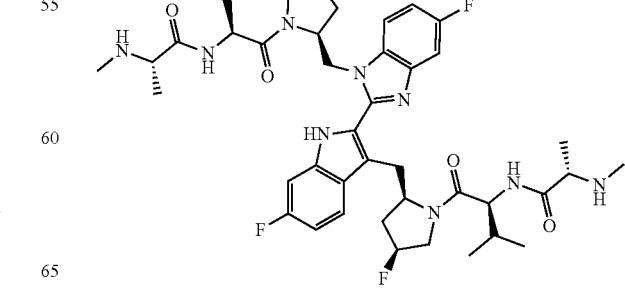
53

54
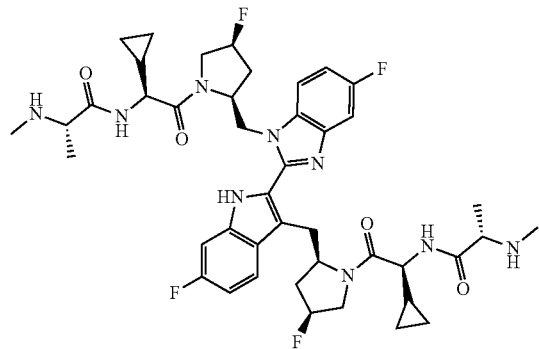
55
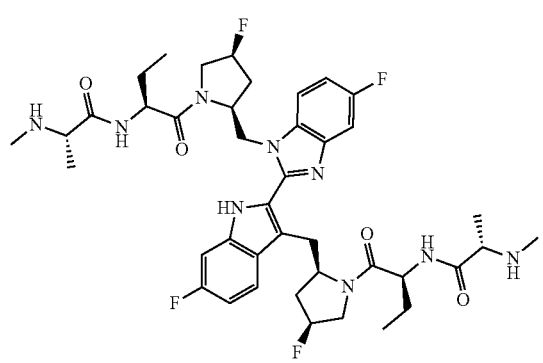
56
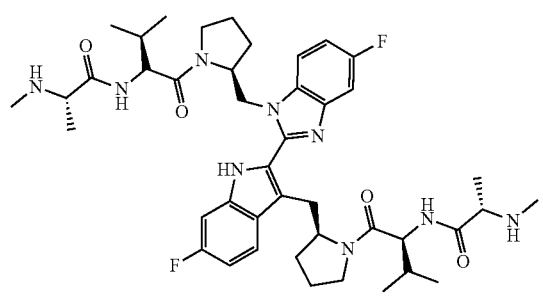
57
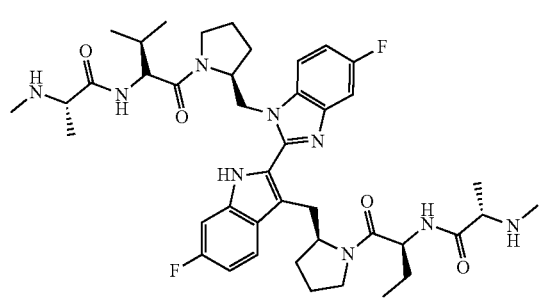
58
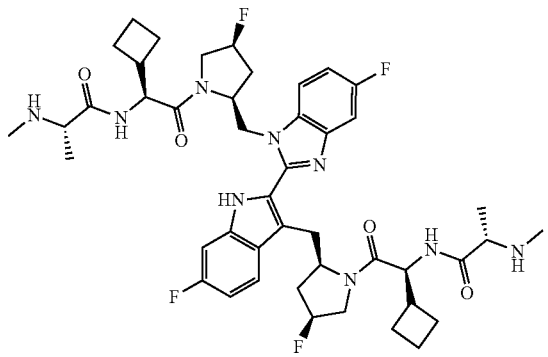
59
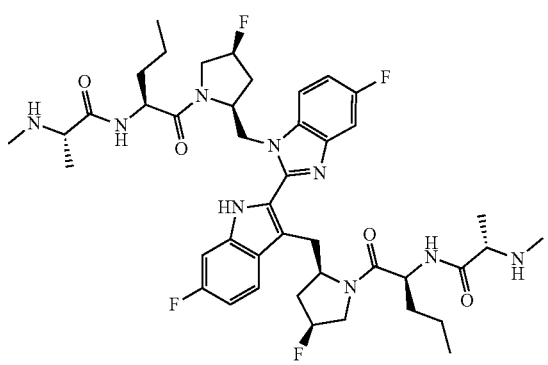
60
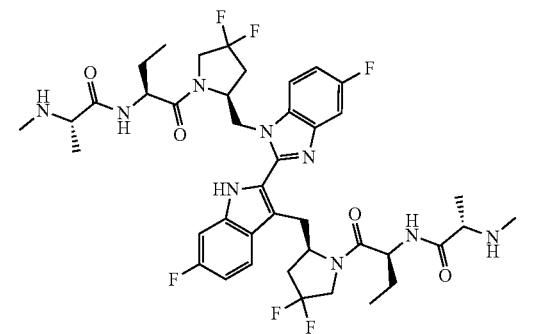
61
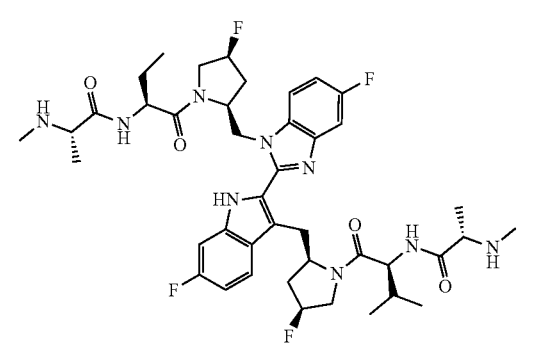

169
-continued
62
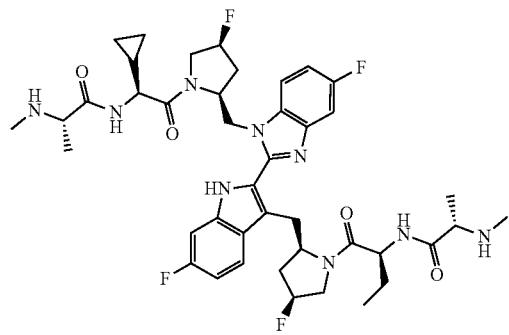
63
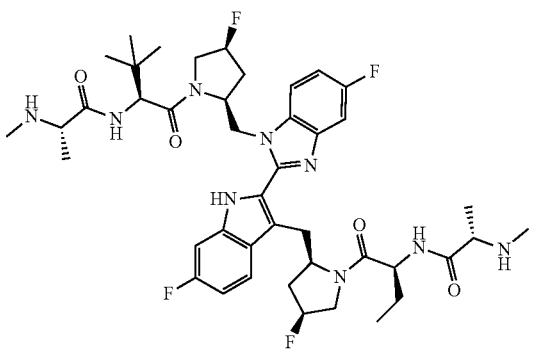
64
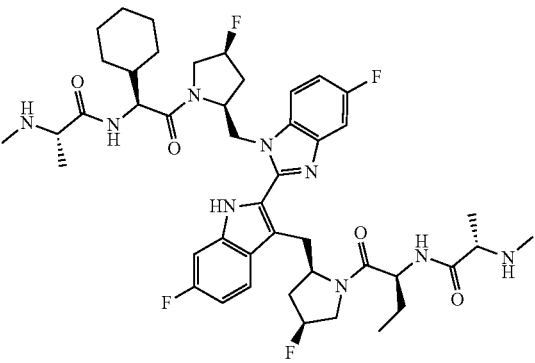
65
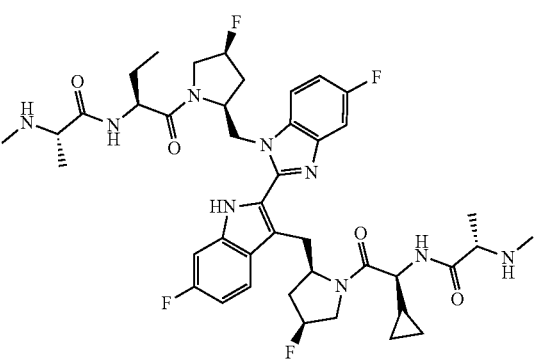
170
-continued
66
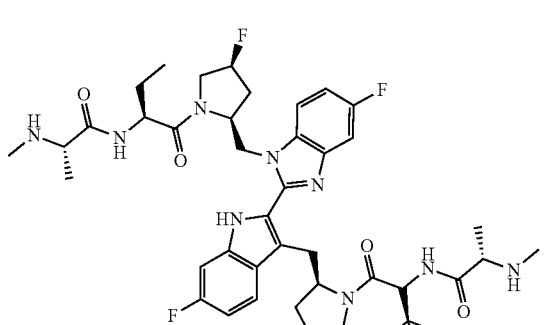
67
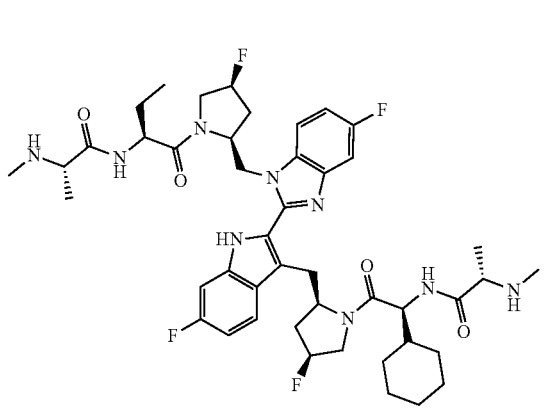
68
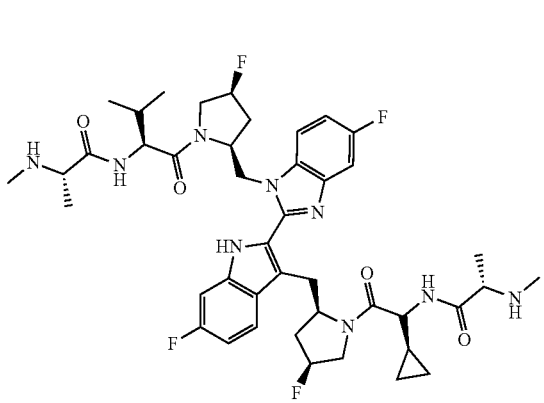
69
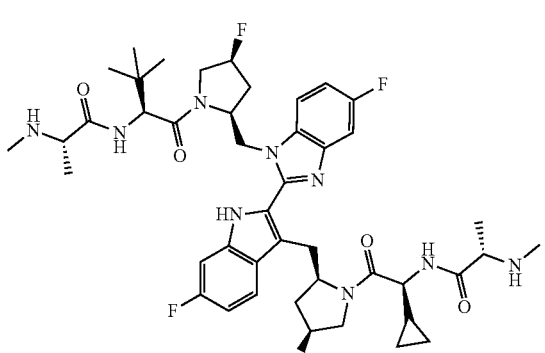

170
-continued
71
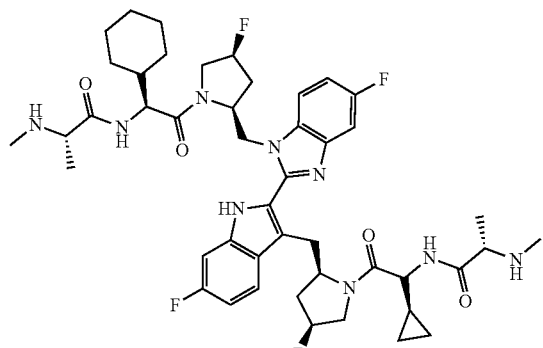
72
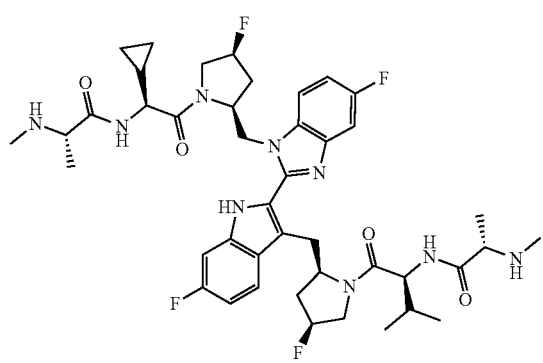
73
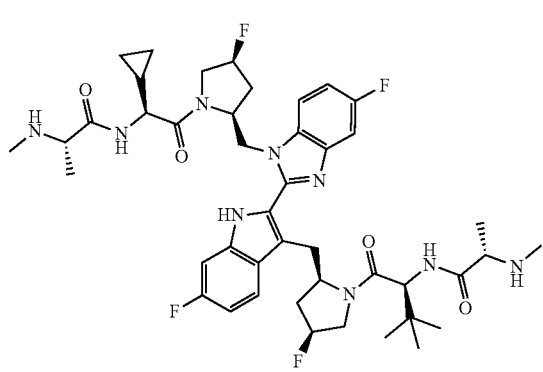
171
-continued
74
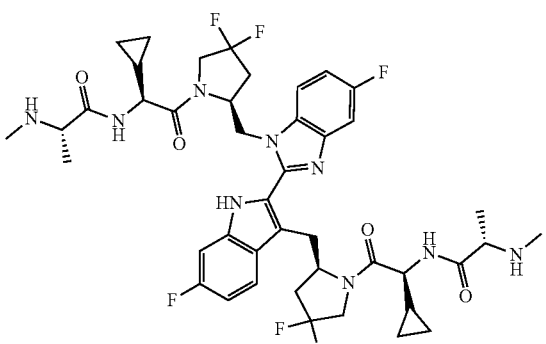
75
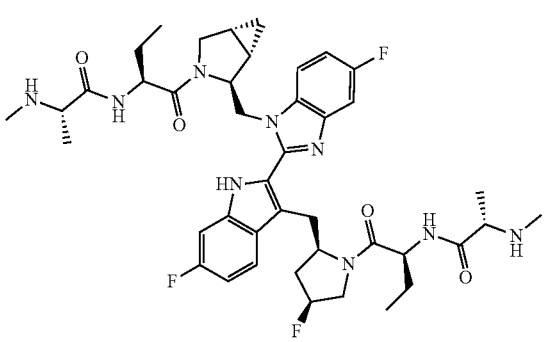
76
77
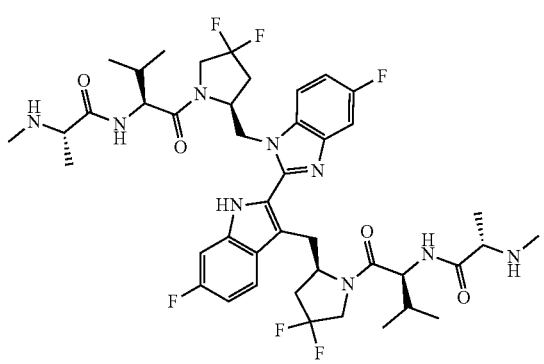

-continued
78
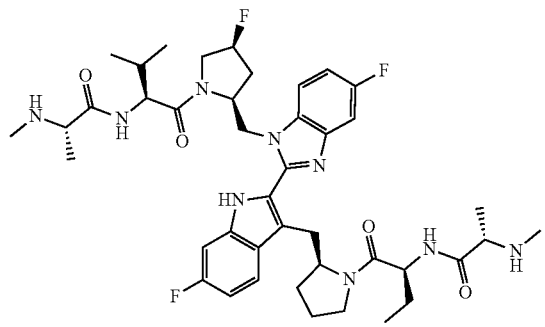
79
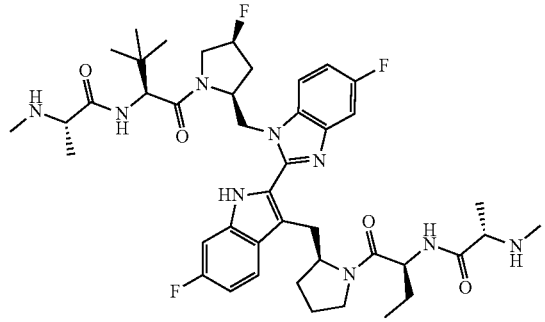
80
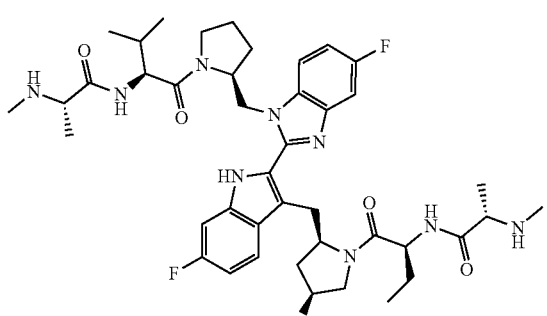
81
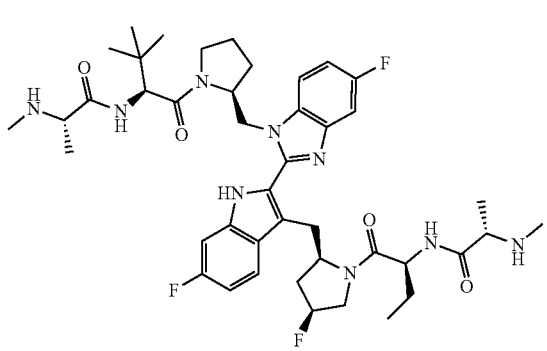
-continued
82
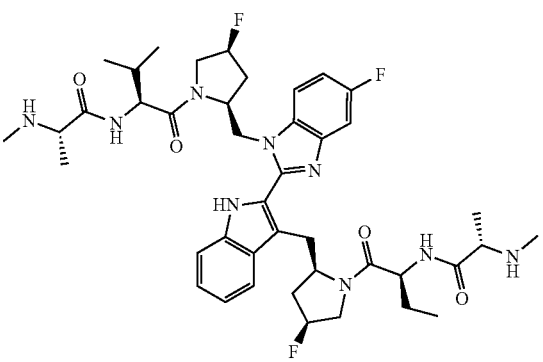
83
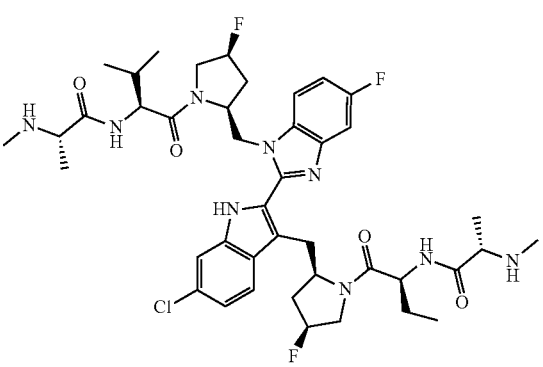
84
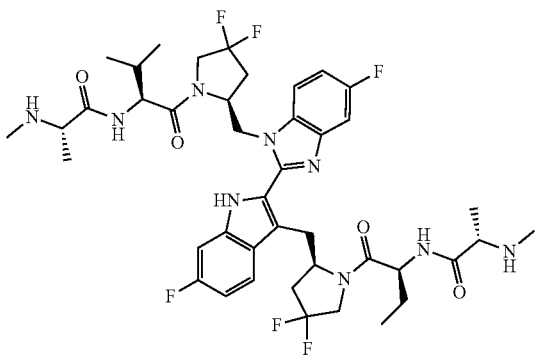
85
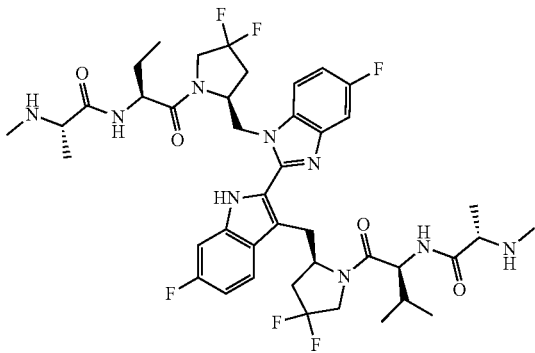

86
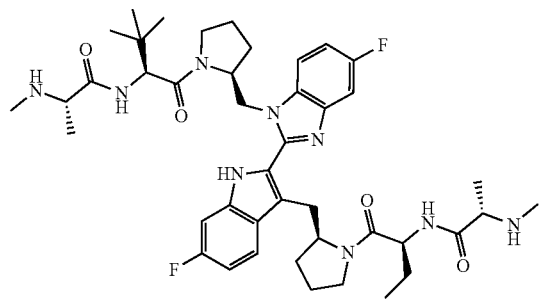
87
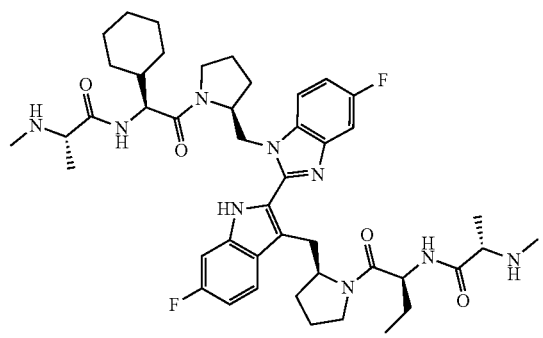
88
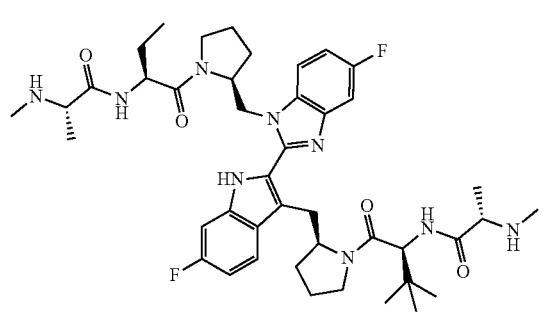
89
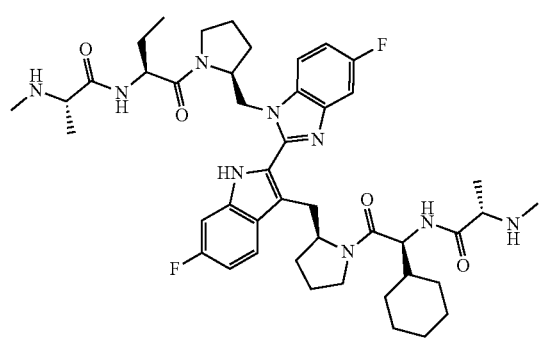
90
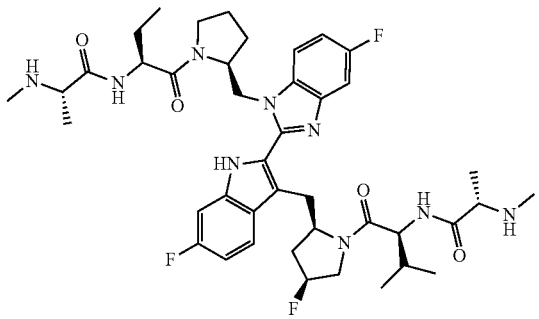
91
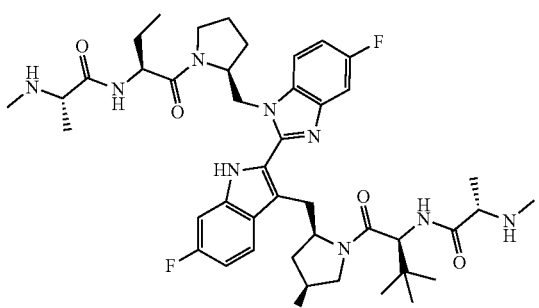
92
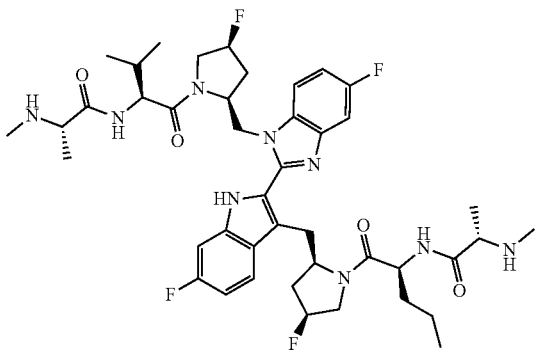
93
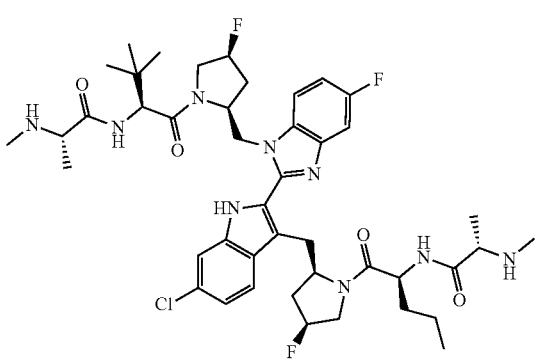

94
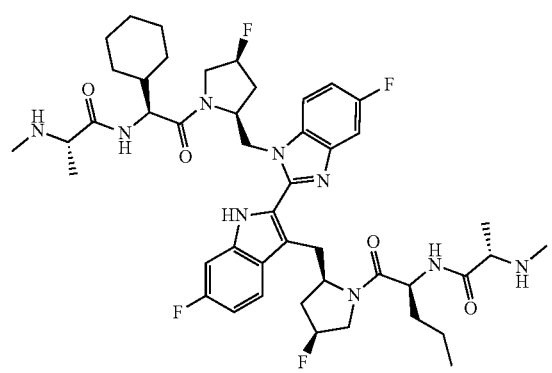
95
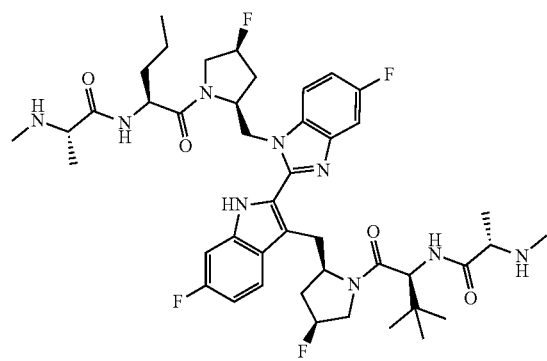
96
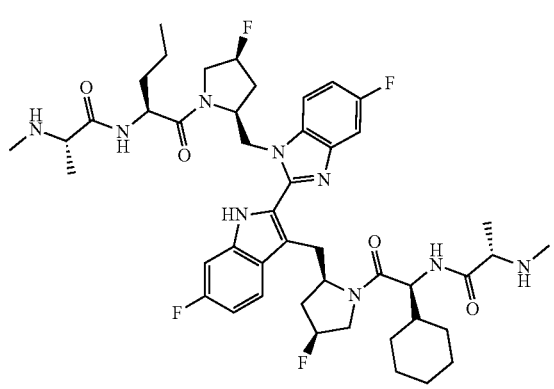
97
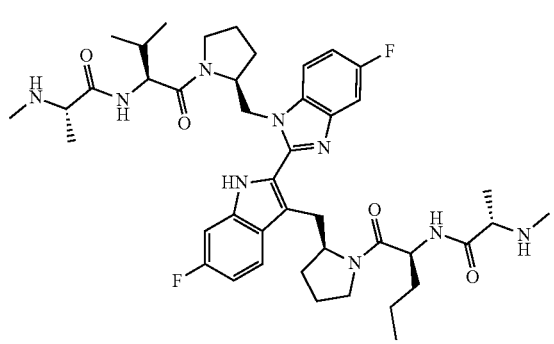
98
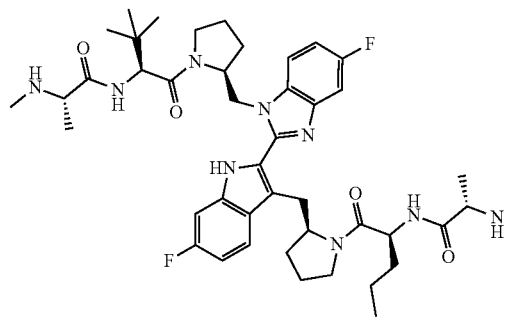
99
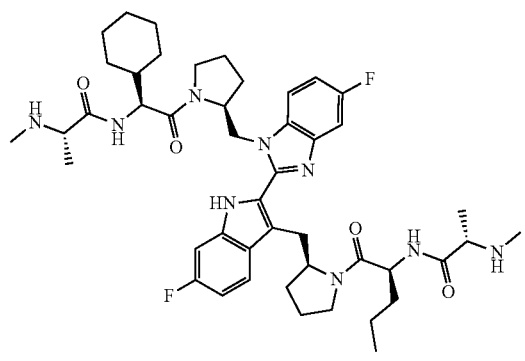
100
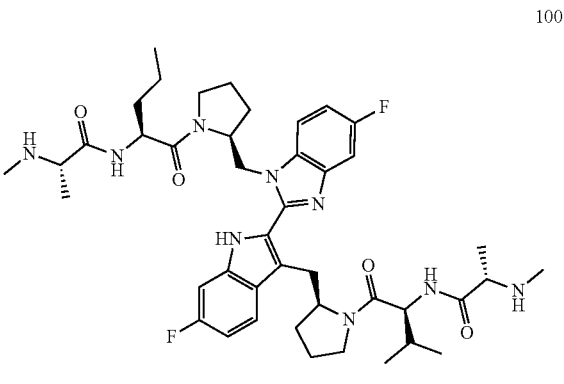
101
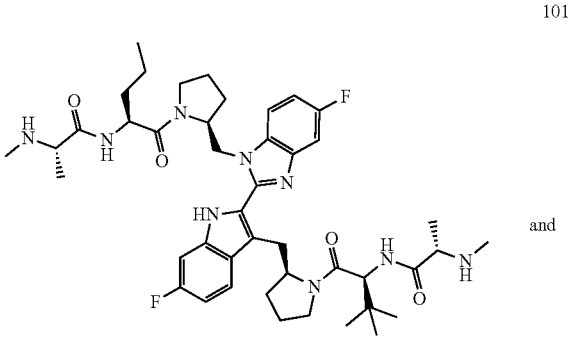
and -continued

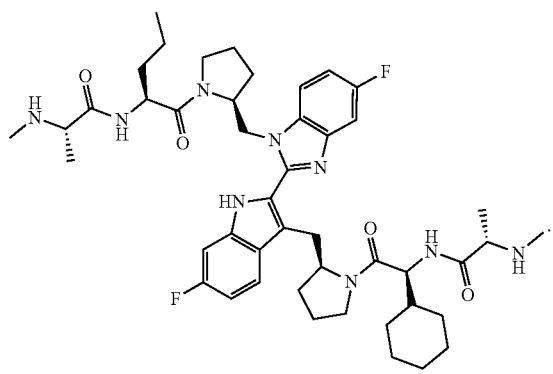

102

30. A pharmaceutical composition comprising an effective amount of the compound or the pharmaceutically acceptable salt thereof of claim 1.

31. A method for treating diseases caused by IAP distortion in a subject in need thereof, comprising administering an effective amount of the compound or the pharmaceutically acceptable salt thereof of claim 1 to the subject, wherein the diseases caused by distortion of IAP are selected from cancers and hepatitis B virus infection.

32. A method for treating diseases caused by IAP distortion in a subject in need thereof, comprising administering an effective amount of the pharmaceutical composition of claim 30 to the subject, wherein the diseases caused by distortion of IAP are selected from cancers and hepatitis B virus infection.

* * * * *